United States Patent
Schaus et al.

(10) Patent No.: US 12,251,372 B2
(45) Date of Patent: Mar. 18, 2025

(54) ANTILEISHMANIAL COMPOUNDS, COMPOSITIONS AND USE THEREOF

(71) Applicants: TRUSTEES OF BOSTON UNIVERSITY, Boston, MA (US); THE REGENTS OF THE UNIVERSITY OF CALIFORNIA, Oakland, CA (US); FUNDAÇÃO OSWALDO CRUZ, Manguinhos (BR)

(72) Inventors: Scott E. Schaus, Boston, MA (US); Lauren E. Brown, Waltham, MA (US); Mark W. Grinstaff, Brookline, MA (US); Danielle M. Fitzgerald, Boston, MA (US); Diana L Diaz, Brighton, MA (US); John A. Kavouris, Woburn, MA (US); Jair Lage De Siqueira-Neto, San Diego, CA (US); James McKerrow, San Diego, CA (US); Camila Indiani De Oliveira, Caminho das Árvores Salvador (BA)

(73) Assignees: TRUSTEES OF BOSTON UNIVERSITY; THE REGENTS OF THE UNIVERSITY OF CALIFORNIA, Oakland, CA (US); FUNDAÇÃO OSWALDO CRUZ, Rio de Janeiro (BR)

( * ) Notice: Subject to any disclaimer, the term of this patent is extended or adjusted under 35 U.S.C. 154(b) by 0 days.

(21) Appl. No.: 18/201,938

(22) Filed: May 25, 2023

(65) Prior Publication Data

US 2023/0381142 A1 Nov. 30, 2023

Related U.S. Application Data

(60) Provisional application No. 63/345,662, filed on May 25, 2022.

(51) Int. Cl.
*A61K 31/4162* (2006.01)
*A61K 9/16* (2006.01)
(Continued)

(52) U.S. Cl.
CPC ........ *A61K 31/4162* (2013.01); *A61K 9/1647* (2013.01); *A61K 31/4178* (2013.01);
(Continued)

(58) Field of Classification Search
CPC ........ A61P 33/00; A61P 33/02; C07D 311/02; C07D 319/02; C07D 405/12;
(Continued)

(56) References Cited

U.S. PATENT DOCUMENTS

| 2010/0167931 A1 | 7/2010 | Mueller |
| 2012/0107365 A1 | 5/2012 | Colson et al. |

(Continued)

FOREIGN PATENT DOCUMENTS

| WO | 2013080141 A1 | 6/2013 |
| WO | 2014115080 A1 | 1/2014 |

OTHER PUBLICATIONS

Nakamura, I. et al. Transition-Metal-Catalyzed Reactions in Heterocyclic Synthesis. Chem. Rev. 2004, vol. 104, p. 2127 (Year: 2004).*

(Continued)

*Primary Examiner* — Savitha M Rao
(74) *Attorney, Agent, or Firm* — NIXON PEABODY LLP; Ronald I. Eisenstein; Ravinderjit S. Braich

(57) ABSTRACT

Provided herein are antileishmanial compounds, compositions comprising the antileishmanial compounds, and use thereof.

23 Claims, 10 Drawing Sheets

(51) Int. Cl.
    A61K 31/4178    (2006.01)
    A61K 31/427     (2006.01)
    A61K 31/437     (2006.01)
    A61K 31/4439    (2006.01)
    A61K 31/454     (2006.01)
    A61K 31/501     (2006.01)
    A61K 31/506     (2006.01)
    A61P 33/02      (2006.01)
(52) U.S. Cl.
    CPC .......... *A61K 31/427* (2013.01); *A61K 31/437* (2013.01); *A61K 31/4439* (2013.01); *A61K 31/454* (2013.01); *A61K 31/501* (2013.01); *A61K 31/506* (2013.01); *A61P 33/02* (2018.01)
(58) Field of Classification Search
    CPC .. C07D 407/12; C07D 409/12; C07D 413/12; C07D 417/12; A61K 31/4162; A61K 31/4178; A61K 31/427; A61K 31/437; A61K 31/4439; A61K 31/454; A61K 31/501; A61K 31/506; A61K 9/1647
    See application file for complete search history.

(56)                References Cited

U.S. PATENT DOCUMENTS

2015/0353563 A1    12/2015  Furet et al.
2020/0056038 A1     2/2020  Grinstaff et al.

OTHER PUBLICATIONS

Anderson (Chem and Biol 10:787-797, 2003), (Year: 2003).*
Thiel (Nature Biotechnol 2:513-519, 2004), (Year: 2004).*
Kavouris et al.(Frontiers in tropical disease, Jan. 2023, pp. 01-19) (Year: 2023).*
Pubchem-750, Dated 2015 (Year: 2015).*
Ait-Oudhia et al. "Leishmania antimony resistance: what we know what we can learn from the field." Parasitology research 109 (2011): 1225-1232.
Bhattacharya et al. "New insights with miltefosine unresponsiveness in Brazilian Leishmania infantum isolates." EBioMedicine 37 (2018): 13-14.
Bunally et al. "The role and impact of high throughput biomimetic measurements in drug discovery." ADMET and DMPK 6.2 (2018): 74-84.
Debie et al. "A confidence level algorithm for the determination of absolute configuration using vibrational circular dichroism or Raman optical activity." ChemPhysChem 12.8 (2011): 1542-1549.
De Muylder et al. "A screen against Leishmania intracellular amastigotes: comparison to a promastigote screen and identification of a host cell-specific hit." PLoS Neglected Tropical Diseases 5.7 (2011): e1253.
De Rycker et al. "Comparison of a high-throughput high-content intracellular Leishmania donovani assay with an axenic amastigote assay." Antimicrobial agents and chemotherapy 57.7 (2013): 2913-2922.
Devegowda et al. "Novel 6-N-arylcarboxamidopyrazolo [4, 3-d] pyrimidin-7-one derivatives as potential anti-cancer agents." Bioorganic & Medicinal Chemistry Letters 20.5 (2010): 1630-1633.
Flynn et al. "Prevention and treatment of cutaneous leishmaniasis in primates by using synthetic type D/A oligodeoxynucleotides expressing CpG motifs." Infection and immunity 73.8 (2005): 4948-4954.
Frezard. "Pentavalent antimonials: new perspectives for old drugs." Molecules 14.7 (2009): 2317-2336.
Furet et al. "Discovery of a novel class of highly potent inhibitors of the p53-MDM2 interaction by structure-based design starting from a conformational argument." Bioorganic & medicinal chemistry letters 26.19 (2016): 4837-4841.
Gein et al. "Three-component reaction of methyl 2, 4-dioxo-4-phenylbutanoate and methyl 2, 4-dioxopentanoate with aromatic aldehydes and propane-1, 2-diamine and chemical properties of the products." Russian journal of organic chemistry 46 (2010): 875-883.
Jacobs et al. "Boron-based drugs as antiprotozoals." Current opinion in infectious diseases 24.6 (2011): 586-592.
Jha et al. "The treatment of visceral leishmaniasis: safety and efficacy." Journal of Nepal Medical Association 52.192 (2013).
Leeson et al. "Molecular property design: does everyone get it?." ACS Medicinal Chemistry Letters 6.7 (2015): 722-725.
Singh et al. "Leishmaniasis: current status of available drugs and new potential drug targets." Asian Pacific journal of tropical medicine 5.6 (2012): 485-497.
Srivastava et al. "Laboratory confirmed miltefosine resistant cases of visceral leishmaniasis from India." Parasites & vectors 10 (2017): 1-11.
Sundar et al. "A cluster of cases of severe cardiotoxicity among kala-azar patients treated with a high-osmolarity lot of sodium antimony gluconate." The American journal of tropical medicine and hygiene 59.1 (1998): 139-143.
Sundar et al. "Antimony toxicity." International journal of environmental research and public health 7.12 (2010): 4267-4277.
Sundar et al. "Chemotherapeutics of visceral leishmaniasis: present and future developments." Parasitology 145.4 (2018): 481-489.
Tahir et al. "Safety and efficacy of miltefosine in cutaneous leishmaniasis: An open label, non-comparative study from Balochistan." Pakistan journal of medical sciences 35.2 (2019): 495.
Thomas et al. "Identification of GSK3186899/DDD853651 as a preclinical development candidate for the treatment of visceral leishmaniasis." Journal of Medicinal Chemistry 62.3 (2018): 1180-1202.
Thompson et al. "7-Substituted 2-nitro-5, 6-dihydroimidazo [2, 1-b][1, 3] oxazines: novel antitubercular agents lead to a new preclinical candidate for visceral leishmaniasis." Journal of medicinal chemistry 60.10 (2017): 4212-4233.
Thompson et al. "Development of (6 R)-2-Nitro-6-[4-(trifluoromethoxy) phenoxy]-6, 7-dihydro-5 H-imidazo [2, 1-b][1, 3] oxazine (DNDI-8219): A New Lead for Visceral Leishmaniasis." Journal of medicinal chemistry 61.6 (2018): 2329-2352.
Thompson et al. "Repositioning antitubercular 6-nitro-2, 3-dihydroimidazo [2, 1-b][1, 3] oxazoles for neglected tropical diseases: structure-activity studies on a preclinical candidate for visceral leishmaniasis." Journal of medicinal chemistry 59.6 (2016): 2530-2550.
World Health Organization. Control of the leishmaniases: report of a meeting of the WHO Expert Commitee on the Control of Leishmaniases, Geneva, Mar. 22-26, 2010. World Health Organization, 2010.
Vakil et al. "Pharmacotherapy for leishmaniasis in the United States: focus on miltefosine." Pharmacotherapy: The Journal of Human Pharmacology and Drug Therapy 35.5 (2015): 536-545.
Valko et al. "Fast gradient HPLC method to determine compounds binding to human serum albumin. Relationships with octanol/water and immobilized artificial membrane lipophilicity." Journal of pharmaceutical sciences 92.11 (2003): 2236-2248.
Van Bocxlaer et al. "Novel benzoxaborole, nitroimidazole and aminopyrazoles with activity against experimental cutaneous leishmaniasis." International Journal for Parasitology: Drugs and Drug Resistance 11 (2019): 129-138.
Van Den Kerkhof et al. "In vitro and in vivo pharmacodynamics of three novel antileishmanial lead series." International Journal for Parasitology: Drugs and Drug Resistance 8.1 (2018): 81-86.
Verthelyi et al. "CpG oligodeoxynucleotides protect normal and SIV-infected macaques from Leishmania infection." The Journal of Immunology 170.9 (2003): 4717-4723.
Veira-Goncalves et al. "First report of treatment failure in a patient with cutaneous leishmaniasis infected by Leishmania (Viannia) naiffi carrying Leishmania RNA virus: a fortuitous combination?." Revista da Sociedade Brasileira de Medicina Tropical 52 (2019).
Vos, et al. "Global, regional, and national incidence, prevalence, and years lived with disability for 310 diseases and injuries, 1990-2015:

(56) References Cited

OTHER PUBLICATIONS a systematic analysis for the Global Burden of Disease Study 2015." The lancet 388.10053 (2016): 1545-1602.

Walker et al. "Immunostimulatory oligodeoxynucleotides promote protective immunity and provide systemic therapy for leishmaniasis via IL-12-and IFN-γ-dependent mechanisms." Proceedings of the National Academy of Sciences 96.12 (1999): 6970-6975.

Wyllie et al. "Cyclin-dependent kinase 12 is a drug target for visceral leishmaniasis." Nature 560.7717 (2018): 192-197.

Wyllie et al. "Preclinical candidate for the treatment of visceral leishmaniasis that acts through proteasome inhibition." Proceedings of the National Academy of Sciences 116.19 (2019): 9318-9323.

Young et al. "Getting physical in drug discovery II: the impact of chromatographic hydrophobicity measurements and aromaticity." Drug discovery today 16.17-18 (2011): 822-830.

Zhou et al. "Design, synthesis and structure-activity relationship of 4, 5-dihydropyrrolo [3, 4-c] pyrazol-6 (1H)-ones as potent p53-MDM2 inhibitors." Chinese Chemical Letters 28.2 (2017): 422-425.

Zhuang et al. "Double-edged swords as cancer therapeutics: novel, orally active, small molecules simultaneously inhibit P53-MDM2 interaction and the NF-κB pathway." Journal of medicinal chemistry 57.3 (2014): 567-577.

Zimmermann et al. "Cutting edge: CpG oligodeoxynucleotides trigger protective and curative Th1 responses in lethal murine leishmaniasis." The Journal of Immunology 160.8 (1998): 3627-3630.

National Center for Biotechnology Information. "PubChem Substance Record for SID 141029750, SID 141029750, Source: SCRIPDB" PubChem, https://pubchem.ncbi.nlm.nih.gov/substance/141029750. Accessed Oct. 25, 2023.

National Center for Biotechnology Information. "PubChem Substance Record for SID 228304358, SCHEMBL2171128, Source: SureChEMBL" PubChem, https://pubchem.ncbi.nlm.nih.gov/substance/228304358. Accessed Oct. 25, 2023.

\* cited by examiner

Black = measured, Gray = predicted for (S)

Black = measured, Gray = predicted for (R)

ANTILEISHMANIAL COMPOUNDS, COMPOSITIONS AND USE THEREOF

CROSS-REFERENCE TO RELATED APPLICATIONS

This application claims benefit under 35 U.S.C. § 119(e) of the U.S. Provisional Application No. 63/345,662 filed May 25, 2022, the content of which is incorporated herein by reference in its entirety.

GOVERNMENT SUPPORT

This invention was made with Government support under Grant No. GM086180, No. GM067041 and No. AI151639 awarded by the National Institutes of Health. The Government has certain rights in the invention.

TECHNICAL FIELD

The disclosure relates generally to antileishmanial compounds, compositions comprising the anti-leishmanial compounds and uses thereof.

BACKGROUND

Leishmaniasis is a neglected disease caused by protozoan parasites from the genus *Leishmania* sp. It is transmitted by the sandfly vector and manifests in different clinical forms including skin ulcers, mucosa destruction, damage to visceral organs such as the liver and spleen, and bone marrow damage. The clinical outcome is determined primarily by the species of the parasite and the immune system of the host. There are 98 countries affected by leishmaniasis with more than 2 million people currently infected and 350 million people at risk. *Leishmania* parasites predominately infect monocytes in the reticulo-endothelial system.

Chemotherapy options for leishmaniasis are limited. Antimonials have been the first line drug for decades in most endemic countries, despite antimony's notorious adverse effects, hospitalization requirements and increasing cases of antimony-resistant parasites. Amphotericin B, the main alternative treatment, also causes significant harmful side effects. Liposomal formulations are better tolerated, but are prohibitively expensive for most affected populations. Miltefosine, an anti-cancer drug, was recently repurposed to treat leishmaniasis and is the only oral treatment available and approved for use in the US. Miltefosine also has toxicity limitations, teratogenicity and lack of efficacy against certain *Leishmania* species.

There remains a need for effective antileishmanial compounds, compositions, and methods for treating leishmaniasis. The present disclosure addresses these needs.

SUMMARY

In one aspect provided herein is a composition comprising an antileishmanial compound and a polymer. In some embodiments of any of the aspects described herein, an anti-leishmanial compound is a compound of Formula (I) or (II):

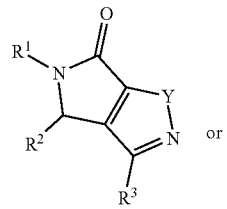

(Formula I)

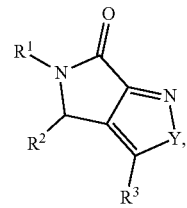

(Formula II)

or a pharmaceutically acceptable salt thereof.

In compounds of Formula (I) or (II), Y can be Y is $NR^4$, $CH_2$, O or S; $R^{11}$ can be aryl, heteroaryl, alkyl, alkenyl, alkynyl, cycloalkyl, or heterocyclyl; $R^{12}$ can be cycloalkyl, heterocyclyl, aryl or heteroaryl; $R^{13}$ can be $-CH_2-R^{15}$; $R^{14}$ is H, alkyl, alkenyl, alkynyl, cycloalkyl, heterocyclyl, aryl or heteroaryl; and $R^5$ can be alkyl, alkenyl, alkynyl, aryl, heteroaryl, cycloalkyl, heterocyclyl, or a nucleophile, It is noted that any alkyl, alkenyl, alkynyl, aryl, heteroaryl, cycloalkyl and heterocyclyl described herein can be optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

In compounds of Formula (I), (I-A), (II) or (II-A), the carbon to which the $R^{12}$ group is attached can have the R or S stereochemistry. For example, the carbon to which the $R^{12}$ group is attached has the R stereochemistry. Preferably, the carbon to which the $R^{12}$ group is attached has the S stereochemistry.

In some embodiments of any one of the aspects described herein, an anti-leishmanial compound is a compound of Formula (I) or (II), where Y is $N-R^4$, e.g., the anti-leishmanial compound is of Formula (I-A) or (II-A):

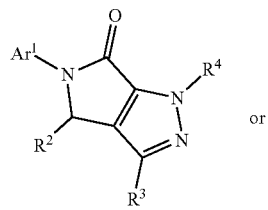

(Formula I-A)

(Formula II-A)

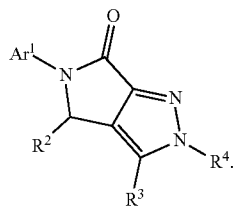

In some embodiments of any one of the aspects described herein, the antileishmanial compound is selected from the group consisting of: CMLD010994, CMLD011572, CMLD011562, CMLD011039, CMLD011574, CMLD010976, CMLD010901, BUCMD00694, BUCMD00729, BUCMD00683, BUCMD00695, BUCMD00730, CMLD010921, BUCMD00669, BUCMD00629, BUCMD00718, BUCMD00717, CMLD010948, CMLD011101, and CMLD011567. In some embodiments, the antileishmanial compound is selected from the group consisting of: BUCMD00694, BUCMD00729, BUCMD00683, BUCMD00695, BUCMD00730, BUCMD00669, BUCMD00629, BUCMD00718, and BUCMD00717.

The composition can be formulated for topical, intravenous (iv) or oral. Accordingly, in some embodiments, the composition is formulated for iv administration. In some other embodiments, the composition is formulated for topical administration.

In some cases, the polymer and the antileishmanial compound are comprised in a particle comprising the polymer and the antileishmanial compound. Generally, the particle is from about 5 nm to about 1500 nm in size, e.g., from about 10 nm to about 1,000 nm in size, optionally from about 50 nm to about 200 nm in size.

In some embodiments, the particle is an expansile particle. For example, the particle comprises a first volume at a neutral pH and a second volume at an acidic pH, wherein the second volume is at least 1× greater than the first volume. Without wishing to be bound by a theory, the change in volume allows the particle to accumulate in the liver of a subject after administration and release the antileishmanial compound in the liver. In some embodiments, the antileishmanial compound is released at higher rate at an acidic pH relative to a release at neutral pH.

In some embodiments of any one of the aspects described herein, the particle is biodegradable.

The particle comprising the antileishmanial compound can be included in formulation comprising the particles and a pharmaceutically acceptable carrier or excipient.

In some embodiments of any one of the aspects described herein, the composition is formulated for topical administration. When the composition is formulated for topical administration, the composition can be in the form of is in the form of a film, a sheet, a dressing, a cream, a spray, a liquid, a gel, a hydrogel, an emulsion, or a suspension. For example, the composition can be in the form of an adhesive.

Embodiments of the various aspects described herein include a polymer. In some embodiments, the polymer can be selected from the group consisting of polycarbonates, polyesters, polyacrylates, polyamindes, and copolymers and mixtures thereof. In some cases, the polymer comprises one or more monomers of Formula (A), Formula (B), and/or Formula (C):

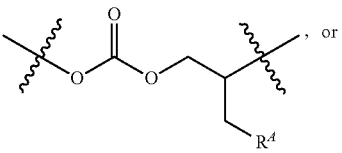
Formula (A)

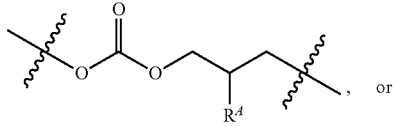
Formula (B)

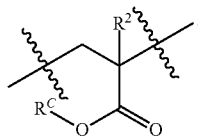
Formula (C)

In monomers of Formula (A) or (B), each $R^A$ is independently —OC(O)—$R^{41}$, —OC(O)O—$R^{41}$, —OC(O)NH—$R^{41}$, —NHC(O)O—$R^{41}$, —NHC(O)NH—$R^{41}$, —O$R^{41}$, —C(O)—$R^{41}$, —C(O)O—$R^{41}$, or —C(O)NH—$R^{41}$; and each $R^{41}$ is independently hydrogen, alkyl, alkenyl, cycloalkyl, aryl, heterocyclyl, heteroaryl, silyl, alkylsilyl, arylsilyl, alkylaryl, arylalkyl, poly(ethylene glycol), poly(ethylene oxide), poly(hydroxyacid)), a carbohydrate, a protein, a polypeptide, an amino acid, a nucleic acid, a nucleotide, a lipid, an oligosaccharide, a polysaccharide, an antibody, a pharmaceutical agent, an imaging agent, an epitope for a biological receptor, a photocrosslinkable group, or an ionically crosslinkable group, wherein alkyl, alkenyl, cycloalkyl, aryl, heterocyclyl, heteroaryl, silyl, alkylsilyl, arylsilyl, alkylaryl, and arylalkyl is optionally substituted by one or more substituents selected independently from the group consisting of hydroxyl, hydroxyether, carboxyl, carboxyester, carboxyamide, amino, mono- or di-substituted amino, thiol, thioester, sulfate, phosphate, phosphonate, and halogen.

In monomers of Formula (C), each $R^C$ is independently:

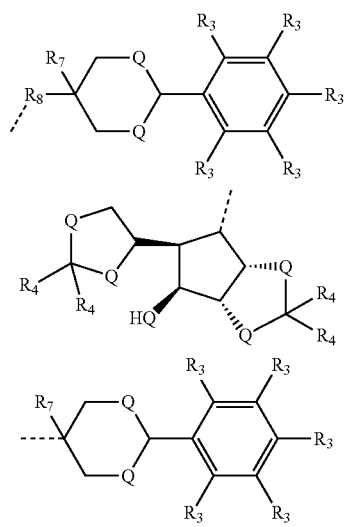

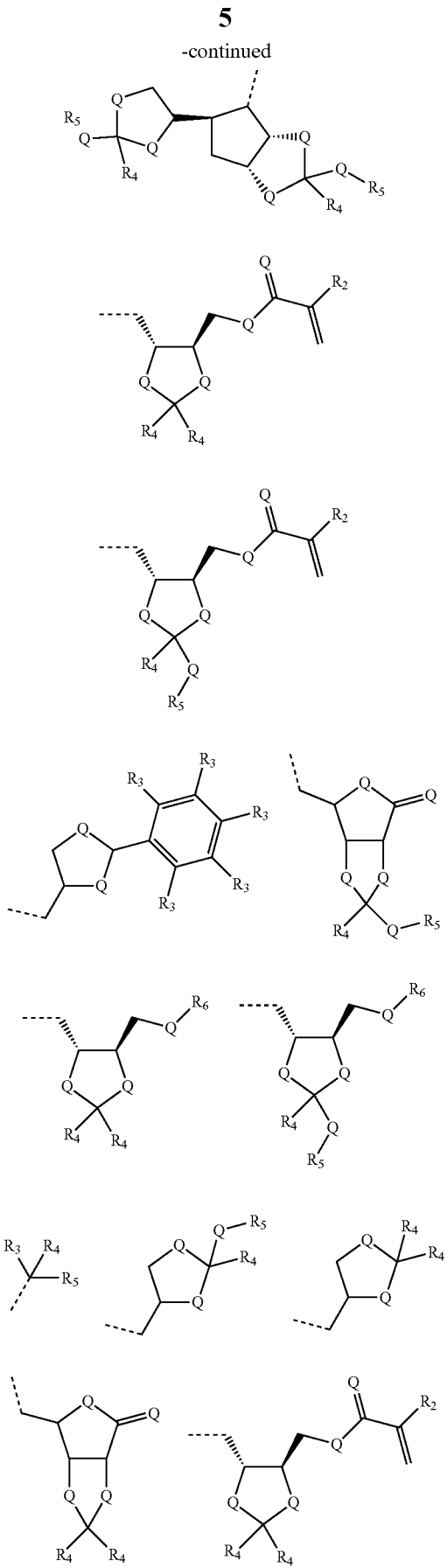

where each Q is O;
each $R^2$ is independently selected from the group consisting of hydrogen, a straight or branched alkyl, cycloalkyl, aryl, olefin, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;
one $R_3$ is selected from the group consisting of methoxy, ethoxy, amino, nitro, cycloalkyl, aryl, and olefin;
and the remaining $R_3$ are each independently selected from the group consisting of hydrogen, methoxy, ethoxy, amino, a straight and branched alkyl, cycloalkyl, aryl, and olefin;
$R_4$, $R_5$, and $R_6$ are each independently selected from the group consisting of a straight or branched alkyl, cycloalkyl, aryl, and olefin; and
$R_7$ and $R_8$ are each independently selected from the group consisting of hydrogen, a straight or branched alkyl, cycloalkyl, aryl, olefin, alkylaryl, and arylalkyl.

In some embodiments of any one of the aspects described herein, the polymer comprises one or more monomers of Formula (A) and/or Formula (B). For example, the polymer comprises at least one monomer of Formula (A). In another example, the polymer comprises at least one monomer of Formula (B).

In some embodiments of any one of the aspects described herein, the polymer is a poly(glycerol carbonate) or a copolymer thereof. For example, the polymer is poly(1,3-glycerol carbonate), poly(1,2-glycerol carbonate), or a copolymer thereof. In some embodiments, the polymer is copolymer comprising poly(glycerol carbonate) and one of polycaprolactone, poly(lactic acid), poly(glycolic acid), poly(lactic-co-glycolic acid), poly(trimethylene carbonate), polyester, polycarbonate, or polyamide. For example, the polymer is copolymer comprising poly(glycerol carbonate) and polycaprolactone. In some embodiments, the copolymer is poly(1,3-glycerol carbonate)-$C_{18}$-co-poly(ε-caprolactone).

In some embodiments of any one of the aspects described herein, the composition is formulated for topical administration and the polymer comprises one or more monomers of Formula (A) and/or Formula (B).

In some embodiments of any one of the aspects described herein, the composition is formulated for iv or oral administration and the polymer comprises one or more monomers of Formula (C).

In some embodiments of any one of the aspects described herein, the composition is formulated for iv or oral administration and the polymer comprises one or more monomers of Formula (A) and/or Formula (B).

In some embodiments of any one of the aspects described herein, the composition is formulated for iv or oral administration and the polymer comprises one or more monomers of Formula (C).

In some embodiments, the composition is a pharmaceutical composition and further comprises a pharmaceutically acceptable carrier or excipient.

In some embodiments of any one of the aspects described herein, the composition further comprises an active agent. Exemplary active agents include, but are not limited to, a second antileishmanial compound. Some exemplary antileishmanial compound include, but are not limited to, antimonials, miltefosine, dronedarone, stibogluconate, meglumine antimonite, pentamidine, amphotericin B, paromomycin, reversed amidines, and pharmaceutically acceptable salts thereof), and/or the active agent is selected from the group consisting of wound-healing agents, anti-scarring agents, antioxidant agents, cooling agents, soothing agents, anti-inflammatory-agents, antibiotics, topical analgesics, counter irritants, penetration enhancers, and permeation enhancers.

In some embodiments of any one of the aspects described herein, the composition can further comprise one or more of binders, viscosity modifiers, preservatives, humectants, emollients, pH stabilizing agents, chelating agents, gelling agents, thickening agents, emulsifiers, buffers, and carriers.

In another aspect provided herein is a compound of Formula (I) or (II) or a pharmaceutically acceptable salt thereof. Optionally, the compound is not pyrrolo[3,4-c]pyrazol-6(1H)-one, 4,5-dihydro-3-(2-hydroxyethyl)-5-[4-(3-isoxazolyl)phenyl]-4-(2-methoxyphenyl)-; Pyrrolo[3,4-c]pyrazol-6(1H)-one, 3-butyl-4,5-dihydro-5-[4-(3-isoxazolyl)phenyl]-4-(2-methoxyphenyl)-; Pyrrolo[3,4-c]pyrazol-6(1H)-one, 3-(2,2-dimethylpropyl)-4,5-dihydro-5-[4-(3-isoxazolyl)phenyl]-4-(2-methoxyphenyl)-; Pyrrolo[3,4-c]pyrazol-6(1H)-one, 4-(4-chlorophenyl)-1-cyclopropyl-4,5-dihydro-3-(methoxymethyl)-; Pyrrolo[3,4-c]pyrazol-6(1H)-one, 3-ethyl-1-(4-fluorophenyl)-4,5-dihydro-4,5-dimethyl-; Pyrrolo[3,4-c]pyrazol-6(1H)-one, 4-(4-chlorophenyl)-5-(3,7-dimethyl-1,2-benzisoxazol-5-yl)-3-ethyl-4,5-dihydro-1-(2-hydroxyethyl)-; Pyrrolo[3,4-c]pyrazol-6(2H)-one, 4-(4-chlorophenyl)-5-(3,7-dimethyl-1,2-benzisoxazol-5-yl)-3-ethyl-4,5-dihydro-2-(2-hydroxyethyl)-; Pyrrolo[3,4-c]pyrazole-4-propanoic acid, 3-[(2,4-dichlorophenyl)methyl]-1,4,5,6-tetrahydro-5-methyl-6-oxo-; Pyrrolo[3,4-c]pyrazol-6(1H)-one, 4-(4-chlorophenyl)-5-(1,6-dihydro-1,5-dimethyl-6-oxo-3-pyridinyl)-3-ethyl-4,5-dihydro-; Pyrrolo[3,4-c]pyrazol-6(2H)-one, 5-(1H-benzimidazol-6-yl)-3-ethyl-4,5-dihydro-2-methyl-4-(4-propoxyphenyl)-; Pyrrolo[3,4-c]pyrazol-6(1H)-one, 5-(4-bromophenyl)-4,5-dihydro-3-(2-methoxyethyl)-4-phenyl-; 2-Propenoic acid, 3-[3-[(2,4-dichlorophenyl)methyl]-1,4,5,6-tetrahydro-5-methyl-6-oxopyrrolo[3,4-c]pyrazol-4-yl]-, (2E)-; Pyrrolo[3,4-c]pyrazol-6(1H)-one, 3-butyl-5-(4-fluorophenyl)-4,5-dihydro-4-(2-methoxyphenyl)-; Pyrrolo[3,4-c]pyrazol-6(1H)-one, 4,5-dihydro-3-(hydroxymethyl)-4-(2-methoxyphenyl)-5-[4-(3-thienyl)phenyl]-; Pyrrolo[3,4-c]pyrazol-6(1H)-one, 4-(4-chlorophenyl)-5-(1,6-dihydro-1,5-dimethyl-6-oxo-3-pyridinyl)-3-ethyl-4,5-dihydro-1-(2-hydroxyethyl)-; Pyrrolo[3,4-c]pyrazol-6(1H)-one, 4-(4-chlorophenyl)-1-cyclopropyl-5-(1,6-dihydro-1,5-dimethyl-6-oxo-3-pyridinyl)-3-ethyl-4,5-dihydro-; Pyrrolo[3,4-c]pyrazol-6(1H)-one, 4-(4-chlorophenyl)-1-cyclopropyl-4,5-dihydro-3-(methoxymethyl)-5-[(4-methoxyphenyl)methyl]-; Pyrrolo[3,4-c]pyrazol-6(1H)-one, 4-(4-chlorophenyl)-1-cyclopropyl-5-(1,6-dihydro-1,5-dimethyl-6-oxo-3-pyridinyl)-4,5-dihydro-3-(hydroxymethyl)-; Pyrrolo[3,4-c]pyrazol-6(1H)-one, 4-(4-chlorophenyl)-5-(1,6-dihydro-1,5-dimethyl-6-oxo-3-pyridinyl)-3-ethyl-4,5-dihydro-1-(1-methyl-1H-pyrazol-5-yl)-; Pyrrolo[3,4-c]pyrazol-6(1H)-one, 4-(4-chlorophenyl)-1-cyclopropyl-5-(1,6-dihydro-1,5-dimethyl-6-oxo-3-pyridinyl)-4,5-dihydro-3-(methoxymethyl)-, (4S)—; Pyrrolo[3,4-c]pyrazol-6(1H)-one, 4-(4-chlorophenyl)-1-cyclopropyl-5-(1,6-dihydro-1,5-dimethyl-6-oxo-3-pyridinyl)-4,5-dihydro-3-(methoxymethyl)-, (4R)—; Pyrrolo[3,4-c]pyrazol-6(1H)-one, 4-(4-chlorophenyl)-1-cyclopropyl-5-(1,6-dihydro-1,5-dimethyl-6-oxo-3-pyridinyl)-4,5-dihydro-3-(methoxymethyl)-; Pyrrolo[3,4-c]pyrazol-6(1H)-one, 4-(4-chlorophenyl)-5-(1,6-dihydro-1,5-dimethyl-6-oxo-3-pyridinyl)-3-ethyl-4,5-dihydro-1-(2-methoxyethyl)-; Pyrrolo[3,4-c]pyrazol-6(1H)-one, 4,5-dihydro-5-[4-(3-isoxazolyl)phenyl]-3-(2-methoxyethyl)-4-(2-methoxyphenyl)-; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-3-ethyl-4,5-dihydro-, (4R)—; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-3-ethyl-4,5-dihydro-, (4S)—; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-3-ethyl-4,5-dihydro-; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-4,5-dihydro-3-(hydroxymethyl)-, (4S)—; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-4,5-dihydro-3-(hydroxymethyl)-, (4R)—; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-4,5-dihydro-3-(hydroxymethyl)-; Pyrrolo[3,4-c]pyrazol-6(1H)-one, 4-(4-chlorophenyl)-3-ethyl-4,5-dihydro-5-(8-methoxy-3-methyl-1,2,4-triazolo[4,3-a]pyridin-6-yl)-1-methyl-; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-3-(fluoromethyl)-4,5-dihydro-; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-4,5-dihydro-3-(methoxymethyl)-, (4S)—; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-4,5-dihydro-3-(methoxymethyl)-, (4R)—; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-4,5-dihydro-3-(methoxymethyl)-; Pyrrolo[3,4-c]pyrazol-6(2H)-one, 4-(4-chlorophenyl)-2-cyclopropyl-5-(1,6-dihydro-1,5-dimethyl-6-oxo-3-pyridinyl)-3-ethyl-4,5-dihydro-; 2-Propenoic acid, 3-[3-[(2,4-dichlorophenyl)methyl]-1,4,5,6-tetrahydro-5-methyl-6-oxopyrrolo[3,4-c]pyrazol-4-yl]-, ethyl ester, (2E)-; Pyrrolo[3,4-c]pyrazole-1(4H)-carboxamide, 4-(4-chlorophenyl)-5-(1,6-dihydro-1,5-dimethyl-6-oxo-3-pyridinyl)-3-ethyl-5,6-dihydro-N,N-dimethyl-6-oxo-; Pyrrolo[3,4-c]pyrazol-6(1H)-one, 4-(4-chlorophenyl)-5-(3,8-dimethyl-1,2,4-triazolo[4,3-a]pyridin-6-yl)-3-ethyl-4,5-dihydro-1-(2-methoxyethyl)-; Pyrrolo[3,4-c]pyrazol-6(2H)-one, 5-(1H-benzimidazol-6-yl)-4-(4-bromo-2-fluorophenyl)-4,5-dihydro-2-methyl-3-[(phenylmethoxy)methyl]-; Pyrrolo[3,4-c]pyrazol-6(1H)-one, 4-(4-chlorophenyl)-1-cyclopropyl-3-ethyl-4,5-dihydro-5-(8-methoxy-3-methyl-1,2,4-triazolo[4,3-a]pyridin-6-yl)-; Pyrrolo[3,4-c]pyrazol-6(1H)-one, 4,5-dihydro-5-[4-(3-isoxazolyl)phenyl]-4-(2-methoxyphenyl)-3-[2-(phenylmethoxy)ethyl]-; Pyrrolo[3,4-c]pyrazol-6(1H)-one, 4-(4-chlorophenyl)-5-(1,6-dihydro-1,5-dimethyl-6-oxo-3-pyridinyl)-1-(2,4-dimethoxy-5-pyrimidinyl)-3-ethyl-4,5- dihydro-; Pyrrolo[3,4-c]pyrazol-6(2H)-one, 4-(4-chlorophenyl)-5-(3,8-dimethyl-1,2,4-triazolo[4,3-a]pyridin-6-yl)-3-ethyl-4,5-dihydro-2-(2-methoxyethyl)-; Pyrrolo[3,4-c]pyrazole-2(4H)-carboxamide, 4-(4-chlorophenyl)-5-(1,6-dihydro-1,5-dimethyl-6-oxo-3-pyridinyl)-3-ethyl-5,6-dihydro-N,N-dimethyl-6-oxo-; Pyrrolo[3,4-c]pyrazol-6(2H)-one, 5-(1H-benzimidazol-6-yl)-4-[4-(3,3-difluoro-1-pyrrolidinyl)-2-fluorophenyl]-4,5-dihydro-3-(hydroxymethyl)-2-methyl-; Pyrrolo[3,4-c]pyrazol-6(2H)-one, 4-(4-bromo-2-fluorophenyl)-4,5-dihydro-2-methyl-3-[(phenylmethoxy)methyl]-5-[1-[[2-(trimethylsilyl)ethoxy]methyl]-1H-benzimidazol-5-yl]-; Pyrrolo[3,4-c]pyrazol-6(1H)-one, 4-(4-chlorophenyl)-3-ethyl-4,5-dihydro-5-(8-methoxy-3-methyl-1,2,4-triazolo[4,3-a]pyridin-6-yl)-1-[2-(2,2,2-trifluoroethoxy)ethyl]-; Pyrrolo[3,4-c]pyrazol-6(2H)-one, 4-[4-(3,3-difluoro-1-pyrrolidinyl)-2-fluorophenyl]-4,5-dihydro-3-(hydroxymethyl)-2-methyl-5-[1-[[2-(trimethylsilyl)ethoxy]methyl]-1H-benzimidazol-5-yl]-; Pyrrolo[3,4-c]pyrazol-6(2H)-one, 4-[4-(3,3-difluoro-1-pyrrolidinyl)-2-fluorophenyl]-4,5-dihydro-2-methyl-3-[(phenylmethoxy)methyl]-5-[1-[[2-(trimethylsilyl)ethoxy]methyl]-1H-benzimidazol-5-yl]-; Pyrrolo[3,4-c]pyrazole-4-propanamide, 3-[(2,4-dichlorophenyl)methyl]-N-[(4,5-dichloro-2-thienyl)sulfonyl]-1,4,5,6-tetrahydro-5-methyl-6-oxo-; Pyrrolo[3,4-c]pyrazole-3-carboxaldehyde, 4-[4-(3,3-difluoro-1-pyrrolidinyl)-2-fluorophenyl]-2,4,5,6-tetrahydro-2-methyl-6-oxo-5-[1-[[2-(trimethylsilyl)ethoxy]methyl]-1H-benzimidazol-5-yl]-; 2-Propenamide, 3-[3-[(2,4-dichlorophenyl)methyl]-1,4,5,6-tetrahydro-5-methyl-6-oxopyrrolo[3,4-c]pyrazol-4-yl]-N-[(4,5-dichloro-2-thienyl)sulfonyl]-, (2E)-; Pyrrolo[3,4-c]pyrazol-6(2H)-one, 4,5-dihydro-3-(methoxymethyl)-4-phenyl-; Pyrrolo[3,4-c]pyrazol-6(2H)-one, 4,5-dihydro-3-(methoxymethyl)-4-(4-methylphenyl)-; Pyrrolo[3,4-c]pyrazol-6(2H)-one, 4-(4-fluorophenyl)-4,5-dihydro-3-(methoxymethyl)-; Pyrrolo[3,4-c]pyrazol-6(2H)-one, 4,5-dihydro-3-(methoxymethyl)-4-[3-(trifluoromethyl)phenyl]-; Pyrrolo[3,4-c]pyrazol-6(2H)-one, 4-(1,3-benzodioxol-5-yl)-4,5-dihydro-3-(methoxymethyl)-5-(2-propen-1-yl)-; Pyrrolo[3,4-c]pyrazol-6(2H)-one, 4,5-dihydro-3-(methoxymethyl)-4-(4-methylphenyl)-5-(2-propen-1-yl)-; Pyrrolo[3,4-c]pyrazol-6(2H)-one, 4,5-dihydro-3-(methoxymethyl)-4-phenyl-5-(phenylmethyl)-; Pyrrolo[3,4-c]pyrazol-6(2H)-one, 4,5-dihydro-3-(methoxymethyl)-4,5-diphenyl-; Pyrrolo[3,4-c]pyrazol-6(2H)-one, 4-(1,3-benzodioxol-5-yl)-4,5-dihydro-3-(methoxymethyl)-5-(phenylmethyl)-; Pyrrolo[3,4-c]pyrazol-6(2H)-one, 4,5-dihydro-3-(methoxymethyl)-4-(4-methylphenyl)-5-(phenylmethyl)-; Pyrrolo[3,4-c]pyrazol-6(2H)-one, 4-(4-fluorophenyl)-4,5-dihydro-3-(methoxymethyl)-5-(2-propen-1-yl)-; Pyrrolo[3,4-c]pyrazol-6(2H)-one, 4-(4-bromophenyl)-4,5-dihydro-3-(methoxymethyl)-5-(2-propen-1-yl)-; Pyrrolo[3,4-c]pyrazol-6(2H)-one, 4-(1,3-benzodioxol-5-yl)-4,5-dihydro-3-(methoxymethyl)-5-(4-methoxyphenyl)-; Pyrrolo[3,4-c]pyrazol-6(2H)-one, 4,5-dihydro-3-(methoxymethyl)-5-(4-methoxyphenyl)-4-(4-methylphenyl)-; Pyrrolo[3,4-c]pyrazol-6(2H)-one, 4-(4-bromophenyl)-4,5-dihydro-3-(methoxymethyl)-5-(phenylmethyl)-; Pyrrolo[3,4-c]pyrazol-6(2H)-one, 4-(4-fluorophenyl)-4,5-dihydro-3-(methoxymethyl)-5-(phenylmethyl)-; Pyrrolo[3,4-c]pyrazol-6(2H)-one, 4-(4-fluorophenyl)-4,5-dihydro-3-(methoxymethyl)-5-phenyl-; Pyrrolo[3,4-c]pyrazol-6(2H)-one, 4,5-dihydro-3-(methoxymethyl)-5-(2-propen-1-yl)-4-[3-(trifluoromethyl)phenyl]-; Pyrrolo[3,4-c]pyrazol-6(2H)-one, 4-(4-bromophenyl)-4,5-dihydro-3-(methoxymethyl)-5-(4-methoxyphenyl)-; Pyrrolo[3,4-c]pyrazol-6(2H)-one, 4-(4-fluorophenyl)-4,5-dihydro-3-(methoxymethyl)-5-(4-methoxyphenyl)-; Pyrrolo[3,4-c]pyrazol-6(2H)-one, 4,5-dihydro-3-(methoxymethyl)-5-phenyl-4-[3-(trifluoromethyl)phenyl]-; Pyrrolo[3,4-c]pyrazol-6(2H)-one, 4,5-dihydro-3-(methoxymethyl)-5-(4-methoxyphenyl)-4-[3-(trifluoromethyl)phenyl]-; 2-Propenoic acid, 2-(phenylamino)-3-(1,4,5,6-tetrahydro-6-oxo-4,5-diphenylpyrrolo[3,4-c]pyrazol-3-yl)-, ethyl ester; 2-Propenoic acid, 2-hydroxy-3-[1,4,5,6-tetrahydro-4-(4-nitrophenyl)-6-oxo-5-phenylpyrrolo[3,4-c]pyrazol-3-yl]-, ethyl ester; 2-Propenoic acid, 3-[4,5-bis(4-bromophenyl)-1,4,5,6-tetrahydro-6-oxopyrrolo[3,4-c]pyrazol-3-yl]-2-[(4-bromophenyl)amino]-, ethyl ester;

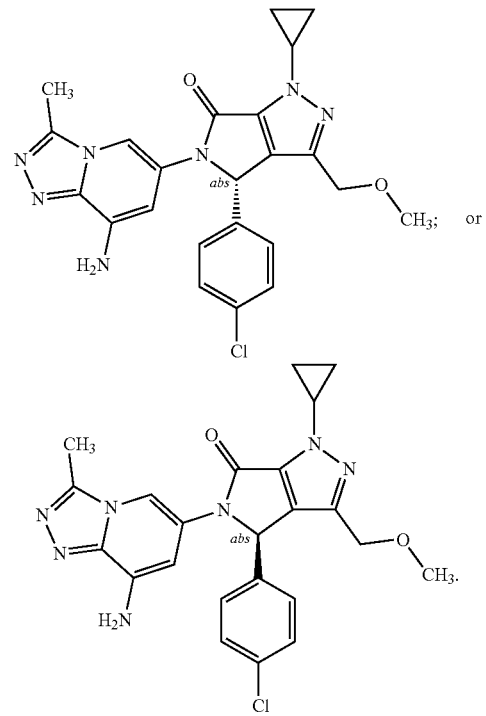

In some embodiments of any one of the aspects described herein, the compound of Formula (I) or (II) has a C Log P from about 3.2 to about 4.3.

Also provided herein is a method for treating leishmaniasis or a disease or disorder associated with leishmaniasis. Generally, the method comprises: administering a therapeutically effective amount of an antileishmanial compound of Formula (I) or (II), or a composition described herein to a subject in need thereof. The leishmaniasis can be cutaneous leishmaniasis (CL), visceral leishmaniasis (VL) or mucosal leishmaniasis (ML).

In another aspect, provided herein is a method for reducing, suppressing or inhibiting a *Leishmania* parasite in a vector. The method comprises: administering to the vector an effective amount of Formula (I) or Formula (II).

BRIEF DESCRIPTION OF THE DRAWINGS

FIG. 4A shows the evaluation of the percentage of infection. FIG. 4B shows the evaluation of the number of amastigotes per 100 macrophages by optical microscopy. FIG. 4C shows the number of viable promastigotes, following exposure to CMLD011494 was evaluated by culture in Schneider medium, free of CMLD011494. Infected macrophages treated with amphotericin B (AB) were used as positive controls. The data are shown as mean±SEM. *p<0.05; p<0.01, *p<0.001; all comparisons were against medium (negative control).

FIG. 5A shows the evaluation for the percentage of infection. FIG. 5B shows the evaluation for the number of amastigotes per 100 macrophages by optical microscopy. The data are shown as mean±SEM. *p<0.05; **p<0.01, all comparisons were against medium (negative control).

FIGS. 6A and 6C show evaluation for the percentage of infection. FIGS. 6B and 6D shows the number of amastigotes per 100 macrophages by optical microscopy. Infected macrophages treated with amphotericin B (AB) were used as positive controls. That data are shown as mean±SEM. *p<0.05; **p<0.01, all comparisons were against medium (negative control).

FIG. 7A shows topical treatment with CMLD011494 or CMLD011948 formulated in BC hydrogel. Lesion development was measured weekly. FIGS. 7B and 7C examine six weeks post infection, mice were euthanized and parasite load was determined by Limited Dilution Analysis *p<0.05, (Kruskal Wallis) (compared to control).

FIGS. 8A and 8C show evaluation for the percentage of infection. FIGS. 8B and 8D shows evaluation for the number of amastigotes per 100 macrophages by optical microscopy. Infected macrophages treated with amphotericin B (AB) were used as positive controls The data are shown as mean±SEM. *p<0.05; **p<0.01, all comparison were against medium (negative control).

DETAILED DESCRIPTION

Figure 2:
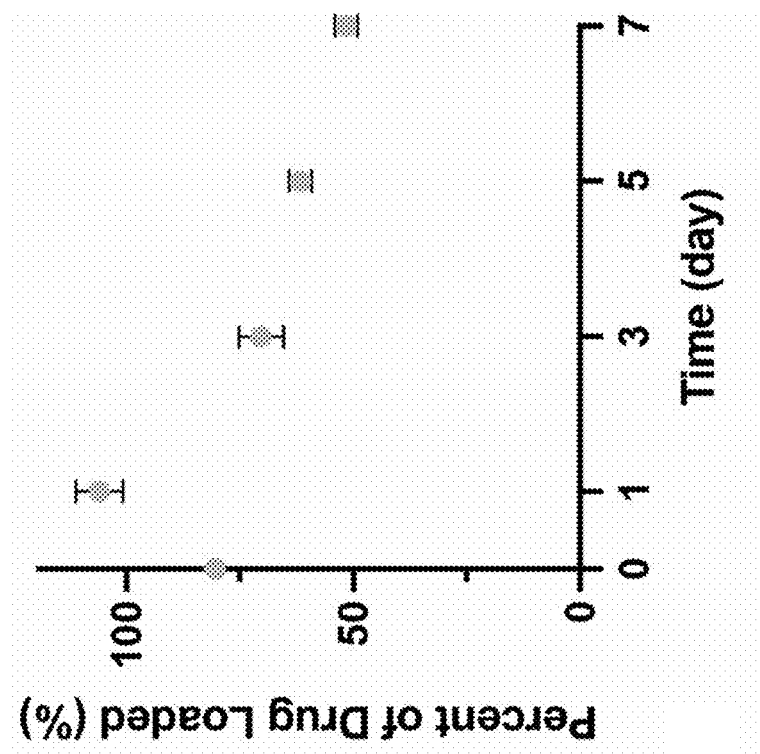
FIG. 2 examines the release of CMLD011128 from nanoparticles over the course of 7 days in physiologically-relevant sodium phosphate buffer (n=2).

It is to be understood that both the foregoing general description and the following detailed description are exemplary and explanatory only and are not restrictive of the invention, as claimed.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Compounds

Embodiments of the various aspects described herein include a compound of Formula (I) or (II):

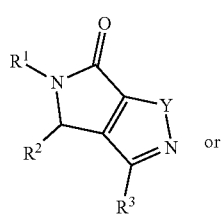

(Formula I)

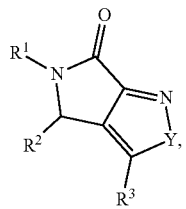

(Formula II)

wherein:
Y is $NR^4$, $CH_2$, O or S; $R^{11}$ is aryl, heteroaryl, alkyl, alkenyl, alkynyl, cycloalkyl, or heterocyclyl;
$R^{12}$ is cycloalkyl, heterocyclyl, aryl or heteroaryl; $R^{13}$ is —$CH_2$—$R^{15}$; $R^{14}$ is H, alkyl, alkenyl, alkynyl, cycloalkyl, heterocyclyl, aryl or heteroaryl; and
$R^{15}$ is alkyl, alkenyl, alkynyl, aryl, heteroaryl, cycloalkyl, heterocyclyl, or a nucleophile; and
a pharmaceutically acceptable salt thereof,
optionally, any alkyl, alkenyl, alkynyl, aryl, heteroaryl, cycloalkyl and heterocyclyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Inventors have discovered inter alia that compounds of Formula (I) or (II) have antileishmanial activity, i.e., compounds are antileshmanial compounds. As used herein, an "antileishmanial" compound is a compound that restrict growth and/or activity of any species that is a part of the *Leishmania* genus. *Leishmania* is a parasitic protozoan, a single-celled organism of the genus *Leishmania* that are responsible for the disease leishmaniasis. They are spread by sandflies of the genus *Phlebotomus* in Africa, Europe, and Asia, and of the genus *Lutzomyia* in North and South America. *Leishmania* currently affects 6 million people in 98 countries. About 0.9-1.6 million new cases occur each year, and 21 species are known to cause disease in humans. *Leishmania* amastigote growth in infected cells can be evaluated using microscopy (e.g., fluorescence, confocal), fluorescence emission spectroscopy, and luminescence spectroscopy. *Leishmania* promastigote growth can be evaluated using standard metabolism-based cell growth assays (e.g., CellTiter-Glo, MTT [3-(4, 5-methylthiazol-2-yl)-2, 5-diphenyltetrazolium bromide]).

Y

In some embodiments of any one of the aspects described herein, Y is N—$R^{14}$. When Y is N—$R^{14}$, the compound is of Formula (I-A) or (II-A):

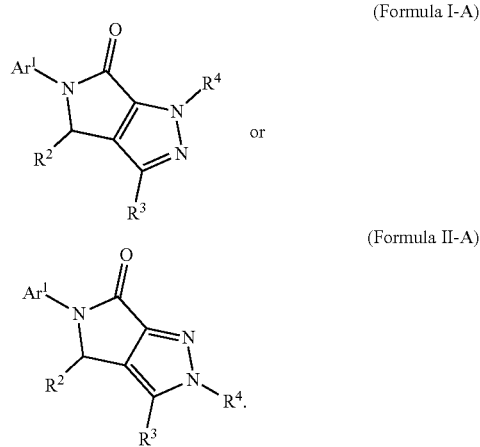

(Formula I-A)

or (Formula II-A)

$R^{15}$

In some embodiments of any one of the aspects described herein, $R^{15}$ is alkyl, alkenyl, alkynyl, cycloalkyl, or heterocyclyl, wherein the alkyl, alkenyl, alkynyl, cycloalkyl and heterocyclyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido. For example, $R^{15}$ is alkyl, alkenyl, cycloalkyl or heterocyclyl, wherein the alkyl, alkenyl, cycloalkyl and heterocyclyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido. In some embodiments, the alkyl of $R^{15}$ can be optionally substituted with a halogen, hydroxyl, alkoxy, amino, alkylamino, dialkylamino, cycloalkyl, heterocyclyl, aryl, heteroaryl, thiol, azide or nitrite.

In some embodiments of any one of the aspects described herein, $R^{15}$ is $C_1$-$C_6$alkyl or —$(CH_2)_a$—$R^{16}$, where a is 0, 1, 2, 3, 4, 5, 6, 7, 8, 9 or 10, optionally, a is 0, 1, 2, 3 or 4 (e.g., a is 1 or 2); and $R^{16}$ is cycloalkyl, —$OR^{17}$, —$NR^{18}R^{19}$, where $R^7$ is H or alkyl, and $R^8$ and $R^9$ are independently H, alkyl, or cycloalkyl. For example, $R^{15}$ is $C_1$-$C_6$ alkyl, —$CH_2$-cycloalkyl, —$CH_2CH_2$-cycloalkyl, —$CH_2$—$OR^7$, —$CH_2CH_2$—$OR^{17}$, —$CH_2$—$NR^{18}N^{19}$ or —$CH_2CH_2$—$NR^{18}N^{19}$. In some embodiments of the any one of the aspects described herein, $R^{15}$ is isopropyl, isobutyl, t-butyl, propyl, propen-3-yl, 2-methylpropen-3-yl, 2-methylbutene-4-yl, cyclohexylmethyl, 2-cyclohexylethyl, benzyl, —$CH_2$—$OR^{17}$, —$CH_2CH_2$—$OR^{17}$, —$CH_2$—$NR^{18}N^{19}$ or —$CH_2CH_2$—$NR^{18}N^{19}$. For example, $R^{15}$ is isopropyl.

In some embodiments of any one of the aspects described herein, $R^{15}$ is a nucleophile. As used herein, a nucleophile is a is a chemical species that forms bonds by donating an electron pair. All molecules and ions with a free pair of electrons or at least one pi bond can act as nucleophiles. Some exemplary nucleophiles include but, are not limited to, hydroxyl, amino, thiol, carboxyl, cyanide, azide, and nitrite groups.

$R^{14}$

In some embodiments of any of the aspects described herein, $R^{14}$ is H, alkyl, alkenyl, alkynyl, aryl or heteroaryl, wherein the alkyl, alkenyl, alkynyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido. For example, $R^{14}$ is H, $C_1$-$C_6$alkyl, $C_2$-$C_6$alkenyl, $C_2$-$C_6$alkynyl, or 5-12 membered aryl, wherein the $C_1$-$C_6$alkyl, $C_2$-$C_6$alkenyl, $C_2$-$C_6$alkynyl, and 5-12 membered aryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

In some embodiments, $R^{14}$ is H, $C_1$-$C_6$alkyl, methoxymethyl, phenyl, 4-trifluoromethylphenyl, or —$(CH_2)_a$—$R^{16}$, where a is 0, 1, 2, 3, 4, 5, 6, 7, 8, 9 or 10, optionally, a is 0, 1, 2, 3 or 4 (e.g., a is 1 or 2); and $R^{16}$ is cycloalkyl, —$OR^{17}$, —$NR^{18}R^{19}$, where $R^7$ is H or alkyl, and $R^8$ and $R^9$ are independently H, alkyl, or cycloalkyl. For example, $R^{14}$ is H, $C_1$-$C_6$ alkyl, —$CH_2$-cycloalkyl, —$CH_2CH_2$-cycloalkyl, —$CH_2$—$OR^7$, —$CH_2CH_2$—$OR^{17}$, —$CH_2$—$NR^{18}N^{19}$, —$CH_2CH_2$—$NR^{18}N^{19}$, methoxymethyl, phenyl, 4-trifluoromethylphenyl. In some embodiments, $R^{14}$ is H, methyl, ethyl, propyl, isopropyl, butyl, isobutyl, but-2-yl, t-butyl, pentyl, 5-hexyn-1-yl, 2-propyn-1-yl, propargyl, —$CH_2$—$OR^7$ $CH_2CH_2$—$OR^{17}$ $CH_2$—$NR^{18}N^{19}$ or —$CH_2CH_2$—$NR^{18}N^{19}$.

$R^{12}$

In some embodiments of any one of the aspects described herein, $R^{12}$ is cycloalkyl, heterocyclyl, aryl or heteroaryl, wherein the cycloalkyl, heterocyclyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido. For example, $R^{12}$ is 5-12 membered aryl, 5-12 membered heteroaryl comprising 1, 2 or 3 independently selected heteroatoms, 5-12 membered cycloalkyl, or 5-12 membered heterocyclyl comprising 1, 2 or 3 independently selected heteroatoms, wherein the 5-12 membered aryl, 5-12 membered heteroaryl, 5-12 membered cycloalkyl, and the 5-12 membered heterocyclyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

In some embodiments of any one of the aspects described herein, $R^{12}$ is phenyl, cyclohexyl, cyclopentyl, tetrahydropyranyl, tetrahydrofuranyl, piperidinyl, pyridinyl, diazinyl, furanyl, thiophenyl, or thiazolyl, wherein the phenyl, cyclohexyl, cyclopentyl, tetrahydropyranyl, tetrahydrofuranyl, piperidinyl, pyridinyl, diazinyl, furanyl, thiophenyl and thiazolyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido. For example, $R^{12}$ is a phenyl (optionally substituted at position 2 and/or 4 with substituents selected independently from halogen, hydroxyl, alkoxy, amino, mono-substituted amino, and di-substituted amino), cyclohexyl, cyclopentyl, tetrahydropyran-4-yl, piperdin-4-yl (optionally substituted at position 1 with an alkyl or cycloalkyl), pyridine-2-yl (optionally substituted at position 3 and/or 5 with substituents selected independently from halogen, hydroxyl, alkoxy, amino, mono-substituted amino, and di-substituted amino), pyridine-5-yl (optionally substituted at position 2 and/or 4 with substituents selected independently from halogen, hydroxyl, alkoxy, amino, mono-substituted amino, and di-substituted amino), pyridin-3-yl (optionally substituted at position 2 and/or 6 with substituents selected independently from halogen, hydroxyl, alkoxy, amino, mono-substituted amino, and di-substituted amino), furan-5-yl (optionally substituted at position 2 and/or 4 with substituents selected independently from halogen, hydroxyl, alkoxy, amino, mono-substituted amino, and di-substituted amino), furan-4-yl (optionally substituted at position 2 and/or 4 with substituents selected independently from halogen, hydroxyl, alkoxy, amino, mono-substituted amino, and di-substituted amino), thiopen-5-yl (optionally substituted at position 2 and/or 4 with substituents selected independently from halogen, hydroxyl, alkoxy, amino, mono-substituted amino, and di-substituted amino), or thiophen-4-yl (optionally substituted at position 2 and/or 4 with substituents selected independently from halogen, hydroxyl, alkoxy, amino, mono-substituted amino, and di-substituted amino).

In some embodiments of any one of the aspects described herein, $R^{12}$ is 4-fluorophenyl, 4-chlorophenyl, 4-bromophenyl, 4-trifluoromethylphenyl, 4-methoxyphenyl, 4-carboxylphenyl, 4-methoxycarbonylphenyl, 4-methylphenyl, 3-fluorophenyl, 3-chlorophenyl, 3-bromophenyl, 3-trifluoromethylphenyl, 3-methoxyphenyl, 2-fluorophenyl, 2-chlorophenyl, 2-bromophenyl, 2-trifluoromethylphenyl, 2-methoxyphenyl, 2-methylphenyl, 3,4-difluorophenyl, 2,4-difluorophenyl, 4-fluoro-2-methylphenyl, 2-chloro-4-fluorophenyl, 2-bromo-4-fluorophenyl, 2-fluoro-4-chlorophenyl, 2-fluoro-4-bromophenyl, 1,6-dichlorophenyl, phenyl, cyclohexyl, cyclopentyl, 3-methoxypyridin-2-yl, 2-methoxypyridin-3-yl, 2-methoxypyridin-5-yl, thiophen-3-yl, thiopen-2-yl, 3-methylthiophen-2-yl, 2-methylthiophen-5-yl, pyridine-4-yl, 4-fluoro-2-methoxyphenyl, 3-methoxypyridin-5-yl, 3-fluoropyridin-6-yl, 4-carboxylphenyl, 2-bromo-5-trifluoromethylphenyl, 1,3-thiazol-5-yl, 3-trifluoromethyl-4-fluorophenyl, pyrimidin-4-yl, 4-chloro-pyridin-3-yl, 2,6-difluoropyridin-4-yl, 4-trifluoromethoxyphenyl, pyridazine-4-yl, but-3-ynyl, but-3-enyl, hex-5-ynyl, 2,5-ditriflouromethylphenyl, thiaz-5-yl, 3-trifluoromethyl-4-fluorophenyl, 3-trifluoromethylphenyl, 4-fluoro-2-methylphenyl, 3-fluropyridin-6-yl, and 3-bromothiophen-2-yl.

In some embodiments, $R^{12}$ is 4-fluorophenyl, 2-chlorophenyl, 2-bromophenyl, 2-methoxyphenyl, 2-methyl-4-fluorophenyl, 2-methoxy-4-fluorophenyl, 2-methylphenyl, 2-bromo-4-fluorophenyl, or 2-chloro-4-fluorophenyl.

$R^{11}$

In some embodiments in any of the aspects, $R^{11}$ is aryl, heteroaryl, alkyl, alkenyl or alkynyl, wherein the aryl, heteroaryl, alkyl, alkenyl, and alkynyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido. For example, $R^{11}$ is $C_1$-$C_{10}$alkyl, $C_2$-$C_{10}$alkenyl, $C_2$-$C_{10}$alkynyl, 5-12 membered aryl, or 5-12 membered heteroaryl comprising 1, 2 or 3 independently selected heteroatoms, wherein the $C_1$-$C_{10}$alkyl, $C_2$-$C_{10}$alkenyl, $C_2$-$C_{10}$alkynyl, 5-12 membered aryl, and 5-12 membered heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

In some other embodiments of any one of the aspects described herein, $R^{11}$ is phenyl, pyridinyl, 1,3-benzodioxolyl, 2,2-difluoro-1,3-benzodioxolyl, 1,3,3a-triazaindenyl, benzimidazolyl, 2,3-dihydro-1,4-benzodioxinyl, cyclohexyl, cyclopentyl, tetrahydropyranyl, tetrahydrofuranyl, piperidinyl, pyridinyl, diazinyl, furanyl, thiophenyl, thiazolyl, $C_1$-$C_6$alkyl, $C_2$-$C_6$alkenyl or $C_2$-$C_6$alkynyl, wherein the phenyl, cyclohexyl, cyclopentyl, tetrahydropyranyl, tetrahydrofuranyl, piperidinyl, pyridinyl, diazinyl, furanyl, thiophenyl thiazolyl, $C_1$-$C_6$alkyl, $C_2$-$C_6$alkenyl and $C_2$-$C_6$alkynyl and alkyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido. In some preferred embodiments, $R^{11}$ is phenyl (optionally substituted at position 4 with a substituent selected independently from halogen, hydroxyl, alkoxy, amino, mono-substituted amino, and di-substituted amino), furan-4-yl (optionally substituted at position 2 and/or 4 with substituents selected independently from halogen, hydroxyl, alkoxy, amino, mono-substituted amino, and di-substituted amino), pyridine-5-yl (optionally substituted at position 2 and/or 3 with a substituent selected independently from halogen, hydroxyl, alkoxy, amino, mono-substituted amino, and di-substituted amino), furan-6-yl (optionally substituted at position 3 and/or 4 with substituents selected independently from halogen, hydroxyl, alkoxy, amino, mono-substituted amino, and di-substituted amino), pyridine-6-yl (optionally substituted at position 2 and/or 3 with a substituent selected independently from halogen, hydroxyl, alkoxy, amino, mono-substituted amino, and di-substituted amino), 1,3-benzodioxolyl, 2,2-difluoro-1,3-benzodioxolyl, or 1,3,3a-triazaindenyl.

In some embodiments of any one of the aspects described herein, $R^{11}$ is 4-methoxyphenyl, 2-methoxyphenyl, 2-methoxypyridin-5-yl, 3-fluoropyridin-5-yl, 1,3-benzodioxolyl, 4-(methoxycarbonyl)phenyl, 4-carboxyphenyl, 4-dimethylaminoaphenyl, benzimidazole-5-yl, 4-sulfamoylphenyl, 4-trifluromethoxyphenyl, 3-methoxyphenyl, 3-fluoro-4-methoxyphenyl, 4-bromophenyl, 4-fluorophenyl, 4-chlorophenyl, 2-pyridinylethyl, N-methylpiperazinyl, N-isopropylpyrazol-4-yl, 4-pyrrolidonylphenyl, 2,3-dihydro-1,4-benzodioxinyl, 1,3,3a-triazaindenyl, 1-acetyl-3-hydroxypropyl, 4-imidazolylphenyl, 3-fluoropyridin-5-yl, 4-dimethylaminophenyl, N-methylpyrrolidin-3-yl, 2-hydroxymethyl-2-methyl-3-hydroxypropyl, 2-methoxyethyl, 5-hexyn-1-yl, 4-hydroxyphenyl, 2-(3-butyn-1-yl)pyridin-4-yl, N-ethylpyrrolidin-3-yl, hydrogen, phenyl, 2-methoxypyridin-5-yl, 3-fluoro-2-methoxypyridin-5-yl, 4-methoxyphenylmethyl, 4-(1-Pyrrolidinylsulfonyl)phenyl, 4-imidazole-1-ylphenyl, 2-hydroxybenzimidazoly-5-yl, 3,4,5-trimethoxyphenyl, 4-ethoxyphenyl, 2,4-dimethoxyphenyl, 4-t-butylphenyl, 4-ethylphenyl, 3-methoxypyridin-6-ylmethyl, 4-cyanophenyl, 3-trifluoromethylpyridin-6-yl, 2-pyrrolidinylethyl, tetrahydropyran-4-yl, 3-caynophenyl, 4-trifluoromethoxyphenyl, 1,3-dihydroxypropy-2-yl, 2-methylpyridin-4-yl, N-ethylpyrrolidin-4-yl, 3-oxo-3,4-dihydro-2H-1,4-benzoxazine-7-yl, 4-(2-oxo-1-pyrrolidinyl)phenyl, 2-methylpyridin-5-yl, 2-(N-methylpiperazinyl)pirpdin-5-yl, 3-fluoropyridin-5-yl, 2-methoxy-3-methylpyridin-5-yl, 4-(1-ethyl-1H-pyrazol-4-yl)phenyl, 4-(1-ethyl-1H-pyrazol-3-yl)phenyl, 2-fluoropyridin-5-yl, 4-(1-isopropyl-1H-pyrazol-4-yl)phenyl, 4-(1-isopropyl-1H-pyrazol-3-yl)phenyl, 4-(1-ethyl-1H-pyrazol-3-yl)phenyl, 4-(1-methyl-1H-pyrazol-4-yl)phenyl, 3-methoxypyridin-6-yl, 4-(1-methyl-1H-pyrazol-3-yl)phenyl, 4-(1-pyrrolidinylcarbonyl)-phenyl, 2-(1-methylpiperzin-4-yl)pyridine-5-yl, 4-(5-hexyn-1-oxy)phenyl, 4-triflouromethoxyphenyl, 4-methylphenyl, 4-ethylphenyl, pyridine-3-yl, pyridine-2-yl, 2-methylfuran-5-yl, 4-methoxycyclohexyl, 4-dimethylaminohexyl, and 1-methylpyrrolidin-3-yl methyl.

In some preferred embodiments, $R^{11}$ is 4-methoxyphenyl, 1,3-benzodioxolyl, 3-fluoro-4-methoxyphenyl, 4-bromophenyl, 4-dimethylaminophenyl, 2'-methoxypyridin-5-yl, 1,3,3a-triazaindenyl, 2'-methoxy-3'-fluoropyridin-5-yl or 2'-methylpyridin-5-yl.

Narrower Genus

In some embodiments of any one of the aspects described herein, $R^{15}$ is alkyl, alkenyl, cycloalkyl or heterocyclyl; $R^4$ is H, $C_1$-$C_6$alkyl, $C_2$-$C_6$alkenyl, $C_2$-$C_6$alkynyl, or 5-12 membered aryl; $R^{12}$ is 5-12 membered aryl, 5-12 membered heteroaryl comprising one heteroatom, 5-12 membered cycloalkyl, or 5-12 membered heterocyclyl comprising one heteroatom; and $R^{11}$ is $C_1$-$C_{10}$alkyl, $C_2$-$C_{10}$alkenyl, $C_2$-$C_{10}$alkynyl, 5-12 membered aryl, or 5-12 membered heteroaryl comprising 1, 2 or 3 independently selected heteroatoms, and where any alkyl, alkenyl, alkynyl, cycloalkyl, heterocyclyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

In some embodiments of any one of the aspects described herein, $R^{15}$ is $C_1$-$C_6$alkyl or —$(CH_2)_a$—$R^{16}$, where a is 0, 1, 2, 3, 4, 5, 6, 7, 8, 9 or 10, and $R^{16}$ is cycloalkyl, —$OR^{17}$, or —$NR^{18}R^{19}$, where $R^{17}$ is H or alkyl, and $R^{18}$ and $R^{19}$ are independently H, alkyl, or cycloalkyl; $R^{14}$ is H, methyl, ethyl, propyl, isopropyl, butyl, isobutyl, but-2-yl, t-butyl, pentyl, 5-hexyn-1-yl, 2-propyn-1-yl, propargyl, methoxymethyl, phenyl, or 4-trifluoromethylphenyl; $R^{12}$ is phenyl, cyclohexyl, cyclopentyl, tetrahydropyranyl, tetrahydrofuranyl, piperidinyl, pyridinyl, diazinyl, furanyl, thiophenyl, or thiazolyl; and $R^{11}$ is phenyl, pyridinyl, 1,3-benzodioxolyl, 2,2-difluoro-1,3-benzodioxolyl, 1,3,3a-triazaindenyl, benzimidazolyl, 2,3-dihydro-1,4-benzodioxinyl, cyclohexyl, cyclopentyl, tetrahydropyranyl, tetrahydrofuranyl, piperidinyl, pyridinyl, diazinyl, furanyl, thiophenyl, thiazolyl, $C_1$-$C_6$alkyl, $C_2$-$C_6$alkenyl or $C_2$-$C_6$alkynyl, and where any phenyl, cyclohexyl, cyclopentyl, tetrahydropyranyl, tetrahydrofuranyl, piperidinyl, pyridinyl, diazinyl, furanyl, thiophenyl, or thiazolyl; and $R^1$ is phenyl, pyridinyl, 1,3-benzodioxolyl, 2,2-difluoro-1,3-benzodioxolyl, 1,3,3a-triazaindenyl, benzimidazolyl, 2,3-dihydro-1,4-benzodioxinyl, cyclohexyl, cyclopentyl, tetrahydropyranyl, tetrahydrofuranyl, piperidinyl, pyridinyl, diazinyl, furanyl, thiophenyl, thiazolyl, $C_1$-$C_6$alkyl, $C_2$-$C_6$alkenyl, $C_2$-$C_6$alkynyl, alkyl, alkenyl, alkynyl, cycloalkyl, heterocyclyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido Isomers All structures of Formula (I), (I-A), (II) and (II-A) are provided herein for illustrative purpose and disclose a particular isomer. However, one of ordinary skill in the art will recognize all possible isomers of the structures of any of Formula (I), (I-A), (II) and (II-A). Therefore, other isomers such as enantiomers of any of Formula (I), (I-A), (II) and (II-A) are considered to fall within the scope of the invention. As used herein, the term "isomer" refers to a compound having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. The designations "R" and "S" are used to denote the absolute configuration of the molecule about its chiral center. The designations may appear as a prefix or as a suffix; they may or may not be separated from the isomer by a hyphen; they may or may not be hyphenated; and they may or may not be surrounded by parentheses. The designations "(+)" and "(−)" are employed to designate the sign of rotation of plane-polarized light by the compound, with (−) meaning that the compound is levorotatory (rotates to the left). A compound prefixed with (+) is dextrorotatory (rotates to the right). Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

It is noted that in compounds of Formula (I), (I-A), (II) or (II-A), the carbon to which the $R^{12}$ group is attached can have the R or S stereochemistry. For example, the carbon to which the $R^{12}$ group is attached has the R stereochemistry. Preferably, the carbon to which the $R^{12}$ group is attached has the S stereochemistry.

Derivatives and Prodrugs

In various embodiments, compounds of Formula (I), (I-A), (II) or (II-A) include enantiomers, derivatives, prodrugs, and pharmaceutically acceptable salts thereof. The term "derivative" as used herein refers to a chemical substance related structurally to another, i.e., an "original" substance, which can be referred to as a "parent" compound. A "derivative" can be made from the structurally-related parent compound in one or more steps. The general physical and chemical properties of a derivative are also similar to the parent compound.

Exemplary Compounds

In some embodiments of any one of the aspects described herein, a compound of Formula (I) or (II) is selected from the group consisting of: CMLD007431, CMLD011128, CMLD007427, CMLD011024, CMLD011025, CMLD010981, CMLD010849, CMLD010980, CMLD010979, CMLD011029, CMLD010900, CMLD010885, CMLD011039, CMLD010899, CMLD011113, CMLD010897, CMLD011033, CMLD011031, CMLD011046, CMLD010895, CMLD011098, CMLD011095, CMLD011026, CMLD011092, CMLD011036, CMLD011124, CMLD011030, CMLD011072, CMLD011129, CMLD011117, CMLD010884, CMLD010992, CMLD010901, CMLD011101, CMLD010888, CMLD011096, CMLD010889, CMLD011121, CMLD011032, CMLD011034, CMLD010892, CMLD010978, CMLD011102, CMLD010893, CMLD010894, CMLD010994, CMLD010890, CMLD011099, CMLD010891, CMLD011088, CMLD007432, CMLD011079, CMLD010902, CMLD011548, CMLD011546, CMLD011564, CMLD012217, CMLD011566, CMLD011562, CMLD010986, CMLD011139, BUCMD00647,
CMLD011551, CMLD011549, CMLD011565, BUCMD00627, BUCMD00653, BUCMD00641,
CMLD011494, CMLD010920, CMLD011554, BUCMD00645, BUCMD00646, BUCMD00648,
CMLD011552, CMLD011561, CMLD011572, BUCMD00652, BUCMD00654, BUCMD00655,
CMLD012218, CMLD011567, CMLD011574, BUCMD00656, BUCMD00657, BUCMD00658,
CMLD010921, CMLD010948, CMLD010882, BUCMD00659, BUCMD00660, BUCMD00661,
CMLD011104, CMLD010991, CMLD011075, BUCMD00662, BUCMD00664, BUCMD00665,
CMLD011142, CMLD011125, CMLD010887, BUCMD00666, BUCMD00667, BUCMD00670,
CMLD011100, CMLD010886, CMLD011575, BUCMD00671, BUCMD00675, BUCMD00676,
CMLD011496, CMLD011027, CMLD011120, BUCMD00677, BUCMD00678, BUCMD00680,
CMLD011579, CMLD011559, CMLD011028, BUCMD00693, BUCMD00696, BUCMD00701,
CMLD011577, CMLD011578, CMLD007169, BUCMD00711, BUCMD00712, BUCMD00713,
CMLD007188, CMLD007203, CMLD007219, BUCMD00714, BUCMD00715, BUCMD00716,
CMLD007221, CMLD007235, CMLD007247, BUCMD00719, BUCMD00722, BUCMD00724,
CMLD007262, CMLD007286, CMLD007424, BUCMD00725, BUCMD00726, BUCMD00727,
CMLD007425, CMLD007430, CMLD010949, BUCMD00731, BUCMD00739, BUCMD00741,
CMLD011573, BUCMD00800, BUCMD00797, BUCMD00156, BUCMD00157, BUCMD00158,
CMLD010987, CMLD010898, CMLD011119, BUCMD00159, BUCMD00160, BUCMD00161,
CMLD011547, CMLD011131, CMLD011105, BUCMD00162, BUCMD00163, BUCMD00164,
BUCMD00815, CMLD011499, BUCMD00812, BUCMD00165, BUCMD00166, BUCMD00167,
CMLD010896, CMLD011111, CMLD011135, BUCMD00168, BUCMD00169, BUCMD00170,
BUCMD00809, CMLD011569, CMLD011132, BUCMD00171, BUCMD00172, BUCMD00173,
CMLD011133, CMLD013640, CMLD011116, BUCMD00174, BUCMD00175, BUCMD00176,
CMLD011140, BUCMD00802, BUCMD00803, BUCMD00177, BUCMD00178, BUCMD00179,
BUCMD00805, CMLD011109, CMLD011122, BUCMD00180, BUCMD00181, BUCMD00182,
CMLD011568, CMLD011106, CMLD010881, BUCMD00183, BUCMD00184, BUCMD00185,
CMLD011110, CMLD011134, CMLD011138, BUCMD00186, BUCMD00187, BUCMD00188,
CMLD011550, CMLD011141, BUCMD00804, BUCMD00189, BUCMD00190, BUCMD00191,
CMLD011103, CMLD011137, BUCMD00808, BUCMD00192, BUCMD00193, BUCMD00194,
BUCMD00811, BUCMD00816, CMLD011112, BUCMD00195, BUCMD00196, BUCMD00197,
CMLD011115, CMLD011097, BUCMD00807, BUCMD00198, and BUCMD00199.

BUCMD00813, BUCMD00814, CMLD011130, In some embodiments of any one of the aspects described herein, a compound of Formula (I) or (II) is selected from the group consisting of: BUCMD00800, BUCMD00797, BUCMD00815, BUCMD00812, BUCMD00809, BUCMD00802, BUCMD00803, BUCMD00805, BUCMD00804, BUCMD00808, BUCMD00811, BUCMD00807, BUCMD00813, CMLD010880, CMLD010903, CMLD011126,
CMLD011093, BUCMD00799, BUCMD00810,
CMLD011576, BUCMD00806, CMLD010883,
BUCMD00798, CMLD010848, CMLD011094,
CMLD011557, CMLD011495, CMLD011556,
CMLD011558, BUCMD00801, BUCMD00817, BUCMD00816, BUCMD00807, BUCMD00813,
CMLD010926, CMLD011040, CMLD010925, BUCMD00814, BUCMD00799, BUCMD00810,
CMLD011042, CMLD010996, CMLD011043, BUCMD00806, BUCMD00798, BUCMD00801,
CMLD010998, CMLD010993, CMLD011081, BUCMD00817, BUCMD00694, BUCMD00729,
CMLD010976, CMLD010989, BUCMD00694, BUCMD00639, BUCMD00695, BUCMD00730,
BUCMD00729, BUCMD00639, CMLD011035, BUCMD00669, BUCMD00629, BUCMD00686,
BUCMD00695, BUCMD00730, CMLD010982, BUCMD00717, BUCMD00718, BUCMD00733,
BUCMD00669, CMLD010985, CMLD010950, BUCMD00643, BUCMD00642, BUCMD00700,
CMLD011497, CMLD011560, BUCMD00629, BUCMD00699, BUCMD00734, BUCMD00685,
BUCMD00686, BUCMD00717, BUCMD00718, BUCMD00732, BUCMD00698, BUCMD00697,
CMLD011080, CMLD010977, BUCMD00733, BUCMD00628, BUCMD00688, BUCMD00640,
CMLD010984, CMLD010990, BUCMD00643, BUCMD00663, BUCMD00691, BUCMD00721,
BUCMD00642, BUCMD00700, BUCMD00699, BUCMD00720, BUCMD00668, BUCMD00651,
BUCMD00734, BUCMD00685, CMLD011555, BUCMD00672, BUCMD00702, BUCMD00630,
CMLD011076, CMLD006598, BUCMD00732, BUCMD00683, BUCMD00690, BUCMD00674,
CMLD010988, BUCMD00698, CMLD011077, BUCMD00723, BUCMD00679, BUCMD00650,
CMLD011123, BUCMD00697, CMLD011553, BUCMD00684, BUCMD00687, BUCMD00649,
BUCMD00628, BUCMD00688, BUCMD00640, BUCMD00673, BUCMD00689, BUCMD00692,
CMLD011047, CMLD011136, CMLD011073, BUCMD00728, BUCMD00738, BUCMD00647,
BUCMD00663, CMLD011045, BUCMD00691, BUCMD00627, BUCMD00653, BUCMD00641,
BUCMD00721, CMLD009657, BUCMD00720, BUCMD00645, BUCMD00646, BUCMD00648,
CMLD010924, BUCMD00668, BUCMD00651, BUCMD00652, BUCMD00654, BUCMD00655,
BUCMD00672, BUCMD00702, BUCMD00630, BUCMD00656, BUCMD00657, BUCMD00658,
BUCMD00683, CMLD011037, BUCMD00690, BUCMD00659, BUCMD00660, BUCMD00661,
CMLD011038, BUCMD00674, BUCMD00723, BUCMD00662, BUCMD00664, BUCMD00665,
BUCMD00679, BUCMD00650, BUCMD00684, BUCMD00666, BUCMD00667, BUCMD00670,
BUCMD00687, BUCMD00649, BUCMD00673, BUCMD00671, BUCMD00675, BUCMD00676,
BUCMD00689, BUCMD00692, BUCMD00728, BUCMD00677, BUCMD00678, BUCMD00680,
BUCMD00738, CMLD011078, CMLD011090, BUCMD00693, BUCMD00696, BUCMD00701,
CMLD011044, CMLD011087, CMLD013629, BUCMD00711, BUCMD00712, BUCMD00713, BUCMD00714, BUCMD00715, BUCMD00716, BUCMD00719, BUCMD00722, BUCMD00724, BUCMD00725, BUCMD00726, BUCMD00727, BUCMD00731, BUCMD00739, BUCMD00741, BUCMD00156, BUCMD00157, BUCMD00158, BUCMD00159, BUCMD00160, BUCMD00161, BUCMD00162, BUCMD00163, BUCMD00164, BUCMD00165, BUCMD00166, BUCMD00167, BUCMD00168, BUCMD00169, BUCMD00170, BUCMD00171, BUCMD00172, BUCMD00173, BUCMD00174, BUCMD00175, BUCMD00176, BUCMD00177, BUCMD00178, BUCMD00179, BUCMD00180, BUCMD00181, BUCMD00182, BUCMD00183, BUCMD00184, BUCMD00185, BUCMD00186, BUCMD00187, BUCMD00188, BUCMD00189, BUCMD00190, BUCMD00191, BUCMD00192, BUCMD00193, BUCMD00194, BUCMD00195, BUCMD00196, BUCMD00197, BUCMD00198, and BUCMD00199.

In some embodiments, the compound is selected from the group consisting of: CMLD010994, CMLD011572, CMLD011562, CMLD011039, CMLD011574, CMLD010976, CMLD010901, BUCMD00694, BUCMD00729, BUCMD00683, BUCMD00695, BUCMD00730, CMLD010921, BUCMD00669, BUCMD00629, BUCMD00718, BUCMD00717, CMLD010948, CMLD011101, and CMLD011567. In some embodiments, the compound is selected from the group consisting of: BUCMD00694, BUCMD00729, BUCMD00683, BUCMD00695, BUCMD00730, BUCMD00669, BUCMD00629, BUCMD00718, and BUCMD00717.

Without wishing to be bound by a theory, inventors have discovered inter alia that compounds of Formula (I) or (II) having a C Log P from about 3.0 to about 4.5, unexpectedly and surprisingly have antileishmanial activity. Accordingly, in some embodiments of any one of the aspects described herein, the compound of Formula (I) or (II) has a C Log P from about 3.0 to about 4.5, e.g., from about 3.2 to about 4.3.

As used herein, C Log P is also known as "fragment/compound log P". A C Log P is a method that uses a dataset from full compounds, or fragments, which are experimentally determined, and then modelled using quantitative structure-activity relationship or other regression techniques in small fragments rather than per atom. Fragment contributions are then added up, with correction factors. This method tends to be better for systems with complex aromaticity, and larger molecules—on the condition that the molecule contains features that are similar to those from which the modelling was conducted. In the case of very obscure motifs in the molecules, then the model from which the prediction is made may not have a very good correlation.

Polymers

Embodiments of the various aspects described herein include a polymer. It is noted the polymer can be homopolymer, copolymer or blockpolymer. Some exemplary polymers include, but are not limited to, polycarbonates, polyesters, polyacrylates, polyamindes, and copolymers, blockpolymers and mixtures thereof.

In some embodiments, the polymer comprises one or more monomers of Formula (A), Formula (B), Formula (C):

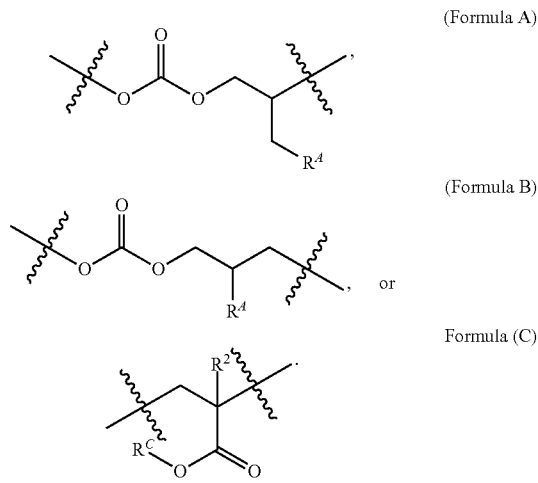

(Formula A)

(Formula B)

Formula (C)

In some embodiments of any of the aspects, each $R^A$ is independently —OC(O)—$R^{A1}$, —OC(O)O—$R^{A1}$, —OC(O)NH—$R^{A1}$, —NHC(O)O—$R^{A1}$, —NHC(O)NH—$R^{A1}$, —OR, —C(O)—$R^{A1}$, or —C(O)O—$R^{A1}$. For example, each $R^{A1}$ is independently —OC(O)—$R^{A2}$, —OC(O)O—$R^{A1}$, —OR$^{A1}$, —C(O)R$^{A1}$, or C(O)O—$R^{A1}$. Preferably, each $R^{A1}$ is independently —OC(O)—$R^{A2}$, —OR$^{A2}$, —C(O)R$^{A1}$, or —C(O)O—$R^{A1}$.

In some embodiments of any of the aspects, each $R^{A1}$ is independently H, $C_1$-$C_6$alkyl, $C_2$-$C_6$alkenyl, $C_2$-$C_6$alkynyl, poly(ethylene glycol), poly(ethylene oxide), a photocrosslinkable group, or an ionically crosslinkable group, wherein $C_1$-$C_6$alkyl, $C_2$-$C_6$alkenyl, $C_2$-$C_6$alkynyl is optionally substituted with one, two, three or four substituents selected independently from the group consisting of hydroxyl, hydroxyether, carboxyl, amino, mono- or di-substituted amino, thiol, thioester, and halogen. For example, each $R^{A1}$ is independently H, methyl, ethyl, propyl, iso-propyl, butyl, but-2-yl, 2-methylpropyl, t-butyl, pentyl, hexyl, poly(ethylene glycol), or poly(ethylene oxide). In some embodiments, each $R^{A1}$ is independently H, methyl, ethyl, propyl, iso-propyl, or butyl.

Exemplary monomers of Formula (A) and polymers comprising same are described in US patent publication US20200056038, content of which is incorporated herein by reference in its entirety.

Exemplary monomers of Formula (B) and polymers comprising same are described in US patent publication US20120107365 content of which is incorporated herein by reference in its entirety.

In some embodiments of any one of the aspects described herein, each $R^2$ is independently straight or branched alkyl, hydrogen or cycloalkyl. For example, $R^2$ is H or $C_1$-$C_6$alkyl, hydrogen. In some embodiments, $R^2$ is methyl, ethyl, propyl, isopropyl, butyl, isobutyl, tert-butyl or pentyl. For example, $R^2$ is methyl.

In some embodiments of anyone of the aspects described herein, each $R^3$ is independently hydrogen, hydroxyl, alkoxy, amino, nitro, cycloalkyl, aryl. For example, each $R^3$ is independently hydrogen, hydroxyl, $C_1$-$C_6$alkoxy, amino, nitro, or cycloalkyl. In some embodiments, each $R^3$ is independently H, $C_1$-$C_6$alkoxy, amino, or nitro. For example, each $R^3$ is independently H, methoxy, ethoxy, amino, or nitro. In some embodiments, each $R^3$ is H or methoxy.

In some embodiments of any one of the aspects described herein, $R_4$, $R_5$, and $R_6$ are each independently selected from the group consisting of a straight or branched alkyl, cycloalkyl, aryl, and olefin.

In some embodiments of any one of the aspects described herein, each $R_7$ is independently hydrogen, a straight or branched alkyl, cycloalkyl, aryl, alkylaryl, or arylalkyl. For example, each $R_7$ is independently hydrogen, a straight or branched alkyl, or cycloalkyl. For example, each $R_7$ is independently hydrogen or $C_1$-$C_6$ alkyl. For example, each $R_7$ is independently hydrogen, methyl, ethyl, propyl, isopropyl, butyl, or pentyl. In some cases, each $R_7$ is independently hydrogen or methyl.

In some embodiments of any one of the aspects described herein, each $R_8$ is independently $R_8$ is absent, alkylene or alkenylene. For example, each $R_8$ is absent or $C_1$-$C_6$alkylene. In some embodiments, each $R_8$ is independently absent, methylene, ethylene, propylene, butylene or pentylene. For example, each $R_8$ is absent or methylene.

In some embodiments, of any one of the aspects described herein, $R^C$ is

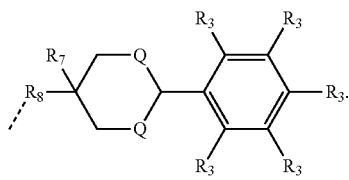

For example, a monomer of Formula (C) is:

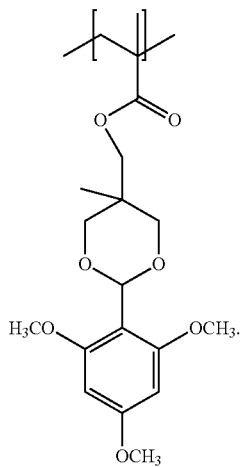

Exemplary monomers of Formula (B) and polymers comprising same are described in US patent publication US20120107365 content of which is incorporated herein by reference in its entirety.

In some embodiments of any of the aspects, the polymer comprises one or more monomers of Formula (A) and/or Formula (B). For example, the polymer comprises one or more monomers of Formula (A). In another example, the polymer comprises one or more monomers of Formula (B).

In some embodiments of any one of the aspects described herein, the polymer comprises one or more monomers of Formula (C).

In some embodiments of any one of the aspects described herein, the polymer is poly(glycerol carbonate) or a copolymer thereof. For example, the polymer is poly(1,3-glycerol carbonate), poly(1,2-glycerol carbonate), or a copolymer thereof. In some embodiments, the polymer is copolymer comprising poly(glycerol carbonate) and one of polycaprolactone, poly(lactic acid), poly(glycolic acid), poly(lactic-co-glycolic acid), poly(trimethylene carbonate), polyester, polycarbonate, or polyamide. For example, the polymer is copolymer comprising poly(glycerol carbonate) and polycaprolactone. In some embodiments, the copolymer is poly(1,3-glycerol carbonate)-$C_{18}$-co-poly(ε-caprolactone)

Cross-Linkers

The polymer can be cross-linked. Accordingly, in some embodiments of any one of the aspects described herein, the composition further comprises a cross-linker, e.g., a cross-linker linking the polymer chains. Suitable crosslinkers include compounds with at least two (meth)acryloyl groups. As used herein, the term "(meth)acryloyl" refers to an acryloyl group, a methacryloyl group, or both. Likewise, the term "(meth)acrylate" refers to an acrylate, a methacrylate, or both; the term "(meth)acrylamide" refers to an acrylamide, a methacrylamide, or both; and the term "(meth)acrylic acid" refers to acrylic acid, methacrylic acid, or both. The crosslinkers can be di(meth)acrylates, tri(meth)acrylates, tetra(meth)acrylates, penta(meth)acrylates, and the like. These crosslinkers can be formed, for example, by reacting (meth)acrylic acid with a polyhydric alcohol (i.e., an alcohol having at least two hydroxyl groups). The polyhydric alcohol often has two, three, four, or five hydroxyl groups. Mixtures of crosslinkers can be used. In some embodiments, the crosslinkers contain at least two acryloyl groups. Exemplary crosslinkers with two acryloyl groups include 1,2-ethanediol diacrylate, 1,3-propanediol diacrylate, 1,9-nonanediol diacrylate, 1,12-dodecanediol diacrylate, 1,4-butanediol diacrylate, 1,6-hexanediol diacrylate, butylene glycol diacrylate, bisphenol A diacrylate, diethylene glycol diacrylate, triethylene glycol diacrylate, tetraethylene glycol diacrylate, tripropylene glycol diacrylate, polyethylene glycol diacrylate, polypropylene glycol diacrylate, polyethylene/polypropylene copolymer diacrylate, and neopentylglycol hydroxypivalate diacrylate modified caprolactone. Exemplary crosslinkers with three or four (meth)acryloyl groups include, but are not limited to, trimethylolpropane triacrylate (e.g., commercially available under the trade designation TMPTA-N from Surface Specialties, Smyrna, Ga. and under the trade designation SR-351 from Sartomer, Exton, Pa.), pentaerythritol triacrylate (e.g., commercially available under the trade designation SR-444 from Sartomer), tris(2-hydroxyethylisocyanurate)triacrylate (commercially available under the trade designation SR-368 from Sartomer), a mixture of pentaerythritol triacrylate and pentaerythritol tetraacrylate (e.g., commercially available from Surface Specialties under the trade designation PETIA with an approximately 1:1 ratio of tetraacrylate to triacrylate and under the trade designation PETA-K with an approximately 3:1 ratio of tetraacrylate to triacrylate), pentaerythritol tetraacrylate (e.g., commercially available under the trade designation SR-295 from Sartomer), di-trimethylolpropane tetraacrylate (e.g., commercially available under the trade designation SR-355 from Sartomer), and ethoxylated pentaerythritol tetraacrylate (e.g., commercially available under the trade designation SR-494 from Sartomer). An exemplary crosslinker with five (meth)acryloyl groups includes, but is not limited to, dipentaerythritol pentaacrylate (e.g., commercially available under the trade designation SR-399 from Sartomer).

In some embodiments, the crosslinkers are polymeric material that contains at least two (meth)acryloyl groups.

For example, the crosslinkers can be poly(alkylene oxides) with at least two acryloyl groups (e.g., polyethylene glycol diacrylates commercially available from Sartomer such as SR210, SR252, and SR603) or poly(urethanes) with at least two (meth)acryloyl groups (e.g., polyurethane diacrylates such as CN9018 from Sartomer). As the higher molecular weight of the crosslinkers increases, the resulting acrylic copolymer tends to have a higher elongation before breaking Polymeric crosslinkers tend to be used in greater weight percent amounts compared to their non-polymeric counterparts.

In some embodiments, the cross-linker is 1,4-O-methacryloylhydroquinone or 1,4-phenylene-bis(2-methylacrylate).

Particles

In some embodiments of any one of the aspects described herein, the polymer and the antileishmanial compound can be comprised in a particle. The particle can be between about 5 nm and about 1500 nm in size. For example, the particle can be between about 10 nm, and about 1000 nm in size. In some embodiments, the particle can be between about 50 nm and about 200 nm in size. Polymer nanoparticles of similar size and polymer compositions are known to demonstrate significant uptake in the liver following injection.

In some embodiments, the particle is a an expansile particle. As used herein, an "expansile particle" is a particle and expansile in the presence of a particular stimulus. The expansile particle can expand in the presence of a particular pH. For example, the particle comprises a first volume at a first pH and a second volume at a second pH, optionally, the second volume is at least 1× greater than the first volume. In some embodiments, the particle comprises a first volume at a higher pH and a second volume at a lower pH. For example, the particle comprises a first volume at a neutral pH and a second volume at an acidic pH. In some embodiments, the particle comprises a first volume at a pH from about 6.5 to about 7.5 (e.g., a pH of about 7) and a second volume at a pH from about 4 to about 6 (e.g., pH of about 5), and where the second volume is at least 1× greater than the first volume. Expansile particles are known to show significant uptake in the liver (~40%) and spleen (~2%) following i.v. injection.

Without wishing to be bound by a theory, the change in volume allows the particle to accumulate in the liver of a subject after administration and release the antileishmanial compound in the liver. In some embodiments, the antileishmanial compound is released from the particle at higher rate at an acidic pH relative to a release at neutral pH.

The particles can be formed through water-in-oil ultrasonication methods and purified via dialysis. Particle size, monodispersity can be controlled by varying cross-linker, surfactant (e.g., polymer to surfactant ratio) and sonication parameters (e.g., sonication time and sonication pulse parameters) during preparation of the particles.

Pharmaceutical Compositions

The compositions described herein can be in form of a pharmaceutical composition. For example, the composition comprising the particle and the antileishmanial can further comprise with one or more pharmaceutically acceptable carriers (additives), excipient and/or diluents. It is noted that the compounds of Formula (I) or (II) described herein can be formulated into pharmaceutical compositions for therapeutic use without the polymer. Accordingly, in another aspect, the invention provides a composition, e.g., a pharmaceutical composition, comprising an effective amount of a compound of Formula (I) or (II) (e.g., without a polymer) formulated together with one or more pharmaceutically acceptable carriers (additives), excipient and/or diluents.

The compositions can be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; or (3) topical application, for example, as a film, sheet, dressing, cream, ointment, liquid, gel, hydrogel, emulsion, suspension or a controlled-release patch or spray applied to the skin. Delivery using topical, oral or intravenous methods can be particularly advantageous. Accordingly, in some embodiments, the composition is formulated for oral or intravenous administration.

In some embodiments, the composition is formulated for topical administration. For topical administration, the composition can be in the form of a film, sheet, dressing, cream, ointment, liquid, gel, hydrogel, emulsion, suspension or a controlled-release patch or spray applied. In some embodiments, the composition formulated for topical administration is in the form of an adhesive.

In some embodiments, the composition is formulated for oral or intravenous administration.

Generally, the composition, e.g., pharmaceutical composition comprises an effective or therapeutically effective amount of the antileishmanial compound. The phrase "therapeutically effective amount" as used herein means that amount of a compound, material, or composition comprising a compound described herein which is effective for producing some desired therapeutic effect in a subject at a reasonable benefit/risk ratio applicable to any medical treatment, e.g., treatment of *Leishmania* or a disease or disorder due to *Leishmania*.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Embodiments of the compositions described herein include pharmaceutically acceptable carriers (additives), excipient and/or diluents. The phrase "pharmaceutically acceptable carrier" as used herein means a pharmaceutically-acceptable material, composition, or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

In some embodiments, the composition is formulated as a unit dosage formulation.

Techniques and formulations generally can be found in Remington's Pharmaceutical Sciences, Meade Publishing Co., Easton, PA. For systemic administration, injection is preferred, including intramuscular, intravenous, intraperitoneal, and subcutaneous. For injection, antileishmanial compounds described herein can be formulated in liquid solutions, preferably in physiologically compatible buffers such as Hank's solution or Ringer's solution. In addition, the antileishmanial compound described herein can be formulated in solid form and redissolved or suspended immediately prior to use. Lyophilized forms are also included.

For oral administration, the pharmaceutical composition can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups, or suspensions, or they may be presented as a dry product for constitution with water or other suitable vehicle before use. Such liquid preparations can be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., pharmaceutically acceptable oils, oily esters, ethyl alcohol or fractionated vegetable oils); and preservatives (e.g., methyl or propyl-p-hydroxybenzoates or sorbic acid). The preparations can also contain buffer salts, flavoring, coloring, and sweetening agents as appropriate.

Preparations for oral administration can be suitably formulated to give controlled release of the active compound. For buccal administration the compositions can take the form of tablets or lozenges formulated in conventional manner. For administration by inhalation, the compounds for use as described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The antileishmanial compound can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

In addition to the formulations described previously, the antileishmanial compound can also be formulated as a depot preparation. Such long-acting formulations can be administered by implantation (for example subcutaneously or intramuscularly) or by intramuscular injection. Thus, for example, the antibodies can be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents can be used to facilitate permeation. Transmucosal administration can be through nasal sprays or using suppositories. For topical administration, the antileishmanial compound can be formulated into ointments, salves, gels, or creams as generally known in the art. A wash solution can be used locally to treat an injury or inflammation to accelerate healing.

The compositions can, if desired, be presented in a pack or dispenser device which can contain one or more-unit dosage forms containing the active ingredient. The pack can for example comprise metal or plastic foil, such as a blister pack. The pack or dispenser device can be accompanied by instructions for administration.

In some embodiments, the composition further comprises one or more of binders, viscosity modifiers, preservatives, humectants, emollients, pH stabilizing agents, chelating agents, gelling agents, thickening agents, emulsifiers, buffers, and carriers.

Second Active Agent

A composition described herein can an active agent, e.g., a second antileishmanial compound and/or another active agent. Accordingly, in some embodiments, the composition further comprises a second antileishmanial compound. Exemplary antileishmanial compounds include, but are not limited to, antimonials, miltefosine, dronedarone, stibogluconate, meglumine antimonite, pentamidine, amphotericin B, paromomycin, reversed amidines, Cpg-D35, DNDI-6148, DNDI-0690, DDD853651, DDD1305143, LXE408, DNDI-6174, proteasome inhibitors, CRK12 inhibitors, and pharmaceutically acceptable salts thereof.

In some embodiments, the active agent is selected from the group consisting of wound-healing agents, anti-scarring agents, antioxidant agents, cooling agents, soothing agents, anti-inflammatory-agents, antibiotics, topical analgesics, counter irritants, penetration enhancers, and permeation enhancers.

Method of Treatment

In another aspect provided herein is a method for treating leishmaniasis or a disease or disorder associated with leishmaniasis. The method comprises: administering a therapeutically effective amount of an antileishmanial compound of Formula (I) or Formula (II) to a subject in need thereof. Exemplary *Leishmania* parasites causing leishmaniasis or a disease or disorder associated with leishmaniasis include, but are not limited to *Leishmania major, Leishmania tropica, Leishmania Mexicana, Leishmania braziliensis, Leishmania amazonensis, Leishmania aethiopica, Leishmania panamensis, Leishmania guyanensis, Leishmania infantum, Leishmania donovani, Leishmania promastigotes, Leishmania adleri, Leishmania agamae, Leishmania arabica, Leishmania aristidesi, Leishmania ceramodactyli, Leishmania enriettii, Leishmania forattinii, Leishmania gerbilli, Leishmania gulikae, Leishmania gymnodactyli, Leishmania helioscopi, Leishmania hemidactyli, Leishmania hoogstraali, Leishmania killicki, Leishmania lainsoni, Leishmania lindenbergi, Leishmania macropodum, Leishmania martiniquensis, Leishmania naiffi, Leishmania nicollei, Leishmania orientalis, Leishmania peruviana, Leishmania phrynocephali, Leishmania pifanoi, Leishmania platycephala, Leishmania senegalensis, Leishmania shawl, Leishmania* softeffi, *Leishmania tarentolae, Leishmania turanica, Leishmania utingensis, Leishmania venezeulensis, Leishmania waltoni* Shaw, *Leishmania zmeevi,* and *Leishmania zuckermani.*

In some embodiments, the leishmaniasis or a disease or disorder associated with leishmaniasis is caused by a *Leishmania* parasite selected from the group consisting of *Leishmania major, Leishmania tropica, Leishmania Mexicana, Leishmania braziliensis, Leishmania amazonensis, Leishmania aethiopica, Leishmania panamensis, Leishmania guyanensis, Leishmania infantum, Leishmania donovani.* For example, leishmaniasis or a disease or disorder associated with leishmaniasis is caused by a *Leishmania* parasite selected from the group consisting of *Leishmania major, Leishmania braziliensis,* and *Leishmania donovani.*

It is noted that the leishmaniasis can be cutaneous leishmaniasis (CL), visceral leishmaniasis (VL) or mucosal leishmaniasis (ML). In some embodiments, the leishmaniasis is cutaneous leishmaniasis (CL). In other embodiments, the leishmaniasis is visceral leishmaniasis (VL).

In some embodiments, the leishmaniasis is cutaneous leishmaniasis. Cutaneous leishmaniasis is a more common form of leishmaniasis that affects 1.5 million to 2 million worldwide per year. CL is a skin infection that is characterized by symptoms which include skin sores. Skin sores typically develop within a few weeks or months of the sand fly bite. The sores can change in size and appearance over time. The sores may start out as papules (bumps) or nodules (lumps) and may end up as ulcers (like a volcano, with a raised edge and central crater); skin ulcers might be covered by scab or crust. The sores usually are painless but can be painful. Additional symptoms can include swollen lymph nodes near the sores (e.g., under the arm, if the sores are on the arm or hand).

In some embodiments, the leishmaniasis is visceral leishmaniasis. Viserceral leishmaniasis is characterized by symptoms which affects several internal organs (usually spleen, liver, and bone marrow) and can be life threatening. The illness typically develops within months (sometimes as long as years) of the sand fly bite. Affected people usually have fever, weight loss, enlargement (swelling) of the spleen and liver, and low blood counts—a low red blood cell count (anemia), a low white blood cell count (leukopenia), and a low platelet count (thrombocytopenia).

In some embodiments, the leishmaniasis is mucosal leishmaniasis. Mucosal leishmaniasis is a less common form of leishmaniasis. This form can be a consequence of infection with some of the species of the parasite that cause cutaneous leishmaniasis in parts of Latin America: certain types of the parasite might spread from the skin and cause sores in the mucous membranes of the nose, which is the most common location, mouth, or throat.

Diagnosis of leishmaniasis includes, but is not limited to, examination of tissue specimens through a skin biopsy (e.g., from skin sores (in suspected cases of cutaneous leishmaniasis) or from bone marrow (in suspected cases of visceral leishmaniasis)) for presence of the parasite, serological tests, and needle biopsy. As disclosed herein, antileishmanial compounds can reduce, suppress, or inhibit the expression or presence of a *Leishmania* parasite in a vector by at least 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of antileishmanial compounds.

Current treatments of leishmaniasis include, but are not limited to, amphotericin B, miltefosin, pentavalent antimonials (e.g., sodium stibogluconate and meglumine antimoniate), ambisome, pentamidine isethionate, and paromomycin. Pentavalent antimonials can only be given by injection and there are no oral preparations currently available. Additional treatments include thermotherapy, cryotherapy, and laser therapy. Complications from leishmaniasis include, but are not limited to bacterial infections, scarring, relapse, septal perforation or collapse, pneumonia or gastrointestinal tract infections, Post kala-azar dermal leishmaniasis (PKDL), severe bleeding, hemophagocytic lymphohistiocytosis, and sepsis.

In some embodiments, compounds and compositions described herein can inhibit or decrease the development and/or presence of symptoms of CL, VL or ML by at least 10%, relative to the development and/or presence of symptoms in the absence of antileishmanial compounds, e.g., at least about 15%, at least about 20%, at least about 30%, at least about 40%, at least about 50%, at least about 60%, at least about 70%, at least about 80%, at least about 90%, 95%, 99% or even 100%.

Vectors

The compounds and compositions described herein can be useful in reducing, suppressing or inhibiting a *Leishmania* parasite in a *Leishmania* parasite vector. Thus, in another aspect provided herein is a method of reducing, suppressing or inhibiting a *Leishmania* parasite in a vector. The method comprises administering to the vector an effective amount of Formula (I) or Formula (II).

Administration of an effective amount of Formula (I) or Formula (II) to the vector can comprise including an effective amount of Formula (I) or Formula (II) as part of an insect repellent or insecticide. Insect repellents that can include Formula (I) or Formula (II) include, but are not limited to benzaldehyde, butopyronoxyl, N,N-diethyl-m-toluamide (DEET), dimethyl carbate, dimethyl phthalate, ethyl butylacetylaminopropionate, ethylhexanediol, icaridin, methyl anthranilate, N,N-dimethylanthranilic acid (DMA), ethyl anthranilate (EA), butyl anthranilate (BA), metofluthrin, permethrin, SS220, tricyclodecenyl allyl ether, beautyberry (Callicarpa) leaves, nepetalactone, citronella oil, essential oil of *Corymbia citriodora* (lemon eucalyptus) and its active compound p-menthane-3,8-diol (PMD), lemongrass, neem oil, tea tree oil from the leaves of *Melaleuca alternifolia,* and tobacco. Formula (I) or Formula (II) can also be a part of bed netting and/or clothing that has been treated with a pyrethroid-containing insecticide.

As used herein, a "vector" is a living organism that can transmit infectious pathogens between humans, or from animals to humans. Many of these vectors are bloodsucking insects, which ingest disease-producing microorganisms during a blood meal from an infected host (human or animal) and later transmit it into a new host, after the pathogen has replicated. Often, once a vector becomes infectious, they are capable of transmitting the pathogen for the rest of their life during each subsequent bite/blood meal. In some embodiments, the vector that transmits a *Leishmania* parasite is Phlembotominae. The Phlebotominae are a subfamily of the family Psychodidae. Phlebotominae are commonly known as sandflies, but the name is applied to other flies. The genera that is found in Phlebotominae subfamily include Australophlebotomus, Bichromomyia, Brumptomyia, Chinius, Dampfomyia, Datzia, Deanemyia, Evandromyia, Edentomyia, Expapillata, Hertigia, Idiophlebotomus, Libanophlebotomus, *Lutzomyia*, Mandalayia, Martinsmyia, Mesophlebotomites, Micropygomyia, Migonemyia, Nyssomyia, Oligodontomyia, Palaeomyia, Phlebotomites, Phlebotoiella, *Phlebotomus*, Pintomyia, Pressatia, Protopsychodinae, Protopsychoda, Psathyromyia, Psychodopygus, Sciopemyia, Sergentomyia, Trichophoromyia, Viannamyia, and Warileya. In North, Central, and South America, leishmaniasis is spread by the genus *Lutzomyia*. In Africa, Europe, and Asia, leishmaniasis is spread by the genus *Phlebotomus*.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials can be used in the practice or testing of the invention, the methods, devices, and materials in this regard are described herein.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximating the number that the term precedes. In determining whether a number is near to or approximately a specifically recited number, the near or approximating unrecited number can be a number which, in the context in which it is presented, provides the substantial equivalent of the specifically recited number.

As used herein the term "comprising" or "comprises" is used in reference to compositions, methods, and respective component(s) thereof, that are essential to the invention, yet open to the inclusion of unspecified elements, whether essential or not. In other words, except where the context requires otherwise, the term "comprise" and variations of the term, such as "comprising", "comprises" and "comprised", are not intended to exclude further additives, components, integers or steps.

The singular terms "a," "an," and "the" include plural referents unless context clearly indicates otherwise. Similarly, the word "or" is intended to include "and" unless the context clearly indicates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "subject" or "patient" refers to any organism to which a compound or composition disclosed herein can be administered, e.g., for experimental, diagnostic, and/or therapeutic purposes. Typical subjects include animals (e.g., mammals such as mice, rats, rabbits, non-human primates, and humans) and/or plants. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of human diseases and disorders. In addition, compounds, compositions and methods described herein can be used to with domesticated animals and/or pets.

A subject can be one who has been previously diagnosed with or identified as suffering from or having leishmaniasis or a disease or disorder associated with leishmaniasis. Alternatively, a subject can also be one who has not been previously diagnosed. A "subject in need" of treatment for leishmaniasis or a disease or disorder associated with leishmaniasis can be a subject having leishmaniasis or a disease or disorder associated with leishmaniasis, diagnosed as having that condition, or at risk of developing that condition.

In some embodiments, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species. In some embodiments, the subject can be of European ancestry. In some embodiments, the subject can be of African American ancestry. In some embodiments, the subject can be of Asian ancestry.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "parenteral administration," refers to administration through injection or infusion. Parenteral administration includes, but is not limited to, subcutaneous administration, intravenous administration, or intramuscular administration.

As used herein, the term "subcutaneous administration" refers to administration just below the skin. "Intravenous administration" means administration into a vein.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

As used herein, the term "dosage unit" refers to a form in which a pharmaceutical agent is provided. In certain embodiments, a dosage unit is a vial comprising lyophilized composition or compound described herein. In certain embodiments, a dosage unit is a vial comprising reconstituted composition or compound descried herein.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of leishmaniasis or a disease or disorder associated with leishmaniasis.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

As used herein, the term "aliphatic" means a saturated or unsaturated and straight, branched, and/or cyclic hydrocarbon having the defined number of carbon atom. Examples include alkyl, alkenyl, alkynyl, cycloalkyl, cycloalkylalkyl, cycloalkylalkenyl, and cycloalkylalkynyl, having the defined number of carbon atoms.

As used herein, the term "alkyl" refers to an aliphatic hydrocarbon group which can be straight or branched having 1 to about 60 carbon atoms in the chain, and which preferably have about 6 to about 50 carbons in the chain. "Lower alkyl" refers to an alkyl group having 1 to about 8 carbon atoms. "Higher alkyl" refers to an alkyl group having about 10 to about 20 carbon atoms. The alkyl group can be optionally substituted with one or more alkyl group substituents which can be the same or different, where "alkyl group substituent" includes halo, amino, aryl, hydroxyl, alkoxy, aryloxy, alkyloxy, alkylthio, arylthio, aralkyloxy, aralkylthio, carboxy, alkoxycarbonyl, oxo and cycloalkyl. "Branched" refers to an alkyl group in which a lower alkyl group, such as methyl, ethyl or propyl, is attached to a linear alkyl chain. Exemplary alkyl groups include methyl, ethyl, propyl, i-propyl, n-butyl, t-butyl, n-pentyl, hexyl, heptyl, octyl, decyl, dodecyl, tridecyl, tetradecyl, pentadecyl and hexadecyl. Useful alkyl groups include branched or straight chain alkyl groups of 6 to 50 carbon, and also include the lower alkyl groups of 1 to about 4 carbons and the higher alkyl groups of about 12 to about 16 carbons.

A "heteroalkyl" group substitutes any one of the carbons of the alkyl group with a heteroatom having the appropriate number of hydrogen atoms attached (e.g., a $CH_2$ group to an NH group or an O group). The term "heteroalkyl" include optionally substituted alkyl, alkenyl and alkynyl radicals which have one or more skeletal chain atoms selected from an atom other than carbon, e.g., oxygen, nitrogen, sulfur, phosphorus, silicon, or combinations thereof. In certain embodiments, the heteroatom(s) is placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —Si($CH_3$)$_3$, —$CH_2$—CH=N—O$CH_3$, and —CH=CH—N($CH_3$)—$CH_3$. In some embodiments, up to two heteroatoms are consecutive, such as, by way of example, —$CH_2$—NH—O$CH_3$ and —$CH_2$—O—Si($CH_3$)$_3$ As used herein, the term "alkenyl" refers to an alkyl group containing at least one carbon-carbon double bond. The alkenyl group can be optionally substituted with one or more "alkyl group substituents." Exemplary alkenyl groups include vinyl, ally, n-pentenyl, decenyl, dodecenyl, tetradecadienyl, heptadec-8-en-1-yl and heptadec-8,11-dien-1-yl.

As used herein, the term "alkynyl" refers to an alkyl group containing a carbon-carbon triple bond. The alkynyl group can be optionally substituted with one or more "alkyl group substituents." Exemplary alkynyl groups include ethynyl, propargyl, n-pentynyl, decynyl and dodecynyl. Useful alkynyl groups include the lower alkynyl groups.

As used herein, the term "cycloalkyl" refers to a non-aromatic mono- or multicyclic ring system of about 3 to about 12 carbon atoms. The cycloalkyl group can be optionally partially unsaturated. The cycloalkyl group can be also optionally substituted with an aryl group substituent, oxo and/or alkylene. Representative monocyclic cycloalkyl rings include cyclopentyl, cyclohexyl and cycloheptyl. Useful multicyclic cycloalkyl rings include adamantyl, octahydronaphthyl, decalin, camphor, camphane, and noradamantyl.

"Heterocyclyl" refers to a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyland the like.

"Aryl" refers to an aromatic carbocyclic radical containing about 3 to about 13 carbon atoms. The aryl group can be optionally substituted with one or more aryl group substituents, which can be the same or different, where "aryl group substituent" includes alkyl, alkenyl, alkynyl, aryl, aralkyl, hydroxyl, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, alkylene and —NRR', where R and R' are each independently hydrogen, alkyl, aryl and aralkyl. Exemplary aryl groups include substituted or unsubstituted phenyl and substituted or unsubstituted naphthyl.

"Heteroaryl" refers to an aromatic 3-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively.

Exemplary aryl and heteroaryls include, but are not limited to, phenyl, pyridinyl, pyrimidinyl, furanyl, thienyl, imidazolyl, thiazolyl, pyrazolyl, pyridazinyl, pyrazinyl, triazinyl, tetrazolyl, indolyl, benzyl, naphthyl, anthracenyl, azulenyl, fluorenyl, indanyl, indenyl, naphthyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

As used herein, the term "halogen" or "halo" refers to an atom selected from fluorine, chlorine, bromine and iodine.

The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application.

The term "haloalkyl" as used herein refers to alkyl and alkoxy structures structure with at least one substituent of fluorine, chorine, bromine or iodine, or with combinations thereof. In embodiments, where more than one halogen is included in the group, the halogens are the same or they are different. The terms "fluoroalkyl" and "fluoroalkoxy" include haloalkyl and haloalkoxy groups, respectively, in which the halo is fluorine. Exemplary halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl ($CF_3$), perfluoroethyl, 2,2,2-trifluoroethyl, 2,2,2-trifluoro-1,1-dichloroethyl, and the like).

As used herein, the term "amino" means —$NH_2$. The term "alkylamino" means a nitrogen moiety having one straight or branched unsaturated aliphatic, cyclyl, or heterocyclyl radicals attached to the nitrogen, e.g., —NH(alkyl). The term "dialkylamino" means a nitrogen moiety having at two straight or branched unsaturated aliphatic, cyclyl, or heterocyclyl radicals attached to the nitrogen, e.g., —N(alkyl) (alkyl). The term "alkylamino" includes "alkenylamino," "alkynylamino," "cyclylamino," and "heterocyclylamino." The term "arylamino" means a nitrogen moiety having at least one aryl radical attached to the nitrogen. For example, —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like. Exemplary alkylamino includes, but is not limited to, NH($C_1$-$C_{10}$alkyl), such as —$NHCH_3$, —$NHCH_2CH_3$, $NHCH_2CH_2CH_3$, and —$NHCH(CH_3)_2$. Exemplary dialkylamino includes, but is not limited to, —N($C_1$-$C_{10}$alkyl)$_2$, such as N($CH_3$)$_2$, —N($CH_2CH_3$)$_2$, —N($CH_2CH_2CH_3$)$_2$, and —N($CH(CH_3)_2$)$_2$.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

The terms "hydroxyl" and "hydroxyl" mean the radical —OH.

The terms "alkoxyl" or "alkoxy" as used herein refers to an alkyl group, as defined above, having an oxygen radical attached thereto, and can be represented by one of —O-alkyl, —O— alkenyl, and —O-alkynyl. Aroxy can be represented by —O-aryl or O-heteroaryl, wherein aryl and heteroaryl are as defined herein. The alkoxy and aroxy groups can be substituted as described above for alkyl. Exemplary alkoxy groups include, but are not limited to O-methyl, O-ethyl, O-n-propyl, O-isopropyl, O-n-butyl, O-isobutyl, O-sec-butyl, O-tert-butyl, O-pentyl, O-hexyl, O-cyclopropyl, O-cyclobutyl, O-cyclopentyl, O-cyclohexyl and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

As used herein, the term "oxo" means double bonded oxygen, i.e., =O.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. As used herein, a carboxy group includes —COOH, i.e., carboxyl group.

The term "ester" refers to a chemical moiety with formula —C(=O)OR, where R is selected from the group consisting of alkyl, cycloalkyl, aryl, heteroaryl and heterocycloalkyl.

The term "cyano" means the radical —CN.

The term "nitro" means the radical —NO$_2$.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —NR$^N$—, —N$^+$(O$^-$)=, —O—, —S— or —S(O)$_2$—, —OS(O)$_2$—, and —SS—, wherein R$^N$ is H or a further substituent.

The terms "alkylthio" and "thioalkoxy" refer to an alkoxy group, as defined above, where the oxygen atom is replaced with a sulfur. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —SO$_2$—. It is noted that the sulfonyl radical can be further substituted with a variety of substituents to form different sulfonyl groups including sulfonic acids (—SO$_3$H), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

"Acyl" refers to an alkyl-CO— group, wherein alkyl is as previously described. Exemplary acyl groups comprise alkyl of 1 to about 30 carbon atoms. Exemplary acyl groups also include acetyl, propanoyl, 2-methylpropanoyl, butanoyl and palmitoyl.

"Aroyl" means an aryl-CO— group, wherein aryl is as previously described. Exemplary aroyl groups include benzoyl and 1- and 2-naphthoyl.

"Arylthio" refers to an aryl-S— group, wherein the aryl group is as previously described. Exemplary arylthio groups include phenylthio and naphthylthio.

"Aralkyl" refers to an aryl-alkyl- group, wherein aryl and alkyl are as previously described. Exemplary aralkyl groups include benzyl, phenylethyl and naphthylmethyl.

"Aralkyloxy" refers to an aralkyl-O— group, wherein the aralkyl group is as previously described. An exemplary aralkyloxy group is benzyloxy.

"Aralkylthio" refers to an aralkyl-S— group, wherein the aralkyl group is as previously described. An exemplary aralkylthio group is benzylthio.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an H$_2$N—CO— group.

"Alkylcarbamoyl" refers to a R'RN—CO— group, wherein one of R and R' is hydrogen and the other of R and R' is alkyl as previously described.

"Dialkylcarbamoyl" refers to R'RN—CO— group, wherein each of R and R' is independently alkyl as previously described.

"Acyloxy" refers to an acyl-O— group, wherein acyl is as previously described. "Acylamino" refers to an acyl-NH— group, wherein acyl is as previously described. "Aroylamino" refers to an aroyl-NH— group, wherein aroyl is as previously described.

The term "optionally substituted" means that the specified group or moiety is unsubstituted or is substituted with one or more (typically 1, 2, 3, 4, 5 or 6 substituents) independently selected from the group of substituents listed below in the definition for "substituents" or otherwise specified. The term "substituents" refers to a group "substituted" on a substituted group at any atom of the substituted group. Suitable substituents include, without limitation, halogen, hydroxyl, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxylalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

For example, any alkyl, alkenyl, cycloalkyl, heterocyclyl, heteroaryl or aryl is optionally substituted with 1, 2, 3, 4 or 5 groups selected from OH, CN, —SC(O)Ph, oxo (=O), SH, SO$_2$NH$_2$, SO$_2$(C$_1$-C$_4$)alkyl, SO$_2$NH(C$_1$-C$_4$)alkyl, halogen, carbonyl, thiol, cyano, NH$_2$, NH(C$_1$-C$_4$)alkyl, N[(C$_1$-C$_4$)alkyl]$_2$, C(O)NH$_2$, COOH, COOMe, acetyl, (C$_1$-C$_8$) alkyl, O(C$_1$-C$_8$)alkyl, O(C$_1$-C$_8$)haloalkyl, (C$_2$-C$_8$)alkenyl, (C$_2$-C$_8$)alkynyl, haloalkyl, thioalkyl, cyanomethylene, alkylaminyl, aryl, heteroaryl, substituted aryl, NH$_2$—C(O)-alkylene, NH(Me)-C(O)-alkylene, CH$_2$—C(O)-alkyl, C(O)-alkyl, alkylcarbonylaminyl, CH$_2$—[CH(OH)]$_m$—(CH$_2$)$_p$—OH, CH$_2$—[CH(OH)]$_m$—(CH$_2$)$_p$—NH$_2$ or CH$_2$-arylalkoxy; "m" and "p" are independently 1, 2, 3, 4, 5 or 6.

In some embodiments, an optionally substituted group is substituted with 1 substituent. In some other embodiments, an optionally substituted group is substituted with 2 independently selected substituents, which can be same or different. In some other embodiments, an optionally substituted group is substituted with 3 independently selected substituents, which can be same, different or any combination of same and different. In still some other embodiments, an optionally substituted group is substituted with 4 independently selected substituents, which can be same, different or any combination of same and different. In yet some other embodiments, an optionally substituted group is substituted with 5 independently selected substituents, which can be same, different or any combination of same and different.

An "isocyanato" group refers to a NCO group.
A "thiocyanato" group refers to a CNS group.
An "isothiocyanato" group refers to a NCS group.
"Alkoyloxy" refers to a RC(=O)O— group.
"Alkoyl" refers to a RC(=O)— group.

It should be understood that this disclosure is not limited to the particular methodology, protocols, and reagents, etc., provided herein and as such may vary. The terminology used herein is for the purpose of describing particular embodiments only, and is not intended to limit the scope of the present disclosure, which is defined solely by the claims. The invention is further illustrated by the following example, which should not be construed as further limiting.

The technology may be as described in any one of the following numbered Embodiments:

Embodiment 1: A composition comprising: (a) a polymer; and (b) an antileishmanial compound, optionally, the antileishmnial compound is of Formula (I) or (II):

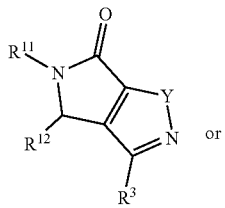
(Formula I)

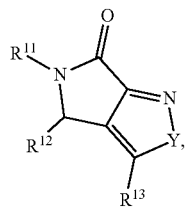
(Formula II)

wherein:
Y is $NR^{14}$, $CH_2$, O or S;
$R^{11}$ is aryl, heteroaryl, alkyl, alkenyl, alkynyl, cycloalkyl, or heterocyclyl;
$R^{12}$ is cycloalkyl, heterocyclyl, aryl or heteroaryl;
$R^{13}$ is —$CH_2$—$R^{15}$;
$R^{14}$ is H, alkyl, alkenyl, alkynyl, cycloalkyl, heterocyclyl, aryl or heteroaryl; and
$R^{15}$ is alkyl, alkenyl, alkynyl, aryl, heteroaryl, cycloalkyl, heterocyclyl, or a nucleophile; and
a pharmaceutically acceptable salt thereof,
optionally, any alkyl, alkenyl, alkynyl, aryl, heteroaryl, cycloalkyl and heterocyclyl is optionally substituted with one or more (e.g., 1, 2, 3, 4 or more) substituents selected
independently from the group consisting of halogen, hydroxyl, alkoxy, carboxyl, oxo,
nitro, haloalkyl, alkyl, alkenyl, alkynyl, alkaryl, aryl, heteroaryl, cycloalkyl, heterocyclyl,
aralkyl, acyl, aryloxy, amino, alkylamino dialkylamino, acylamino, alkylcarbanoyl,
arylcarbanoyl, aminoalkyl, aminocarbonyl, alkoxycarbonyl, carboxy, hydroxylalkyl,
alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl,
sulfonamide, sulfate, phosphate, haloalkyl, thioalkyl, cyanomethylene, alkylaminyl,
cyano and ureido.

Embodiment 2: The composition of Embodiment 1, wherein Y is N—$R^{14}$, e.g., the compound is of Formula (I-A) or (II-A):

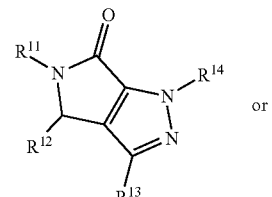
(Formula I-A)

or

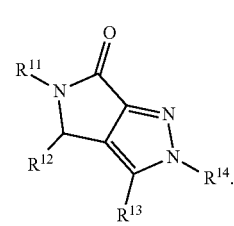
(Formula II-A)

Embodiment 3: The composition of Embodiment 2, wherein $R^{15}$ is alkyl, alkenyl, alkynyl, cycloalkyl, or heterocyclyl, wherein the alkyl, alkenyl, alkynyl, cycloalkyl and heterocyclyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 4: The composition of Embodiment 3, wherein $R^{15}$ is alkyl, alkenyl, cycloalkyl or heterocyclyl, wherein the alkyl, alkenyl, cycloalkyl and heterocyclyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 5: The composition of Embodiment 4, wherein $R^{15}$ is an alkyl, optionally substituted with a halogen, hydroxyl, alkoxy, amino, alkylamino, dialkylamino, cycloalkyl, heterocyclyl, aryl, heteroaryl, thiol, azide or nitrite.

Embodiment 6: The composition of Embodiment 5, wherein $R^{15}$ is $C_1$-$C_6$alkyl or —$(CH_2)_a$—$R^{16}$, where a is 0, 1, 2, 3, 4, 5, 6, 7, 8, 9 or 10; and $R^{16}$ is cycloalkyl, —$OR^{17}$, —$NR^{18}R^{19}$, where $R^7$ is H or alkyl, and $R^8$ and $R^9$ are independently H, alkyl, or cycloalkyl.

Embodiment 7: The composition of Embodiment 6, wherein a is 0, 1, 2, 3 or 4.

Embodiment 8: The compound of Embodiment 7, wherein $R^{15}$ is $C_1$-$C_6$ alkyl, —$CH_2$-cycloalkyl, —$CH_2CH_2$-cycloalkyl, —$CH_2$—$OR^7$, —$CH_2CH_2$—$OR^{17}$, —$CH_2$—$NR^{18}N^{19}$ or —$CH_2CH_2$—$NR^{18}N^{19}$.

Embodiment 9: The composition of Embodiment 8, wherein $R^{15}$ is isopropyl, isobutyl, t-butyl, propyl, propen-3-yl, 2-methylpropen-3-yl, 2-methylbutene-4-yl, cyclohexylmethyl, 2-cyclohexylethyl, benzyl, —$CH_2$—$OR^{17}$, —$CH_2CH_2$—$OR^{17}$, —$CH_2$—$NR^{18}N^{19}$ or —$CH_2CH_2$—$NR^{18}N^{19}$.

Embodiment 10: The composition of Embodiment 9, wherein $R^{15}$ is isopropyl.

Embodiment 11: The composition of Embodiments 1 or 2, wherein $R^{15}$ is a nucleophile.

Embodiment 12: The composition of Embodiment 11, wherein $R^{15}$ is hydroxyl, amino, thiol, carboxyl, cyanide, azide, or nitrite.

Embodiment 13: The composition of any one of Embodiments 1-12, wherein $R^{14}$ is H, alkyl, alkenyl, alkynyl, aryl or heteroaryl, wherein the alkyl, alkenyl, alkynyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 14: The composition of Embodiment 13, wherein $R^{14}$ is H, $C_1$-$C_6$alkyl, $C_2$-$C_6$alkenyl, $C_2$-$C_6$alkynyl, or 5-12 membered aryl, wherein the $C_1$-$C_6$alkyl, $C_2$-$C_6$alkenyl, $C_2$-$C_6$alkynyl, and 5-12 membered aryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 15: The composition of Embodiment 14, wherein $R^{14}$ is H, methyl, ethyl, propyl, isopropyl, butyl, isobutyl, but-2-yl, t-butyl, pentyl, 5-hexyn-1-yl, 2-propyn-1-yl, propargyl, methoxymethyl, phenyl, 4-trifluoromethylphenyl or —$(CH_2)_a$—$R^{16}$, where a is 0, 1, 2, 3, 4, 5, 6, 7, 8, 9 or 10, optionally, a is 0, 1, 2, 3 or 4 (e.g., a is 1 or 2); and $R^{16}$ is cycloalkyl, —$OR^{17}$, —$NR^{18}R^{19}$, where $R^7$ is H or alkyl, and $R^8$ and $R^9$ are independently H, alkyl, or cycloalkyl.

Embodiment 16: The composition of Embodiment 15, wherein $R^{14}$ is H, $R^4$ is H, methyl, ethyl, propyl, isopropyl, butyl, isobutyl, but-2-yl, pentyl, hexyl, 5-hexyn-1-yl, 2-propyn-1-yl, propargyl, —$CH_2$—$OR^7$, —$CH_2CH_2$—$OR^{17}$, —$CH_2$—$NR^{18}N^{19}$ or —$CH_2CH_2$—$NR^{18}N^{19}$.

Embodiment 17: The composition of any one of Embodiments 1-16, wherein $R^{12}$ is cycloalkyl, heterocyclyl, aryl or heteroaryl, wherein the cycloalkyl, heterocyclyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 18: The composition of Embodiment 17, wherein $R^{12}$ is 5-12 membered aryl, 5-12 membered heteroaryl comprising 1, 2 or 3 independently selected heteroatoms, 5-12 membered cycloalkyl, or 5-12 membered heterocyclyl comprising 1, 2 or 3 independently selected heteroatoms, wherein the 5-12 membered aryl, 5-12 membered heteroaryl, 5-12 membered cycloalkyl, and the 5-12 membered heterocyclyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 19: The composition of Embodiment 18, wherein $R^{12}$ is phenyl, cyclohexyl, cyclopentyl, tetrahydropyranyl, tetrahydrofuranyl, piperidinyl, pyridinyl, diazinyl, furanyl, thiophenyl, or thiazolyl, wherein the phenyl, cyclohexyl, cyclopentyl, tetrahydropyranyl, tetrahydrofuranyl, piperidinyl, pyridinyl, diazinyl, furanyl, thiophenyl and thiazolyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 20: The composition of Embodiment 19, wherein $R^{12}$ is phenyl (optionally substituted at position 2 and/or 4 with substituents selected independently from halogen, hydroxyl, alkoxy, amino, mono-substituted amino, and di-substituted amino), cyclohexyl, cyclopentyl, tetrahydropyran-4-yl, piperdin-4-yl (optionally substituted at position 1 with an alkyl or cycloalkyl), pyridine-2-yl (optionally substituted at position 3 and/or 5 with substituents selected independently from halogen, hydroxyl, alkoxy, amino, mono-substituted amino, and di-substituted amino), pyridine-5-yl (optionally substituted at position 2 and/or 4 with substituents selected independently from halogen, hydroxyl, alkoxy, amino, mono-substituted amino, and di-substituted amino), pyridin-3-yl (optionally substituted at position 2 and/or 6 with substituents selected independently from halogen, hydroxyl, alkoxy, amino, mono-substituted amino, and di-substituted amino), furan-5-yl (optionally substituted at position 2 and/or 4 with substituents selected independently from halogen, hydroxyl, alkoxy, amino, mono-substituted amino, and di-substituted amino), furan-4-yl (optionally substituted at position 2 and/or 4 with substituents selected independently from halogen, hydroxyl, alkoxy, amino, mono-substituted amino, and di-substituted amino), thiopen-5-yl (optionally substituted at position 2 and/or 4 with substituents selected independently from halogen, hydroxyl, alkoxy, amino, mono-substituted amino, and di-substituted amino), or thiophen-4-yl (optionally substituted at position 2 and/or 4 with substituents selected independently from halogen, hydroxyl, alkoxy, amino, mono-substituted amino, and di-substituted amino).

Embodiment 21: The composition of Embodiment 19, wherein $R^{12}$ is 4-fluorophenyl, 4-chlorophenyl, 4-bromophenyl, 4-trifluoromethylphenyl, 4-methoxyphenyl, 4-carboxylphenyl, 4-methoxycarbonylphenyl, 4-methylphenyl, 3-fluorophenyl, 3-chlorophenyl, 3-bromophenyl, 3-trifluoromethylphenyl, 3-methoxyphenyl, 2-fluorophenyl, 2-chlorophenyl, 2-bromophenyl, 2-trifluoromethylphenyl, 2-methoxyphenyl, 2-methylphenyl, 3,4-difluorophenyl, 2,4-difluorophenyl, 4-fluoro-2-methylphenyl, 2-chloro-4-fluorophenyl, 2-bromo-4-fluorophenyl, 2-fluoro-4-chlorophenyl, 2-fluoro-4-bromophenyl, 1,6-dichlorophenyl, phenyl, cyclohexyl, cyclopentyl, 3-methoxypyridin-2-yl, 2-methoxypyridin-3-yl, 2-methoxypyridin-5-yl, thiophen-3-yl, thiopen-2-yl, 3-methylthiophen-2-yl, 2-methylthiophen-5-yl, pyridine-4-yl, 4-fluoro-2-methoxyphenyl, 3-methoxypyridin-5-yl, 3-fluoropyridin-6-yl, 4-carboxylphenyl, 2-bromo-5-trifluoromethylphenyl, 1,3-thiazol-5-yl, 3-trifluoromethyl-4-fluorophenyl, pyrimidin-4-yl, 4-cholor-pyridin-3-yl, 2,6-difluoropyridin-4-yl, 4-trifloromethoxyphenyl, pyridazine-4-yl, 2,5-ditrifluromethylphenyl, thiaz-5-yl, 3-trifluromethyl-4-fluorophenyl, 3-trifluoromethylphenyl, 4-fluoro-2-methylphenyl, 3-fluropyridin-6-yl, and 3-bromothiophen-2-yl.

Embodiment 22: The composition of Embodiment 19, wherein $R^{12}$ is 4-fluorophenyl, 2-chlorphenyl, 2-bromophenyl, 2-methoxyphenyl, 2-methyl-4-fluorophenyl, 2-methylphenyl, 2-bromo-4-fluorophenyl, 2-chloro-4-fluorophenyl, or 2-methoxy-4-fluorophenyl.

Embodiment 23: The composition of any one of Embodiments 1-22, wherein $R^{11}$ is aryl, heteroaryl, alkyl, alkenyl or alkynyl, wherein the aryl, heteroaryl, alkyl, alkenyl, and alkynyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido;

Embodiment 24: The composition of Embodiment 23, wherein $R^{11}$ is $C_1$-$C_{10}$alkyl, $C_2$-$C_1$alkenyl, $C_2$-$C_{10}$alkynyl, 5-12 membered aryl, or 5-12 membered heteroaryl comprising 1, 2 or 3 independently selected heteroatoms, wherein the $C_1$-$C_{10}$alkyl, $C_2$-$C_{10}$alkenyl, $C_2$-$C_{10}$alkynyl, 5-12 membered aryl, and 5-12 membered heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 25: The composition of Embodiment 24, wherein $R^{11}$ is phenyl, pyridinyl, 1,3-benzodioxolyl, 2,2-difluoro-1,3-benzodioxolyl, 1,3,3a-triazaindenyl, benzimidazolyl, 2,3-dihydro-1,4-benzodioxinyl, cyclohexyl, cyclopentyl, tetrahydropyranyl, tetrahydrofuranyl, piperidinyl, pyridinyl, diazinyl, furnayl, thiophenyl, thiazolyl, $C_1$-$C_6$alkyl, $C_2$-$C_6$alkenyl or $C_2$-$C_6$alkynyl, wherein the phenyl, cyclohexyl, cyclopentyl, tetrahydropyranyl, tetrahydrofuranyl, piperidinyl, pyridinyl, diazinyl, furnayl, thiophenyl thiazolyl, $C_1$-$C_6$alkyl, $C_2$-$C_6$alkenyl and $C_2$-$C_6$alkynyl and alkyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 26: The composition of Embodiment 25, wherein $R^{11}$ is phenyl (optionally substituted at position 4 with a substituent selected independently from halogen, hydroxyl, alkoxy, amino, mono-substituted amino, and di-substituted amino), furan-4-yl (optionally substituted at position 2 and/or 4 with substituents selected independently from halogen, hydroxyl, alkoxy, amino, mono-substituted amino, and di-substituted amino), pyridine-5-yl (optionally substituted at position 2 and/or 3 with a substituent selected independently from halogen, hydroxyl, alkoxy, amino, mono-substituted amino, and di-substituted amino), furan-6-yl (optionally substituted at position 3 and/or 4 with substituents selected independently from halogen, hydroxyl, alkoxy, amino, mono-substituted amino, and di-substituted amino), pyridine-6-yl (optionally substituted at position 2 and/or 3 with a substituent selected independently from halogen, hydroxyl, alkoxy, amino, mono-substituted amino, and di-substituted amino), 1,3-benzodioxolyl, 2,2-difluoro-1,3-benzodioxolyl, or 1,3,3a-triazaindenyl.

Embodiment 27: The composition of Embodiment 25, wherein $R^{11}$ is 4-methoxyphenyl, 2-methoxyphenyl, 2-methoxypyridin-5-yl, 3-fluoropyridin-5-yl, 1,3-benzodioxolyl, 4-(methoxycarbonyl)phenyl, 4-carboxyphenyl, 4-dimethylaminoaphenyl, benzimidazole-5-yl, 4-sulfamoylphenyl, 4-trifluromethoxyphenyl, 3-methoxyphenyl, 3-fluoro-4-methoxyphenyl, 4-bromophenyl, 4-fluorophenyl, 4-chlorophenyl, 2-pyridinylethyl, N-methylpiperazinyl, N-isopropylpyrazol-4-yl, 4-pyrrolidonylphenyl, 2,3-dihydro-1,4-benzodioxinyl, 1,3,3a-triazaindenyl, 1-acetyl-3-hydroxypropyl, 4-imidazolylphenyl, 3-fluoropyridin-5-yl, 4-dimethylaminophenyl, N-methylpyrrolidin-3-yl, 2-hydroxymethyl-2-methyl-3-hydroxypropyl, 2-methoxyethyl, 5-hexyn-1-yl, 4-hydroxyphenyl, 2-(3-butyn-1-yl)pyridin-4-yl, N-ethylpyrrolidin-3-yl, hydrogen, phenyl, 2-methoxypyridin-5-yl, 3-fluoro-2-methoxypyridin-5-yl, 4-methoxyphenylmethyl, 4-(1-Pyrrolidinylsulfonyl)phenyl, 4-imidazole-1-ylphenyl, 2-hydroxybenzimidazoly-5-yl, 3,4,5-trimethoxyphenyl, 4-ethoxyphenyl, 2,4-dimethoxyphenyl, 4-t-butylphenyl, 4-ethylphenyl, 3-methoxypyridin-6-ylmethyl, 4-cyanophenyl, 3-trifluoromethylpyridin-6-yl, 2-pyrrolidinylethyl, tetrahydropyran-4-yl, 3-caynophenyl, 4-trifluoromethoxyphenyl, 1,3-dihydroxypropy-2-yl, 2-methylpyridin-4-yl, N-ethylpyrrolidin-4-yl, 3-oxo-3,4-dihydro-2H-1,4-benzoxazine-7-yl, 4-(2-oxo-1-pyrrolidinyl)phenyl, 2-methylpyridin-5-yl, 2-(N-methylpiperazinyl)pirpdin-5-yl, 3-fluoropyridin-5-yl, 2-methoxy-3-methylpyridin-5-yl, 4-(1-ethyl-1H-pyrazol-4-yl)phenyl, 4-(1-ethyl-1H-pyrazol-3-yl)phenyl, 2-fluoropyridin-5-yl, 4-(1-isopropyl-1H-pyrazol-4-yl)phenyl, 4-(1-isopropyl-1H-pyrazol-3-yl)phenyl, 4-(1-ethyl-1H-pyrazol-3-yl)phenyl, 4-(1-methyl-1H-pyrazol-4-yl)phenyl, 3-methoxypyridin-6-yl, 4-(1-methyl-1H-pyrazol-3-yl)phenyl, 4-(1-pyrrolidinylcarbonyl)-phenyl, 2-(1-methylpiperzin-4-yl)pyridine-5-yl, 4-(5-hexyn-1-oxy)phenyl, 4-triflouromethoxyphenyl, 4-methylphenyl, 4-ethylphenyl, pyridine-3-yl, pyridine-2-yl, 2-methylfuran-5-yl, 4-methoxycyclohexyl, 4-dimethylaminohexyl, and 1-methylpyrrolidin-3-yl methyl.

Embodiment 28: The composition of Embodiment 27, wherein $R^{11}$ is 4-methoxyphenyl, 1,3-benzodioxolyl, 3-fluoro-4-methoxyphenyl, 4-bromophenyl, 4-dimethylaminophenyl, 2'-methoxypyridin-5-yl, 2'-methoxy-3'-fluoropyridin-5-yl, 2'-methylpyridin-5-yl, or 1,3,3a-triazaindenyl.

Embodiment 29: The composition of Embodiment 1, wherein $R^{15}$ is alkyl, alkenyl, alkynyl, cycloalkyl, or heterocyclyl; $R^{14}$ is H, alkyl, alkenyl, alkynyl, aryl or heteroaryl; $R^{12}$ is cycloalkyl, heterocyclyl, aryl or heteroaryl; and $R^{11}$ is aryl, heteroaryl, alkyl, alkenyl or alkynyl, and where any alkyl, alkenyl, alkynyl, cycloalkyl, heterocyclyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 30: The composition of Embodiment 29, wherein $R^{15}$ is alkyl, alkenyl, cycloalkyl or heterocyclyl; $R^4$ is H, $C_1$-$C_6$alkyl, $C_2$-$C_6$alkenyl, $C_2$-$C_6$alkynyl, or 5-12 membered aryl; $R^{12}$ is 5-12 membered aryl, 5-12 membered heteroaryl comprising one heteroatom, 5-12 membered cycloalkyl, or 5-12 membered heterocyclyl comprising one heteroatom; and $R^{11}$ is $C_1$-$C_{10}$alkyl, $C_2$-$C_{10}$alkenyl, $C_2$-$C_{10}$alkynyl, 5-12 membered aryl, or 5-12 membered heteroaryl comprising 1, 2 or 3 independently selected heteroatoms, and where any alkyl, alkenyl, alkynyl, cycloalkyl, heterocyclyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 31: The composition of Embodiment 30, wherein $R^{15}$ is $C_1$-$C_6$alkyl or —$(CH_2)_a$—$R^{16}$, where a is 0, 1, 2, 3, 4, 5, 6, 7, 8, 9 or 10, and $R^{16}$ is cycloalkyl, —$OR^{17}$, or —$NR^{18}R^{19}$, where $R^{17}$ is H or alkyl, and $R^{18}$ and $R^{19}$ are independently H, alkyl, or cycloalkyl; $R^{14}$ is H, methyl, ethyl, propyl, isopropyl, butyl, isobutyl, but-2-yl, t-butyl, pentyl, 5-hexyn-1-yl, 2-propyn-1-yl, propargyl, methoxymethyl, phenyl, or 4-trifluoromethylphenyl; $R^{12}$ is phenyl, cyclohexyl, cyclopentyl, tetrahydropyranyl, tetrahydrofuranyl, piperidinyl, pyridinyl, diazinyl, furnayl, thiophenyl, or thiazolyl; and $R^{11}$ is phenyl, pyridinyl, 1,3-benzodioxolyl, 2,2-difluoro-1,3-benzodioxolyl, 1,3,3a-triazaindenyl, benzimidazolyl, 2,3-dihydro-1,4-benzodioxinyl, cyclohexyl, cyclopentyl, tetrahydropyranyl, tetrahydrofuranyl, piperidinyl, pyridinyl, diazinyl, furnayl, thiophenyl, thiazolyl, $C_1$-$C_6$alkyl, $C_2$-$C_6$alkenyl or $C_2$-$C_6$alkynyl, and where any phenyl, cyclohexyl, cyclopentyl, tetrahydropyranyl, tetrahydrofuranyl, piperidinyl, pyridinyl, diazinyl, furnayl, thiophenyl, or thiazolyl; and $R^{11}$ is phenyl, pyridinyl, 1,3-benzodioxolyl, 2,2-difluoro-1,3-benzodioxolyl, 1,3,3a-triazaindenyl, benzimidazolyl, 2,3-dihydro-1,4-benzodioxinyl, cyclohexyl, cyclopentyl, tetrahydropyranyl, tetrahydrofuranyl, piperidinyl, pyridinyl, diazinyl, furnayl, thiophenyl, thiazolyl, $C_1$-$C_6$alkyl, $C_2$-$C_6$alkenyl, $C_2$-$C_6$alkynyl, alkyl, alkenyl, alkynyl, cycloalkyl, heterocyclyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 32: The composition of Embodiment 31, wherein $R^{15}$ is $C_1$-$C_6$ alkyl, —$CH_2$-cycloalkyl, —$CH_2CH_2$-cycloalkyl, —$CH_2$—$OR^{17}$, —$CH_2CH_2$—$OR^{17}$, —$CH_2$—$NR^{18}N^{19}$ or —$CH_2CH_2$—$NR^{18}N^{19}$; $R^{14}$ is H, methyl, ethyl, propyl, isopropyl, butyl, isobutyl, but-2-yl, t-butyl, pentyl, 5-hexyn-1-yl, 2-propyn-1-yl, propargyl, methoxymethyl, phenyl, or 4-trifluoromethylphenyl; $R^{12}$ is phenyl, cyclohexyl, cyclopentyl, tetrahydropyranyl, tetrahydrofuranyl, piperidinyl, pyridinyl, diazinyl, furnayl, thiophenyl, or thiazolyl; and $R^{11}$ is phenyl, pyridinyl, 1,3-benzodioxolyl, 2,2-difluoro-1,3-benzodioxolyl, 1,3,3a-triazaindenyl, benzimidazolyl, 2,3-dihydro-1,4-benzodioxinyl, cyclohexyl, cyclopentyl, tetrahydropyranyl, tetrahydrofuranyl, piperidinyl, pyridinyl, diazinyl, furnayl, thiophenyl, thiazolyl, $C_1$-$C_6$alkyl, $C_2$-$C_6$alkenyl or $C_2$-$C_6$alkynyl, and where any phenyl, cyclohexyl, cyclopentyl, tetrahydropyranyl, tetrahydrofuranyl, piperidinyl, pyridinyl, diazinyl, furnayl, thiophenyl, or thiazolyl; and $R^1$ is phenyl, pyridinyl, 1,3-benzodioxolyl, 2,2-difluoro-1,3-benzodioxolyl, 1,3,3a-triazaindenyl, benzimidazolyl, 2,3-dihydro-1,4-benzodioxinyl, cyclohexyl, cyclopentyl, tetrahydropyranyl, tetrahydrofuranyl, piperidinyl, pyridinyl, diazinyl, furnayl, thiophenyl, thiazolyl, $C_1$-$C_6$alkyl, $C_2$-$C_6$alkenyl, $C_2$-$C_6$alkynyl, alkyl, alkenyl, alkynyl, cycloalkyl, heterocyclyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 33: The composition of Embodiment 1, wherein the antileishmanial compound is selected from the group consisting of: CMLD007431, CMLD011128, CMLD007427, CMLD011024, CMLD011025, CMLD010981, CMLD010849, CMLD010980, CMLD010979, CMLD011029, CMLD010900, CMLD010885, CMLD011039, CMLD010899, CMLD011113, CMLD010897, CMLD011033, CMLD011031, CMLD011046, CMLD010895, CMLD011098, CMLD011095, CMLD011026, CMLD011092, CMLD011036, CMLD011124, CMLD011030, CMLD011072, CMLD011129, CMLD011117, CMLD010884, CMLD010992, CMLD010901, CMLD011101, CMLD010888, CMLD011096, CMLD010889, CMLD011121, CMLD011032, CMLD011034, CMLD010892, CMLD010978, CMLD011102, CMLD010893, CMLD010894, CMLD010994, CMLD010890, CMLD011099, CMLD010891, CMLD011088, CMLD007432, CMLD011079, CMLD010902, CMLD011548, CMLD011546, CMLD011564, CMLD012217, CMLD011566, CMLD011562, CMLD011551, CMLD011549, CMLD011565, CMLD011494, CMLD010920, CMLD011554, CMLD011552, CMLD011561, CMLD011572, CMLD012218, CMLD011567, CMLD011574, CMLD010921, CMLD010948, CMLD010882, CMLD011104, CMLD010991, CMLD011075, CMLD011142, CMLD011125, CMLD010887, CMLD011100, CMLD010886, CMLD011575, CMLD011496, CMLD011027, CMLD011120, CMLD011579, CMLD011559, CMLD011028, CMLD011577, CMLD011578, CMLD007169, CMLD007188, CMLD007203, CMLD007219, CMLD007221, CMLD007235, CMLD007247, CMLD007262, CMLD007286, CMLD007424, CMLD007425, CMLD007430, CMLD010949, CMLD011573, BUCMD00800, BUCMD00797, CMLD010987, CMLD010898, CMLD011119, CMLD011547, CMLD011131, CMLD011105, BUCMD00815, CMLD011499, BUCMD00812, CMLD010896, CMLD011111, CMLD011135, BUCMD00809, CMLD011569, CMLD011132, CMLD011133, CMLD011140, BUCMD00805, CMLD011568, CMLD011110, CMLD011550, CMLD011103, BUCMD00811, CMLD011115, BUCMD00813, CMLD010880, CMLD011093, CMLD011576, BUCMD00798, CMLD011557, CMLD011558, CMLD010926, CMLD011042, CMLD010998, CMLD010976, BUCMD00729, BUCMD00695, BUCMD00669, CMLD011497, BUCMD00686, CMLD011080, CMLD010984, BUCMD00642, BUCMD00734, CMLD011076, CMLD010988, CMLD011123, BUCMD00628, CMLD011047, BUCMD00663, BUCMD00721, CMLD010924, BUCMD00672, BUCMD00683, CMLD011038, BUCMD00679, BUCMD00687, BUCMD00689, BUCMD00738, CMLD011044, CMLD010986, BUCMD00627, BUCMD00645, BUCMD00652, BUCMD00656, BUCMD00659, BUCMD00662, BUCMD00666, BUCMD00671, BUCMD00677, BUCMD00693, BUCMD00711, BUCMD00714, BUCMD00719, BUCMD00725, BUCMD00731, BUCMD00156, BUCMD00159, BUCMD00162, BUCMD00165, BUCMD00168, BUCMD00171, CMLD013640, BUCMD00802, CMLD011109, CMLD011106, CMLD011134, CMLD011141, CMLD011137, BUCMD00816, CMLD011097, BUCMD00814, CMLD010903, BUCMD00799, BUCMD00806, CMLD010848, CMLD011495, BUCMD00801, CMLD011040, CMLD010996, CMLD010993, CMLD010989, BUCMD00639, BUCMD00730, CMLD010985, CMLD011560, BUCMD00717, CMLD010977, CMLD010990, BUCMD00700, BUCMD00685, CMLD006598, BUCMD00698, BUCMD00697, BUCMD00688, CMLD011136, CMLD011045, CMLD009657, BUCMD00668, BUCMD00702, CMLD011037, BUCMD00674, BUCMD00650, BUCMD00649, BUCMD00692, CMLD011078, CMLD011087, CMLD011139, BUCMD00653, BUCMD00646, BUCMD00654, BUCMD00657, BUCMD00660, BUCMD00664, BUCMD00667, BUCMD00675, BUCMD00678, BUCMD00696, BUCMD00712, BUCMD00715, BUCMD00722, BUCMD00726, BUCMD00739, BUCMD00157, BUCMD00160, BUCMD00163, BUCMD00166, BUCMD00169, BUCMD00172, CMLD011116, BUCMD00803, CMLD011122, CMLD010881, CMLD011138, BUCMD00804, BUCMD00808, CMLD011112, BUCMD00807, CMLD011130, CMLD011126, BUCMD00810, CMLD010883, CMLD011094, CMLD011556, BUCMD00817, CMLD010925, CMLD011043, CMLD011081, BUCMD00694, CMLD011035, CMLD010982, CMLD010950, BUCMD00629, BUCMD00718, BUCMD00733, BUCMD00643, BUCMD00699, CMLD011555, BUCMD00732, CMLD011077, CMLD011553, BUCMD00640, CMLD011073, BUCMD00691, BUCMD00720, BUCMD00651, BUCMD00630, BUCMD00690, BUCMD00723, BUCMD00684, BUCMD00673, BUCMD00728, CMLD011090, CMLD013629, BUCMD00647, BUCMD00641, BUCMD00648, BUCMD00655, BUCMD00658, BUCMD00661, BUCMD00665, BUCMD00670, BUCMD00676, BUCMD00680, BUCMD00701, BUCMD00713, BUCMD00716, BUCMD00724, BUCMD00727, BUCMD00741, BUCMD00158, BUCMD00161, BUCMD00164, BUCMD00167, BUCMD00170, BUCMD00173, BUCMD00174, BUCMD00175, BUCMD00176, BUCMD00177, BUCMD00178, BUCMD00179, BUCMD00180, BUCMD00181, BUCMD00182, BUCMD00183, BUCMD00184, BUCMD00185, BUCMD00186, BUCMD00187, BUCMD00188, BUCMD00189, BUCMD00190, BUCMD00191, BUCMD00192, BUCMD00193, BUCMD00194, BUCMD00195, BUCMD00196, BUCMD00197, BUCMD00198, and BUCMD00199.

Embodiment 34: The composition of Embodiment 33, wherein the antileishmanial compound is selected from the group consisting of: BUCMD00800, BUCMD00797, BUCMD00815, BUCMD00812, BUCMD00809, BUCMD00802, BUCMD00803, BUCMD00805, BUCMD00804, BUCMD00808, BUCMD00811, BUCMD00816, BUCMD00807, BUCMD00813, BUCMD00814, BUCMD00799, BUCMD00810, BUCMD00806, BUCMD00798, BUCMD00801, BUCMD00817, BUCMD00694, BUCMD00729, BUCMD00639, BUCMD00695, BUCMD00730, BUCMD00669, BUCMD00629, BUCMD00686, BUCMD00717, BUCMD00718, BUCMD00733, BUCMD00643, BUCMD00642, BUCMD00700, BUCMD00699, BUCMD00734, BUCMD00685, BUCMD00732, BUCMD00698, BUCMD00697, BUCMD00628, BUCMD00688, BUCMD00640, BUCMD00663, BUCMD00691, BUCMD00721, BUCMD00720, BUCMD00668, BUCMD00651, BUCMD00672, BUCMD00702, BUCMD00630, BUCMD00683, BUCMD00690, BUCMD00674, BUCMD00723, BUCMD00679, BUCMD00650, BUCMD00684, BUCMD00687, BUCMD00649, BUCMD00673, BUCMD00689, BUCMD00692, BUCMD00728, BUCMD00738, BUCMD00647, BUCMD00627, BUCMD00653, BUCMD00641, BUCMD00645, BUCMD00646, BUCMD00648, BUCMD00652, BUCMD00654, BUCMD00655, BUCMD00656, BUCMD00657, BUCMD00658, BUCMD00659, BUCMD00660, BUCMD00661, BUCMD00662, BUCMD00664, BUCMD00665, BUCMD00666, BUCMD00667, BUCMD00670, BUCMD00671, BUCMD00675, BUCMD00676, BUCMD00677, BUCMD00678, BUCMD00680, BUCMD00693, BUCMD00696, BUCMD00701, BUCMD00711, BUCMD00712, BUCMD00713, BUCMD00714, BUCMD00715, BUCMD00716, BUCMD00719, BUCMD00722, BUCMD00724, BUCMD00725, BUCMD00726, BUCMD00727, BUCMD00731, BUCMD00739, BUCMD00741, BUCMD00156, BUCMD00157, BUCMD00158, BUCMD00159, BUCMD00160, BUCMD00161, BUCMD00162, BUCMD00163, BUCMD00164, BUCMD00165, BUCMD00166, BUCMD00167, BUCMD00168, BUCMD00169, BUCMD00170, BUCMD00171, BUCMD00172, BUCMD00173, BUCMD00174, BUCMD00175, BUCMD00176, BUCMD00177, BUCMD00178, BUCMD00179, BUCMD00180, BUCMD00181, BUCMD00182, BUCMD00183, BUCMD00184, BUCMD00185, BUCMD00186, BUCMD00187, BUCMD00188, BUCMD00189, BUCMD00190, BUCMD00191, BUCMD00192, BUCMD00193, BUCMD00194, BUCMD00195, BUCMD00196, BUCMD00197, BUCMD00198, and BUCMD00199.

Embodiment 35: The composition of any one of Embodiments 1-34, wherein the antileishmanial compound has a C Log P from about 3.2 to about 4.3.

Embodiment 36: The composition of any one of the preceding Embodiments, wherein the composition is formulated for topical, intravenous (iv) or oral.

Embodiment 37: The composition of Embodiment 36, wherein the composition is formulated for iv administration.

Embodiment 38: The composition of any one of Embodiments 1-37, wherein the polymer and the antileishmanial compound are comprised in a particle comprising the polymer and the antileishmanial compound.

Embodiment 39: The composition of Embodiment 38, wherein the particle is an expansile particle.

Embodiment 40: The composition of Embodiment 38 or 39, wherein the particle accumulates in the liver of a subject after administering to said subject and releases the antileishmanial compound in the liver.

Embodiment 41: The composition of any one of Embodiments 38-40, wherein the particle is from about 5 nm to about 1500 nm in size.

Embodiment 42: The composition of Embodiment 36, wherein the composition is formulated for topical administration.

Embodiment 43: The composition of Embodiment 42, wherein the composition is in the form of an adhesive.

Embodiment 44: The composition of Embodiment 42 or 43, wherein the composition is in the form of a film, a sheet, a dressing, a cream, a spray, a liquid, a gel, a hydrogel, an emulsion, or a suspension.

Embodiment 45: The composition of any one of Embodiments 1-44, wherein the polymer is selected from the group consisting of polycarbonates, polyesters, polyacrylates, polyamindes, and copolymers and mixtures thereof.

Embodiment 46: The composition of any one of Embodiments 1-45, wherein the polymer comprises one or more monomers of Formula (A), Formula (B), and/or Formula (C):

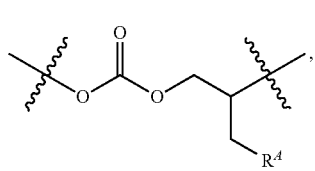

(Formula A)

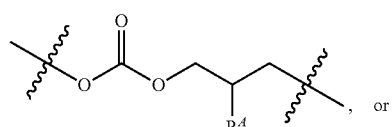

(Formula B) or

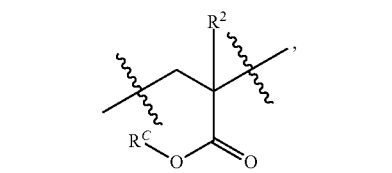

Formula (C)

wherein:
each $R^A$ is independently —OC(O)—$R^{A1}$, —OC(O)O—$R^{A1}$, —OC(O)NH—$R^{A1}$, —NHC(O)O—$R^{A1}$, —NHC(O)NH—$R^{A1}$, —OR, —C(O)—$R^{A1}$, —C(O)O—$R^{A1}$, or —C(O)NH—$R^{A1}$; and
each $R^{A1}$ is independently hydrogen, alkyl, alkenyl, cycloalkyl, aryl, heterocyclyl, heteroaryl, silyl, alkylsilyl, arylsilyl, alkylaryl, arylalkyl, poly(ethylene glycol), poly(ethylene oxide), poly(hydroxyacid)), a carbohydrate, a protein, a polypeptide, an amino acid, a nucleic acid, a nucleotide, a lipid, an oligosaccharide, a polysaccharide, an antibody, a pharmaceutical agent, an imaging agent, an epitope for a biological receptor, a photocrosslinkable group, or an ionically crosslinkable group, wherein alkyl, alkenyl, cycloalkyl, aryl, heterocyclyl, heteroaryl, silyl, alkylsilyl, arylsilyl, alkylaryl, and arylalkyl is optionally substituted by one or more substituents selected independently from the group consisting of hydroxyl, hydroxyether, carboxyl, carboxyester, carboxyamide, amino, mono- or di-substituted amino, thiol, thioester, sulfate, phosphate, phosphonate, and halogen;

each $R^C$ is independently:

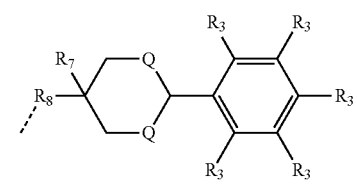

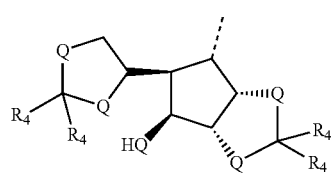

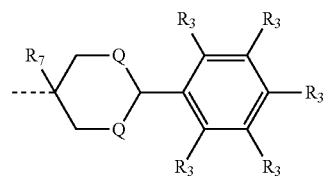

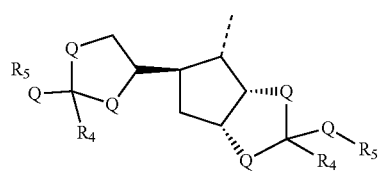

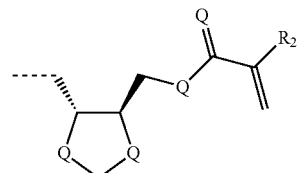

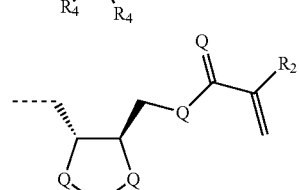

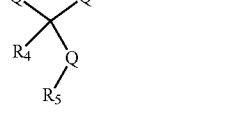

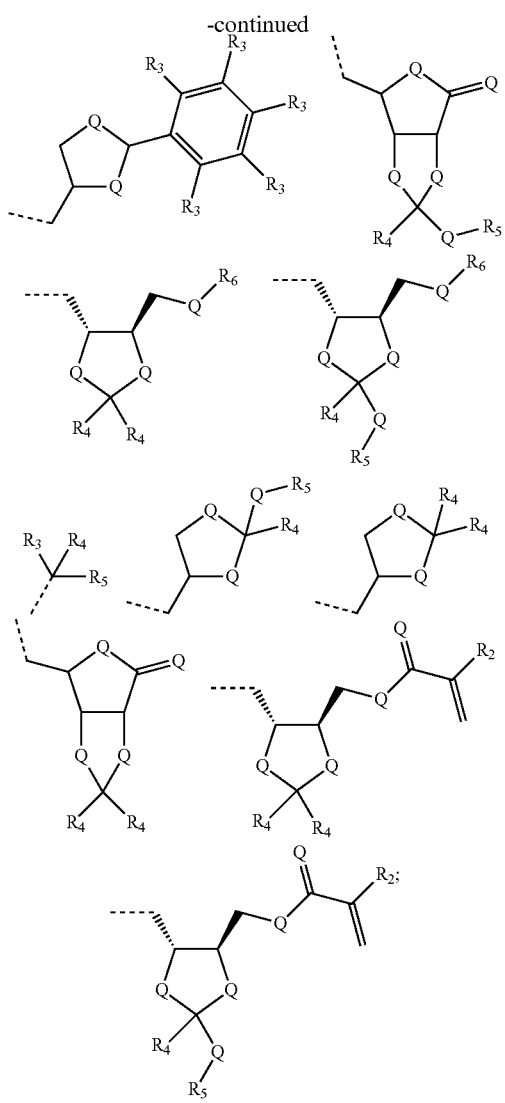

where each Q is O;

each $R^2$ is independently selected from the group consisting of hydrogen, a straight or branched alkyl, cycloalkyl, aryl, olefin, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

one $R_3$ is selected from the group consisting of methoxy, ethoxy, amino, nitro, cycloalkyl, aryl, and olefin;

and the remaining $R_3$ are each independently selected from the group consisting of hydrogen, methoxy, ethoxy, amino, a straight and branched alkyl, cycloalkyl, aryl, and olefin;

$R_4$, $R_5$, and $R_6$ are each independently selected from the group consisting of a straight or branched alkyl, cycloalkyl, aryl, and olefin; and $R_7$ and $R_8$ are each independently selected from the group consisting of hydrogen, a straight or branched alkyl, cycloalkyl, aryl, olefin, alkylaryl, and arylalkyl.

Embodiment 47: The composition of Embodiment 46, wherein the polymer comprises one or more monomers of Formula (A) and/or Formula (B).

Embodiment 48: The composition of Embodiment 47, wherein the polymer comprises one or more monomers of Formula (A).

Embodiment 49: The composition of Embodiment 47 or 48, wherein the polymer comprises one or more monomers of Formula (B).

Embodiment 50: The composition of any one of Embodiments 46-49, wherein $R^A$ is —OC(O)—$R^{42}$, —$OR^{41}$, —C(O)$R^{41}$, or —C(O)O—$R^{41}$.

Embodiment 51: The composition of any one of Embodiments 46-50, wherein each $R^{41}$ is independently H, $C_1$-$C_6$alkyl, $C_2$-$C_6$alkenyl, $C_2$-$C_6$alkynyl, poly(ethylene glycol), poly(ethylene oxide), a photocrosslinkable group, or an conically crosslinkable group, wherein $C_1$-$C_6$alkyl, $C_2$-$C_6$alkenyl, $C_2$-$C_6$alkynyl is optionally substituted with one, two, three or four substituents selected independently from the group consisting of hydroxyl, hydroxyether, carboxyl, amino, mono- or di-substituted amino, thiol, thioester, and halogen.

Embodiment 52: The composition of Embodiment 51, wherein each R is independently H, methyl, ethyl, propyl, iso-propyl, butyl, but-2-yl, 2-methylpropyl, t-butyl, pentyl, hexyl, poly(ethylene glycol), or poly(ethylene oxide).

Embodiment 53: The composition of Embodiment 52, wherein each $R^{41}$ is independently H, methyl, ethyl, propyl, iso-propyl, or butyl.

Embodiment 54: The composition of any one of Embodiments 46-53, wherein the polymer is a poly(glycerol carbonate) or a copolymer thereof.

Embodiment 55: The composition of any one of Embodiments 46-54, wherein the polymer is poly(1,3-glycerol carbonate), poly(1,2-glycerol carbonate), or a copolymer thereof.

Embodiment 56: The composition of any one of Embodiments 46-55, wherein the copolymer comprises poly(glycerol carbonate) and one of polycaprolactone, poly(lactic acid), poly(glycolic acid), poly(lactic-co-glycolic acid), poly(trimethylene carbonate), polyester, polycarbonate, or polyamide.

Embodiment 57: The composition of Embodiment 56, wherein the copolymer comprises a poly(glycerol carbonate) and polycaprolactone.

Embodiment 58: The composition of Embodiment 57, wherein the copolymer is poly(1,3-glycerol carbonate)-$C_{18}$-co-poly(ε-caprolactone).

Embodiment 59: The composition of any one of Embodiments 42-58, wherein the composition is an extended or slow release composition.

Embodiment 60: The composition of any one of Embodiments 42-59, wherein the composition further comprises glycerol.

Embodiment 61: The composition of Embodiments 38-40, wherein the particle comprises a first volume at a neutral pH and a second volume at an acidic pH, wherein the second volume is at least 1× greater than the first volume.

Embodiment 62: The composition of Embodiment 61, wherein the antileishmanial compound is released at higher rate at an acidic pH relative to a release at neutral pH.

Embodiment 63: The composition of any one of Embodiments 38-40 or 61-62, wherein the particle is from about 10 nm to about 1,000 nm in size.

Embodiment 64: The composition of Embodiment 63, wherein the particle is from about 50 nm to about 200 nm in size.

Embodiment 65: The composition of any one of Embodiments 38-40 or 61-64, wherein the polymer comprises one or more monomers of Formula (C).

Embodiment 66: The composition of Embodiment 64, wherein $R^2$ straight or branched alkyl, hydrogen or cycloalkyl.

Embodiment 67: The composition of Embodiment 65, wherein $R^2$ is $C_1$-$C_6$alkyl, hydrogen.

Embodiment 68: The composition of Embodiment 66, wherein $R^2$ is methyl.

Embodiment 69: The composition of any one of Embodiments 65-68, wherein each $R^3$ is independently hydrogen or methoxy.

Embodiment 70: The composition of any one of Embodiments 65-69, wherein $R^C$ is

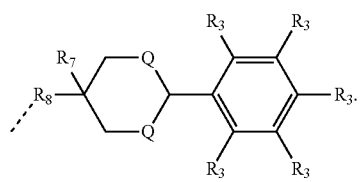

Embodiment 71: The composition of any one of Embodiments 65-70, wherein the monomer of Formula (C) is:

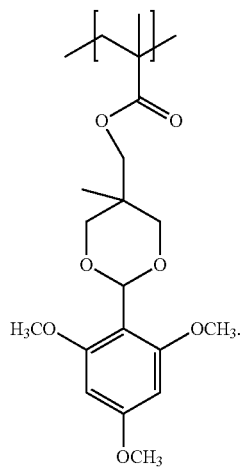

Embodiment 72: The composition of any one of the preceding Embodiments, wherein the composition further comprises a cross-linker.

Embodiment 73: The composition of Embodiment 72, wherein the cross-linker is 1,4-O-methacryloylhydroquinone or 1,4-phenylene-bis(2-methylacrylate).

Embodiment 74: The composition of any one of Embodiments 38-40, wherein the polymer is poly(glycerol carbonate) or a copolymer thereof.

Embodiment 75: The composition of Embodiment 74, wherein the polymer comprises one or more monomers of Formula (A) and/or Formula (B).

Embodiment 76: The composition of Embodiment 75, wherein the polymer comprises one or more monomers of Formula (A).

Embodiment 77: The composition of Embodiment 75 or 76, wherein the polymer comprises one or more monomers of Formula (B).

Embodiment 78: The composition of any one of Embodiments 74-77, wherein $R^A$ is —OC(O)—$R^{42}$, —$OR^{41}$, —C(O)$R^{41}$, or —C(O)O—$R^{41}$.

Embodiment 79: The composition of any one of Embodiments 74-78, wherein each $R^{41}$ is independently H, $C_1$-$C_6$alkyl, $C_2$-$C_6$alkenyl, $C_2$-$C_6$alkynyl, poly(ethylene glycol), poly(ethylene oxide), a photocrosslinkable group, or an ionically crosslinkable group, wherein $C_1$-$C_6$alkyl, $C_2$-$C_6$alkenyl, $C_2$-$C_6$alkynyl is optionally substituted with one, two, three or four substituents selected independently from the group consisting of hydroxyl, hydroxyether, carboxyl, amino, mono- or di-substituted amino, thiol, thioester, and halogen.

Embodiment 80: The composition of Embodiment 79, wherein each $R^{41}$ is independently H, methyl, ethyl, propyl, iso-propyl, butyl, but-2-yl, 2-methylpropyl, t-butyl, pentyl, hexyl, poly(ethylene glycol), or poly(ethylene oxide).

Embodiment 81: The composition of Embodiment 80, wherein each $R^{41}$ is independently H, methyl, ethyl, propyl, iso-propyl, or butyl.

Embodiment 82: The composition of any one of Embodiments 74-81, wherein the polymer is a poly(glycerol carbonate) or a copolymer thereof.

Embodiment 83: The composition of any one of Embodiments 74-82, wherein the polymer is poly(1,3-glycerol carbonate), poly(1,2-glycerol carbonate), or a copolymer thereof.

Embodiment 84: The composition of any one of Embodiments 74-83, wherein the copolymer comprises poly(glycerol carbonate) and one of polycaprolactone, poly(lactic acid), poly(glycolic acid), poly(lactic-co-glycolic acid), poly(trimethylene carbonate), polyester, polycarbonate, or polyamide.

Embodiment 85: The composition of Embodiment 84, wherein the copolymer comprises a poly(glycerol carbonate) and polycaprolactone.

Embodiment 86: The composition of Embodiment 85, wherein the copolymer is poly(1,3-glycerol carbonate)-$C_{18}$-co-poly(ε-caprolactone).

Embodiment 87: The composition of any one of Embodiments 74-86, wherein the particle is from about 10 nm to about 1,000 nm.

Embodiment 88: The composition of Embodiment 87, wherein the particle is from about 50 nm to about 200 nm.

Embodiment 89: The composition of any one of Embodiments 1-88, wherein the composition further comprises a pharmaceutically acceptable carrier or excipient.

Embodiment 90: The composition of any one of Embodiments 1-89, wherein the composition is formulated as a unit dosage formulation.

Embodiment 91: The composition of any one of Embodiments 1-90, wherein the composition further comprises an active agent.

Embodiment 92: The composition of Embodiment 91, wherein the active agent is a second antileishmanial compound (optionally selected from the group consisting of antimonials, miltefosine, dronedarone, stibogluconate, meglumine antimonite, pentamidine, amphotericin B, paromomycin, reversed amidines, and pharmaceutically acceptable salts thereof), and/or the active agent is selected from the group consisting of wound-healing agents, anti-scarring agents, antioxidant agents, cooling agents, soothing agents, anti-inflammatory-agents, antibiotics, topical analgesics, counter irritants, penetration enhancers, Cpg-D35, DNDI-6148, DNDI-0690, DDD853651, DDD1305143, LXE408, DNDI-6174, proteasome inhibitors, CRK12 inhibitors, and permeation enhancers.

Embodiment 93: The composition of any one of Embodiments 1-92, wherein the composition further comprises one or more of binders, viscosity modifiers, preservatives, humectants, emollients, pH stabilizing agents, chelating agents, gelling agents, thickening agents, emulsifiers, buffers, and carriers.

Embodiment 94: A compound of Formula (I) or (II):

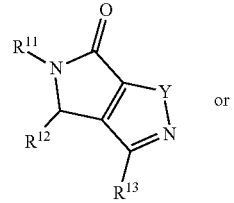

(Formula I)

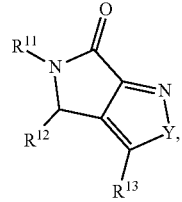

(Formula II)

wherein:
Y is $NR^{14}$, $CH_2$, O or S;
$R^{11}$ is aryl, heteroaryl, alkyl, alkenyl, alkynyl, cycloalkyl, or heterocyclyl;
$R^{12}$ is cycloalkyl, heterocyclyl, aryl or heteroaryl;
$R^{13}$ is —$CH_2$—$R^{15}$;
$R^{14}$ is H, alkyl, alkenyl, alkynyl, cycloalkyl, heterocyclyl, aryl or heteroaryl; and
$R^{15}$ is alkyl, alkenyl, alkynyl, aryl, heteroaryl, cycloalkyl, heterocyclyl, or a nucleophile; and
a pharmaceutically acceptable salt thereof,
optionally, any alkyl, alkenyl, alkynyl, aryl, heteroaryl, cycloalkyl and heterocyclyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido, and
provided that compound is not pyrrolo[3,4-c]pyrazol-6 (1H)-one, 4,5-dihydro-3-(2-hydroxyethyl)-5-[4-(3-isoxazolyl)phenyl]-4-(2-methoxyphenyl)-; Pyrrolo[3,4-c]pyrazol-6(1H)-one, 3-butyl-4,5-dihydro-5-[4-(3-isoxazolyl)phenyl]-4-(2-methoxyphenyl)-; Pyrrolo[3,4-c]pyrazol-6(1H)-one, 3-(2,2-dimethylpropyl)-4,5-dihydro-5-[4-(3-isoxazolyl)phenyl]-4-(2-methoxyphenyl)-; Pyrrolo[3,4-c]pyrazol-6(1H)-one, 4-(4-chlorophenyl)-1-cyclopropyl-4,5-dihydro-3-(methoxymethyl)-; Pyrrolo[3,4-c]pyrazol-6(1H)-one, 3-ethyl-1-(4-fluorophenyl)-4,5-dihydro-4,5-dimethyl-; Pyrrolo[3,4-c]pyrazol-6(1H)-one, 4-(4-chlorophenyl)-5-(3,7-dimethyl-1,2-benzisoxazol-5-yl)-3-ethyl-4,5-dihydro-1-(2-hydroxyethyl)-; Pyrrolo[3,4-c]pyrazol-6(2H)-one, 4-(4-chlorophenyl)-5-(3,7-dimethyl-1,2-benzisoxazol-5-yl)-3-ethyl-4,5-dihydro-2-(2-hydroxyethyl)-; Pyrrolo

[3,4-c]pyrazole-4-propanoic acid, 3-[(2,4-dichlorophenyl)methyl]-1,4,5,6-tetrahydro-5-methyl-6-oxo-; Pyrrolo[3,4-c]pyrazol-6(1H)-one, 4-(4-chlorophenyl)-5-(1,6-dihydro-1,5-dimethyl-6-oxo-3-pyridinyl)-3-ethyl-4,5-dihydro-; Pyrrolo[3,4-c]pyrazol-6(2H)-one, 5-(1H-benzimidazol-6-yl)-3-ethyl-4,5-dihydro-2-methyl-4-(4-propoxyphenyl)-; Pyrrolo[3,4-c]pyrazol-6(1H)-one, 5-(4-bromophenyl)-4,5-dihydro-3-(2-methoxyethyl)-4-phenyl-; 2-Propenoic acid, 3-[3-[(2,4-dichlorophenyl)methyl]-1,4,5,6-tetrahydro-5-methyl-6-oxopyrrolo[3,4-c]pyrazol-4-yl]-, (2E)-; Pyrrolo[3,4-c]pyrazol-6(1H)-one, 3-butyl-5-(4-fluorophenyl)-4,5-dihydro-4-(2-methoxyphenyl)-; Pyrrolo[3,4-c]pyrazol-6(1H)-one, 4,5-dihydro-3-(hydroxymethyl)-4-(2-methoxyphenyl)-5-[4-(3-thienyl)phenyl]-; Pyrrolo[3,4-c]pyrazol-6(1H)-one, 4-(4-chlorophenyl)-5-(1,6-dihydro-1,5-dimethyl-6-oxo-3-pyridinyl)-3-ethyl-4,5-dihydro-1-(2-hydroxyethyl)-; Pyrrolo[3,4-c]pyrazol-6(1H)-one, 4-(4-chlorophenyl)-1-cyclopropyl-5-(1,6-dihydro-1,5-dimethyl-6-oxo-3-pyridinyl)-3-ethyl-4,5-dihydro-; Pyrrolo[3,4-c]pyrazol-6(1H)-one, 4-(4-chlorophenyl)-1-cyclopropyl-4,5-dihydro-3-(methoxymethyl)-5-[(4-methoxyphenyl) methyl]-; Pyrrolo[3,4-c]pyrazol-6(1H)-one, 4-(4-chlorophenyl)-1-cyclopropyl-5-(1,6-dihydro-1,5-dimethyl-6-oxo-3-pyridinyl)-4,5-dihydro-3-(hydroxymethyl)-; Pyrrolo[3,4-c]pyrazol-6(1H)-one, 4-(4-chlorophenyl)-5-(1,6-dihydro-1,5-dimethyl-6-oxo-3-pyridinyl)-3-ethyl-4,5-dihydro-1-(1-methyl-1H-pyrazol-5-yl)-; Pyrrolo[3,4-c]pyrazol-6(1H)-one, 4-(4-chlorophenyl)-1-cyclopropyl-5-(1,6-dihydro-1,5-dimethyl-6-oxo-3-pyridinyl)-4,5-dihydro-3-(methoxymethyl)-, (4S)—; Pyrrolo[3,4-c]pyrazol-6(1H)-one, 4-(4-chlorophenyl)-1-cyclopropyl-5-(1,6-dihydro-1,5-dimethyl-6-oxo-3-pyridinyl)-4,5-dihydro-3-(methoxymethyl)-, (4R)—; Pyrrolo[3,4-c]pyrazol-6(1H)-one, 4-(4-chlorophenyl)-1-cyclopropyl-5-(1,6-dihydro-1,5-dimethyl-6-oxo-3-pyridinyl)-4,5-dihydro-3-(methoxymethyl)-; Pyrrolo[3,4-c]pyrazol-6(1H)-one, 4-(4-chlorophenyl)-5-(1,6-dihydro-1,5-dimethyl-6-oxo-3-pyridinyl)-3-ethyl-4,5-dihydro-1-(2-methoxyethyl)-; Pyrrolo[3,4-c]pyrazol-6(1H)-one, 4,5-dihydro-5-[4-(3-isoxazolyl)phenyl]-3-(2-methoxyethyl)-4-(2-methoxyphenyl)-; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-3-ethyl-4,5-dihydro-, (4R)—; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-3-ethyl-4,5-dihydro-, (4S)—; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-3-ethyl-4,5-dihydro-; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-4,5-dihydro-3-(hydroxymethyl)-, (4S)—; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-4,5-dihydro-3-(hydroxymethyl)-, (4R)—; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-4,5-dihydro-3-(hydroxymethyl)-; Pyrrolo[3,4-c]pyrazol-6(1H)-one, 4-(4-chlorophenyl)-3-ethyl-4,5-dihydro-5-(8-methoxy-3-methyl-1,2,4-triazolo[4,3-a]pyridin-6-yl)-1-methyl-; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-3-(fluoromethyl)-4,5-dihydro-; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-4,5-dihydro-3-(methoxymethyl)-, (4S)—; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-4,5-dihydro-3-(methoxymethyl)-, (4R)—; Pyrrolo[3,4-c]pyrazol-6(1H)-one, 4-(4-chlorophenyl)-1-cyclopropyl-5-(3,8-dimethyl-1,2,4-triazolo[4,3-a]pyridin-6-yl)-4,5-dihydro-3-(methoxymethyl)-; Pyrrolo[3,4-c]pyrazol-6(2H)-one, 4-(4-chlorophenyl)-2-cyclopropyl-5-(1,6-dihydro-1,5-dimethyl-6-oxo-3-pyridinyl)-3-ethyl-4,5-dihydro-; 2-Propenoic acid, 3-[3-[(2,4-dichlorophenyl)methyl]-1,4,5,6-tetrahydro-5-methyl-6-oxopyrrolo[3,4-c]pyrazol-4-yl]-, ethyl ester, (2E)-; Pyrrolo[3,4-c]pyrazole-1(4H)-carboxamide, 4-(4-chlorophenyl)-5-(1,6-dihydro-1,5-dimethyl-6-oxo-3-pyridinyl)-3-ethyl-5,6-dihydro-N,N-dimethyl-6-oxo-; Pyrrolo[3,4-c]pyrazol-6(1H)-one, 4-(4-chlorophenyl)-5-(3,8-dimethyl-1,2,4-triazolo[4,3-a]pyridin-6-yl)-3-ethyl-4,5-dihydro-1-(2-methoxyethyl)-; Pyrrolo[3,4-c]pyrazol-6(2H)-one, 5-(1H-benzimidazol-6-yl)-4-(4-bromo-2-fluorophenyl)-4,5-dihydro-2-methyl-3-[(phenylmethoxy)methyl]-; Pyrrolo[3,4-c]pyrazol-6(1H)-one, 4-(4-chlorophenyl)-1-cyclopropyl-3-ethyl-4,5-dihydro-5-(8-methoxy-3-methyl-1,2,4-triazolo[4,3-a]pyridin-6-yl)-; Pyrrolo[3,4-c]pyrazol-6(1H)-one, 4,5-dihydro-5-[4-(3-isoxazolyl)phenyl]-4-(2-methoxyphenyl)-3-[2-(phenylmethoxy)ethyl]-; Pyrrolo[3,4-c]pyrazol-6(1H)-one, 4-(4-chlorophenyl)-5-(1,6-dihydro-1,5-dimethyl-6-oxo-3-pyridinyl)-1-(2,4-dimethoxy-5-pyrimidinyl)-3-ethyl-4,5-dihydro-; Pyrrolo[3,4-c]pyrazol-6(2H)-one, 4-(4-chlorophenyl)-5-(3,8-dimethyl-1,2,4-triazolo[4,3-a]pyridin-6-yl)-3-ethyl-4,5-dihydro-2-(2-methoxyethyl)-; Pyrrolo[3,4-c]pyrazole-2(4H)-carboxamide, 4-(4-chlorophenyl)-5-(1,6-dihydro-1,5-dimethyl-6-oxo-3-pyridinyl)-3-ethyl-5,6-dihydro-N,N-dimethyl-6-oxo-; Pyrrolo[3,4-c]pyrazol-6(2H)-one, 5-(1H-benzimidazol-6-yl)-4-[4-(3,3-difluoro-1-pyrrolidinyl)-2-fluorophenyl]-4,5-dihydro-3-(hydroxymethyl)-2-methyl-; Pyrrolo[3,4-c]pyrazol-6(2H)-one, 4-(4-bromo-2-fluorophenyl)-4,5-dihydro-2-methyl-3-[(phenylmethoxy)methyl]-5-[1-[[2-(trimethylsilyl)ethoxy]methyl]-1H-benzimidazol-5-yl]-; Pyrrolo[3,4-c]pyrazol-6(1H)-one, 4-(4-chlorophenyl)-3-ethyl-4,5-dihydro-5-(8-methoxy-3-methyl-1,2,4-triazolo[4,3-a]pyridin-6-yl)-1-[2-(2,2,2-trifluoroethoxy)ethyl]-; Pyrrolo[3,4-c]pyrazol-6(2H)-one, 4-[4-(3,3-difluoro-1-pyrrolidinyl)-2-fluorophenyl]-4,5-dihydro-3-(hydroxymethyl)-2-methyl-5-[1-[[2-(trimethylsilyl)ethoxy]methyl]-1H-benzimidazol-5-yl]-; Pyrrolo[3,4-c]pyrazol-6(2H)-one, 4-[4-(3,3-difluoro-1-pyrrolidinyl)-2-fluorophenyl]-4,5-dihydro-2-methyl-3-[(phenylmethoxy)methyl]-5-[1-[[2-(trimethylsilyl)ethoxy]methyl]-1H-benzimidazol-5-yl]-; Pyrrolo[3,4-c]pyrazole-4-propanamide, 3-[(2,4-dichlorophenyl)methyl]-N-[(4,5-dichloro-2-thienyl)sulfonyl]-1,4,5,6-tetrahydro-5-methyl-6-oxo-; Pyrrolo[3,4-c]pyrazole-3-carboxaldehyde, 4-[4-(3,3-difluoro-1-pyrrolidinyl)-2-fluorophenyl]-2,4,5,6-tetrahydro-2-methyl-6-oxo-5-[1-[[2-(trimethylsilyl)ethoxy]methyl]-1H-benzimidazol-5-yl]-; 2-Propenamide, 3-[3-[(2,4-dichlorophenyl)methyl]-1,4,5,6-tetrahydro-5-methyl-6-oxopyrrolo[3,4-c]pyrazol-4-yl]-N-[(4,5-dichloro-2-thienyl)sulfonyl]-, (2E)-; Pyrrolo[3,4-c]pyrazol-6(2H)-one, 4,5-dihydro-3-(methoxymethyl)-4-phenyl-; Pyrrolo[3,4-c]pyrazol-6(2H)-one, 4,5-dihydro-3-(methoxymethyl)-4-(4-methylphenyl)-; Pyrrolo[3,4-c]pyrazol-6(2H)-one, 4-(4-fluorophenyl)-4,5-dihydro-3-

(methoxymethyl)-; Pyrrolo[3,4-c]pyrazol-6(2H)-one, 4,5-dihydro-3-(methoxymethyl)-4-[3-(trifluoromethyl)phenyl]-; Pyrrolo[3,4-c]pyrazol-6(2H)-one, 4-(1,3-benzodioxol-5-yl)-4,5-dihydro-3-(methoxymethyl)-5-(2-propen-1-yl)-; Pyrrolo[3,4-c]pyrazol-6(2H)-one, 4,5-dihydro-3-(methoxymethyl)-4-(4-methylphenyl)-5-(2-propen-1-yl)-; Pyrrolo[3,4-c]pyrazol-6(2H)-one, 4,5-dihydro-3-(methoxymethyl)-4-phenyl-5-(phenylmethyl)-; Pyrrolo[3,4-c]pyrazol-6(2H)-one, 4,5-dihydro-3-(methoxymethyl)-4,5-diphenyl-; Pyrrolo[3,4-c]pyrazol-6(2H)-one, 4-(1,3-benzodioxol-5-yl)-4,5-dihydro-3-(methoxymethyl)-5-(phenylmethyl)-; Pyrrolo[3,4-c]pyrazol-6(2H)-one, 4,5-dihydro-3-(methoxymethyl)-4-(4-methylphenyl)-5-(phenylmethyl)-; Pyrrolo[3,4-c]pyrazol-6(2H)-one, 4-(4-fluorophenyl)-4,5-dihydro-3-(methoxymethyl)-5-(2-propen-1-yl)-; Pyrrolo[3,4-c]pyrazol-6(2H)-one, 4-(4-bromophenyl)-4,5-dihydro-3-(methoxymethyl)-5-(2-propen-1-yl)-; Pyrrolo[3,4-c]pyrazol-6(2H)-one, 4-(1,3-benzodioxol-5-yl)-4,5-dihydro-3-(methoxymethyl)-5-(4-methoxyphenyl)-; Pyrrolo[3,4-c]pyrazol-6(2H)-one, 4,5-dihydro-3-(methoxymethyl)-5-(4-methoxyphenyl)-4-(4-methylphenyl)-; Pyrrolo[3,4-c]pyrazol-6(2H)-one, 4-(4-bromophenyl)-4,5-dihydro-3-(methoxymethyl)-5-(phenylmethyl)-; Pyrrolo[3,4-c]pyrazol-6(2H)-one, 4-(4-fluorophenyl)-4,5-dihydro-3-(methoxymethyl)-5-(phenylmethyl)-; Pyrrolo[3,4-c]pyrazol-6(2H)-one, 4-(4-fluorophenyl)-4,5-dihydro-3-(methoxymethyl)-5-phenyl-; Pyrrolo[3,4-c]pyrazol-6(2H)-one, 4,5-dihydro-3-(methoxymethyl)-5-(2-propen-1-yl)-4-[3-(trifluoromethyl)phenyl]-; Pyrrolo[3,4-c]pyrazol-6(2H)-one, 4-(4-bromophenyl)-4,5-dihydro-3-(methoxymethyl)-5-(4-methoxyphenyl)-; Pyrrolo[3,4-c]pyrazol-6(2H)-one, 4-(4-fluorophenyl)-4,5-dihydro-3-(methoxymethyl)-5-(4-methoxyphenyl)-; Pyrrolo[3,4-c]pyrazol-6(2H)-one, 4,5-dihydro-3-(methoxymethyl)-5-phenyl-4-[3-(trifluoromethyl)phenyl]-; Pyrrolo[3,4-c]pyrazol-6(2H)-one, 4,5-dihydro-3-(methoxymethyl)-5-(4-methoxyphenyl)-4-[3-(trifluoromethyl)phenyl]-; 2-Propenoic acid, 2-(phenylamino)-3-(1,4,5,6-tetrahydro-6-oxo-4,5-diphenylpyrrolo[3,4-c]pyrazol-3-yl)-, ethyl ester; 2-Propenoic acid, 2-hydroxy-3-[1,4,5,6-tetrahydro-4-(4-nitrophenyl)-6-oxo-5-phenylpyrrolo[3,4-c]pyrazol-3-yl]-, ethyl ester; 2-Propenoic acid, 3-[4,5-bis(4-bromophenyl)-1,4,5,6-tetrahydro-6-oxopyrrolo[3,4-c]pyrazol-3-yl]-2-[(4-bromophenyl)amino]-, ethyl ester;

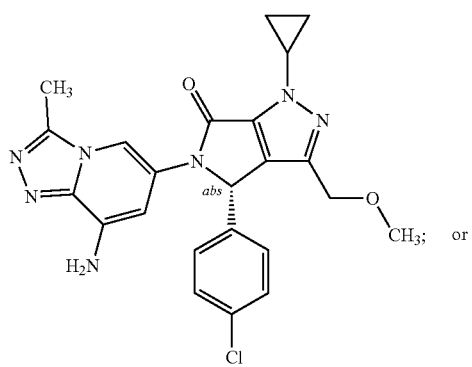 [SMILES: COCc1nn(C2CC2)c2c1[C@H](c1ccc(Cl)cc1)N(c1cc(N)c3nnc(C)n3c1)C2=O]

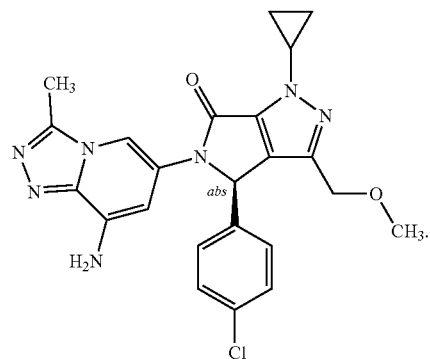 [SMILES: COCc1nn(C2CC2)c2c1[C@@H](c1ccc(Cl)cc1)N(c1cc(N)c3nnc(C)n3c1)C2=O]

Embodiment 95: The compound of Embodiment 94, wherein Y is N—R$^{14}$, e.g., the compound is of Formula (I-A) or (II-A):

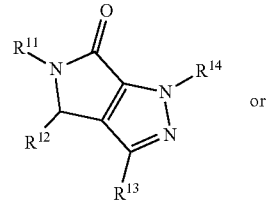
(Formula I-A)

or

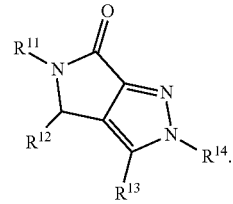
(Formula II-A)

Embodiment 96: The compound of Embodiment 94 or 95, wherein R$^{15}$ is alkyl, alkenyl, alkynyl, cycloalkyl, or heterocyclyl, wherein the alkyl, alkenyl, alkynyl, cycloalkyl and heterocyclyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 97: The compound of Embodiment 96, wherein R$^{15}$ is alkyl, alkenyl, cycloalkyl or heterocyclyl, wherein the alkyl, alkenyl, cycloalkyl and heterocyclyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 97: The compound of Embodiment 96, wherein $R^{15}$ is alkyl, alkenyl, cycloalkyl or heterocyclyl, wherein the alkyl, alkenyl, cycloalkyl and heterocyclyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 98: The compound of Embodiment 96, wherein $R^{15}$ is an alkyl, optionally substituted with a halogen, hydroxyl, alkoxy, amino, alkylamino, dialkylamino, cycloalkyl, heterocyclyl, aryl, heteroaryl, thiol, azide or nitrite.

Embodiment 99: The compound of Embodiment 98, wherein $R^{15}$ is $C_1$-$C_6$alkyl or —$(CH_2)_a$—$R^{16}$, where a is 0, 1, 2, 3, 4, 5, 6, 7, 8, 9 or 10; and $R^{16}$ is cycloalkyl, —$OR^{11}$, —$NR^{18}R^{19}$, where $R^7$ is H or alkyl, and $R^8$ and $R^9$ are independently H, alkyl, or cycloalkyl.

Embodiment 100: The compound of Embodiment 99, wherein a is 0, 1, 2, 3 or 4.

Embodiment 101: The compound of Embodiment 100, wherein $R^{15}$ is $C_1$-$C_6$ alkyl, —$CH_2$-cycloalkyl, —$CH_2CH_2$-cycloalkyl, —$CH_2$—$OR^7$, —$CH_2CH_2$—$OR^{17}$, —$CH_2$—$NR^{18}N^{19}$ or —$CH_2CH_2$—$NR^{18}N^{19}$.

Embodiment 102: The compound of Embodiment 101, wherein $R^{15}$ is isopropyl, isobutyl, t-butyl, propyl, propen-3-yl, 2-methylpropen-3-yl, 2-methylbutene-4-yl, cyclohexylmethyl, 2-cyclohexylethyl, benzyl, —$CH_2$—$OR^{17}$, —$CH_2CH_2$—$OR^{17}$, —$CH_2$—$NR^{18}N^{19}$ or —$CH_2CH_2$—$NR^{18}N^{19}$.

Embodiment 103: The compound of Embodiment 102, wherein $R^{15}$ is isopropyl.

Embodiment 104: The compound of Embodiment 94 or 95, wherein $R^{15}$ is a nucleophile.

Embodiment 105: The compound of Embodiment 104, wherein $R^{15}$ is hydroxyl, amino, thiol, carboxyl, cyanide, azide, or nitrite.

Embodiment 106: The compound of any one of Embodiments 94-105, wherein $R^{14}$ is H, alkyl, alkenyl, alkynyl, aryl or heteroaryl, wherein the alkyl, alkenyl, alkynyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 107: The compound of Embodiment 106, wherein $R^{14}$ is H, $C_1$-$C_6$alkyl, $C_2$-$C_6$alkenyl, $C_2$-$C_6$alkynyl, or 5-12 membered aryl, wherein the $C_1$-$C_6$alkyl, $C_2$-$C_6$alkenyl, $C_2$-$C_6$alkynyl, and 5-12 membered aryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 108: The compound of Embodiment 107, wherein $R^{14}$ is H, methyl, ethyl, propyl, isopropyl, butyl, isobutyl, but-2-yl, t-butyl, pentyl, 5-hexyn-1-yl, 2-propyn-1-yl, propargyl, methoxymethyl, phenyl, or 4-trifluoromethylphenyl.

Embodiment 109: The compound of Embodiment 108, wherein $R^{14}$ is H, $R^4$ is H, methyl, ethyl, propyl, isopropyl, butyl, isobutyl, but-2-yl, pentyl, hexyl, 5-hexyn-1-yl, 2-propyn-1-yl, or propargyl.

Embodiment 110: The compound of any one of Embodiments 94-109, wherein $R^{12}$ is cycloalkyl, heterocyclyl, aryl or heteroaryl, wherein the cycloalkyl, heterocyclyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 111: The compound of Embodiment 110, wherein $R^{12}$ is 5-12 membered aryl, 5-12 membered heteroaryl comprising 1, 2 or 3 independently selected heteroatoms, 5-12 membered cycloalkyl, or 5-12 membered heterocyclyl comprising 1, 2 or 3 independently selected heteroatoms, wherein the 5-12 membered aryl, 5-12 membered heteroaryl, 5-12 membered cycloalkyl, and the 5-12 membered heterocyclyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 112: The composition of Embodiment 111, wherein $R^{12}$ is phenyl, cyclohexyl, cyclopentyl, tetrahydropyranyl, tetrahydrofuranyl, piperidinyl, pyridinyl, diazinyl, furnayl, thiophenyl, or thiazolyl, wherein the phenyl, cyclohexyl, cyclopentyl, tetrahydropyranyl, tetrahydrofuranyl, piperidinyl, pyridinyl, diazinyl, furnayl, thiophenyl and thiazolyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 113: The composition of Embodiment 112, wherein $R^{12}$ is phenyl (optionally substituted at position 2 and/or 4 with substituents selected independently from halogen, hydroxyl, alkoxy, amino, mono-substituted amino, and di-substituted amino), cyclohexyl, cyclopentyl, tetrahydropyran-4-yl, piperdin-4-yl (optionally substituted at position 1 with an alkyl or cycloalkyl), pyridine-2-yl (optionally substituted at position 3 and/or 5 with substituents selected independently from halogen, hydroxyl, alkoxy, amino, mono-substituted amino, and di-substituted amino), pyridine-5-yl (optionally substituted at position 2 and/or 4 with substituents selected independently from halogen, hydroxyl, alkoxy, amino, mono-substituted amino, and di-substituted amino), pyridin-3-yl (optionally substituted at position 2 and/or 6 with substituents selected independently from halogen, hydroxyl, alkoxy, amino, mono-substituted amino, and di-substituted amino), furan-5-yl (optionally substituted at position 2 and/or 4 with substituents selected independently from halogen, hydroxyl, alkoxy, amino, mono-substituted amino, and di-substituted amino), furan-4-yl (optionally substituted at position 2 and/or 4 with substituents selected independently from halogen, hydroxyl, alkoxy, amino, mono-substituted amino, and di-substituted amino), thiopen-5-yl (optionally substituted at position 2 and/or 4 with substituents selected independently from halogen, hydroxyl, alkoxy, amino, mono-substituted amino, and di-substituted amino), or thiophen-4-yl (optionally substituted at position 2 and/or 4 with substituents selected independently from halogen, hydroxyl, alkoxy, amino, mono-substituted amino, and di-substituted amino).

Embodiment 114: The composition of Embodiment 112, wherein $R^{12}$ is 4-fluorophenyl, 4-chlorophenyl, 4-bromophenyl, 4-trifluoromethylphenyl, 4-methoxyphenyl, 4-carboxylphenyl, 4-methoxycarbonylphenyl, 4-methylphenyl, 3-fluorophenyl, 3-chlorophenyl, 3-bromophenyl, 3-trifluoromethylphenyl, 3-methoxyphenyl, 2-fluorophenyl, 2-chlorophenyl, 2-bromophenyl, 2-trifluoromethylphenyl, 2-methoxyphenyl, 2-methylphenyl, 3,4-difluorophenyl, 2,4-difluorophenyl, 4-fluoro-2-methylphenyl, 2-chloro-4-fluorophenyl, 2-bromo-4-fluorophenyl, 2-fluoro-4-chlorophenyl, 2-fluoro-4-bromophenyl, 1,6-dichlorophenyl, phenyl, cyclohexyl, cyclopentyl, 3-methoxypyridin-2-yl, 2-methoxypyridin-3-yl, 2-methoxypyridin-5-yl, thiophen-3-yl, thiopen-2-yl, 3-methylthiophen-2-yl, 2-methylthiophen-5-yl, pyridine-4-yl, 4-fluoro-2-methoxyphenyl, 3-methoxypyridin-5-yl, 3-fluoropyridin-6-yl, 4-carboxylphenyl, 2-bromo-5-trifluoromethylphenyl, 1,3-thiazol-5-yl, 3-trifluoromethyl-4-fluorophenyl, pyrimidin-4-yl, 4-cholor-pyridin-3-yl, 2,6-difluoropyridin-4-yl, 4-trifloromethoxyphenyl, pyridazine-4-yl, but-3-ynyl, but-3-enyl, hex-5-ynyl, 2,5-ditrifluromethylphenyl, thiaz-5-yl, 3-trifluoromethyl-4-fluorophenyl, 3-trifluoromethylphenyl, 4-fluoro-2-methylphenyl, 3-fluropyridin-6-yl, and 3-bromothiophen-2-yl.

Embodiment 115: The compound of Embodiment 112, wherein $R^{12}$ is 4-fluorophenyl, 2-chlorphenyl, 2-bromophenyl, 2-methoxyphenyl, 2-methyl-4-fluorophenyl or 2-methoxy-4-fluorophenyl.

Embodiment 116: The compound of any one of Embodiments 94-115, wherein $R^{11}$ is aryl, heteroaryl, alkyl, alkenyl or alkynyl, wherein the aryl, heteroaryl, alkyl, alkenyl, and alkynyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido;

Embodiment 117: The compound of Embodiment 116, wherein $R^{11}$ is $C_1$-$C_{10}$alkyl, $C_2$-$C_1$alkenyl, $C_2$-$C_{10}$alkynyl, 5-12 membered aryl, or 5-12 membered heteroaryl comprising 1, 2 or 3 independently selected heteroatoms, wherein the $C_1$-$C_{10}$alkyl, $C_2$-$C_1$alkenyl, $C_2$-$C_{10}$alkynyl, 5-12 membered aryl, and 5-12 membered heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 118: The compound of Embodiment 117, wherein $R^{11}$ is phenyl, pyridinyl, 1,3-benzodioxolyl, 2,2-difluoro-1,3-benzodioxolyl, 1,3,3a-triazaindenyl, benzimidazolyl, 2,3-dihydro-1,4-benzodioxinyl, cyclohexyl, cyclopentyl, tetrahydropyranyl, tetrahydrofuranyl, piperidinyl, pyridinyl, diazinyl, furnayl, thiophenyl, thiazolyl, $C_1$-$C_6$alkyl, $C_2$-$C_6$alkenyl or $C_2$-$C_6$alkynyl, wherein the phenyl, cyclohexyl, cyclopentyl, tetrahydropyranyl, tetrahydrofuranyl, piperidinyl, pyridinyl, diazinyl, furnayl, thiophenyl thiazolyl, $C_1$-$C_6$alkyl, $C_2$-$C_6$alkenyl and $C_2$-$C_6$alkynyl and alkyl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 119: The composition of Embodiment 118, wherein $R^{11}$ is phenyl (optionally substituted at position 4 with a substituent selected independently from halogen, hydroxyl, alkoxy, amino, mono-substituted amino, and di-substituted amino), furan-4-yl (optionally substituted at position 2 and/or 4 with substituents selected independently from halogen, hydroxyl, alkoxy, amino, mono-substituted amino, and di-substituted amino), pyridine-5-yl (optionally substituted at position 2 and/or 3 with a substituent selected independently from halogen, hydroxyl, alkoxy, amino, mono-substituted amino, and di-substituted amino), furan-6-yl (optionally substituted at position 3 and/or 4 with substituents selected independently from halogen, hydroxyl, alkoxy, amino, mono-substituted amino, and di-substituted amino), pyridine-6-yl (optionally substituted at position 2 and/or 3 with a substituent selected independently from halogen, hydroxyl, alkoxy, amino, mono-substituted amino, and di-substituted amino), 1,3-benzodioxolyl, 2,2-difluoro-1,3-benzodioxolyl, or 1,3,3a-triazaindenyl.

Embodiment 120: The compound of Embodiment 118, wherein $R^{11}$ is 4-methoxyphenyl, 2-methoxyphenyl, 2-methoxypyridin-5-yl, 3-fluoropyridin-5-yl, 1,3-benzodioxolyl, 4-(methoxycarbonyl)phenyl, 4-carboxyphenyl, 4-dimethylaminoaphenyl, benzimidazole-5-yl, 4-sulfamoylphenyl, 4-trifluromethoxyphenyl, 3-methoxyphenyl, 3-fluoro-4-methoxyphenyl, 4-bromophenyl, 4-fluorophenyl, 4-chlorophenyl, 2-pyridinylethyl, N-methylpiperazinyl, N-isopropylpyrazol-4-yl, 4-pyrrolidonylphenyl, 2,3-dihydro-1,4-benzodioxinyl, 1,3,3a-triazaindenyl, 1-acetyl-3-hydroxypropyl, 4-imidazolylphenyl, 3-fluoropyridin-5-yl, 4-dimethylaminophenyl, N-methylpyrrolidin-3-yl, 2-hydroxymethyl-2-methyl-3-hydroxypropyl, 2-methoxyethyl, 5-hexyn-1-yl, 4-hydroxyphenyl, 2-(3-butyn-1-yl)pyridin-4-yl, N-ethylpyrrolidin-3-yl, hydrogen, phenyl, 2-methoxypyridin-5-yl, 3-fluoro-2-methoxypyridin-5-yl, 4-methoxyphenylmethyl, 4-(1-Pyrrolidinylsulfonyl)phenyl, 4-imidazole-1-ylphenyl, 2-hydroxybenzimidazoly-5-yl, 3,4,5-trimethoxyphenyl, 4-ethoxyphenyl, 2,4-dimethoxyphenyl, 4-t-butylphenyl, 4-ethylphenyl, 3-methoxypyridin-6-yl-methyl, 4-cyanophenyl, 3-trifluoromethylpyridin-6-yl, 2-pyrrolidinylethyl, tetrahydropyran-4-yl, 3-caynophenyl, 4-trifluoromethoxyphenyl, 1,3-dihydroxypropy-2-yl, 2-methylpyridin-4-yl, N-ethylpyrrolidin-4-yl, 3-oxo-3,4-dihydro-2H-1,4-benzoxazine-7-yl, 4-(2-oxo-1-pyrrolidinyl)phenyl, 2-methylpyridin-5-yl, 2-(N-methylpiperazinyl)pirpdin-5-yl, 3-fluoropyridin-5-yl, 2-methoxy-3-methylpyridin-5-yl, 4-(1-ethyl-1H-pyrazol-4-yl)phenyl, 4-(1-ethyl-1H-pyrazol-3-yl)phenyl, 2-fluoropyridin-5-yl, 4-(1-isopropyl-1H-pyrazol-4-yl)phenyl, 4-(1-isopropyl-1H-pyrazol-3-yl)phenyl, 4-(1-ethyl-1H-pyrazol-3-yl)phenyl, 4-(1-methyl-1H-pyrazol-4-yl)phenyl, 3-methoxypyridin-6-yl, 4-(1-methyl-1H-pyrazol-3-yl)phenyl, 4-(1-pyrrolidinylcarbonyl)-phenyl, 2-(1-methylpiperzin-4-yl)pyridine-5-yl, 4-(5-hexyn-1-oxy)phenyl, 4-triflouromethoxyphenyl, 4-methylphenyl, 4-ethylphenyl, pyridine-3-yl, pyridine-2-yl, 2-methylfuran-5-yl, 4-methoxycyclohexyl, 4-dimethylaminohexyl, and 1-methylpyrrolidin-3-yl methyl.

Embodiment 121: The compound of Embodiment 120, wherein $R^{11}$ is 4-methoxyphenyl, 1,3-benzodioxolyl, 3-fluoro-4-methoxyphenyl, 4-bromophenyl, 4-dimethylaminophenyl, 2'-methoxypyridin-5-yl, or 1,3,3a-triazaindenyl.

Embodiment 122: The compound of Embodiment 94, wherein $R^{15}$ is alkyl, alkenyl, alkynyl, cycloalkyl, or heterocyclyl; $R^{14}$ is H, alkyl, alkenyl, alkynyl, aryl or heteroaryl; $R^{12}$ is cycloalkyl, heterocyclyl, aryl or heteroaryl; and $R^{11}$ is aryl, heteroaryl, alkyl, alkenyl or alkynyl, and where any alkyl, alkenyl, alkynyl, cycloalkyl, heterocyclyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 123: The compound of Embodiment 122, wherein $R^{15}$ is alkyl, alkenyl, cycloalkyl or heterocyclyl; $R^4$ is H, $C_1$-$C_6$alkyl, $C_2$-$C_6$alkenyl, $C_2$-$C_6$alkynyl, or 5-12 membered aryl; $R^{12}$ is 5-12 membered aryl, 5-12 membered heteroaryl comprising one heteroatom, 5-12 membered cycloalkyl, or 5-12 membered heterocyclyl comprising one heteroatom; and $R^{11}$ is $C_1$-$C_{10}$alkyl, $C_2$-$C_1$alkenyl, $C_2$-$C_{10}$alkynyl, 5-12 membered aryl, or 5-12 membered heteroaryl comprising 1, 2 or 3 independently selected heteroatoms, and where any alkyl, alkenyl, alkynyl, cycloalkyl, heterocyclyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 124: The compound of Embodiment 123, wherein $R^{15}$ is $C_1$-$C_6$alkyl or —$(CH_2)_a$—$R^{16}$, where a is 0, 1, 2, 3, 4, 5, 6, 7, 8, 9 or 10, and $R^{16}$ is cycloalkyl, —$OR^{11}$, or —$NR^{18}R^{19}$, where $R^{17}$ is H or alkyl, and $R^{18}$ and $R^{19}$ are independently H, alkyl, or cycloalkyl; $R^{14}$ is H, methyl, ethyl, propyl, isopropyl, butyl, isobutyl, but-2-yl, t-butyl, pentyl, 5-hexyn-1-yl, 2-propyn-1-yl, propargyl, methoxymethyl, phenyl, or 4-trifluoromethylphenyl; $R^{12}$ is phenyl, cyclohexyl, cyclopentyl, tetrahydropyranyl, tetrahydrofuranyl, piperidinyl, pyridinyl, diazinyl, furnayl, thiophenyl, or thiazolyl; and $R^{11}$ is phenyl, pyridinyl, 1,3-benzodioxolyl, 2,2-difluoro-1,3-benzodioxolyl, 1,3,3a-triazaindenyl, benzimidazolyl, 2,3-dihydro-1,4-benzodioxinyl, cyclohexyl, cyclopentyl, tetrahydropyranyl, tetrahydrofuranyl, piperidinyl, pyridinyl, diazinyl, furnayl, thiophenyl, thiazolyl, $C_1$-$C_6$alkyl, $C_2$-$C_6$alkenyl or $C_2$-$C_6$alkynyl, and where any phenyl, cyclohexyl, cyclopentyl, tetrahydropyranyl, tetrahydrofuranyl, piperidinyl, pyridinyl, diazinyl, furnayl, thiophenyl, or thiazolyl; and $R^{11}$ is phenyl, pyridinyl, 1,3-benzodioxolyl, 2,2-difluoro-1,3-benzodioxolyl, 1,3,3a-triazaindenyl, benzimidazolyl, 2,3-dihydro-1,4-benzodioxinyl, cyclohexyl, cyclopentyl, tetrahydropyranyl, tetrahydrofuranyl, piperidinyl, pyridinyl, diazinyl, furnayl, thiophenyl, thiazolyl, $C_1$-$C_6$alkyl, $C_2$-$C_6$alkenyl, $C_2$-$C_6$alkynyl, alkyl, alkenyl, alkynyl, cycloalkyl, heterocyclyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 125: The compound of Embodiment 124, wherein $R^{15}$ is $C_1$-$C_6$ alkyl, —$CH_2$-cycloalkyl, —$CH_2CH_2$-cycloalkyl, —$CH_2$—$OR^{17}$, —$CH_2CH_2$—$OR^{17}$, —$CH_2$—$NR^{18}N^{19}$ or —$CH_2CH_2$—$NR^{18}N^{19}$; $R^{14}$ is H, methyl, ethyl, propyl, isopropyl, butyl, isobutyl, but-2-yl, t-butyl, pentyl, 5-hexyn-1-yl, 2-propyn-1-yl, propargyl, methoxymethyl, phenyl, or 4-trifluoromethylphenyl; $R^{12}$ is phenyl, cyclohexyl, cyclopentyl, tetrahydropyranyl, tetrahydrofuranyl, piperidinyl, pyridinyl, diazinyl, furnayl, thiophenyl, or thiazolyl; and $R^{11}$ is phenyl, pyridinyl, 1,3-benzodioxolyl, 2,2-difluoro-1,3-benzodioxolyl, 1,3,3a-triazaindenyl, benzimidazolyl, 2,3-dihydro-1,4-benzodioxinyl, cyclohexyl, cyclopentyl, tetrahydropyranyl, tetrahydrofuranyl, piperidinyl, pyridinyl, diazinyl, furnayl, thiophenyl, thiazolyl, $C_1$-$C_6$alkyl, $C_2$-$C_6$alkenyl or $C_2$-$C_6$alkynyl, and where any phenyl, cyclohexyl, cyclopentyl, tetrahydropyranyl, tetrahydrofuranyl, piperidinyl, pyridinyl, diazinyl, furnayl, thiophenyl, or thiazolyl; and $R^1$ is phenyl, pyridinyl, 1,3-benzodioxolyl, 2,2-difluoro-1,3-benzodioxolyl, 1,3,3a-triazaindenyl, benzimidazolyl, 2,3-dihydro-1,4-benzodioxinyl, cyclohexyl, cyclopentyl, tetrahydropyranyl, tetrahydrofuranyl, piperidinyl, pyridinyl, diazinyl, furnayl, thiophenyl, thiazolyl, $C_1$-$C_6$alkyl, $C_2$-$C_6$alkenyl, $C_2$-$C_6$alkynyl, alkyl, alkenyl, alkynyl, cycloalkyl, heterocyclyl, aryl and heteroaryl is optionally substituted with one or more (e.g., 1, 2, 3, 4 or more) substituents selected independently from the group consisting of halogen, hydroxyl, alkoxy, carboxyl, oxo, nitro, haloalkyl, alkyl, alkenyl, alkynyl, alkaryl, aryl, heteroaryl, cycloalkyl, heterocyclyl, aralkyl, acyl, aryloxy, amino, alkylamino dialkylamino, acylamino, alkylcarbanoyl, arylcarbanoyl, aminoalkyl, aminocarbonyl, alkoxycarbonyl, carboxy, hydroxylalkyl, alkanesulfonyl, arenesulfonyl, alkanesulfonamido, arenesulfonamido, aralkylsulfonamido, alkylcarbonyl, alkoxycarbonyl, acyloxy, thiol, sulfinyl, sulfonyl, sulfonamide, sulfate, phosphate, haloalkyl, thioalkyl, cyanomethylene, alkylaminyl, cyano and ureido.

Embodiment 126: The compound of Embodiment 94, wherein the antileishmanial compound is selected from the group consisting of: CMLD007431, CMLD011128, CMLD007427, CMLD011024, CMLD011025, CMLD010981, CMLD010849, CMLD010980, CMLD010979, CMLD011029, CMLD010900, CMLD010885, CMLD011039, CMLD010899, CMLD011113, CMLD010897, CMLD011033, CMLD011031, CMLD011046, CMLD010895, CMLD011098, CMLD011095, CMLD011026, CMLD011092, CMLD011036, CMLD011124, CMLD011030, CMLD011072, CMLD011129, CMLD011117, CMLD010884, CMLD010992, CMLD010901, CMLD011101, CMLD010888, CMLD011096, CMLD010889, CMLD011121, CMLD011032, CMLD011034, CMLD010892, CMLD010978, CMLD011102, CMLD010893, CMLD010894, CMLD010994, CMLD010890, CMLD011099, CMLD010891, CMLD011088, CMLD007432, CMLD011079, CMLD010902, CMLD011548, CMLD011546, CMLD011564, CMLD012217, CMLD011566, CMLD011562, CMLD011551, CMLD011549, CMLD011565, CMLD011494, CMLD010920, CMLD011554, CMLD011552, CMLD011561, CMLD011572, CMLD012218, CMLD011567, CMLD011574, CMLD010921, CMLD010948, CMLD010882, CMLD011104, CMLD010991, CMLD011075, CMLD011142, CMLD011125, CMLD010887, CMLD011100, CMLD010886, CMLD011575, CMLD011496, CMLD011027, CMLD011120, CMLD011579, CMLD011559, CMLD011028, CMLD011577, CMLD011578, CMLD007169, CMLD007188, CMLD007203, CMLD007219, CMLD007221, CMLD007235, CMLD007421, CMLD007247, CMLD007262, CMLD007286, CMLD007424, CMLD007425, CMLD007430, CMLD010949, CMLD011573, BUCMD00800, BUCMD00797, CMLD010987, CMLD010898, CMLD011119, CMLD011547, CMLD011131, CMLD011105, BUCMD00815, CMLD011499, BUCMD00812, CMLD010896, CMLD011111, CMLD011135, BUCMD00809, CMLD011569, CMLD011132, CMLD011133, CMLD013640, CMLD011116, CMLD011140, BUCMD00802, BUCMD00803, BUCMD00805, CMLD011109, CMLD011122, CMLD011568, CMLD011106, CMLD010881, CMLD011110, CMLD011134, CMLD011138, CMLD011550, CMLD011141, BUCMD00804, CMLD011103, CMLD011137, BUCMD00808, BUCMD00811, BUCMD00816, CMLD011112, CMLD011115, CMLD011097, BUCMD00807, BUCMD00813, BUCMD00814, CMLD011130, CMLD010880, CMLD010903, CMLD011126, CMLD011093, BUCMD00799, BUCMD00810, CMLD011576, BUCMD00806, CMLD010883, BUCMD00798, CMLD010848, CMLD011094, CMLD011557, CMLD011495, CMLD011556, CMLD011558, BUCMD00801, BUCMD00817, CMLD010926, CMLD011040, CMLD010925, CMLD011042, CMLD010996, CMLD011043, CMLD010998, CMLD010993, CMLD011081, CMLD010976, CMLD010989, BUCMD00694, BUCMD00729, BUCMD00639, CMLD011035, BUCMD00695, BUCMD00730, CMLD010982, BUCMD00669, CMLD010985, CMLD010950, CMLD011497, CMLD011560, BUCMD00629, BUCMD00686, BUCMD00717, BUCMD00718, CMLD011080, CMLD010977, BUCMD00733, CMLD010984, CMLD010990, BUCMD00643, BUCMD00642, BUCMD00700, BUCMD00699, BUCMD00734, BUCMD00685, CMLD011555, CMLD011076, CMLD006598, BUCMD00732, CMLD010988, BUCMD00698, CMLD011077, CMLD011123, BUCMD00697, CMLD011553, BUCMD00628, BUCMD00688, BUCMD00640, CMLD011047, CMLD011136, CMLD011073, BUCMD00663, CMLD011045, BUCMD00691, BUCMD00721, CMLD009657, BUCMD00720, CMLD010924, BUCMD00668, BUCMD00651, BUCMD00672, BUCMD00702, BUCMD00630, BUCMD00683, CMLD011037, BUCMD00690, CMLD011038, BUCMD00674, BUCMD00723, BUCMD00679, BUCMD00650, BUCMD00684, BUCMD00687, BUCMD00649, BUCMD00673, BUCMD00689, BUCMD00692, BUCMD00728, BUCMD00738, CMLD011078, CMLD011090, CMLD011044, CMLD011087, CMLD013629, CMLD010986, CMLD011139, BUCMD00647, BUCMD00627, BUCMD00653, BUCMD00641, BUCMD00645, BUCMD00646, BUCMD00648, BUCMD00652, BUCMD00654, BUCMD00655, BUCMD00656, BUCMD00657, BUCMD00658, BUCMD00659, BUCMD00660, BUCMD00661, BUCMD00662, BUCMD00664, BUCMD00665, BUCMD00666, BUCMD00667, BUCMD00670, BUCMD00671, BUCMD00675, BUCMD00676, BUCMD00677, BUCMD00678, BUCMD00680, BUCMD00693, BUCMD00696, BUCMD00701, BUCMD00711, BUCMD00712, BUCMD00713, BUCMD00714, BUCMD00715, BUCMD00716, BUCMD00719, BUCMD00722, BUCMD00724, BUCMD00725, BUCMD00726, BUCMD00727, BUCMD00731, BUCMD00739, BUCMD00741, BUCMD00156, BUCMD00157, BUCMD00158, BUCMD00159, BUCMD00160, BUCMD00161, BUCMD00162, BUCMD00163, BUCMD00164, BUCMD00165, BUCMD00166, BUCMD00167, BUCMD00168, BUCMD00169, BUCMD00170, BUCMD00171, BUCMD00172, BUCMD00173, BUCMD00174, BUCMD00175, BUCMD00176, BUCMD00177, BUCMD00178, BUCMD00179, BUCMD00180, BUCMD00181, BUCMD00182, BUCMD00183, BUCMD00184, BUCMD00185, BUCMD00186, BUCMD00187, BUCMD00188, BUCMD00189, BUCMD00190, BUCMD00191, BUCMD00192, BUCMD00193, BUCMD00194, BUCMD00195, BUCMD00196, BUCMD00197, BUCMD00198, and BUCMD00199.

Embodiment 127: The compound of Embodiment 126, wherein the antileishmanial compound is selected from the group consisting of: BUCMD00800, BUCMD00797, BUCMD00815, BUCMD00812, BUCMD00809, BUCMD00802, BUCMD00803, BUCMD00805, BUCMD00804, BUCMD00808, BUCMD00811, BUCMD00816, BUCMD00807, BUCMD00813, BUCMD00814, BUCMD00799, BUCMD00810, BUCMD00806, BUCMD00798, BUCMD00801, BUCMD00817, BUCMD00694, BUCMD00729, BUCMD00639, BUCMD00695, BUCMD00730, BUCMD00669, BUCMD00629, BUCMD00686, BUCMD00717, BUCMD00718, BUCMD00733, BUCMD00643, BUCMD00642, BUCMD00700, BUCMD00699, BUCMD00734, BUCMD00685, BUCMD00732, BUCMD00698, BUCMD00697, BUCMD00628, BUCMD00688, BUCMD00640, BUCMD00663, BUCMD00691, BUCMD00721, BUCMD00720, BUCMD00668, BUCMD00651, BUCMD00672, BUCMD00702, BUCMD00630, BUCMD00683, BUCMD00690, BUCMD00674, BUCMD00723, BUCMD00679, BUCMD00650, BUCMD00684, BUCMD00687, BUCMD00649, BUCMD00673, BUCMD00689, BUCMD00692, BUCMD00728, BUCMD00738, BUCMD00647, BUCMD00627, BUCMD00653, BUCMD00641, BUCMD00645, BUCMD00646, BUCMD00648, BUCMD00652, BUCMD00654, BUCMD00655, BUCMD00656, BUCMD00657, BUCMD00658, BUCMD00659, BUCMD00660, BUCMD00661, BUCMD00662, BUCMD00664, BUCMD00665, BUCMD00666, BUCMD00667, BUCMD00670, BUCMD00671, BUCMD00675, BUCMD00676, BUCMD00677, BUCMD00678, BUCMD00680, BUCMD00693, BUCMD00696, BUCMD00701, BUCMD00711, BUCMD00712, BUCMD00713, BUCMD00714, BUCMD00715, BUCMD00716, BUCMD00719, BUCMD00722, BUCMD00724, BUCMD00725, BUCMD00726, BUCMD00727, BUCMD00731, BUCMD00739, BUCMD00741, BUCMD00156, BUCMD00157, BUCMD00158, BUCMD00159, BUCMD00160, BUCMD00161, BUCMD00162, BUCMD00163, BUCMD00164, BUCMD00165, BUCMD00166, BUCMD00167, BUCMD00168, BUCMD00169, BUCMD00170, BUCMD00171, BUCMD00172, BUCMD00173, BUCMD00174, BUCMD00175, BUCMD00176, BUCMD00177, BUCMD00178, BUCMD00179, BUCMD00180, BUCMD00181, BUCMD00182, BUCMD00183, BUCMD00184, BUCMD00185, BUCMD00186, BUCMD00187, BUCMD00188, BUCMD00189, BUCMD00190, BUCMD00191, BUCMD00192, BUCMD00193, BUCMD00194, BUCMD00195, BUCMD00196, BUCMD00197, BUCMD00198, and BUCMD00199.

Embodiment 128: The compound of any one of Embodiments 94-127, wherein the antileishmanial compound has a C Log P from about 3.2 to about 4.3.

Embodiment 129: The compound of any one of Embodiments 94-128, wherein the carbon to which the $R^{12}$ group is attached has the S stereochemistry.

Embodiment 130: The compound of any one of Embodiments 94-128, wherein the carbon to which the $R^{12}$ group is attached has the R stereochemistry.

Embodiment 131: A method for treating leishmaniasis or a disease or disorder associated with leishmaniasis, the method comprising: administering a therapeutically effective amount of an antileishmanial compound of Formula (I) or Formula (II) to a subject in need thereof.

Embodiment 132: The method of Embodiment 131, wherein the leishmaniasis is caused by a *Leishmania* parasite selected from the group consisting of *Leishmania major, Leishmania tropica, Leishmania Mexicana, Leishmania braziliensis, Leishmania amazonensis, Leishmania aethiopica, Leishmania panamensis, Leishmania guyanensis, Leishmania infantum, Leishmania donovani, Leishmania promastigotes, Leishmania adleri, Leishmania agamae, Leishmania arabica, Leishmania aristidesi, Leishmania ceramodactyli, Leishmania enriettii, Leishmania forattinii, Leishmania gerbilli, Leishmania gulikae, Leishmania gymnodactyli, Leishmania helioscopi, Leishmania hemidactyli, Leishmania hoogstraali, Leishmania killicki, Leishmania lainsoni, Leishmania lindenbergi, Leishmania macropodum, Leishmania martiniquensis, Leishmania naiffi, Leishmania nicollei, Leishmania orientalis, Leishmania peruviana, Leishmania phrynocephali, Leishmania pifanoi, Leishmania platycephala, Leishmania senegalensis, Leishmania shawi, Leishmania sofieffi, Leishmania tarentolae, Leishmania turanica, Leishmania utingensis, Leishmania venezeulensis, Leishmania waltoni* Shaw, *Leishmania zmeevi*, and *Leishmania zuckermani*

Embodiment 133: The method of Embodiment 132, wherein the *Leishmania* parasite is selected from the group consisting of *Leishmania major, Leishmania tropica, Leishmania Mexicana, Leishmania braziliensis, Leishmania amazonensis, Leishmania aethiopica, Leishmania panamensis, Leishmania guyanensis, Leishmania infantum, Leishmania donovani*.

Embodiment 134: The method of Embodiment 133, wherein the *Leishmania* parasite is selected from the group consisting of *Leishmania major, Leishmania braziliensis*, and *Leishmania donovani*.

Embodiment 135: The method of any one of Embodiments 131-134, wherein the leishmaniasis is cutaneous leishmaniasis (CL).

Embodiment 136: The method of any one of Embodiments 131-134, wherein the leishmaniasis is visceral leishmaniasis (VL).

Embodiment 137: The method of any one of Embodiments 131-136, wherein the antileishmanial compound is formulated in a composition for administering to the subject.

Embodiment 138: The method of Embodiment 137, wherein the composition is a composition of any one of claims 1-93.

Embodiment 139: A method of reducing, suppressing or inhibiting a *Leishmania* parasite in a vector, the method comprising: administering to the vector an effective amount of Formula (I) or Formula (II).

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The technology described herein is further illustrated by the following examples which in no way should be construed as being further limiting.

Example 1

Figure 1:
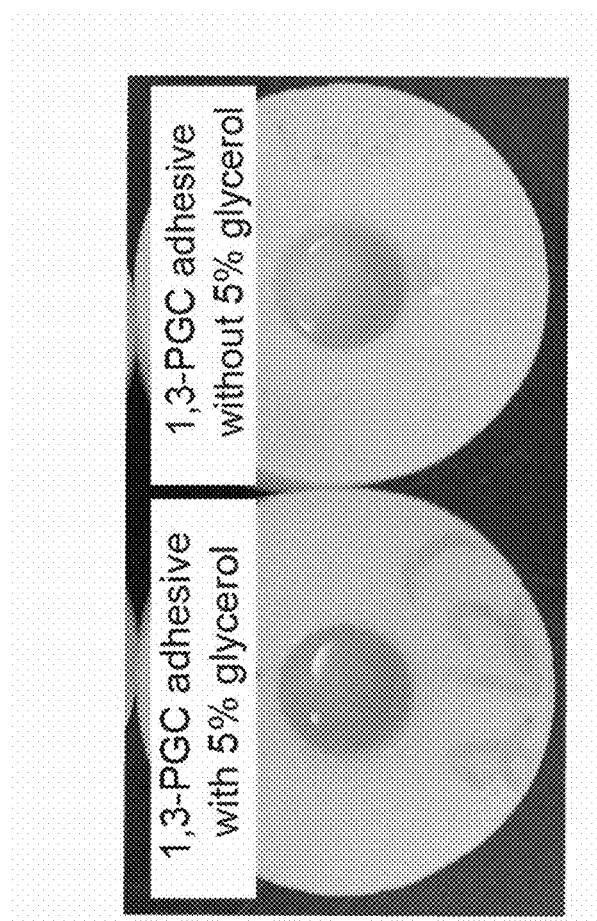
FIG. 1 shows CMLD011128-loaded 1,3-PGC polymer adhesive with and without a 5% glycerol additive during the solvent evaporation manufacturing process.

In order to improve topical administration to CL lesions, the inventors have demonstrated an adhesive that can be formulated into a transdermal patch. The structure of the polymer, 1,3-poly(glycerol carbonate) (1,3-PGC), is promising as an adhesive in that it is biodegradable into natural metabolites, tunable in adhesive strength via pendant chain modifications, and structurally similar to poly(acrylate) adhesives. The inventors demonstrated proof-of-concept in drug-loading the adhesive with CMLD011128 through a solvent evaporation method in ethyl acetate with 5% glycerol. Including the glycerol as an additive slowed down the rate of solvent evaporation, ultimately yielding a more uniform adhesive disk (FIG. 1).

A new poly(glycerol carbonate) co-polymer nanoparticles was also developed and used for the delivery of active agent to the liver in systemic VL infections. This polymer, 1,3-poly(glycerol carbonate)-C18-co-poly(ε-caprolactone) is formulated into nanoparticles via a oil-in-water nanoemulsion sonication method. This method was optimized to achieve particle sizes of 100-130 nm, which is ideal for cellular uptake and in vivo delivery to the liver. In a preliminary drug release study conducted in sodium phosphate buffer and sodium dodecyl sulfate at pH 7.4, these nanoparticles demonstrate approximately 30% drug release within 7 days (FIG. 2).

Figure 3:
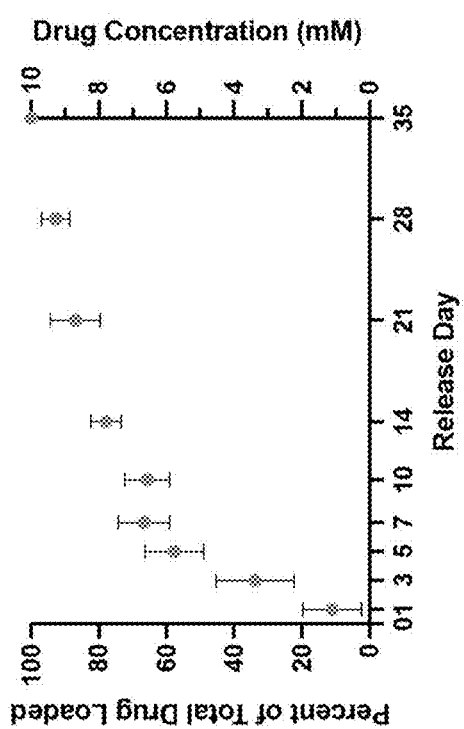
FIG. 3 examines the release of CMLD011128 from PGC-co-PCL nanoparticles in 10 mM phosphate release buffer (n=4) over the course of 35 days.

In a longer-term study, the PGC-co-PCL nanoparticles demonstrated a sustained release of payload, with 65% of the loaded drug released in Week 1 and the remaining 35% released over the next 3-4 weeks (FIG. 3). The release media for these experiments was 10 mM phosphate buffer (pH 7.4) containing 0.5% w/v sodium dodecyl sulfate and maintained at 37° C.

TABLE 1

Compiled Leishmania Data after Treatment with Antileishmanial Compounds

| Compound | Structure | LogP a | *L. donovani* amastigotes % GI at 10 μM (THP-1 cells)b | THP-1 host cell % growth inhibition at 10 μMb | *L. donovani* amastigotes EC50 (μM, THP-1c or B10Rd cells) | THP-1 Host Cell CC50 (μM)c | *L. donovani* amastigotes EC75 (μM B10R cells)d | B10R Host Cell CC50 (μM)d | SI (Host cell potency/ *L. donovani* potency) | *L. braziliensis* amastigotes EC75 (μM J774 cells)e | *L. major* amastigotes EC75 (μM, THP-1 b or J774e cells) | *L. donovani* promastigotes EC50 (μM)f | *L. major* promastigotes EC50 (μM)f |
|---|---|---|---|---|---|---|---|---|---|---|---|---|---|
| CMLD007431 | 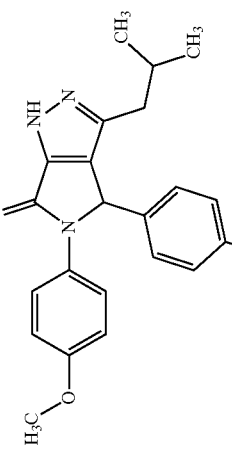 | 4.2 | 99.0 | 13.0 | 2.5c | >20 | 1.0 | >4.7 | >8 | | 1.3b | 2.0 | 4.4 |
| CMLD011128 | 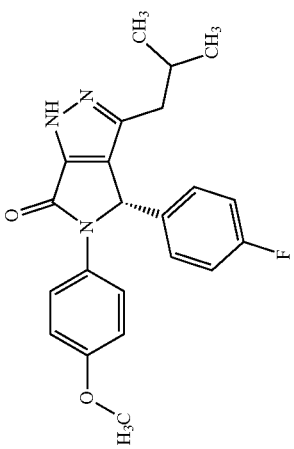 | 4.2 | | | 0.8c | >20 | 0.5 | >4.7 | >25 | 7.5 | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µM | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 or J774e cells) | L. donovani promastigotes EC50 (µM)f | L. major promastigotes EC50 (µM)f |
|---|---|---|---|---|---|---|---|---|---|---|---|---|---|
| CMLD007427 | 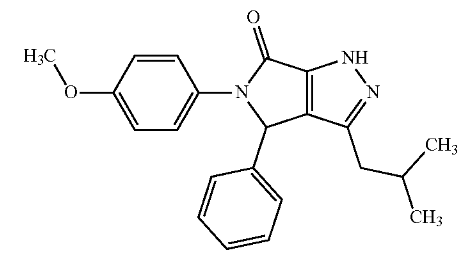 [SMILES: COc1ccc(N2C(=O)c3[nH]nc(CC(C)C)c3C2c2ccccc2)cc1] | 4.1 | 100.0 | 11.0 | 3.2c | 31.6 | 1.1 | >4.7 | 9.9 | | 1.7b | 2.4 | 4.2 |
| CMLD011024 | 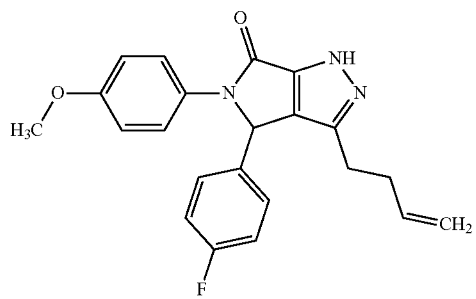 [SMILES: C=CCCc1n[nH]c2c1C(c1ccc(F)cc1)N(c1ccc(OC)cc1)C2=O] | 4.1 | | | 1.6c | 3.2 | | | 2.0 | | | | |
| CMLD011025 | 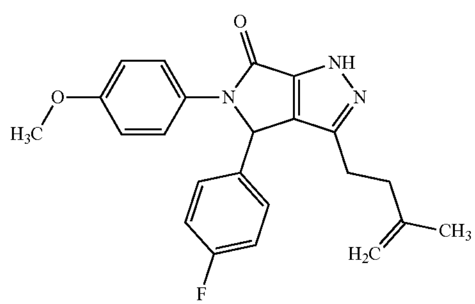 [SMILES: C=C(C)CCc1n[nH]c2c1C(c1ccc(F)cc1)N(c1ccc(OC)cc1)C2=O] | 4.2 | | | 0.5c | 1.6 | | | 3.2 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μM b | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD010981 | 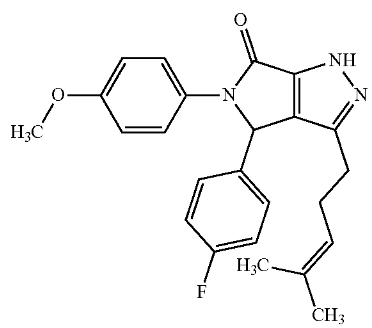 [SMILES: COc1ccc(N2C(=O)c3[nH]nc(CCC=C(C)C)c3C2c2ccc(F)cc2)cc1] | 4.2 | | | 6.3c | 20.0 | | | 3.2 | | | | |
| CMLD010849 | 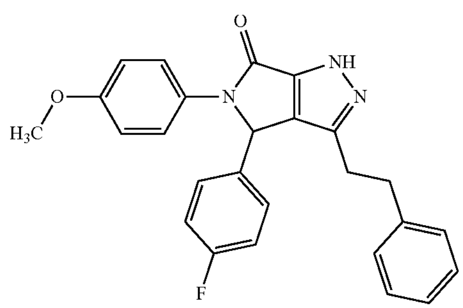 [SMILES: COc1ccc(N2C(=O)c3[nH]nc(CCc4ccccc4)c3C2c2ccc(F)cc2)cc1] | 3.5 | | | 6.3c | 25.1 | | | 4.0 | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| CMLD010980 | 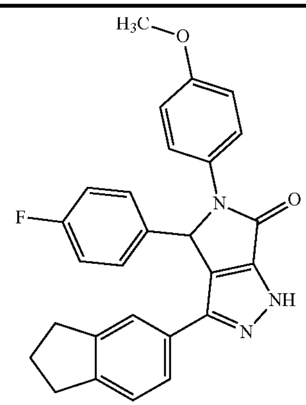 | 4.2 | | | 5.0c | 7.9 | | | 1.6 | | | | |
| CMLD010979 | 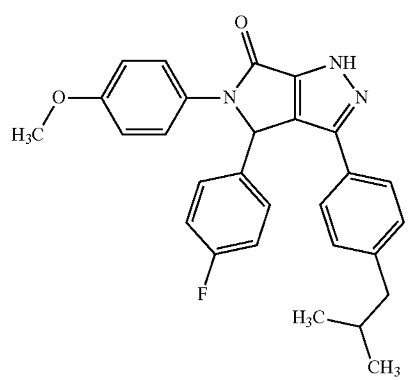 [SMILES: COc1ccc(N2C(=O)c3[nH]nc(-c4ccc(CC(C)C)cc4)c3C2c2ccc(F)cc2)cc1] | 4.1 | | | 4.0c | 7.9 | | | 2.0 | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| CMLD011029 | 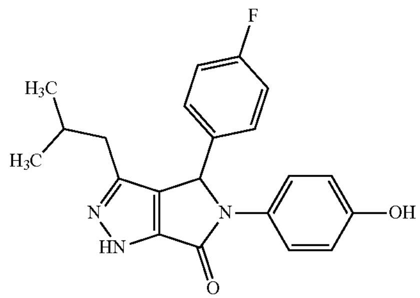 [SMILES: CC(C)Cc1n[nH]c2c1C(c1ccc(F)cc1)N(c1ccc(O)cc1)C2=O] | 4.5 | | | 5.0c | 39.8 | | | 8.0 | | | | |
| CMLD010990 | 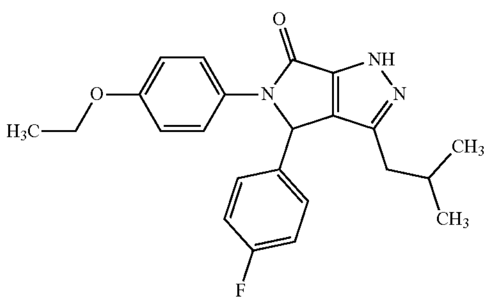 [SMILES: CCOc1ccc(N2C(=O)c3[nH]nc(CC(C)C)c3C2c2ccc(F)cc2)cc1] | 3.0 | | | 1.6c | 20.0 | | | 12.5 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD010885 | 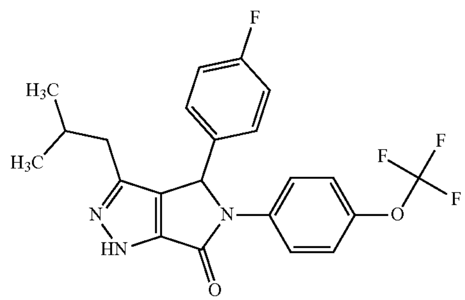 [SMILES: CC(C)Cc1n[nH]c2c1C(c1ccc(F)cc1)N(c1ccc(OC(F)(F)F)cc1)C2=O] | 4.1 | | | 3.2c | 7.9 | | | 2.5 | | | | |
| CMLD011039 | 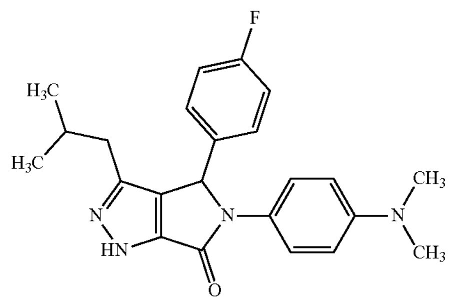 [SMILES: CC(C)Cc1n[nH]c2c1C(c1ccc(F)cc1)N(c1ccc(N(C)C)cc1)C2=O] | 4.5 | | | 1.0c | 39.8 | 0.3 | 5.2 | 39.8 | | | | |

TABLE 1-continued

Compiled Leishmania Data after Treatment with Antileishmanial Compounds

| Compound | Structure | LogPa | L. donovani amast-igotes % GI at 10 µM (THP-1 cells)b | THP-1 host cell % growth inhib-ition at 10 µMb | L. donovani amast-igotes EC50 (µM, THP-1c or B10Rd cells) | THP-1 Host Cell CC50 (µM)c | L. donovani amast-igotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promast-igotes EC50 (µM)f | L. major promast-igotes EC50 (µM)f |
|---|---|---|---|---|---|---|---|---|---|---|---|---|---|
| CMLD010899 | 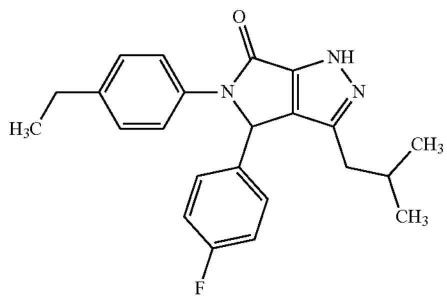 [SMILES: CCc1ccc(N2C(=O)c3[nH]nc(CC(C)C)c3C2c2ccc(F)cc2)cc1] | 3.7 | | | 4.0c | 20.0 | | | 5.0 | | | | |
| CMLD011113 | 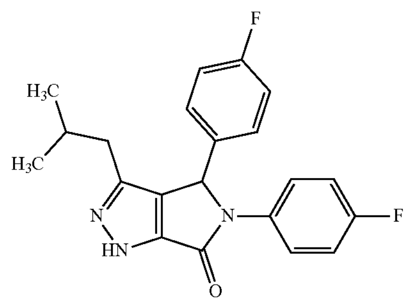 [SMILES: CC(C)Cc1n[nH]c2c1C(c1ccc(F)cc1)N(c1ccc(F)cc1)C2=O] | 4.3 | | | 6.3c | 25.1 | | | 4.0 | | | | |

TABLE 1-continued

Compiled Leishmania Data after Treatment with Antileishmanial Compounds

| Compound | Structure | LogPa | L. donovani amast-igotes % GI at 10 µM (THP-1 cells)b | THP-1 host cell % growth inhib-ition at 10 µMb | L. donovani amast-igotes EC50 (µM, THP-1c or B10Rd cells) | THP-1 Host Cell CC50 (µM)c | L. donovani amast-igotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promast-igotes EC50 (µM)f | L. major promast-igotes EC50 (µM)f |
|---|---|---|---|---|---|---|---|---|---|---|---|---|---|
| CMLD010897 | 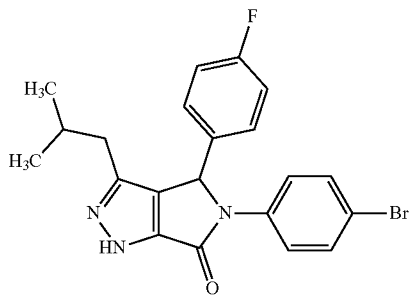 [SMILES: CC(C)Cc1n[nH]c2c1C(c1ccc(F)cc1)N(c1ccc(Br)cc1)C2=O] | 3.7 | | | 1.3c | 15.9 | | | 12.2 | | | | |
| CMLD011033 | 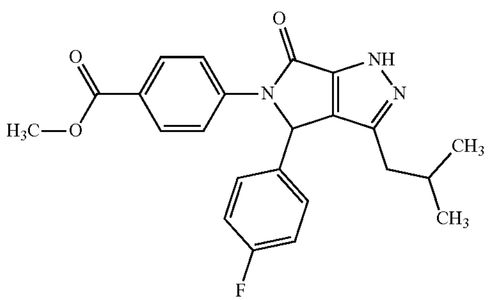 [SMILES: COC(=O)c1ccc(N2C(=O)c3[nH]nc(CC(C)C)c3C2c2ccc(F)cc2)cc1] | 5.0 | | | 1.6c | 31.6 | | | 20.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μM b | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011031 | 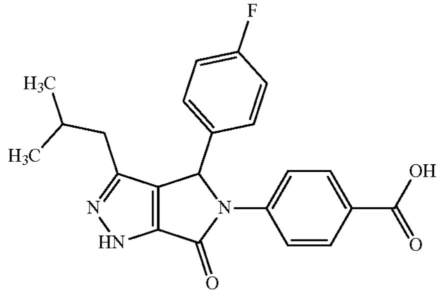 [SMILES: CC(C)Cc1n[nH]c2c1C(c1ccc(F)cc1)N(c1ccc(C(=O)O)cc1)C2=O] | 3.5 | | | >50c | >50 | | | n/a | | | | |
| CMLD011046 | 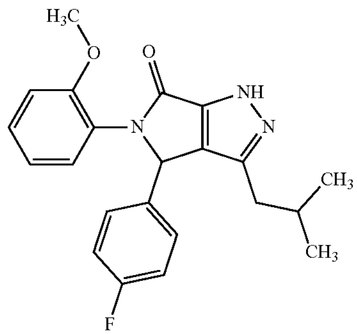 [SMILES: COc1ccccc1N1C(=O)c2[nH]nc(CC(C)C)c2C1c1ccc(F)cc1] | 3.9 | | | 20.0c | >50 | | | >2.5 | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µM b | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| CMLD010895 | 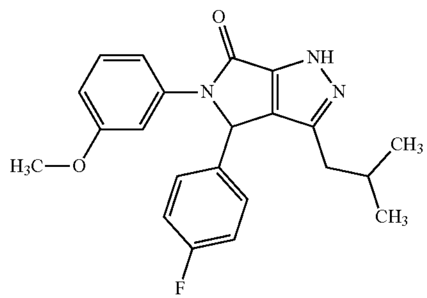 [SMILES: COc1cccc(N2C(=O)c3[nH]nc(CC(C)C)c3C2c2ccc(F)cc2)c1] | 3.0 | | | 12.6c | 31.6 | | | 2.5 | | | | |
| CMLD011098 | 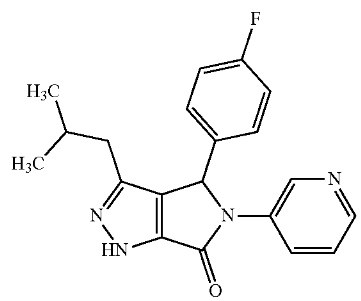 [SMILES: CC(C)Cc1n[nH]c2c1C(c1ccc(F)cc1)N(c1cccnc1)C2=O] | 5.8 | | | 25.1c | >50 | | | >2.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μM b | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011095 | | 4.7 | | | 20.2c | >50 | | | >2.5 | | | | |
| CMLD011026 | | 4.9 | | | 12.6c | 31.6 | | | >2.5 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011092 | 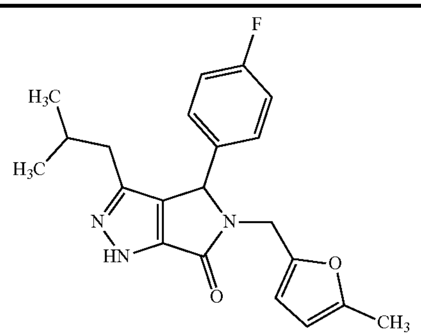 | 5.0 | | | 15.9c | 39.8 | | | >2.5 | | | | |
| CMLD011036 | 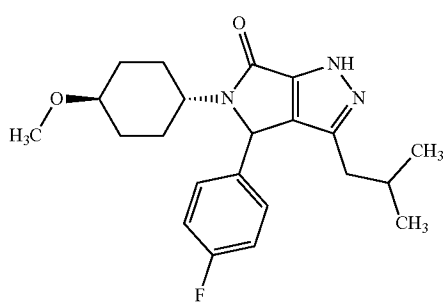 [SMILES: CO[C@H]1CC[C@H](N2C(=O)c3[nH]nc(CC(C)C)c3C2c2ccc(F)cc2)CC1] | 5.8 | | | 25.1c | >50 | | | >2.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μM b | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011124 | 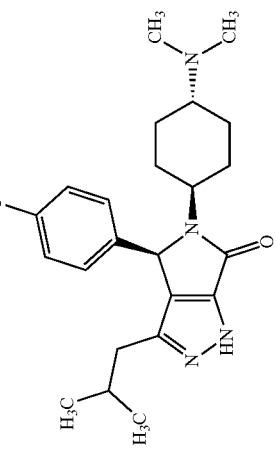 | 4.8 | | | 25.1c | >50 | | | >2.0 | | | | |
| CMLD011030 | 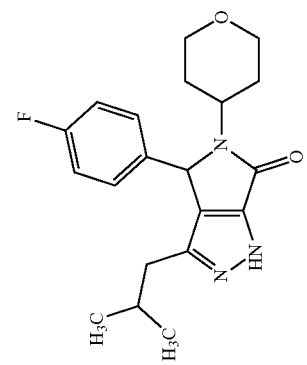 | 4.6 | | | 31.6c | >50 | | | >1.6 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011072 | 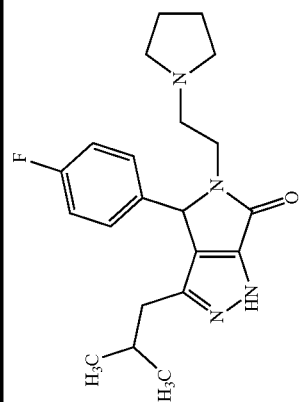 | 3.2 | | | 15.9c | >50 | >10 | >4.7 | >3.2 | | | | |
| CMLD011129 | 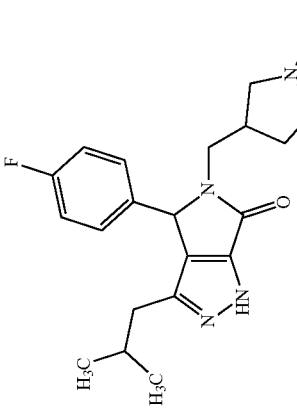 | 4.1 | | | >50c | >50 | | | >1.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J1774 cells)e | L. major amastigotes EC75 (μM, THP-1 b or J1774e cells) | L. donovani promastigotes EC50 (μM)f | L. major promastigotes EC50 (μM)f |
|---|---|---|---|---|---|---|---|---|---|---|---|---|---|
| CMLD011117 | 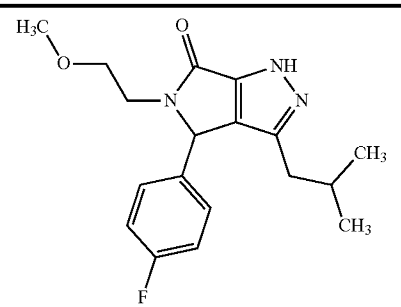 | 4.2 | | | >50c | >50 | | | >1.0 | | | | |
| CMLD010884 | 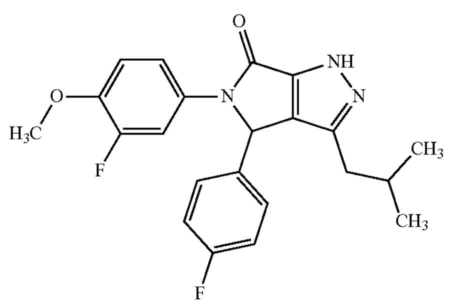 [SMILES: COc1ccc(N2C(=O)c3[nH]nc(CC(C)C)c3C2c2ccc(F)cc2)cc1F] | 4.4 | | | 1.3c | 25.1 | 0.8 | 4.7 | 19.3 | >10 | 7.2e | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD010992 | 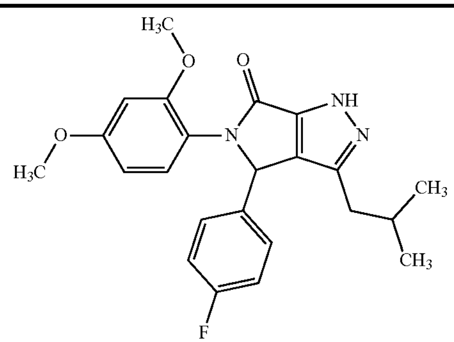 | 3.7 | | | 20.0c | 31.6 | | | 1.6 | | | | |
| CMLD010901 | 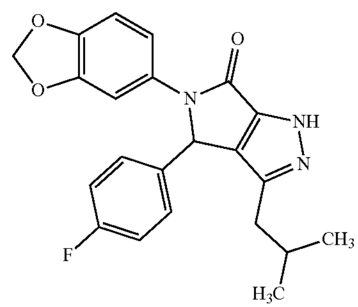 [SMILES: CC(C)Cc1n[nH]c2c1C(c1ccc(F)cc1)N(c1ccc3c(c1)OCO3)C2=O] | 4.0 | | | 0.6c | 25.1 | 0.4 | 4.9 | 41.8 | 8.7 | 6.0e | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011101 | 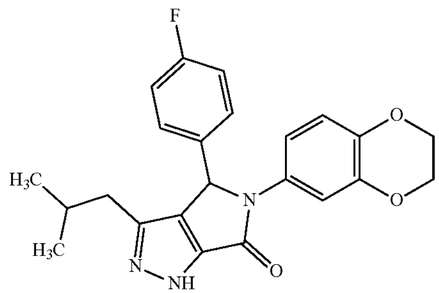 [SMILES: CC(C)Cc1n[nH]c2c1C(c1ccc(F)cc1)N(c1ccc3c(c1)OCCO3)C2=O] | 3.9 | | | 3.2c | 25.1 | 1.2 | 4.8 | 7.9 | | | | |
| CMLD010888 | 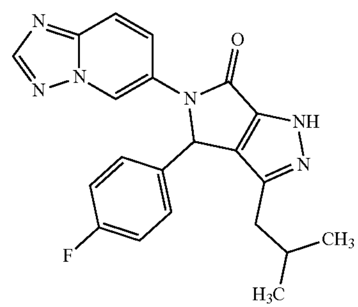 [SMILES: CC(C)Cc1n[nH]c2c1C(c1ccc(F)cc1)N(c1ccc3ncnn3c1)C2=O] | 3.6 | | | 5.0c | >50 | 2.3 | >4.7 | >10 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J1774 cells)e | L. major amastigotes EC75 (μM, THP-1 b or J1774e cells) | L. donovani promastigotes EC50 (μM)f | L. major promastigotes EC50 (μM)f |
|---|---|---|---|---|---|---|---|---|---|---|---|---|---|
| CMLD011096 | 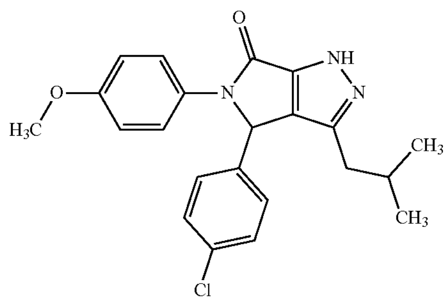 | 3.6 | | | 4.0c | 15.9 | | | 4.0 | | | | |
| CMLD010889 | 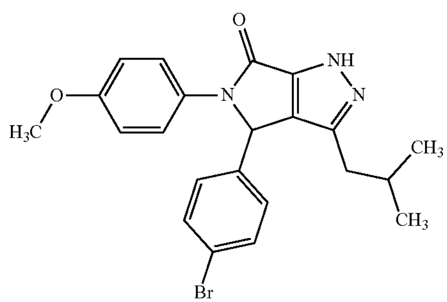 [SMILES: COc1ccc(N2C(=O)c3[nH]nc(CC(C)C)c3C2c2ccc(Br)cc2)cc1] | 1.9 | | | 6.3c | 15.9 | | | 2.5 | | | | |

TABLE 1-continued

Compiled Leishmania Data after Treatment with Antileishmanial Compounds

| Compound | Structure | LogPa | *L. donovani* amastigotes % GI at 10 μM (THP-1 cells)b | THP-1 host cell % growth inhibition at 10 μMb | *L. donovani* amastigotes EC50 (μM, THP-1c or B10Rd cells) | THP-1 Host Cell CC50 (μM)c | *L. donovani* amastigotes EC75 (μM B10R cells)d | B10R Host Cell CC50 (μM)d | SI (Host cell potency/ *L. donovani* potency) | *L. braziliensis* amastigotes EC75 (μM J774 cells)e | *L. major* amastigotes EC75 (μM, THP-1 b or J774e cells) | *L. donovani* promastigotes EC50 (μM)f | *L. major* promastigotes EC50 (μM)f |
|---|---|---|---|---|---|---|---|---|---|---|---|---|---|
| CMLD011121 | 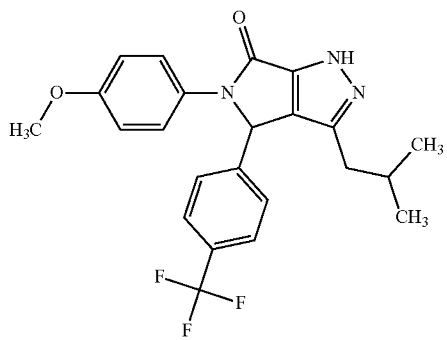 [SMILES: COc1ccc(N2C(=O)c3[nH]nc(CC(C)C)c3C2c2ccc(C(F)(F)F)cc2)cc1] | 4.6 | | | 8.0c | 15.9 | | | 2.0 | | | | |
| CMLD011032 | 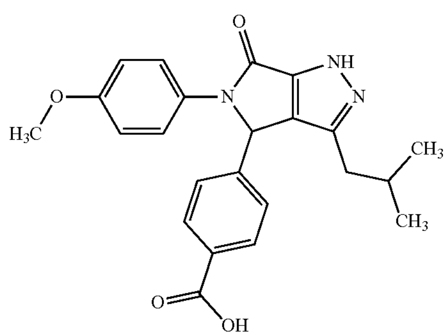 [SMILES: COc1ccc(N2C(=O)c3[nH]nc(CC(C)C)c3C2c2ccc(C(=O)O)cc2)cc1] | 3.6 | | | >50c | >50 | | | 1.0 | | | | |

TABLE 1-continued

Compiled Leishmania Data after Treatment with Antileishmanial Compounds

| Compound | Structure | LogP[a] | L. donovani amastigotes % GI at 10 μM (THP-1 cells)[b] | THP-1 host cell % growth inhibition at 10 μM[b] | L. donovani amastigotes EC50 (μM, THP-1c or B10Rd cells) | THP-1 Host Cell CC50 (μM)[c] | L. donovani amastigotes EC75 (μM B10R cells)[d] | B10R Host Cell CC50 (μM)[d] | SI (Host cell potency/ L. donovani potency) | L. braziliensis amastigotes EC75 (μM J774 cells)[e] | L. major amastigotes EC75 (μM, THP-1 b or J774e cells) | L. donovani promastigotes EC50 (μM)[f] | L. major promastigotes EC50 (μM)[f] |
|---|---|---|---|---|---|---|---|---|---|---|---|---|---|
| CMLD011034 | 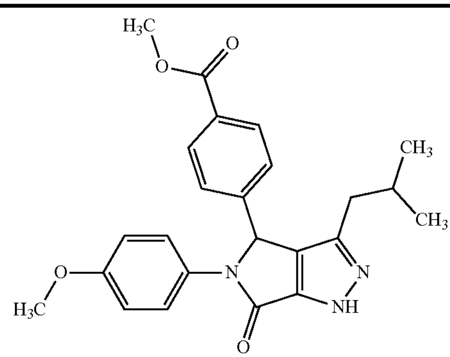 | 5.0 | | | 25.1c | 39.8 | | | 1.6 | | | | |
| CMLD010892 | 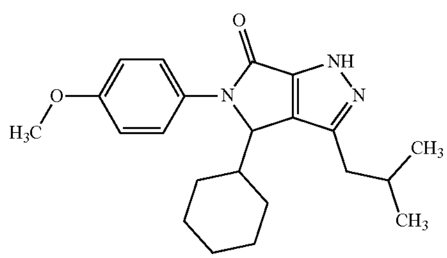 [SMILES: COc1ccc(N2C(=O)c3[nH]nc(CC(C)C)c3C2C2CCCCC2)cc1] | 2.6 | | | 7.9c | 25.1 | | | 3.2 | | | | |
| CMLD010978 | 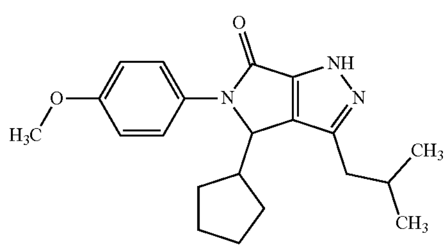 [SMILES: COc1ccc(N2C(=O)c3[nH]nc(CC(C)C)c3C2C2CCCC2)cc1] | 3.3 | | | 12.6c | 20.0 | | | 1.6 | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| CMLD011102 | 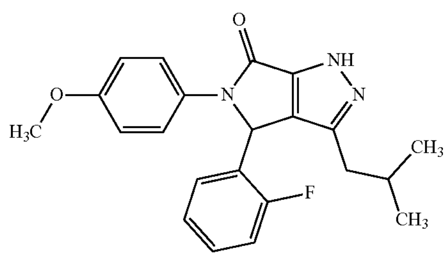 [SMILES: COc1ccc(N2C(=O)c3[nH]nc(CC(C)C)c3C2c2ccccc2F)cc1] | 4.9 | | | 3.2c | 31.6 | | | 9.9 | | | | |
| CMLD010893 | 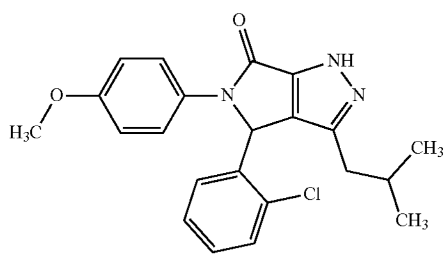 | 4.7 | | | 1.3c | 20.0 | 0.3 | 5.2 | 15.3 | >10 | 8.3e | | |
| CMLD010894 | 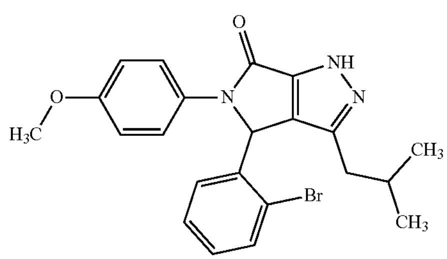 | 2.9 | | | 0.5c | 25.1 | | | 50.2 | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| CMLD010994 | | 5.0 | | | 0.5c | 25.1 | | | 50.2 | | | | |
| CMLD010890 | | 1.8 | | | 5.0c | 12.6 | | | 2.5 | | | | |
| CMLD011099 | | 2.7 | | | 7.9c | 39.8 | | | 5.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD010891 | 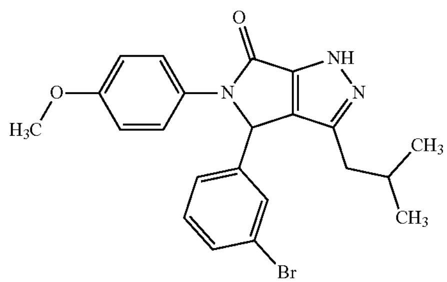 [SMILES: COc1ccc(N2C(=O)c3[nH]nc(CC(C)C)c3C2c2cccc(Br)c2)cc1] | 2.7 | | | 7.9c | 25.1 | | | 3.2 | | | | |
| CMLD011088 | 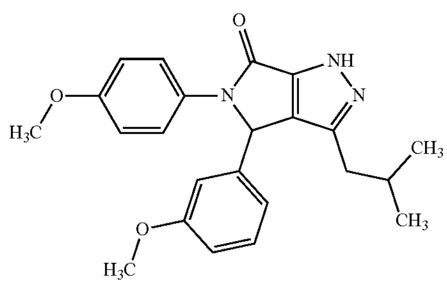 [SMILES: COc1ccc(N2C(=O)c3[nH]nc(CC(C)C)c3C2c2cccc(OC)c2)cc1] | 5.6 | | | 4.0c | 20.0 | | | 5.0 | | | | |
| CMLD007432 | 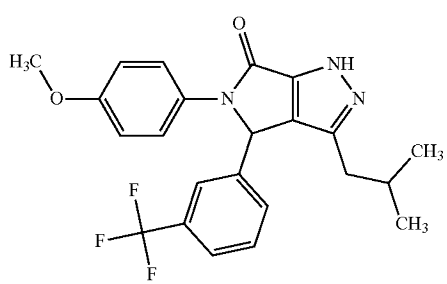 [SMILES: COc1ccc(N2C(=O)c3[nH]nc(CC(C)C)c3C2c2cccc(C(F)(F)F)c2)cc1] | 4.5 | | | 6.3c | 15.9 | | | 2.5 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011079 | 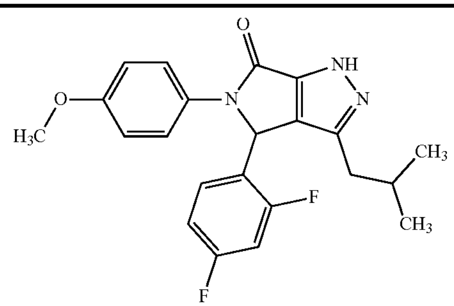 | 4.2 | | | 2.0c | 25.1 | | | 12.6 | | | | |
| CMLD010902 | 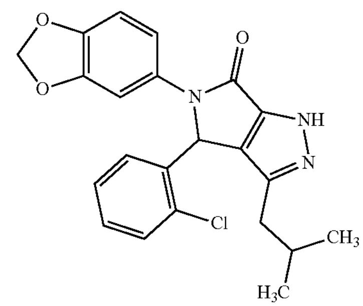 [SMILES: CC(C)Cc1n[nH]c2c1C(c1ccccc1Cl)N(c1ccc3c(c1)OCO3)C2=O] | 4.5 | | | 0.2d | 12.2 | | | 76.4 | >10 | 7.3e | | |
| CMLD011548 | 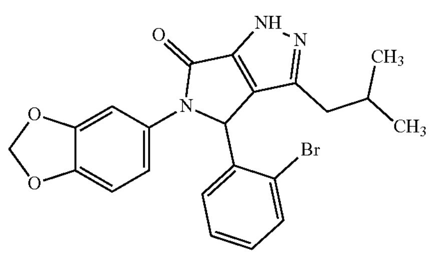 [SMILES: CC(C)Cc1n[nH]c2c1C(c1ccccc1Br)N(c1ccc3c(c1)OCO3)C2=O] | 4.6 | | | 0.3d | >20 | | | >69.0 | 5.2 | 1.8e | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011546 | 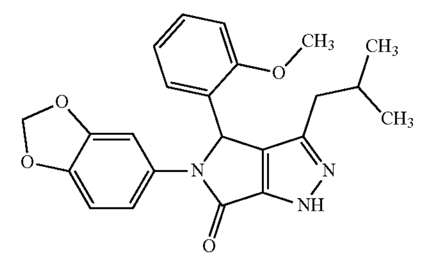 [SMILES: COc1ccccc1C1c2c(CC(C)C)n[nH]c2C(=O)N1c1ccc2c(c1)OCO2] | 3.7 | | | 0.3d | >20 | 0.3 | >4.7 | >74.1 | | | | |
| CMLD011564 | 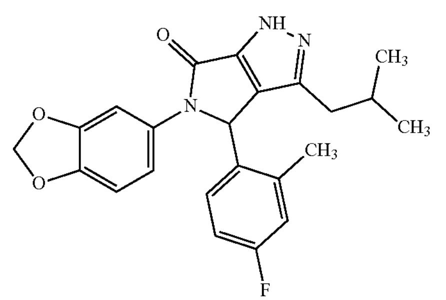 [SMILES: Cc1cc(F)ccc1C1c2c(CC(C)C)n[nH]c2C(=O)N1c1ccc2c(c1)OCO2] | 4.5 | | | 0.1d | 12.1 | 0.1 | 4.9 | 120.8 | 4.9 | 1.4e | | |
| CMLD012217 | 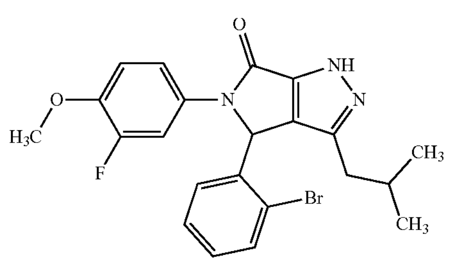 [SMILES: COc1ccc(N2C(=O)c3[nH]nc(CC(C)C)c3C2c2ccccc2Br)cc1F] | 5.0 | | | 0.4d | 3.0 | 0.5 | 5.4 | 7.2 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011566 | 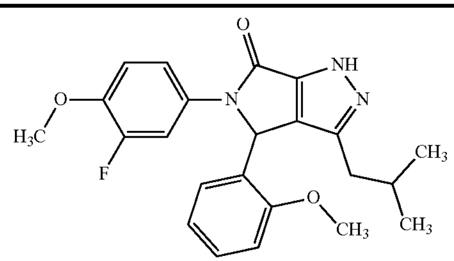 | 4.1 | | | 0.4d | 0.3 | 0.4 | 6.5 | 0.7 | | | | |
| CMLD011562 | 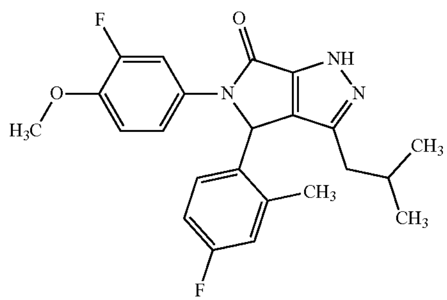 [SMILES: COc1ccc(N2C(=O)c3[nH]nc(CC(C)C)c3C2c2ccc(F)cc2C)cc1F] | 4.9 | | | 0.2d | 10.9 | 0.2 | 5.0 | 68.1 | 5.2 | 2.7e | | |
| CMLD011551 | 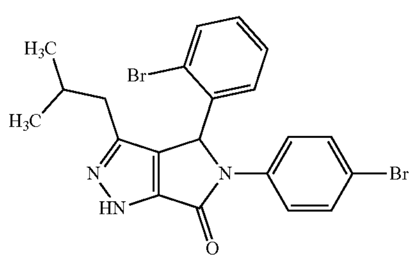 [SMILES: CC(C)Cc1n[nH]c2c1C(c1ccccc1Br)N(c1ccc(Br)cc1)C2=O] | 5.8 | | | 0.4d | 5.0 | 0.5 | 5.2 | 12.8 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011549 | | 4.9 | | | 0.2d | 1.1 | 0.3 | 6.0 | 4.8 | | | | |
| CMLD011565 | | 5.7 | | | 0.1d | 3.0 | 0.1 | 5.4 | 25.3 | 5.0 | | | |
| CMLD011494 | | 5.0 | | | 0.1d | 4.0 | 0.1 | 5.4 | 33.7 | 5.2 | 2.8e | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD010920 | 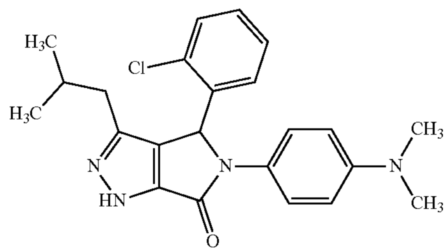 [SMILES: CC(C)Cc1n[nH]c2c1C(c1ccccc1Cl)N(c1ccc(N(C)C)cc1)C2=O] | 5.0 | | | 0.3d | 7.3 | 0.3 | 5.2 | 28.2 | | | | |
| CMLD011554 | 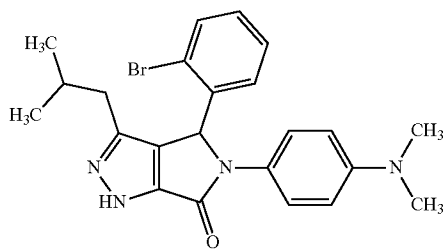 [SMILES: CC(C)Cc1n[nH]c2c1C(c1ccccc1Br)N(c1ccc(N(C)C)cc1)C2=O] | 5.1 | | | 0.1d | 5.7 | 0.1 | 5.2 | 71.5 | 2.9 | 5.2e | | |
| CMLD011552 | 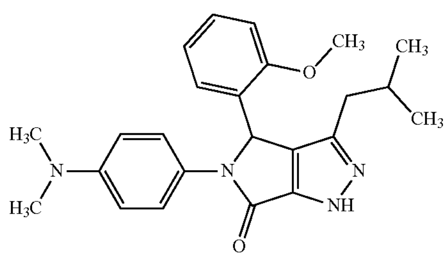 [SMILES: COc1ccccc1C1c2c(CC(C)C)n[nH]c2C(=O)N1c1ccc(N(C)C)cc1] | 4.2 | | | 0.1d | 3.5 | 0.1 | 5.4 | 49.3 | >10 | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μM b | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011561 | 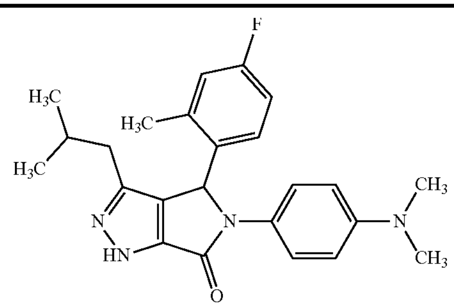 | 5.0 | | | 0.1d | 7.5 | 0.1 | 5.1 | 68.3 | 2.1 | 1.9e | | |
| CMLD011572 | 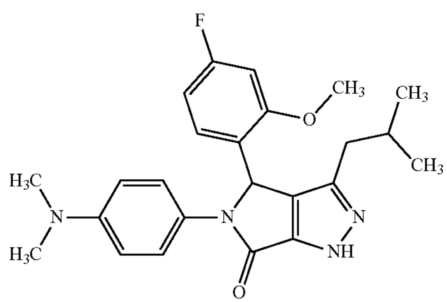 [SMILES: COc1cc(F)ccc1C1c2c(CC(C)C)n[nH]c2C(=O)N1c1ccc(N(C)C)cc1] | 4.3 | | | 0.0d | 8.5 | 0.0 | 5.0 | 212.5 | 1.9 | 1.3e | | |
| BUCMD00686 | 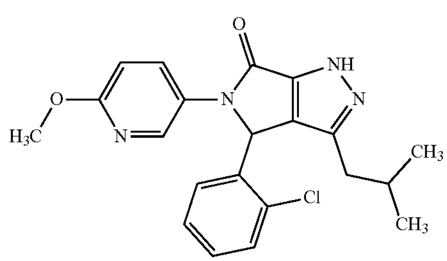 [SMILES: COc1ccc(N2C(=O)c3[nH]nc(CC(C)C)c3C2c2ccccc2Cl)cn1] | 4.1 | | | 1.1d | 9.9 | 0.5 | 5.0 | 8.9 | 1.0 | >10e | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774 cells) | L. donovani promastigotes EC50 (µM)f | L. major promastigotes EC50 (µM)f |
|---|---|---|---|---|---|---|---|---|---|---|---|---|---|
| CMLD012218 | 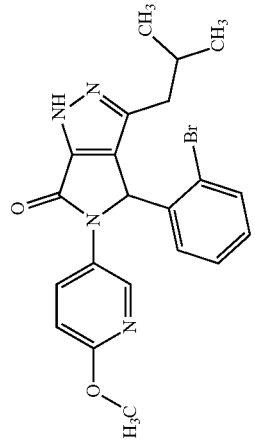 | 4.2 | | | 1.0d | >20 | 0.4 | >4.7 | >54.1 | | | | |
| CMLD011567 | 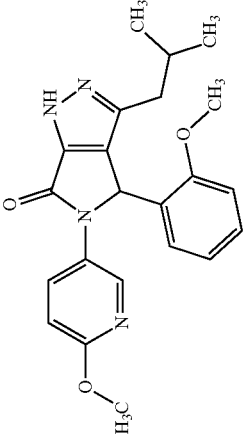 | 3.3 | | | 1.1d | >20 | 1.2 | 4.7 | >76.9 | | | | |
| BUCMD00683 | 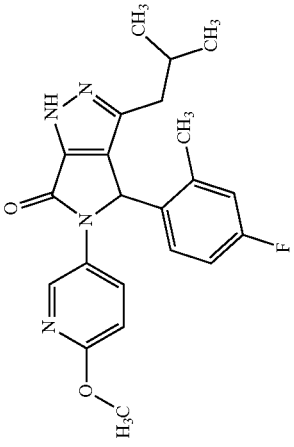 | 4.1 | | | 0.4d | >20 | 0.6 | >4.7 | >36.4 | | | | |

TABLE 1-continued

Compiled Leishmania Data after Treatment with Antileishmanial Compounds

| Compound | Structure | LogP a | L. donovani amast- igotes % GI at 10 µM (THP-1 cells)b | THP-1 host cell % growth inhib- ition at 10 µMb | L. donovani amast- igotes EC50 (µM, THP-1c or B10Rd cells) | THP-1 Host Cell CC50 (µM)c | L. donovani amast- igotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promast- igotes EC50 (µM)f | L. major pronast- igotes EC50 (µM)f |
|---|---|---|---|---|---|---|---|---|---|---|---|---|---|
| CMLD011574 | 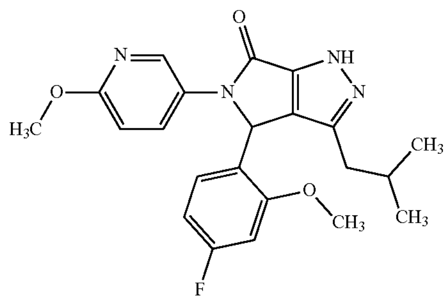 [SMILES: COc1ccc(N2C(=O)c3[nH]nc(CC(C)C)c3C2c2ccc(F)cc2OC)cn1] | 3.5 | | | 0.3d | >20 | 0.3 | >4.7 | >23.0 | 8.2 | 4.8e | | |
| CMLD010921 | 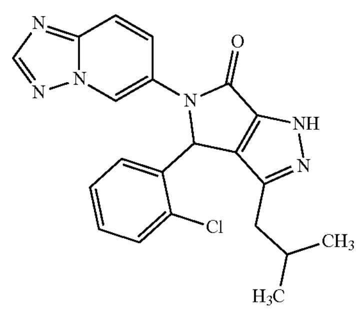 | 4.0 | | | 0.6d | >20 | 0.6 | >4.7 | >55.6 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μM b | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD010948 | 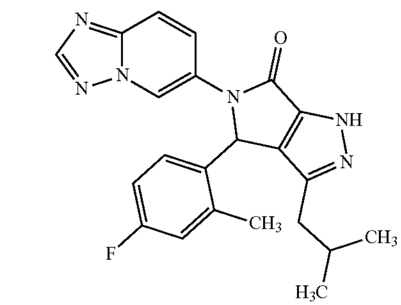 [SMILES: Cc1cc(F)ccc1C1c2c(CC(C)C)n[nH]c2C(=O)N1c1ccc2ncnn2c1] | 4.1 | | | 0.9d | >20 | 1.1 | >4.7 | >24.4 | 5.5 | | | |
| CMLD010882 | 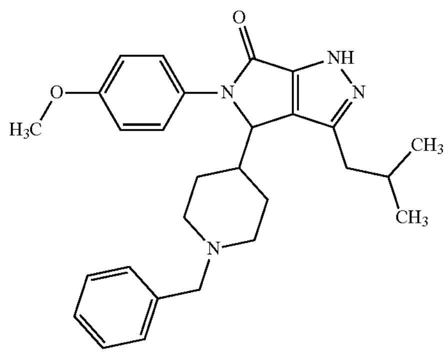 [SMILES: COc1ccc(N2C(=O)c3[nH]nc(CC(C)C)c3C2C2CCN(Cc3ccccc3)CC2)cc1] | 3.3 | | | 15.9c | 20.0 | | | 1.3 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011104 | 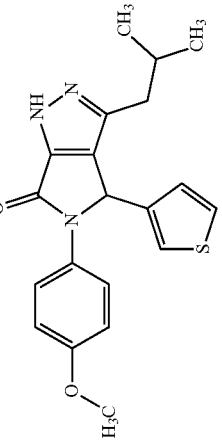 | 3.9 | | | 6.3c | >50 | | | >7.9 | | | | |
| CMLD010991 | 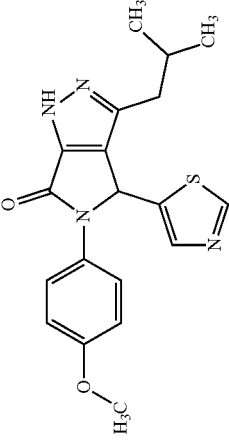 | 3.7 | | | 15.9c | >50 | | | >3.1 | | | | |
| CMLD011075 | 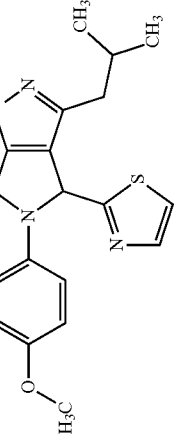 | 4.1 | | | 20.0c | >50 | | | >2.5 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011142 | 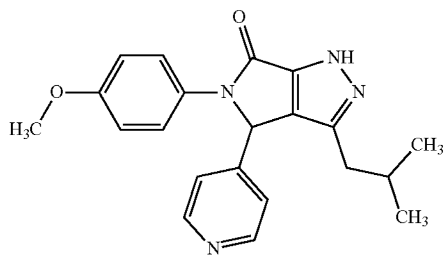 [SMILES: COc1ccc(N2C(=O)c3[nH]nc(CC(C)C)c3C2c2ccncc2)cc1] | 4.3 | | | >50c | >50 | | | 1.0 | | | | |
| CMLD011125 | 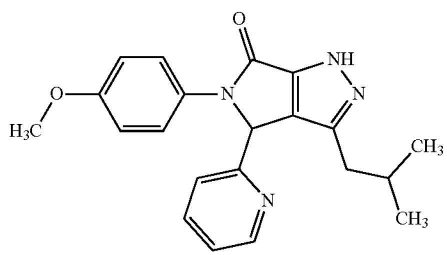 [SMILES: COc1ccc(N2C(=O)c3[nH]nc(CC(C)C)c3C2c2ccccn2)cc1] | 4.0 | | | 31.6c | >50 | | | >1.6 | | | | |
| CMLD010887 | 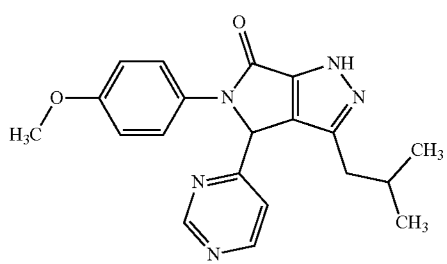 [SMILES: COc1ccc(N2C(=O)c3[nH]nc(CC(C)C)c3C2c2ccncn2)cc1] | 6.1 | | | >50c | >50 | | | 1.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011100 | 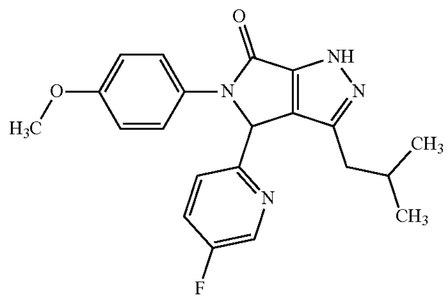 | 3.3 | | | 10.0c | >50 | 4.4 | >4.7 | >5.0 | >10 | | | |
| CMLD010886 | 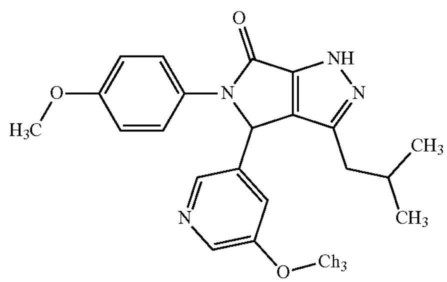 | 3.8 | | | 10.0c | 20.0 | | | 2.0 | | | | |
| CMLD011575 | 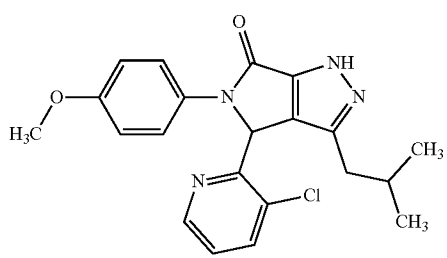 [SMILES: COc1ccc(N2C(=O)c3[nH]nc(CC(C)C)c3C2c2ncccc2Cl)cc1] | 4.1 | | | 10.0c | 20.0 | | | 2.0 | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µM b | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| CMLD011496 | 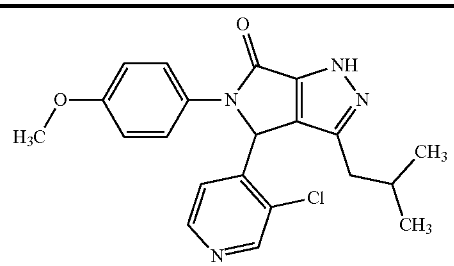 | 3.6 | | | 10.0c | 20.0 | | | 2.0 | | | | |
| CMLD011027 | 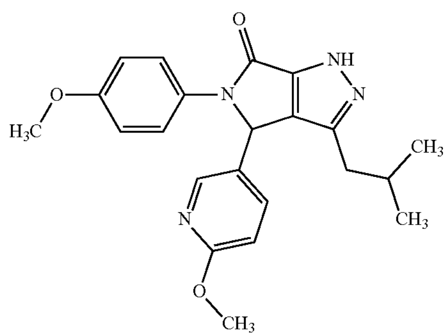 [SMILES: COc1ccc(N2C(=O)c3[nH]nc(CC(C)C)c3C2c2ccc(OC)nc2)cc1] | 4.1 | | | >50c | >50 | | | 1.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011120 | 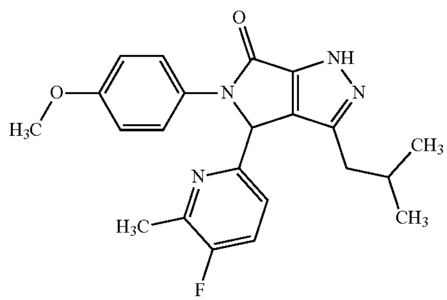 [SMILES: COc1ccc(N2C(=O)c3[nH]nc(CC(C)C)c3C2c2ccc(F)c(C)n2)cc1] | 5.2 | | | 12.6c | >50 | | | >4.0 | | | | |
| CMLD011579 | 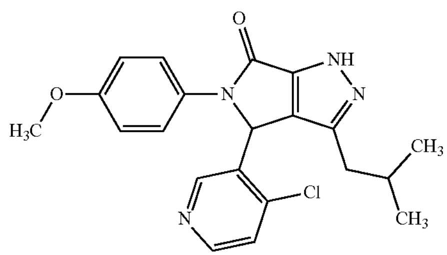 [SMILES: COc1ccc(N2C(=O)c3[nH]nc(CC(C)C)c3C2c2cnccc2Cl)cc1] | 2.7 | | | >100c | 20.0 | | | <0.2 | | | | |
| CMLD011559 | 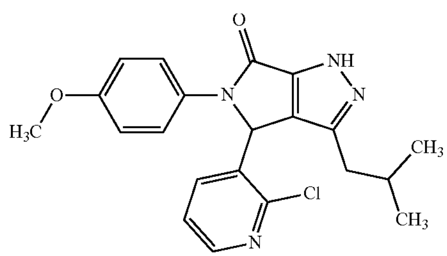 | 4.4 | | | >100c | 20.0 | | | <0.2 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μM b | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011028 | 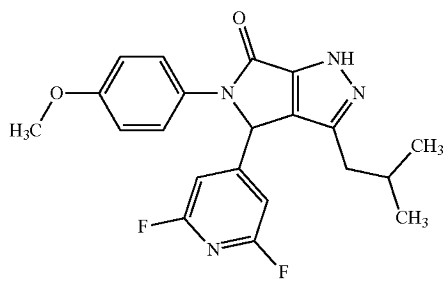 [SMILES: COc1ccc(N2C(=O)c3[nH]nc(CC(C)C)c3C2c2cc(F)nc(F)c2)cc1] | 3.5 | | | >50c | >50 | | | 1.0 | | | | |
| CMLD011577 | 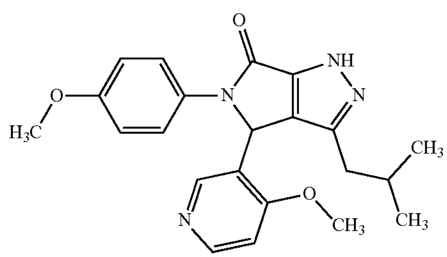 [SMILES: COc1ccc(N2C(=O)c3[nH]nc(CC(C)C)c3C2c2cnccc2OC)cc1] | 4.4 | | | 10.0c | 20.0 | | | 2.0 | | | | |
| CMLD011578 | 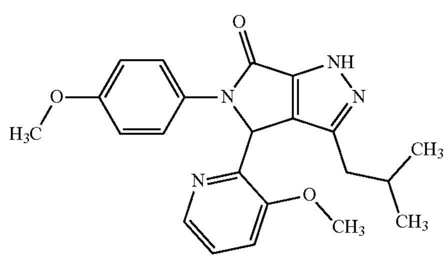 [SMILES: COc1ccc(N2C(=O)c3[nH]nc(CC(C)C)c3C2c2ncccc2OC)cc1] | 5.1 | | | >100c | 20.0 | | | <0.2 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| CMLD007169 | 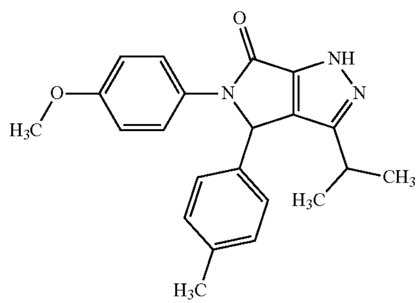 [SMILES: COc1ccc(N2C(=O)c3[nH]nc(C(C)C)c3C2c2ccc(C)cc2)cc1] | 4.4 | 0.0 | <10 | | | | | | | | | |
| CMLD007188 | 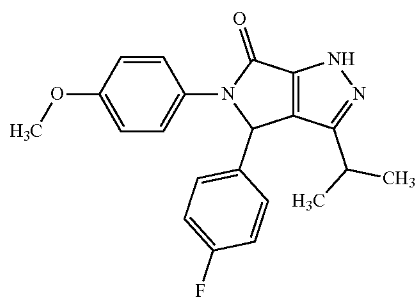 [SMILES: COc1ccc(N2C(=O)c3[nH]nc(C(C)C)c3C2c2ccc(F)cc2)cc1] | 4.0 | 0.0 | <10 | | | | | | | | | |
| CMLD007203 | 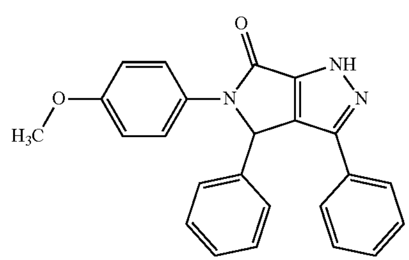 [SMILES: COc1ccc(N2C(=O)c3[nH]nc(-c4ccccc4)c3C2c2ccccc2)cc1] | 4.6 | 0.0 | <10 | | | | | | | | | |

TABLE 1-continued

Compiled Leishmania Data after Treatment with Antileishmanial Compounds

| Compound | Structure | LogPa | L. donovani amast- igotes % GI at 10 µM (THP- 1 cells)b | THP-1 host cell % growth inhib- ition at 10 µM | L. donovani amast- igotes EC50 (µM, THP-1c or B10Rd cells) | THP-1 Host Cell CC50 (µM)c | L. donovani amast- igotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promast- igotes EC50 (µM)f | L. major pronast- igotes EC50 (µM)f |
|---|---|---|---|---|---|---|---|---|---|---|---|---|---|
| CMLD007219 | 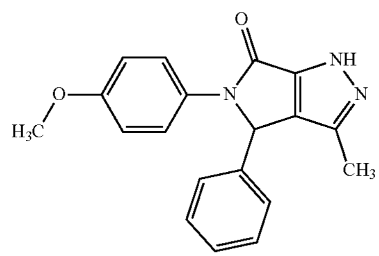 [SMILES: COc1ccc(N2C(=O)c3[nH]nc(C)c3C2c2ccccc2)cc1] | 2.7 | 0.0 | <10 | | | | | | | | | |
| CMLD007221 | 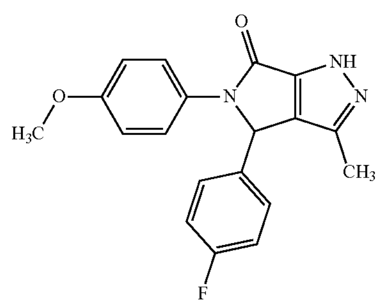 [SMILES: COc1ccc(N2C(=O)c3[nH]nc(C)c3C2c2ccc(F)cc2)cc1] | 2.8 | 0.0 | <10 | | | | | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| CMLD007235 | 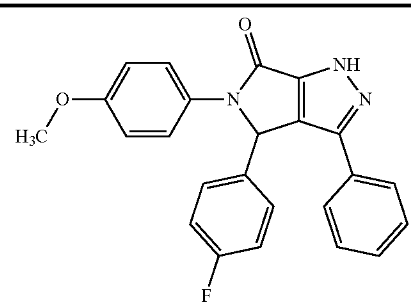 | 4.7 | 0.0 | 30.0 | | | | | | | | | |
| CMLD007421 | 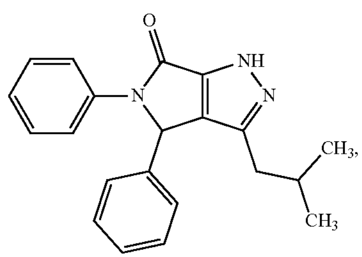 [SMILES: CC(C)Cc1n[nH]c2c1C(c1ccccc1)N(c1ccccc1)C2=O] | 2.7 | 0.0 | <10 | | | | | | | | | |
| CMLD007247 | 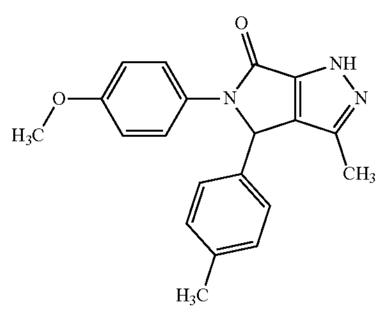 [SMILES: COc1ccc(N2C(=O)c3[nH]nc(C)c3C2c2ccc(C)cc2)cc1] | 3.2 | 0.0 | <10 | | | | | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD007262 | 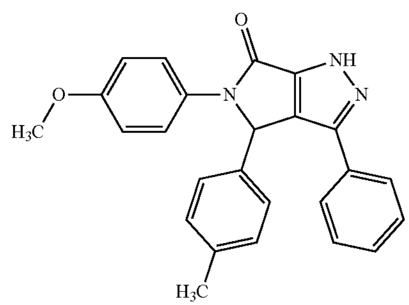 [SMILES: COc1ccc(N2C(=O)c3[nH]nc(-c4ccccc4)c3C2c2ccc(C)cc2)cc1] | 5.1 | 0.0 | <10 | | | | | | | | | |
| CMLD007286 | 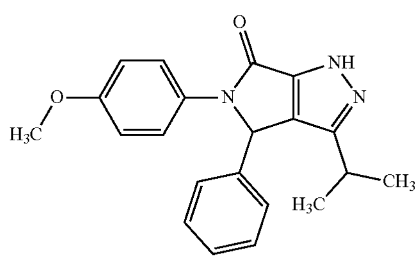 [SMILES: COc1ccc(N2C(=O)c3[nH]nc(C(C)C)c3C2c2ccccc2)cc1] | 3.9 | 0.0 | <10 | | | | | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD007424 | 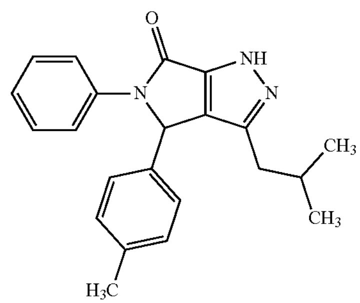 [SMILES: Cc1ccc(C2c3c(CC(C)C)n[nH]c3C(=O)N2c2ccccc2)cc1] | 4.8 | 81.0 | 35.0 | | | | | | | | | |
| CMLD007425 | 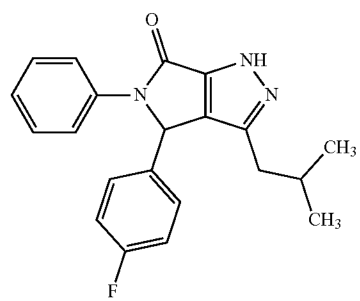 [SMILES: CC(C)Cc1n[nH]c2c1C(c1ccc(F)cc1)N(c1ccccc1)C2=O] | 4.4 | 15.0 | 13.0 | | | | | | | | | |

TABLE 1-continued

Compiled Leishmania Data after Treatment with Antileishmanial Compounds

| Compound | Structure | LogP[a] | L. donovani amastigotes % GI at 10 μM (THP-1 cells)[b] | THP-1 host cell % growth inhibition at 10 μM[b] | L. donovani amastigotes EC50 (μM, THP-1c or B10Rd cells) | THP-1 Host Cell CC50 (μM)[c] | L. donovani amastigotes EC75 (μM B10R cells)[d] | B10R Host Cell CC50 (μM)[d] | SI (Host cell potency/ L. donovani potency) | L. braziliensis amastigotes EC75 (μM J774 cells)[e] | L. major amastigotes EC75 (μM, THP-1 b or J774e cells) | L. donovani promastigotes EC50 (μM)[f] | L. major promastigotes EC50 (μM)[f] |
|---|---|---|---|---|---|---|---|---|---|---|---|---|---|
| CMLD007430 | 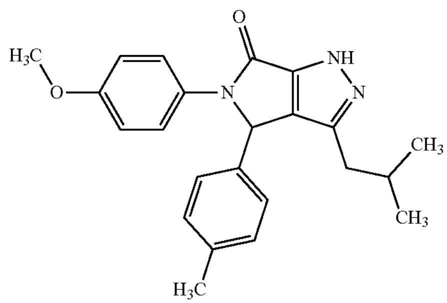 [SMILES: COc1ccc(N2C(=O)c3[nH]nc(CC(C)C)c3C2c2ccc(C)cc2)cc1] | 4.2 | 0.0 | <10 | | | | | | | | | |
| CMLD010949 | 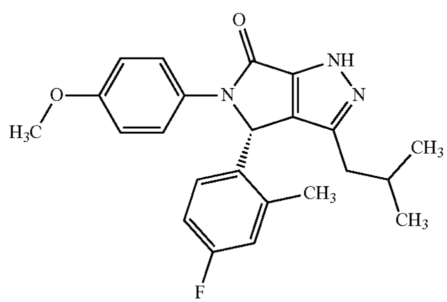 | 4.1 | | | 0.5c | 39.8 | | | 79.4 | | | | |

TABLE 1-continued

Compiled Leishmania Data after Treatment with Antileishmanial Compounds

| Compound | Structure | LogPa | *L. donovani* amastigotes % GI at 10 μM (THP-1 cells)b | THP-1 host cell % growth inhibition at 10 μMb | *L. donovani* amastigotes EC50 (μM, THP-1c or B10Rd cells) | THP-1 Host Cell CC50 (μM)c | *L. donovani* amastigotes EC75 (μM B10R cells)d | B10R Host Cell CC50 (μM)d | SI (Host cell potency/ *L. donovani* potency) | *L. braziliensis* amastigotes EC75 (μM J774 cells)e | *L. major* amastigotes EC75 (μM, THP-1 b or J774 cells) | *L. donovani* promastigotes EC50 (μM)f | *L. major* promastigotes EC50 (μM)f |
|---|---|---|---|---|---|---|---|---|---|---|---|---|---|
| CMLD011573 | 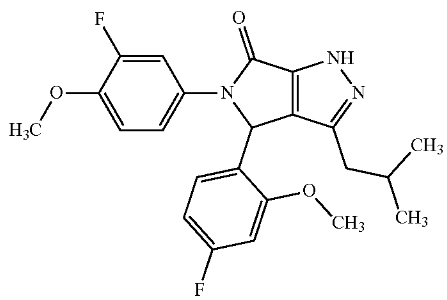 [SMILES: COc1ccc(N2C(=O)c3[nH]nc(CC(C)C)c3C2c2ccc(F)cc2OC)cc1F] | 4.3 | | | 0.5c | 7.9 | | | 15.8 | | | | |
| BUCMD00800 | 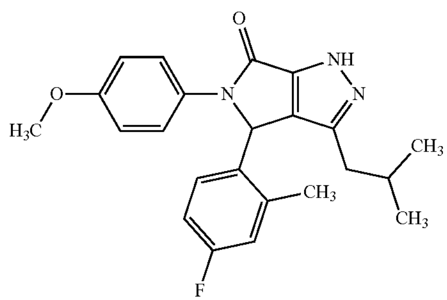 [SMILES: COc1ccc(N2C(=O)c3[nH]nc(CC(C)C)c3C2c2ccc(F)cc2C)cc1] | 4.8 | | | 0.5c | 25.1 | | | 50.1 | | | | |
| BUCMD00797 | 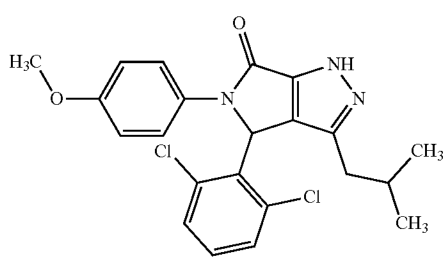 [SMILES: COc1ccc(N2C(=O)c3[nH]nc(CC(C)C)c3C2c2c(Cl)cccc2Cl)cc1] | 5.3 | | | 1.0c | 2.5 | | | | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| CMLD010987 | 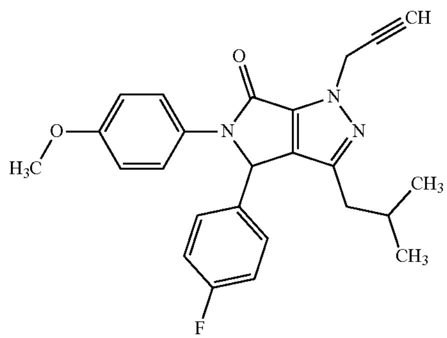 [SMILES: C#CCn1nc(CC(C)C)c2c1C(=O)N(c1ccc(OC)cc1)C2c1ccc(F)cc1] | 4.6 | | | 1.6c | 20.0 | 4.0 | >5 | 12.6 | | | | |
| CMLD010898 | 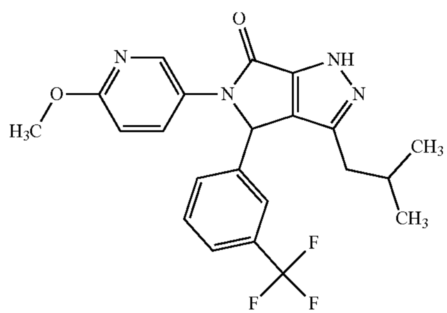 [SMILES: COc1ccc(N2C(=O)c3[nH]nc(CC(C)C)c3C2c2cccc(C(F)(F)F)c2)cn1] | 3.9 | | | 2.0c | 20.0 | | | 10.0 | | | | |

TABLE 1-continued

Compiled Leishmania Data after Treatment with Antileishmanial Compounds

| Compound | Structure | LogPa | *L. donovani* amastigotes % GI at 10 μM (THP-1 cells)b | THP-1 host cell % growth inhibition at 10 μMb | *L. donovani* amastigotes EC50 (μM, THP-1c or B10Rd cells) | THP-1 Host Cell CC50 (μM)c | *L. donovani* amastigotes EC75 (μM B10R cells)d | B10R Host Cell CC50 (μM)d | SI (Host cell potency/ *L. donovani* potency) | *L. braziliensis* amastigotes EC75 (μM J774 cells)e | *L. major* amastigotes EC75 (μM, THP-1 b or J774e cells) | *L. donovani* promastigotes EC50 (μM)f | *L. major* promastigotes EC50 (μM)f |
|---|---|---|---|---|---|---|---|---|---|---|---|---|---|
| CMLD011119 | 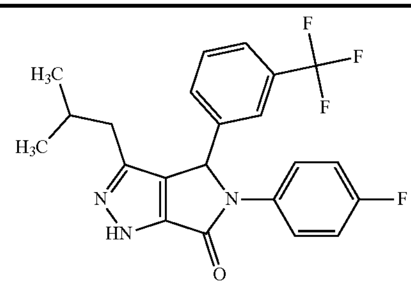 | 3.9 | | | 2.5c | 25.1 | | | 10.0 | | | | |
| CMLD011547 | 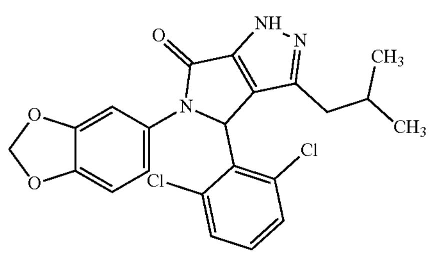 [SMILES: CC(C)Cc1n[nH]c2c1C(c1c(Cl)cccc1Cl)N(c1ccc3c(c1)OCO3)C2=O] | 5.9 | | | 2.5c | 20.0 | | | 7.9 | | | | |
| CMLD011131 | 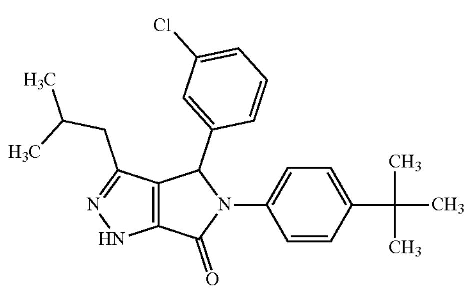 [SMILES: CC(C)Cc1n[nH]c2c1C(c1cccc(Cl)c1)N(c1ccc(C(C)(C)C)cc1)C2=O] | 4.7 | | | 2.5c | 15.8 | | | 6.3 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011105 | 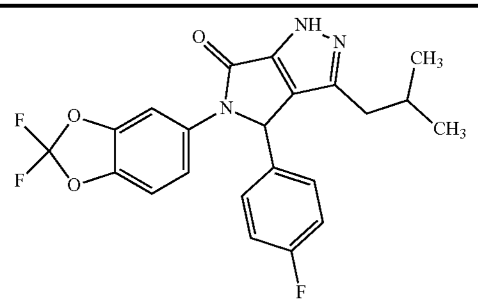 | 4.9 | | | 2.5c | 12.6 | | | 5.0 | | | | |
| BUCMD00815 | 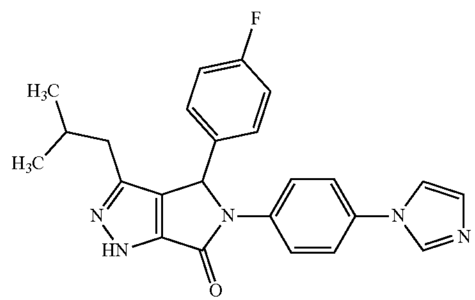 [SMILES: CC(C)Cc1n[nH]c2c1C(c1ccc(F)cc1)N(c1ccc(-n3ccnc3)cc1)C2=O] | 4.1 | | | 2.5c | >50 | | | >20 | | | | |

TABLE 1-continued

Compiled Leishmania Data after Treatment with Antileishmanial Compounds

| Compound | Structure | LogPa | L. donovani amast- igotes % GI at 10 µM (THP- 1 cells)b | THP-1 host cell % growth inhib- ition at 10 µMb | L. donovani amast- igotes EC50 (µM, THP-1c or B10Rd cells) | THP-1 Host Cell CC50 (µM)c | L. donovani amast- igotes EC75 (µM B10R cells)d | B10R Host Cell CC50 (µM)d | SI (Host cell potency/ L. donovani potency) | L. braziliensis amastigotes EC75 (µM J1774 cells)e | L. major amastigotes EC75 (µM, THP-1 b or J1774e cells) | L. donovani promast- igotes EC50 (µM)f | L. major promast- igotes EC50 (µM)f |
|---|---|---|---|---|---|---|---|---|---|---|---|---|---|
| CMLD011499 | 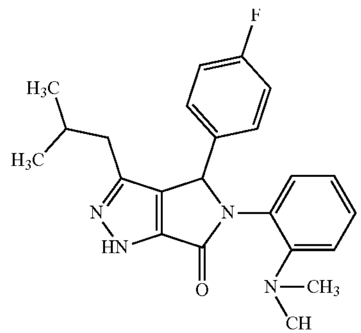 [SMILES: CC(C)Cc1n[nH]c2c1C(c1ccc(F)cc1)N(c1ccccc1N(C)C)C2=O] | 3.9 | | | 3.2c | 10.0 | | | 3.2 | | | | |
| BUCMD00812 | 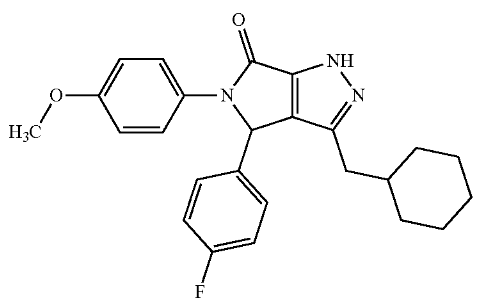 [SMILES: COc1ccc(N2C(=O)c3[nH]nc(CC4CCCCC4)c3C2c2ccc(F)cc2)cc1] | 5.1 | | | 3.2c | 20.0 | | | 6.3 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| CMLD010896 | 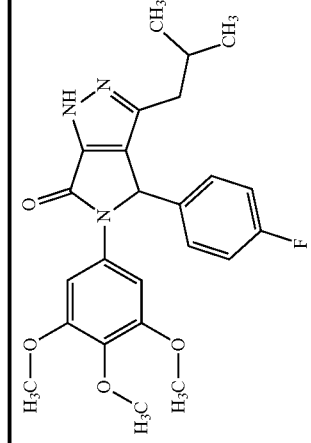 | 4.1 | | | 4.0c | 3.2 | | | 0.8 | | | | |
| CMLD011111 | 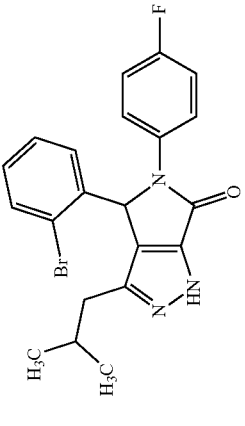 | 3.9 | | | 4.0c | 15.8 | | | 4.0 | | | | |
| CMLD011135 | 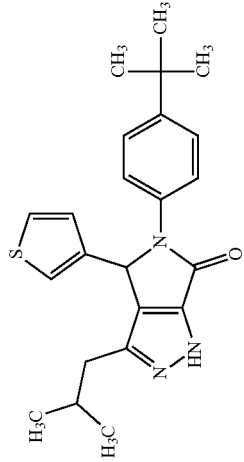 | 4.7 | | | 4.0c | >50 | | | >12.9 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μM b | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00809 | 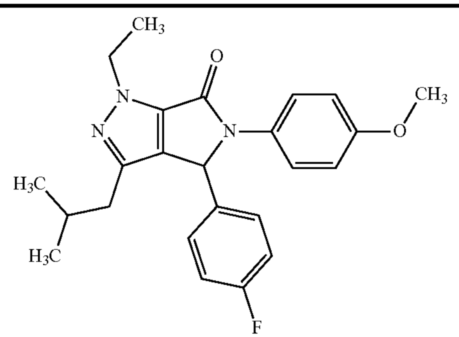 | 4.7 | | | 4.0c | 39.8 | | | 10.0 | | | | |
| CMLD011569 | 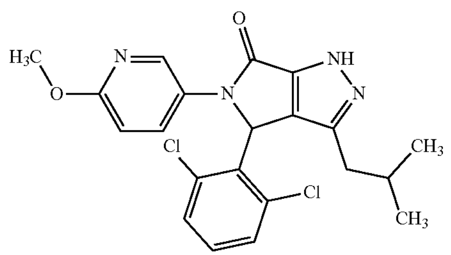 [SMILES: COc1ccc(N2C(=O)c3[nH]nc(CC(C)C)c3C2c2c(Cl)cccc2Cl)cn1] | 4.3 | | | 5.0c | 20.0 | | | 4.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| CMLD011132 | 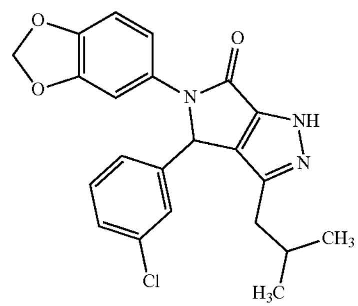 [SMILES: CC(C)Cc1n[nH]c2c1C(c1cccc(Cl)c1)N(c1ccc3c(c1)OCO3)C2=O] | 5.2 | | | 5.0c | 20.0 | | | 4.0 | | | | |
| CMLD011133 | 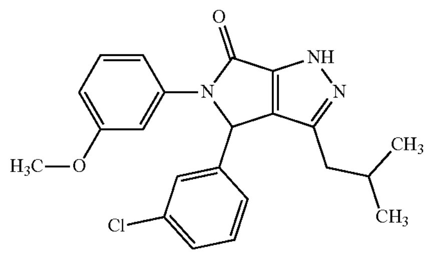 [SMILES: COc1cccc(N2C(=O)c3[nH]nc(CC(C)C)c3C2c2cccc(Cl)c2)c1] | 5.4 | | | 5.0c | 25.1 | | | 5.0 | | | | |
| CMLD013640 | 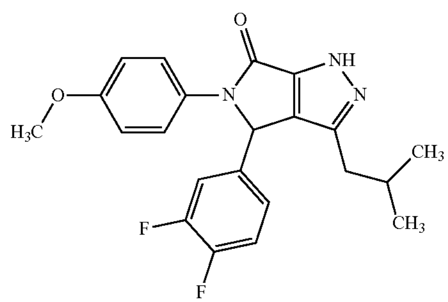 [SMILES: COc1ccc(N2C(=O)c3[nH]nc(CC(C)C)c3C2c2ccc(F)c(F)c2)cc1] | 2.2 | | | 5.0c | 25.1 | | | 5.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011116 | 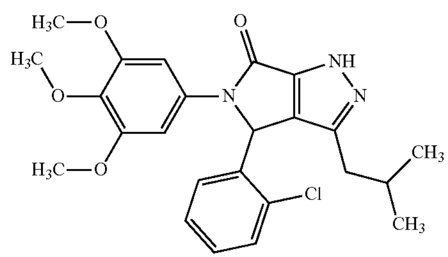 [SMILES: COc1cc(N2C(=O)c3[nH]nc(CC(C)C)c3C2c2ccccc2Cl)cc(OC)c1OC] | 4.6 | | | 5.0c | 6.3 | | | 1.3 | | | | |
| CMLD011140 | 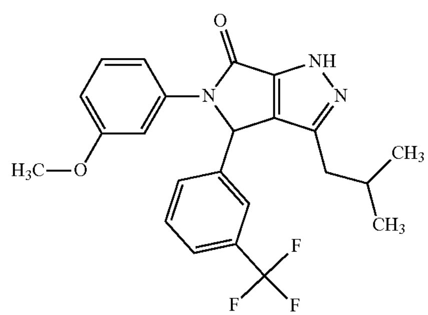 [SMILES: COc1cccc(N2C(=O)c3[nH]nc(CC(C)C)c3C2c2cccc(C(F)(F)F)c2)c1] | 2.9 | | | 5.0c | 20.0 | | | 4.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00802 | 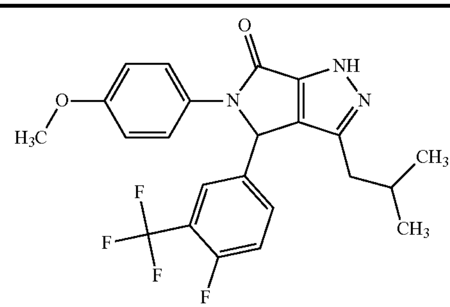 | 5.1 | | | 5.0c | 25.1 | | | 5.0 | | | | |
| BUCMD00803 | 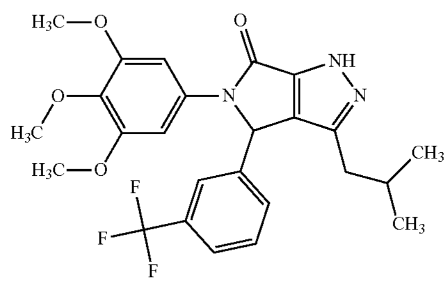 [SMILES: COc1cc(N2C(=O)c3[nH]nc(CC(C)C)c3C2c2cccc(C(F)(F)F)c2)cc(OC)c1OC] | 4.7 | | | 5.0c | 12.6 | | | 2.5 | | | | |
| BUCMD00805 | 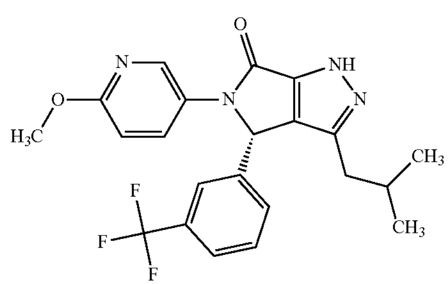 [SMILES: COc1ccc(N2C(=O)c3[nH]nc(CC(C)C)c3[C@@H]2c2cccc(C(F)(F)F)c2)cn1] | 4.3 | | | 5.0c | 25.1 | 1.6 | 5.2 | 5.0 | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J1774 cells)e | L. major amastigotes EC75 (µM, THP-1 b or J1774e cells) | L. donovani promastigotes EC50 (µM)f | L. major promastigotes EC50 (µM)f |
|---|---|---|---|---|---|---|---|---|---|---|---|---|---|
| CMLD011109 | 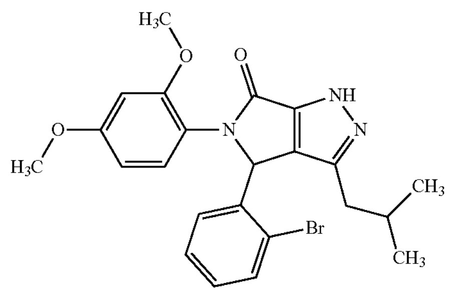 [SMILES: COc1ccc(N2C(=O)c3[nH]nc(CC(C)C)c3C2c2ccccc2Br)c(OC)c1] | 4.9 | | | 6.3c | 15.8 | | | 2.5 | | | | |
| CMLD011122 | 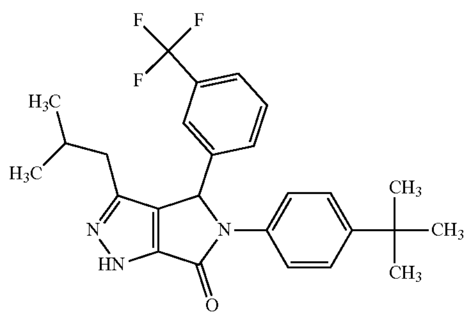 [SMILES: CC(C)Cc1n[nH]c2c1C(c1cccc(C(F)(F)F)c1)N(c1ccc(C(C)(C)C)cc1)C2=O] | 4.8 | | | 6.3c | 10.0 | | | 1.6 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011568 | 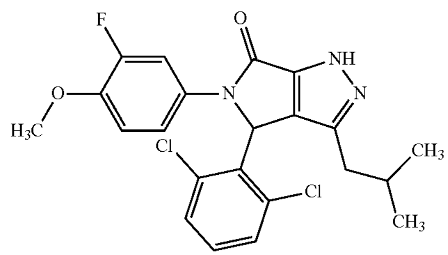 [SMILES: COc1ccc(N2C(=O)c3[nH]nc(CC(C)C)c3C2c2c(Cl)cccc2Cl)cc1F] | 4.1 | | | 6.3c | 20.0 | | | 3.2 | | | | |
| CMLD011106 | 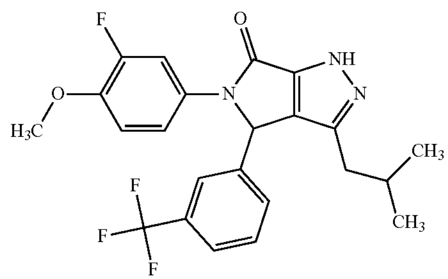 [SMILES: COc1ccc(N2C(=O)c3[nH]nc(CC(C)C)c3C2c2cccc(C(F)(F)F)c2)cc1F] | 4.5 | | | 6.3c | 25.1 | | | 4.0 | | | | |
| CMLD010881 | 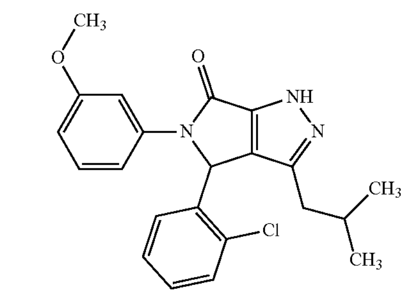 [SMILES: COc1cccc(N2C(=O)c3[nH]nc(CC(C)C)c3C2c2ccccc2Cl)c1] | 4.8 | | | 7.9c | 15.8 | | | 2.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μM b | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| CMLD011110 | 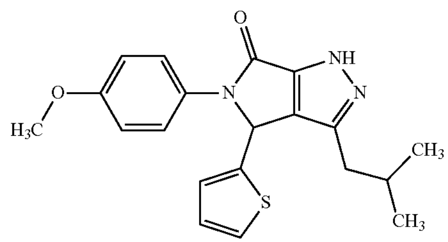 [SMILES: COc1ccc(N2C(=O)c3[nH]nc(CC(C)C)c3C2c2cccs2)cc1] | 4.2 | | | 7.9c | >50 | | | >6.3 | | | | |
| CMLD011134 | 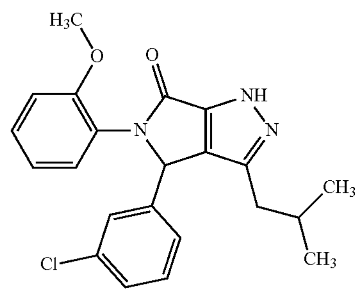 [SMILES: COc1ccccc1N1C(=O)c2[nH]nc(CC(C)C)c2C1c1cccc(Cl)c1] | 5.1 | | | 7.9c | 15.8 | | | 2.0 | | | | |
| CMLD011138 | 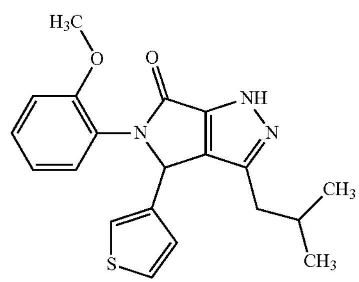 [SMILES: COc1ccccc1N1C(=O)c2[nH]nc(CC(C)C)c2C1c1ccsc1] | 5.6 | | | 7.9c | 15.8 | | | 2.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011550 | 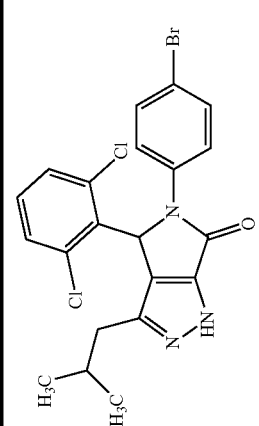 | 4.5 | | | 7.9c | 20.0 | | | 2.5 | | | | |
| CMLD011141 | 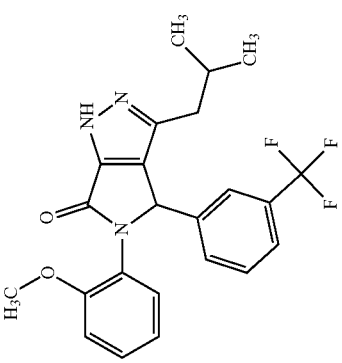 | 4.1 | | | 7.9c | 20.0 | | | 2.5 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00804 | 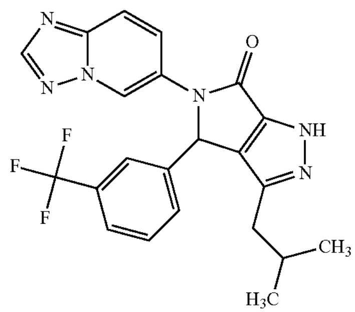 [SMILES: CC(C)Cc1n[nH]c2c1C(c1cccc(C(F)(F)F)c1)N(c1ccc3ncnn3c1)C2=O] | 4.3 | | | 7.9c | 50.1 | | | 6.3 | | | | |
| CMLD011103 | 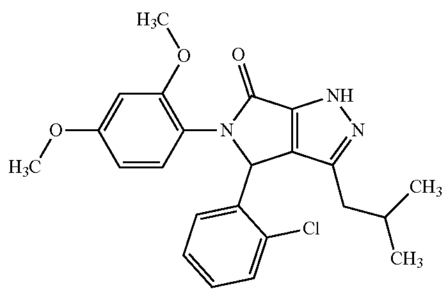 | 4.2 | | | 10.0c | 20.0 | | | 2.0 | | | | |
| CMLD011137 | 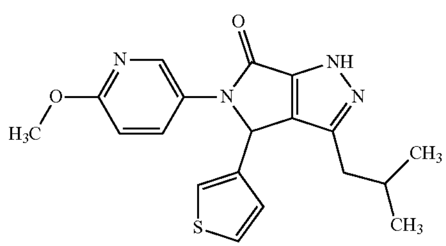 [SMILES: COc1ccc(N2C(=O)c3[nH]nc(CC(C)C)c3C2c2ccsc2)cn1] | 4.4 | | | 10.0c | 25.1 | | | 2.5 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00808 | 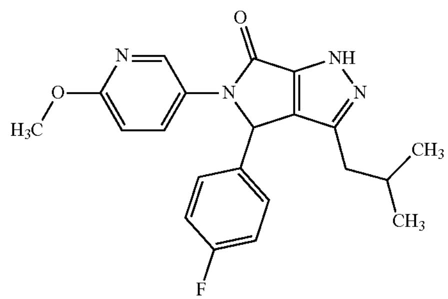 [SMILES: COc1ccc(N2C(=O)c3[nH]nc(CC(C)C)c3C2c2ccc(F)cc2)cn1] | 3.6 | | | 10.0c | >50 | | | >5 | | | | |
| BUCMD00811 | 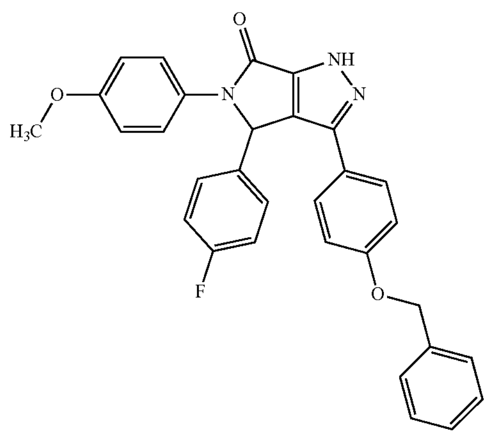 [SMILES: COc1ccc(N2C(=O)c3[nH]nc(-c4ccc(OCc5ccccc5)cc4)c3C2c2ccc(F)cc2)cc1] | 6.3 | | | 10.0c | 15.8 | | | 1.6 | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00816 | 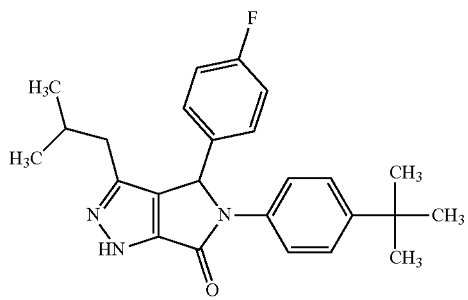 [SMILES: CC(C)Cc1n[nH]c2c1C(c1ccc(F)cc1)N(c1ccc(C(C)(C)C)cc1)C2=O] | 5.9 | | | 10.0c | >50 | | | >5 | | | | |
| CMLD011112 | 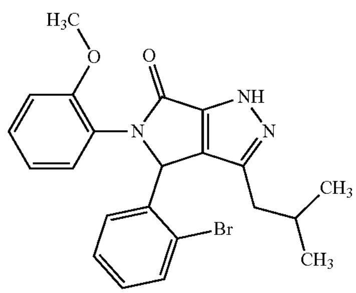 [SMILES: COc1ccccc1N1C(=O)c2[nH]nc(CC(C)C)c2C1c1ccccc1Br] | 5.2 | | | 12.6c | 25.1 | | | 2.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011115 | 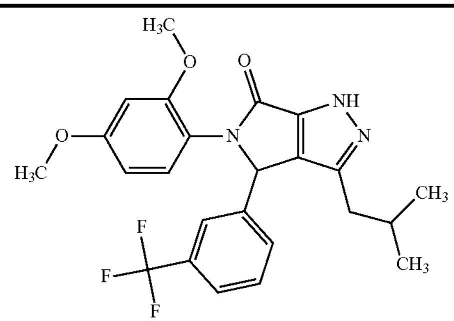 | 5.4 | | | 12.6c | 20.0 | | | 1.6 | | | | |
| CMLD011097 | 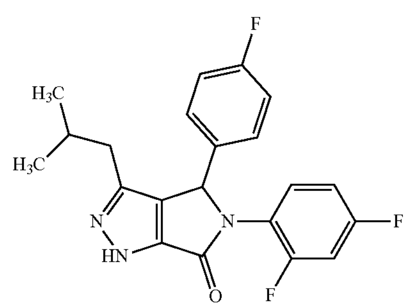 [SMILES: CC(C)Cc1n[nH]c2c1C(c1ccc(F)cc1)N(c1ccc(F)cc1F)C2=O] | 3.2 | | | 12.6c | 39.8 | | | 3.2 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00807 | 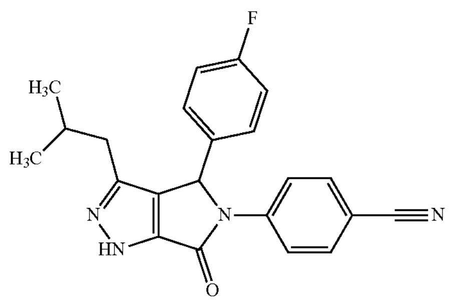 [SMILES: CC(C)Cc1n[nH]c2c1C(c1ccc(F)cc1)N(c1ccc(C#N)cc1)C2=O] | 4.3 | | | 12.6c | 25.1 | | | 2.0 | | | | |
| BUCMD00813 | 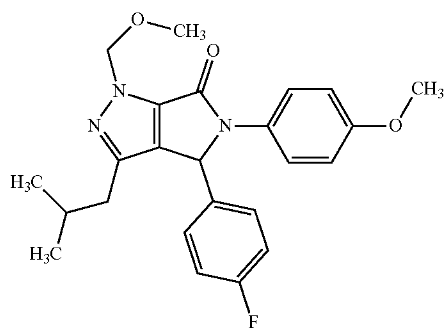 [SMILES: COCn1nc(CC(C)C)c2c1C(=O)N(c1ccc(OC)cc1)C2c1ccc(F)cc1] | 4.4 | | | 12.6c | 31.6 | | | 2.5 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| BUCMD00814 | 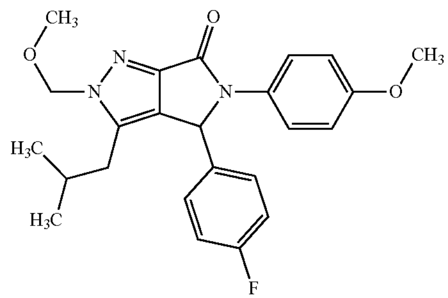 [SMILES: COCn1nc2c(c1CC(C)C)C(c1ccc(F)cc1)N(c1ccc(OC)cc1)C2=O] | 4.8 | | | 12.6c | >50 | | | >4 | | | | |
| CMLD011130 | 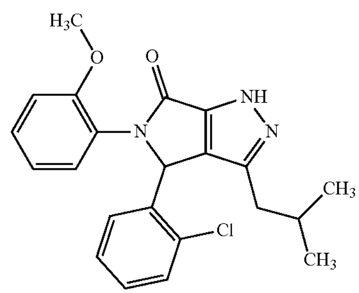 [SMILES: COc1ccccc1N1C(=O)c2[nH]nc(CC(C)C)c2C1c1ccccc1Cl] | 5.7 | | | 15.8c | 25.1 | | | 1.6 | | | | |
| CMLD010880 | 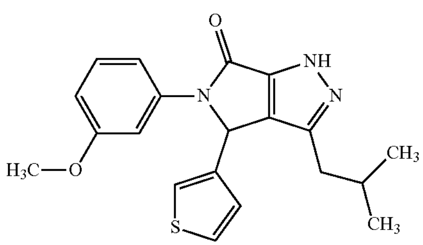 [SMILES: COc1cccc(N2C(=O)c3[nH]nc(CC(C)C)c3C2c2ccsc2)c1] | 2.4 | | | 20.0c | 39.8 | | | 2.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD010903 | 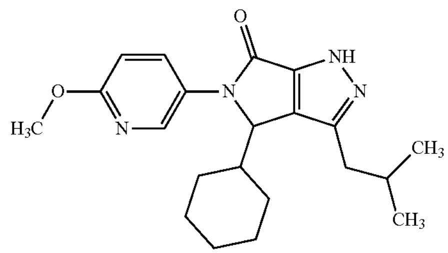 [SMILES: COc1ccc(N2C(=O)c3[nH]nc(CC(C)C)c3C2C2CCCCC2)cn1] | 3.5 | | | 20.0c | 31.6 | | | 1.6 | | | | |
| CMLD011126 | 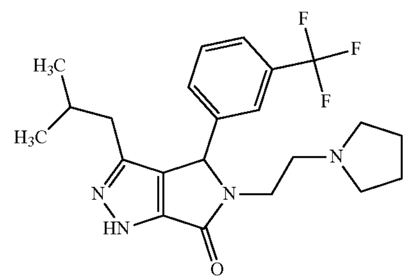 [SMILES: CC(C)Cc1n[nH]c2c1C(c1cccc(C(F)(F)F)c1)N(CCN1CCCC1)C2=O] | 6.4 | | | 20.0c | 39.8 | | | 2.0 | | | | |
| CMLD011093 | 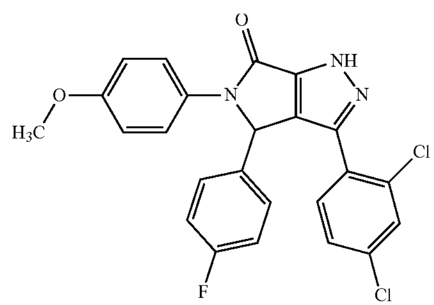 [SMILES: COc1ccc(N2C(=O)c3[nH]nc(-c4ccc(Cl)cc4Cl)c3C2c2ccc(F)cc2)cc1] | 4.2 | | | 20.0c | >50 | | | >2.5 | | | | |

TABLE 1-continued

Compiled Leishmania Data after Treatment with Antileishmanial Compounds

| Compound | Structure | LogPa | *L. donovani* amastigotes % GI at 10 μM (THP-1 cells)b | THP-1 host cell % growth inhibition at 10 μMb | *L. donovani* amastigotes EC50 (μM, THP-1c or B10Rd cells) | THP-1 Host Cell CC50 (μM)c | *L. donovani* amastigotes EC75 (μM B10R cells)d | B10R Host Cell CC50 (μM)d | SI (Host cell potency/ *L. donovani* potency) | *L. braziliensis* amastigotes EC75 (μM J774 cells)e | *L. major* amastigotes EC75 (μM, THP-1 b or J774e cells) | *L. donovani* promastigotes EC50 (μM)f | *L. major* promastigotes EC50 (μM)f |
|---|---|---|---|---|---|---|---|---|---|---|---|---|---|
| BUCMD00799 | 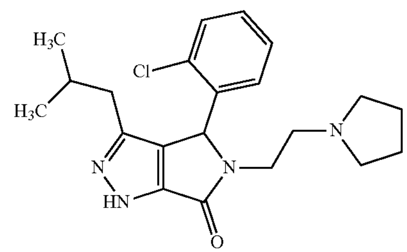 [SMILES: CC(C)Cc1n[nH]c2c1C(c1ccccc1Cl)N(CCN1CCCC1)C2=O] | 3.6 | | | 20.0c | >50 | | | >2.5 | | | | |
| BUCMD00810 | 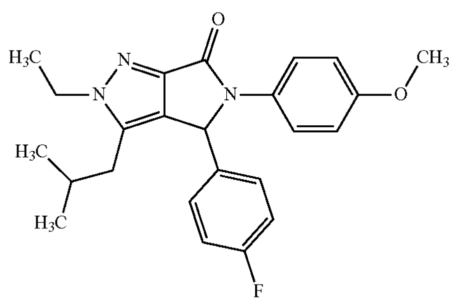 [SMILES: CCn1nc2c(c1CC(C)C)C(c1ccc(F)cc1)N(c1ccc(OC)cc1)C2=O] | 5.1 | | | 20.0c | >50 | | | >2.5 | | | | |
| CMLD011576 | 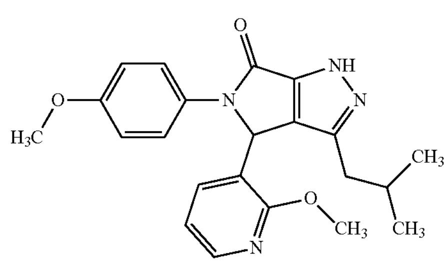 [SMILES: COc1ccc(N2C(=O)c3[nH]nc(CC(C)C)c3C2c2cccnc2OC)cc1] | 2.7 | | | 25.1c | 10.0 | | | 0.4 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00806 | 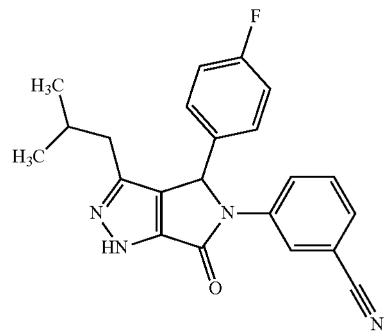 [SMILES: CC(C)Cc1n[nH]c2c1C(c1ccc(F)cc1)N(c1cccc(C#N)c1)C2=O] | 4.3 | | | 25.1c | >50 | | | >2.0 | | | | |
| CMLD010883 | 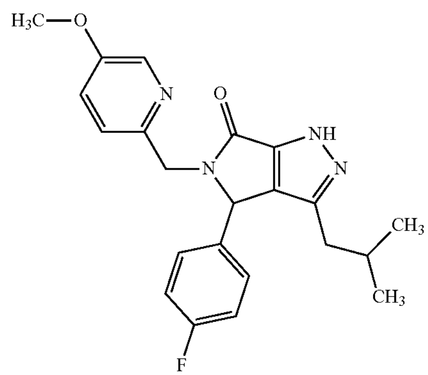 [SMILES: COc1ccc(CN2C(=O)c3[nH]nc(CC(C)C)c3C2c2ccc(F)cc2)nc1] | 4.0 | | | 31.6c | >50 | | | >1.5 | | | | |

TABLE 1-continued

Compiled Leishmania Data after Treatment with Antileishmanial Compounds

| Compound | Structure | LogPa | *L. donovani* amastigotes % GI at 10 µM (THP-1 cells)b | THP-1 host cell % growth inhibition at 10 µMb | *L. donovani* amastigotes EC50 (µM, THP-1c or B10Rd cells) | THP-1 Host Cell CC50 (µM)c | *L. donovani* amastigotes EC75 (µM B10R cells)d | B10R Host Cell CC50 (µM)d | SI (Host cell potency/ *L. donovani* potency) | *L. braziliensis* amastigotes EC75 (µM J774 cells)e | *L. major* amastigotes EC75 (µM, THP-1 b or J774e cells) | *L. donovani* promastigotes EC50 (µM)f | *L. major* promastigotes EC50 (µM)f |
|---|---|---|---|---|---|---|---|---|---|---|---|---|---|
| BUCMD00798 | 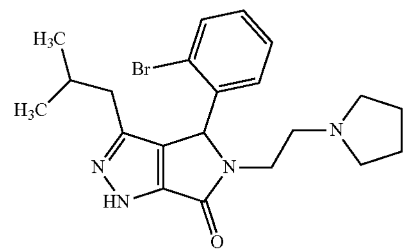 | 3.8 | | | 31.6c | >50 | | | >1.6 | | | | |
| CMLD010848 | 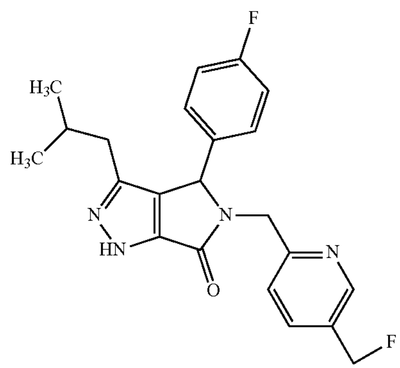 [SMILES: CC(C)Cc1n[nH]c2c1C(c1ccc(F)cc1)N(Cc1ccc(CF)cn1)C2=O] | 5.6 | | | 39.8c | >50 | | | >1.25 | | | | |

TABLE 1-continued

Compiled Leishmania Data after Treatment with Antileishmanial Compounds

| Compound | Structure | LogPa | *L. donovani* amastigotes % GI at 10 μM (THP-1 cells)b | THP-1 host cell % growth inhibition at 10 μMb | *L. donovani* amastigotes EC50 (μM, THP-1c or B10Rd cells) | THP-1 Host Cell CC50 (μM)c | *L. donovani* amastigotes EC75 (μM B10R cells)d | B10R Host Cell CC50 (μM)d | SI (Host cell potency/ *L. donovani* potency) | *L. braziliensis* amastigotes EC75 (μM J774 cells)e | *L. major* amastigotes EC75 (μM, THP-1 b or J774e cells) | *L. donovani* promastigotes EC50 (μM)f | *L. major* promastigotes EC50 (μM)f |
|---|---|---|---|---|---|---|---|---|---|---|---|---|---|
| CMLD011094 | 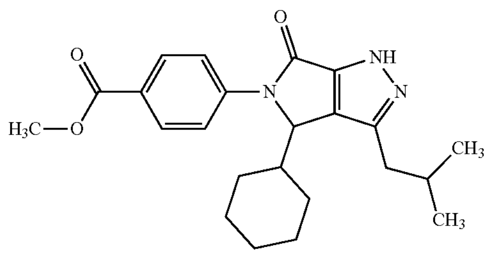 [SMILES: COC(=O)c1ccc(N2C(=O)c3[nH]nc(CC(C)C)c3C2C2CCCCC2)cc1] | 3.9 | | | 39.8c | >50 | | | >1.25 | | | | |
| CMLD011557 | 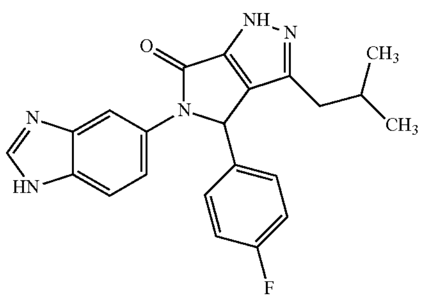 [SMILES: CC(C)Cc1n[nH]c2c1C(c1ccc(F)cc1)N(c1ccc3[nH]cnc3c1)C2=O] | 3.4 | | | >100c | 20.0 | | | <1 | | | | |
| CMLD011495 | 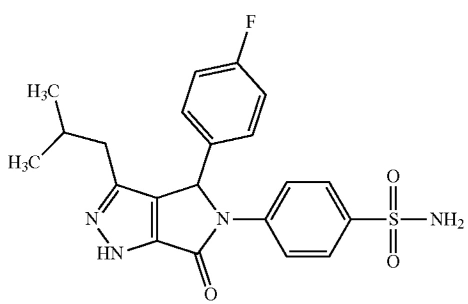 [SMILES: CC(C)Cc1n[nH]c2c1C(c1ccc(F)cc1)N(c1ccc(S(N)(=O)=O)cc1)C2=O] | 4.0 | | | >100c | 20.0 | | | <1 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011556 | 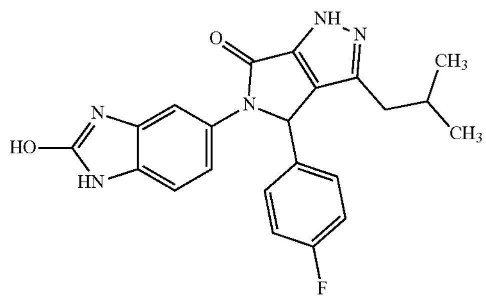 [SMILES: CC(C)Cc1n[nH]c2c1C(c1ccc(F)cc1)N(c1ccc3[nH]c(O)nc3c1)C2=O] | 3.8 | | | >100c | 20.0 | | | <1 | | | | |
| CMLD011558 | 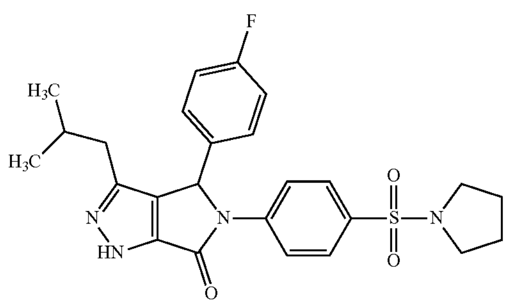 [SMILES: CC(C)Cc1n[nH]c2c1C(c1ccc(F)cc1)N(c1ccc(S(=O)(=O)N3CCCC3)cc1)C2=O] | 3.3 | | | >100c | 20.0 | | | <1 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μM b | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00801 | 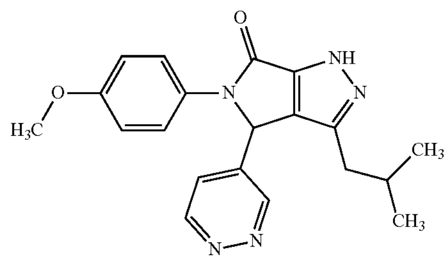 [SMILES: COc1ccc(N2C(=O)c3[nH]nc(CC(C)C)c3C2c2ccnnc2)cc1] | 1.9 | | | >50c | >50 | | | 1.0 | | | | |
| BUCMD00817 | 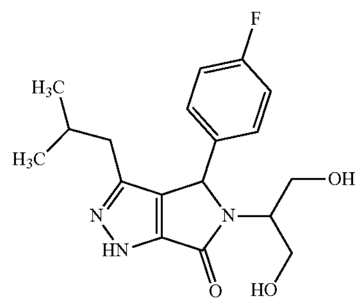 [SMILES: CC(C)Cc1n[nH]c2c1C(c1ccc(F)cc1)N(C(CO)CO)C2=O] | 1.4 | | | >50c | >50 | | | 1.0 | | | | |
| CMLD010926 | 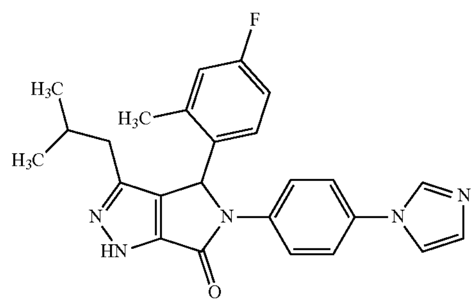 [SMILES: Cc1cc(F)ccc1C1c2c(CC(C)C)n[nH]c2C(=O)N1c1ccc(-n2ccnc2)cc1] | 4.3 | | | 1.3c | 25.1 | | | 20.0 | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| CMLD011040 | | 5.1 | | | 25.1c | 50.1 | | | 2.0 | | | | |
| CMLD010925 | | 4.2 | | | 7.9c | 20.0 | | | 2.5 | | | | |

TABLE 1-continued

Compiled Leishmania Data after Treatment with Antileishmanial Compounds

| Compound | Structure | LogPa | *L. donovani* amastigotes % GI at 10 μM (THP-1 cells)b | THP-1 host cell % growth inhibition at 10 μMb | *L. donovani* amastigotes EC50 (μM, THP-1c or B10Rd cells) | THP-1 Host Cell CC50 (μM)c | *L. donovani* amastigotes EC75 (μM B10R cells)d | B10R Host Cell CC50 (μM)d | SI (Host cell potency/ *L. donovani* potency) | *L. braziliensis* amastigotes EC75 (μM J774 cells)e | *L. major* amastigotes EC75 (μM, THP-1 b or J774e cells) | *L. donovani* promastigotes EC50 (μM)f | *L. major* promastigotes EC50 (μM)f |
|---|---|---|---|---|---|---|---|---|---|---|---|---|---|
| CMLD011042 | 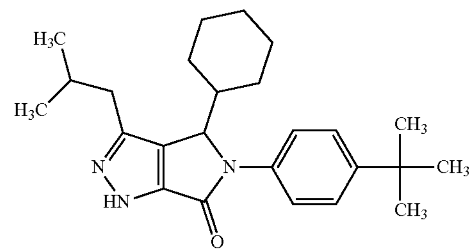 [SMILES: CC(C)Cc1n[nH]c2c1C(C1CCCCC1)N(c1ccc(C(C)(C)C)cc1)C2=O] | 5.7 | | | 2.5c | 50.1 | | | 20.0 | | | | |
| CMLD010996 | 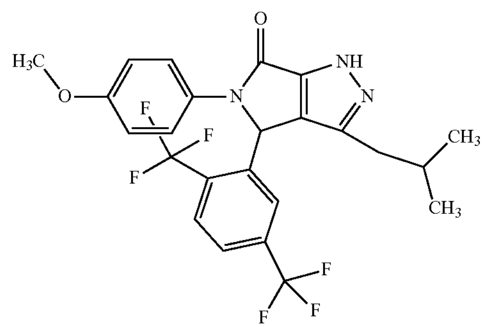 | 5.0 | | | 6.3c | 25.1 | | | 4.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μM b | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011043 | 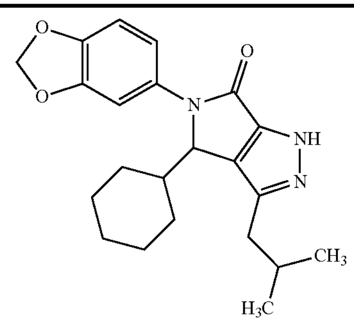 | 4.9 | | | 5.0c | 15.8 | | | 3.2 | | | | |
| CMLD010998 | 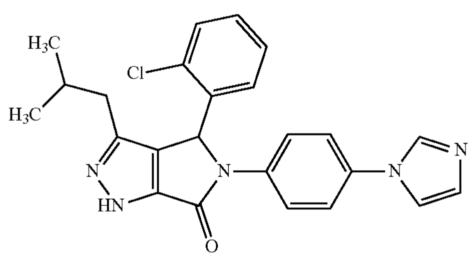 [SMILES: CC(C)Cc1n[nH]c2c1C(c1ccccc1Cl)N(c1ccc(-n3ccnc3)cc1)C2=O] | 4.5 | | | 6.3c | 50.1 | | | 7.9 | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| CMLD010993 | 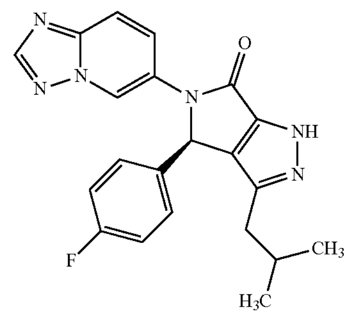 [SMILES: CC(C)Cc1n[nH]c2c1[C@@H](c1ccc(F)cc1)N(c1ccc3ncnn3c1)C2=O] | 3.5 | | | 10.0c | 25.1 | | | 2.5 | | | | |
| CMLD011081 | 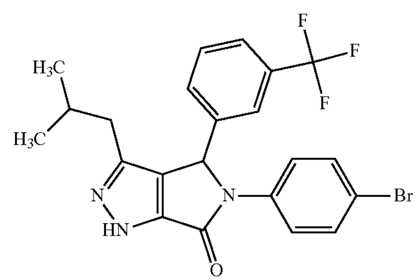 [SMILES: CC(C)Cc1n[nH]c2c1C(c1cccc(C(F)(F)F)c1)N(c1ccc(Br)cc1)C2=O] | 4.7 | | | 31.6c | 31.6 | | | 1.0 | | | | |
| CMLD010976 | 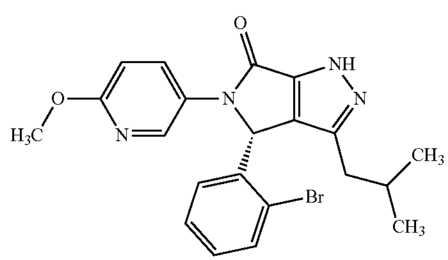 [SMILES: COc1ccc(N2C(=O)c3[nH]nc(CC(C)C)c3[C@@H]2c2ccccc2Br)cn1] | 4.2 | | | 1.0c | 20.0 | | | 20.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD010989 | 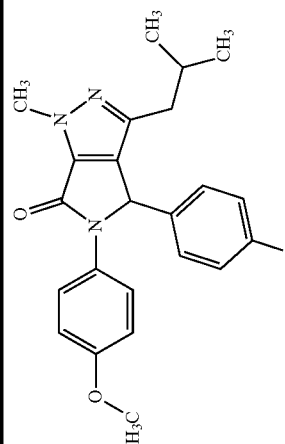 | 4.0 | | | 1.6c | 25.1 | | | 15.8 | | | | |
| BUCMD00694 | 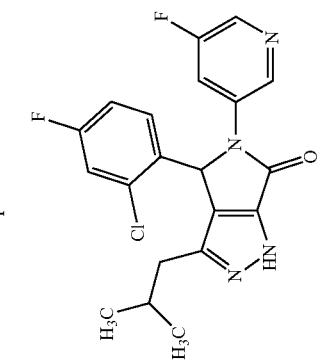 | 3.9 | | | | | 0.4 | 5.0 | 12.7 | >10 | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00729 | 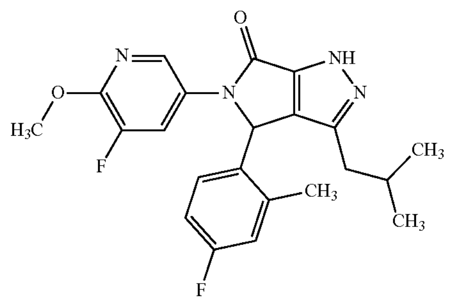 | 4.3 | | | | | 0.4 | 5.2 | 12.9 | 2.0 | | | |
| BUCMD00639 | 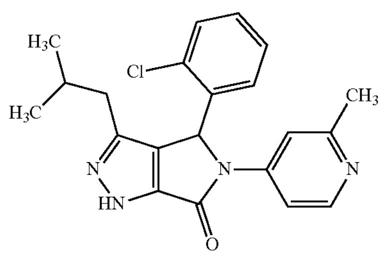 [SMILES: Cc1cc(N2C(=O)c3[nH]nc(CC(C)C)c3C2c2ccccc2Cl)ccn1] | 3.8 | | | | | 0.4 | 4.7 | 11.0 | >10 | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011035 | 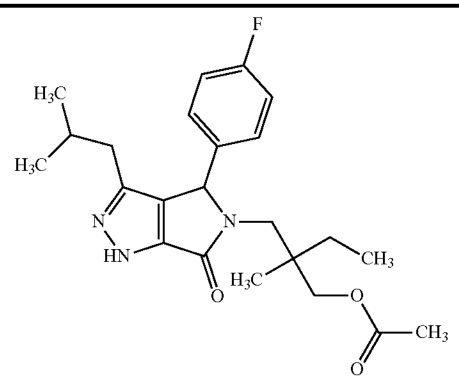 | 5.0 | | | 5.0c | 25.1 | | | 5.0 | | | | |
| BUCMD00695 | 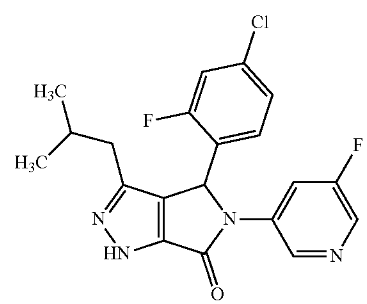 [SMILES: CC(C)Cc1n[nH]c2c1C(c1ccc(Cl)cc1F)N(c1cncc(F)c1)C2=O] | 3.9 | | | | | 0.5 | >5 | >10 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00730 | 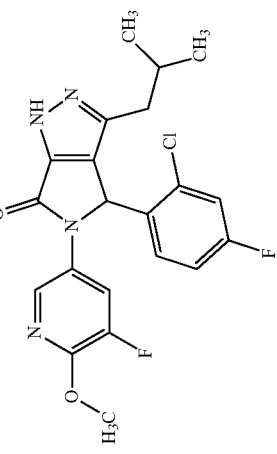 | 4.4 | | | | | 0.6 | 5.0 | 9.0 | | | | |
| CMLD010982 | 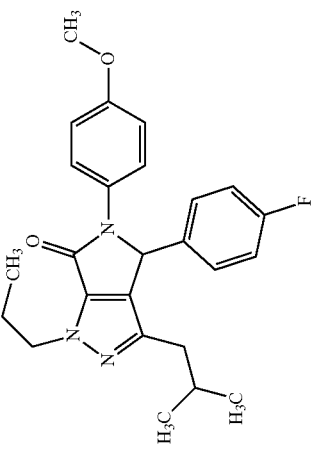 | 4.0 | | | 5.0c | 25.1 | | | 5.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00669 | 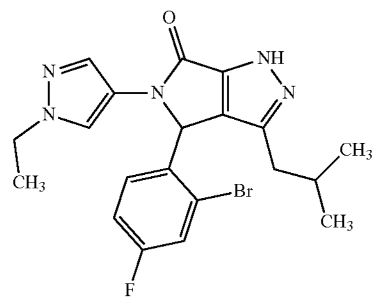 [SMILES: CCn1cc(N2C(=O)c3[nH]nc(CC(C)C)c3C2c2ccc(F)cc2Br)cn1] | 3.9 | | | | | 0.7 | >5 | >7.4 | | | | |
| CMLD010985 | 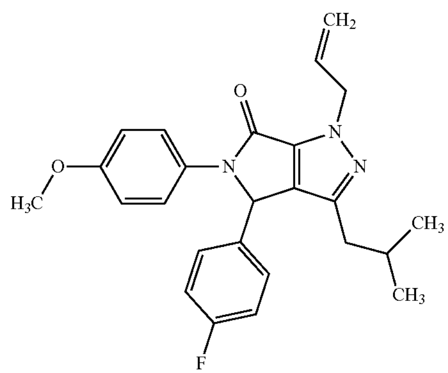 [SMILES: C=CCn1nc(CC(C)C)c2c1C(=O)N(c1ccc(OC)cc1)C2c1ccc(F)cc1] | 4.4 | | | 2.5c | 31.6 | | | 12.6 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| CMLD010950 | 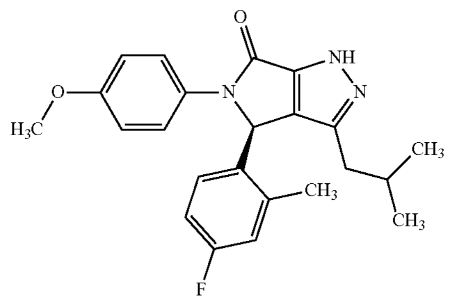 [SMILES: COc1ccc(N2C(=O)c3[nH]nc(CC(C)C)c3[C@H]2c2ccc(F)cc2C)cc1] | 3.8 | | | 6.3c | 31.6 | | | 5.0 | | | | |
| CMLD011497 | 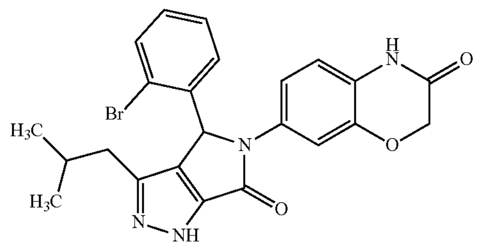 [SMILES: CC(C)Cc1n[nH]c2c1C(c1ccccc1Br)N(c1ccc3c(c1)OCC(=O)N3)C2=O] | 3.8 | | | 2.0c | 20.0 | 0.9 | 5.2 | 10.0 | | | | |
| CMLD011560 | 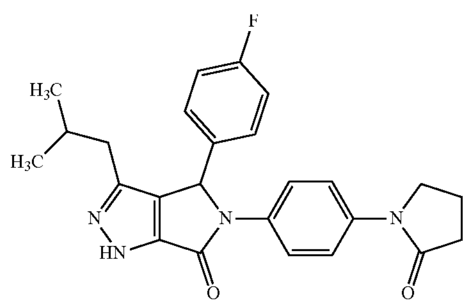 [SMILES: CC(C)Cc1n[nH]c2c1C(c1ccc(F)cc1)N(c1ccc(N3CCCC3=O)cc1)C2=O] | 3.7 | | | 4.0c | 20.0 | 1.0 | >4.7 | 5.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| BUCMD00629 | 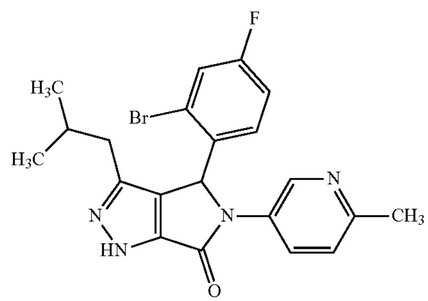 [SMILES: Cc1ccc(N2C(=O)c3[nH]nc(CC(C)C)c3C2c2ccc(F)cc2Br)cn1] | 4.1 | | | | | 1.0 | >4.7 | >4.7 | | | | |
| BUCMD00717 | 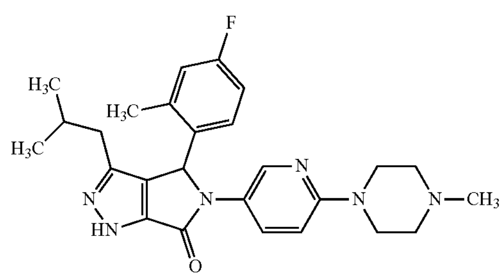 [SMILES: Cc1cc(F)ccc1C1c2c(CC(C)C)n[nH]c2C(=O)N1c1ccc(N2CCN(C)CC2)nc1] | 3.8 | | | | | 1.0 | 5.1 | 5.1 | | | | |
| BUCMD00718 | 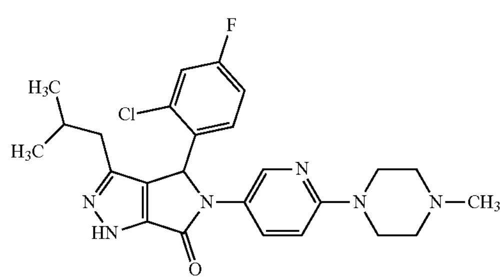 [SMILES: CC(C)Cc1n[nH]c2c1C(c1ccc(F)cc1Cl)N(c1ccc(N3CCN(C)CC3)nc1)C2=O] | 3.9 | | | | | 1.0 | 5.2 | 5.2 | | | | |

TABLE 1-continued

Compiled Leishmania Data after Treatment with Antileishmanial Compounds

| Compound | Structure | LogPa | *L. donovani* amastigotes % GI at 10 μM (THP-1 cells)b | THP-1 host cell % growth inhibition at 10 μMb | *L. donovani* amastigotes EC50 (μM, THP-1c or B10Rd cells) | THP-1 Host Cell CC50 (μM)c | *L. donovani* amastigotes EC75 (μM B10R cells)d | B10R Host Cell CC50 (μM)d | SI (Host cell potency/ *L. donovani* potency) | *L. braziliensis* amastigotes EC75 (μM J774 cells)e | *L. major* amastigotes EC75 (μM, THP-1 b or J774 cells) | *L. donovani* promastigotes EC50 (μM)f | *L. major* promastigotes EC50 (μM)f |
|---|---|---|---|---|---|---|---|---|---|---|---|---|---|
| CMLD011080 | | 4.2 | | | 10.0c | 39.8 | | | 4.0 | | | | |
| CMLD010977 | | 4.2 | | | 2.0c | 25.1 | 1.0 | 4.8 | 12.6 | | | | |
| BUCMD00733 | | 4.1 | | | | | 1.0 | >5 | >5 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD010984 | 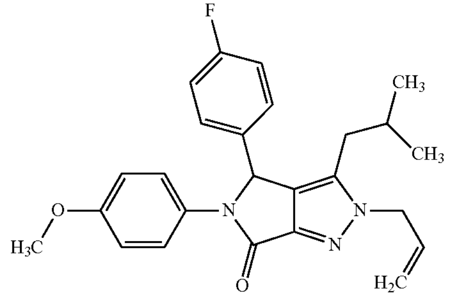 [SMILES: C=CCn1nc2c(c1CC(C)C)C(c1ccc(F)cc1)N(c1ccc(OC)cc1)C2=O] | 4.1 | | | 6.3c | 31.6 | | | 5.0 | | | | |
| CMLD010990 | 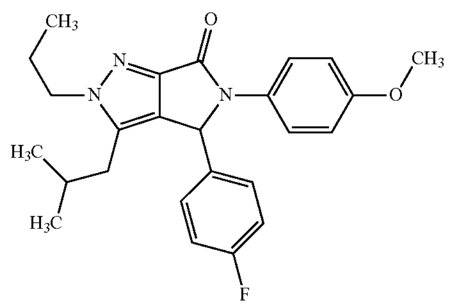 [SMILES: CCCn1nc2c(c1CC(C)C)C(c1ccc(F)cc1)N(c1ccc(OC)cc1)C2=O] | 3.9 | | | 7.9c | 25.1 | | | 3.2 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| BUCMD00643 | 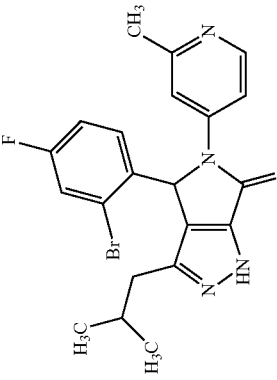 | 4.1 | | | | | 1.2 | >4.7 | >3.95 | | | | |
| BUCMD00642 | 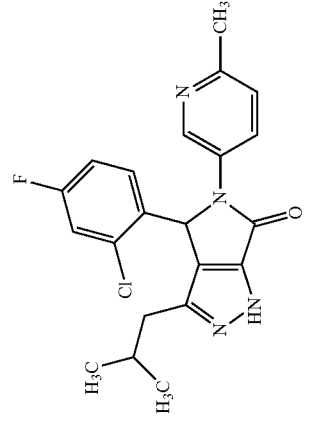 | 3.9 | | | | | 1.3 | 5.0 | 4.0 | | | | |
| BUCMD00700 | 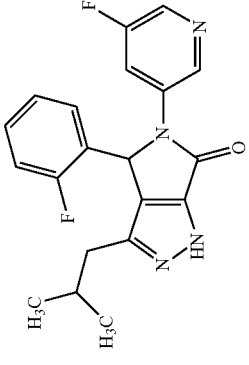 | 3.3 | | | | | 1.3 | 5.0 | 3.7 | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00699 | | 4.1 | | | | | 1.4 | 5.3 | 3.7 | | | | |
| BUCMD00734 | | 3.9 | | | | | 1.5 | >5 | >3.4 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00685 | 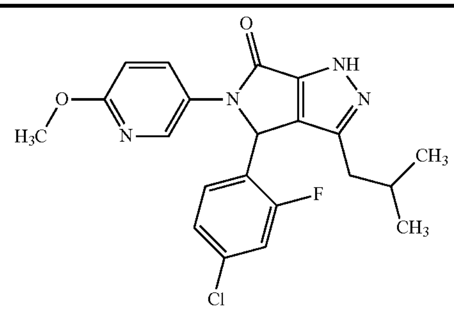 | 4.2 | | | | | 1.7 | >5 | | >10 | | | |
| CMLD011555 | 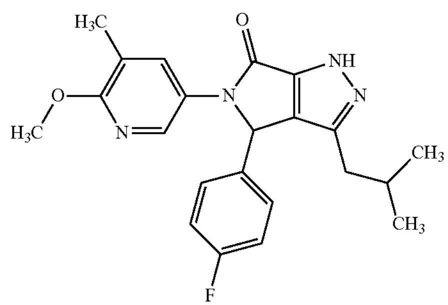 [SMILES: COc1ncc(N2C(=O)c3[nH]nc(CC(C)C)c3C2c2ccc(F)cc2)cc1C] | 4.1 | | | 10.0c | 20.0 | 1.7 | >4.7 | 2.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J1774 cells)e | L. major amastigotes EC75 (μM, THP-1 b or J1774 cells) | L. donovani promastigotes EC50 (μM)f | L. major promastigotes EC50 (μM)f |
|---|---|---|---|---|---|---|---|---|---|---|---|---|---|
| CMLD011076 | 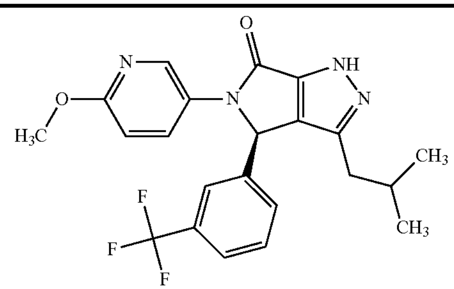 | 4.1 | | | 10.0c | 15.8 | | | 1.6 | | | | |
| CMLD006598 | 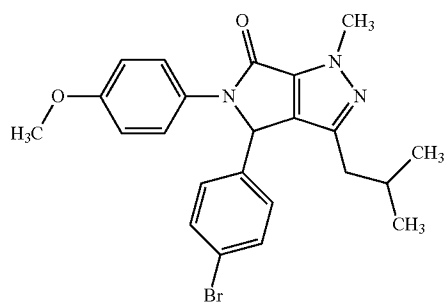 [SMILES: COc1ccc(N2C(=O)c3c(c(CC(C)C)nn3C)C2c2ccc(Br)cc2)cc1] | 4.3 | | | | 50.1 | | | | | | | |
| BUCMD00732 | 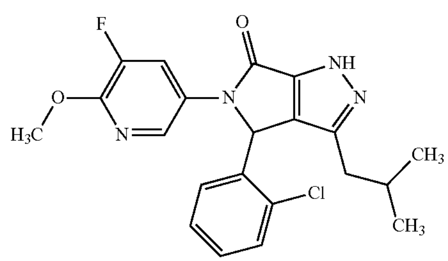 [SMILES: COc1ncc(N2C(=O)c3[nH]nc(CC(C)C)c3C2c2ccccc2Cl)cc1F] | 4.2 | | | | | 1.9 | >5 | >2.67 | | | | |

TABLE 1-continued

Compiled Leishmania Data after Treatment with Antileishmanial Compounds

| Compound | Structure | LogP[a] | L. donovani amastigotes % GI at 10 μM (THP-1 cells)[b] | THP-1 host cell % growth inhibition at 10 μM[b] | L. donovani amastigotes EC50 (μM, THP-1[c] or B10R[d] cells) | THP-1 Host Cell CC50 (μM)[c] | L. donovani amastigotes EC75 (μM B10R cells)[d] | B10R Host Cell CC50 (μM)[d] | SI (Host cell potency/ L. donovani potency) | L. braziliensis amastigotes EC75 (μM J774 cells)[e] | L. major amastigotes EC75 (μM, THP-1[b] or J774[e] cells) | L. donovani promastigotes EC50 (μM)[f] | L. major promastigotes EC50 (μM)[f] |
|---|---|---|---|---|---|---|---|---|---|---|---|---|---|
| CMLD010988 | 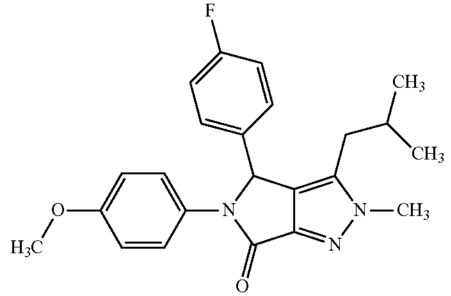 [SMILES: COc1ccc(N2C(=O)c3nn(C)c(CC(C)C)c3C2c2ccc(F)cc2)cc1] | 3.6 | | | 7.9c | 25.1 | | | 3.2 | | | | |
| BUCMD00698 | 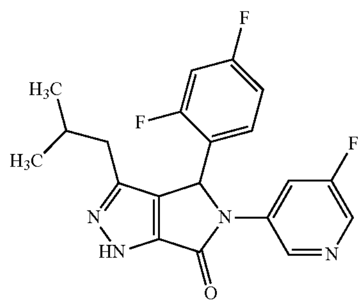 [SMILES: CC(C)Cc1n[nH]c2c1C(c1ccc(F)cc1F)N(c1cncc(F)c1)C2=O] | 3.5 | | | | | 2.3 | >5 | >2.17 | | | | |
| CMLD011077 | 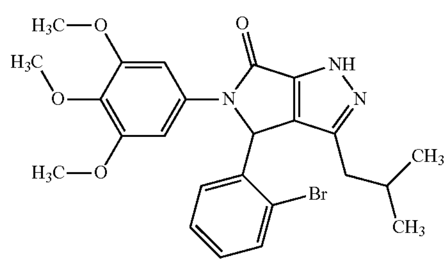 [SMILES: COc1cc(N2C(=O)c3[nH]nc(CC(C)C)c3C2c2ccccc2Br)cc(OC)c1OC] | 4.7 | | | 6.3c | 6.3 | | | 1.0 | | | | |

TABLE 1-continued

Compiled Leishmania Data after Treatment with Antileishmanial Compounds

| Compound | Structure | LogP a | L. donovani amastigotes % GI at 10 μM (THP-1 cells) b | THP-1 host cell % growth inhibition at 10 μM b | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| CMLD011123 | 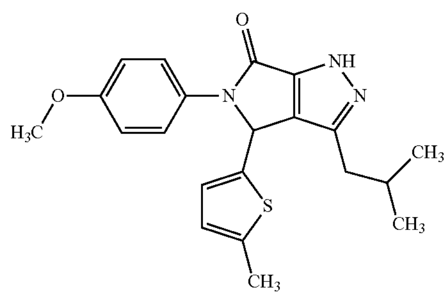 [SMILES: COc1ccc(N2C(=O)c3[nH]nc(CC(C)C)c3C2c2ccc(C)s2)cc1] | 4.7 | | | 5.0c | 20.0 | 2.5 | 4.8 | 4.0 | | | | |
| BUCMD00697 | 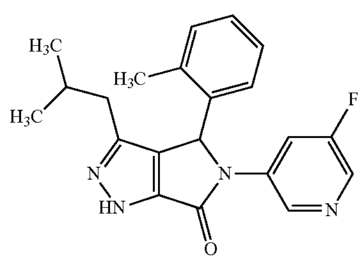 [SMILES: Cc1ccccc1C1c2c(CC(C)C)n[nH]c2C(=O)N1c1cncc(F)c1] | 3.7 | | | | | 2.6 | >5 | >1.95 | | | | |
| CMLD011553 | 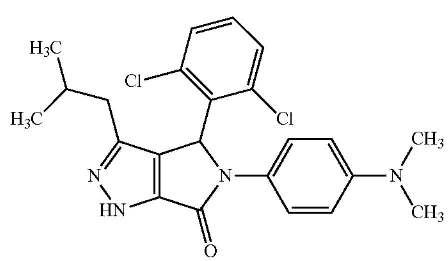 [SMILES: CC(C)Cc1n[nH]c2c1C(c1c(Cl)cccc1Cl)N(c1ccc(N(C)C)cc1)C2=O] | 5.6 | | | 4.0c | 20.0 | 3.0 | 5.3 | 5.0 | | | | |

TABLE 1-continued

Compiled Leishmania Data after Treatment with Antileishmanial Compounds

| Compound | Structure | LogPa | *L. donovani* amastigotes % GI at 10 μM (THP-1 cells)b | THP-1 host cell % growth inhibition at 10 μMb | *L. donovani* amastigotes EC50 (μM, THP-1c or B10Rd cells) | THP-1 Host Cell CC50 (μM)c | *L. donovani* amastigotes EC75 (μM B10R cells)d | B10R Host Cell CC50 (μM)d | SI (Host cell potency/ *L. donovani* potency) | *L. braziliensis* amastigotes EC75 (μM J774 cells)e | *L. major* amastigotes EC75 (μM, THP-1 b or J774 cells) | *L. donovani* promastigotes EC50 (μM)f | *L. major* promastigotes EC50 (μM)f |
|---|---|---|---|---|---|---|---|---|---|---|---|---|---|
| BUCMD00628 | 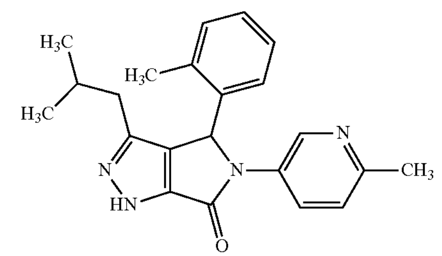 | 3.7 | | | | | 3.2 | 4.8 | 1.5 | | | | |
| BUCMD00688 | 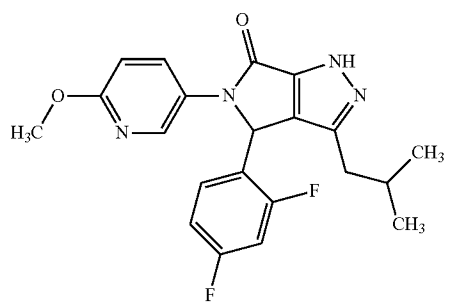 | 3.8 | | | | | 3.3 | >5 | >1.52 | >10 | | | |
| BUCMD00640 | 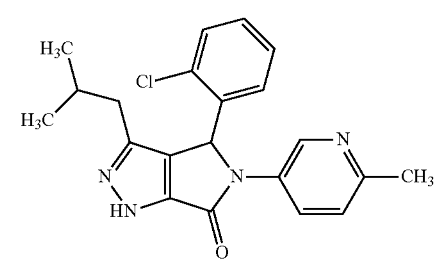 [SMILES: Cc1ccc(N2C(=O)c3[nH]nc(CC(C)C)c3C2c2ccccc2Cl)cn1] | 3.8 | | | | | 3.4 | 4.9 | 1.5 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011047 | 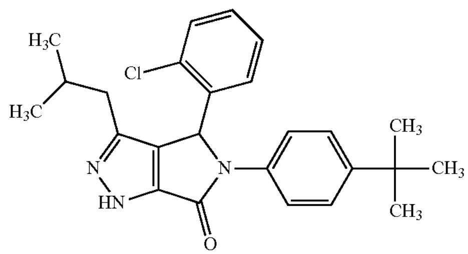 [SMILES: CC(C)Cc1n[nH]c2c1C(c1ccccc1Cl)N(c1ccc(C(C)(C)C)cc1)C2=O] | 3.7 | | | 3.2c | 7.9 | | | 2.5 | | | | |
| CMLD011136 | 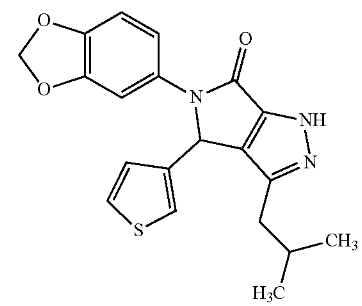 [SMILES: CC(C)Cc1n[nH]c2c1C(c1ccsc1)N(c1ccc3c(c1)OCO3)C2=O] | 3.7 | | | 5.0c | 50.1 | 3.6 | >4.7 | 10.0 | | | | |
| CMLD011073 | 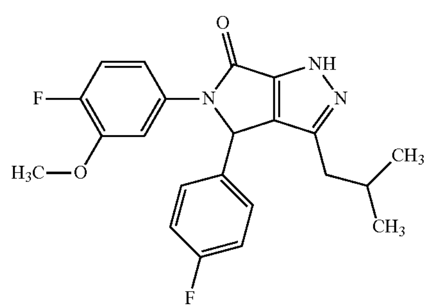 [SMILES: COc1cc(N2C(=O)c3[nH]nc(CC(C)C)c3C2c2ccc(F)cc2)ccc1F] | 4.6 | | | 20.0c | 15.8 | | | 0.8 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00663 | 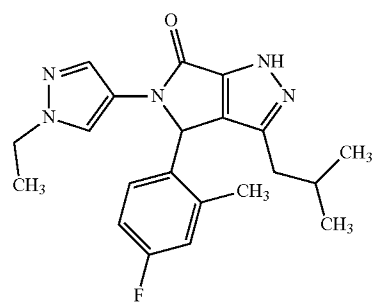 [SMILES: CCn1cc(N2C(=O)c3[nH]nc(CC(C)C)c3C2c2ccc(F)cc2C)cn1] | 3.7 | | | | | 4.0 | >5 | >1.26 | | | | |
| CMLD011045 | 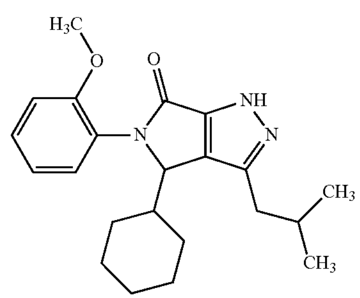 [SMILES: COc1ccccc1N1C(=O)c2[nH]nc(CC(C)C)c2C1C1CCCCC1] | 3.3 | | 10.0c | 25.1 | | | | 2.5 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μM b | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00691 | 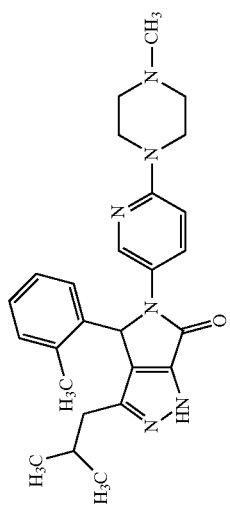 | 3.6 | | | | | 4.9 | >5 | 1.0 | >10 | | | |
| BUCMD00721 | 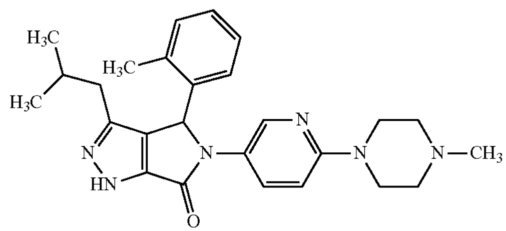 [SMILES: Cc1ccccc1C1c2c(CC(C)C)n[nH]c2C(=O)N1c1ccc(N2CCN(C)CC2)nc1] | 3.7 | | | | | 5.0 | >50 | >10 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μM b | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| CMLD009657 | 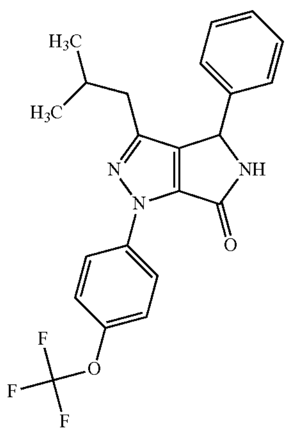 [SMILES: CC(C)Cc1nn(-c2ccc(OC(F)(F)F)cc2)c2c1C(c1ccccc1)NC2=O] | 3.8 | | | 12.6c | 50.1 | | | 4.0 | | | | |
| BUCMD00720 | 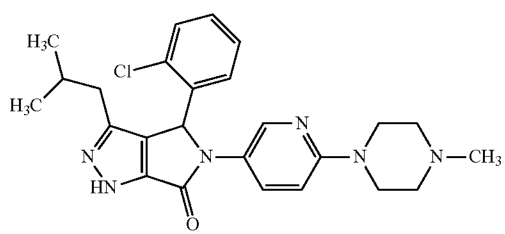 | 3.8 | | | 5.1 | | >5 | | 1.0 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| CMLD010924 | 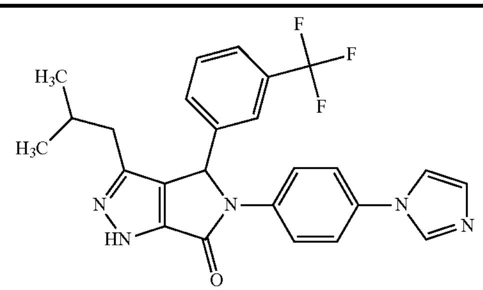 | 3.6 | | | 50.1c | 39.8 | | | 0.8 | | | | |
| BUCMD00668 | 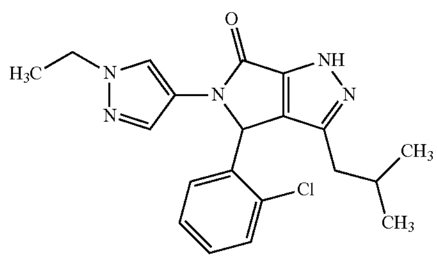 [SMILES: CCn1cc(N2C(=O)c3[nH]nc(CC(C)C)c3C2c2ccccc2Cl)cn1] | 3.6 | | | | | 5.8 | >5 | <1 | | | | |
| BUCMD00651 | 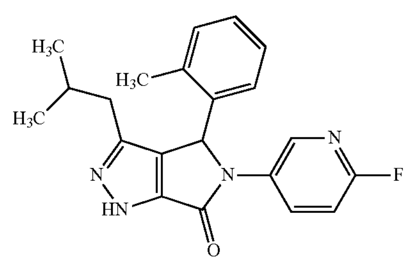 [SMILES: Cc1ccccc1C1c2c(CC(C)C)n[nH]c2C(=O)N1c1ccc(F)nc1] | 4.1 | | | | | 6.3 | >4.7 | <1 | >10 | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| BUCMD00672 | 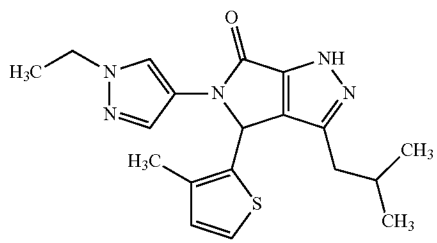 [SMILES: CCn1cc(N2C(=O)c3[nH]nc(CC(C)C)c3C2c2sccc2C)cn1] | 3.5 | | | | | 6.9 | >5 | <1 | | | | |
| BUCMD00702 | 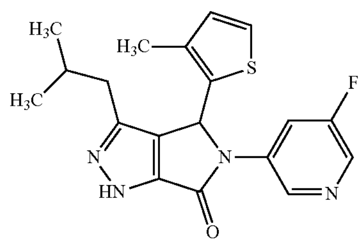 [SMILES: Cc1ccsc1C1c2c(CC(C)C)n[nH]c2C(=O)N1c1cncc(F)c1] | 3.6 | | | | | 7.3 | >5 | <1 | | | | |
| BUCMD00360 | 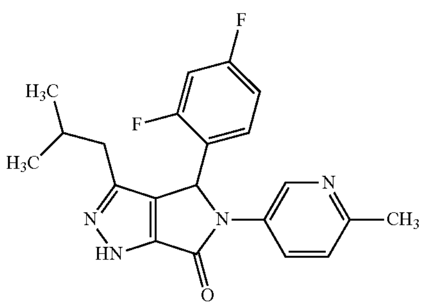 [SMILES: Cc1ccc(N2C(=O)c3[nH]nc(CC(C)C)c3C2c2ccc(F)cc2F)cn1] | 3.5 | | | | | 7.3 | >4.7 | <1 | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J1774 cells)e | L. major amastigotes EC75 (µM, THP-1 b or J1774e cells) | L. donovani promastigotes EC50 (µM)f | L. major promastigotes EC50 (µM)f |
|---|---|---|---|---|---|---|---|---|---|---|---|---|---|
| BUCMD00683 | 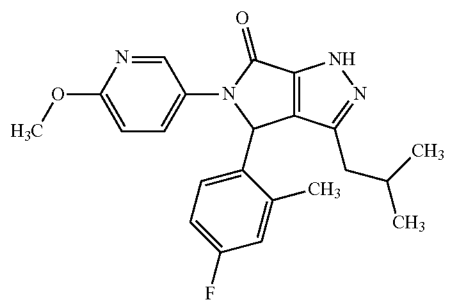 [SMILES: COc1ccc(N2C(=O)c3[nH]nc(CC(C)C)c3C2c2ccc(F)cc2C)cn1] | 4.1 | | | 10.0c | 20.0 | 9.1 | >4.7 | 2.0 | >10 | | | |
| CMLD011037 | 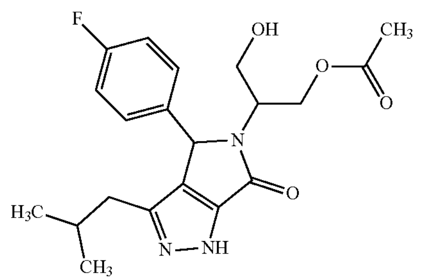 [SMILES: CC(=O)OCC(CO)N1C(=O)c2[nH]nc(CC(C)C)c2C1c1ccc(F)cc1] | 4.1 | | | 50.1c | 50.1 | | | 1.0 | | | | |
| BUCMD00690 | 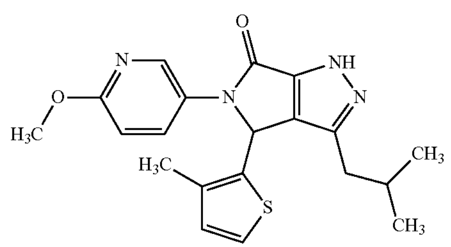 [SMILES: COc1ccc(N2C(=O)c3[nH]nc(CC(C)C)c3C2c2sccc2C)cn1] | 3.9 | | | | | 9.7 | >5 | <1 | >10 | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 or J774e cells) | L. donovani promastigotes EC50 (μM)f | L. major promastigotes EC50 (μM)f |
|---|---|---|---|---|---|---|---|---|---|---|---|---|---|
| CMLD011038 | 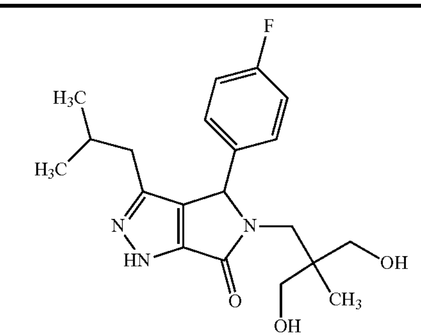 | 3.9 | | | 50.1c | 50.1 | | | 1.0 | | | | |
| BUCMD00674 | 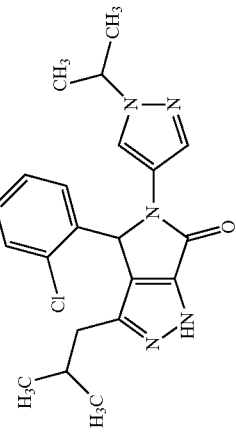 | 4.2 | | | | | 10.0 | >5 | <1 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| BUCMD00723 | 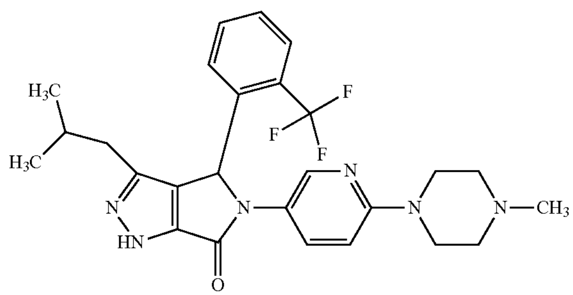 [SMILES: CC(C)Cc1n[nH]c2c1C(c1ccccc1C(F)(F)F)N(c1ccc(N3CCN(C)CC3)nc1)C2=O] | 4.1 | | | | | 10.0 | 5.1 | <1 | | | | |
| BUCMD00679 | 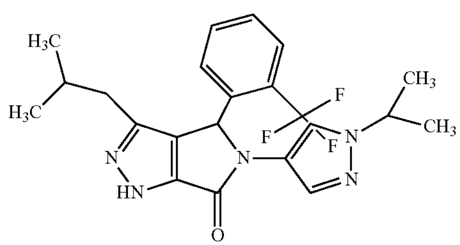 | 4.3 | | | | | 10.4 | >5 | <1 | | | | |
| BUCMD00650 | 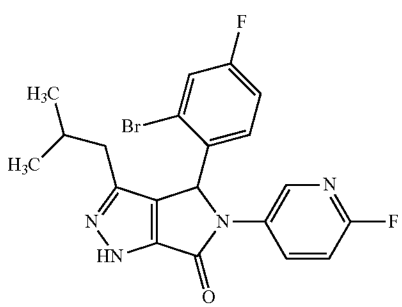 [SMILES: CC(C)Cc1n[nH]c2c1C(c1ccc(F)cc1Br)N(c1ccc(F)nc1)C2=O] | 4.5 | | | | | >10 | >5 | | 9.0 | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00684 | 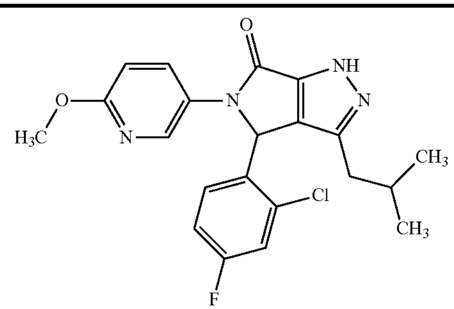 | 4.2 | | | | | >10 | >5 | | 10.0 | | | |
| BUCMD00687 | 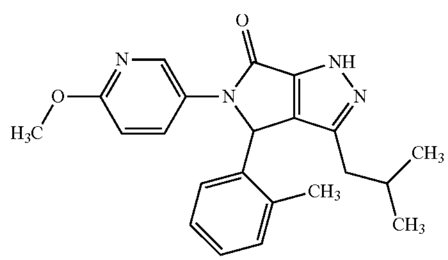 [SMILES: COc1ccc(N2C(=O)c3[nH]nc(CC(C)C)c3C2c2ccccc2C)cn1] | 4.0 | | | | | >10 | >5 | | >10 | | | |
| BUCMD00649 | 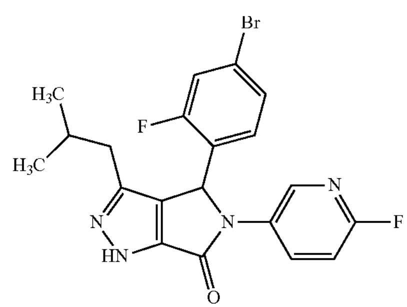 [SMILES: CC(C)Cc1n[nH]c2c1C(c1ccc(Br)cc1F)N(c1ccc(F)nc1)C2=O] | 4.5 | | | | | >10 | >5 | | >10 | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00673 | 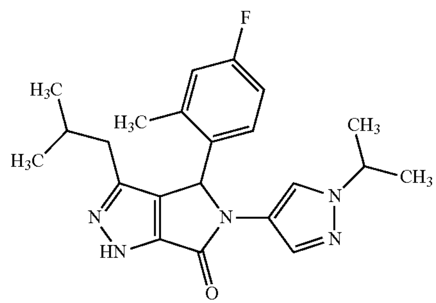 [SMILES: Cc1cc(F)ccc1C1c2c(CC(C)C)n[nH]c2C(=O)N1c1cnn(C(C)C)c1] | 4.1 | | | | | >10 | >5 | | >10 | | | |
| BUCMD00689 | 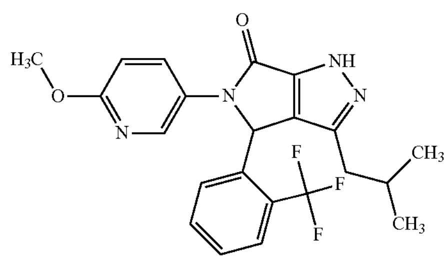 [SMILES: COc1ccc(N2C(=O)c3[nH]nc(CC(C)C)c3C2c2ccccc2C(F)(F)F)cn1] | 4.3 | | | | | >10 | >5 | | >10 | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00692 | 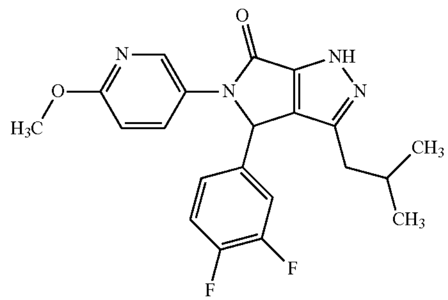 [SMILES: COc1ccc(N2C(=O)c3[nH]nc(CC(C)C)c3C2c2ccc(F)c(F)c2)cn1] | 3.8 | | | | | >10 | >5 | | >10 | | | |
| BUCMD00728 | 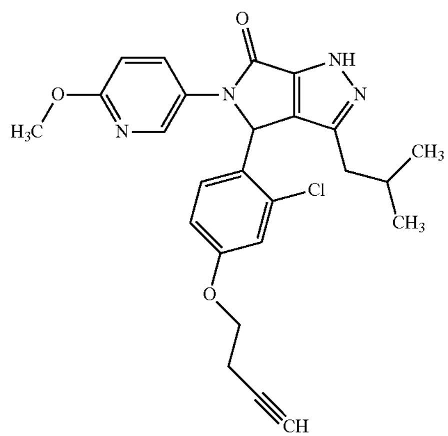 [SMILES: C#CCCOc1ccc(C2c3c(CC(C)C)n[nH]c3C(=O)N2c2ccc(OC)nc2)c(Cl)c1] | 4.4 | | | | | >10 | >5 | | >10 | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00738 | 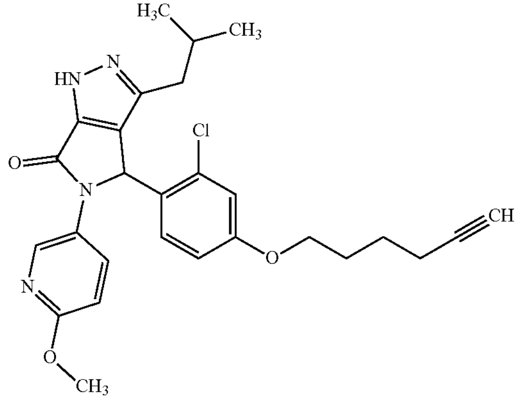 [SMILES: C#CCCCCOc1ccc(C2c3c(CC(C)C)n[nH]c3C(=O)N2c2ccc(OC)nc2)c(Cl)c1] | 5.3 | | | | | >10 | 5.1 | | >10 | | | |
| CMLD011078 | 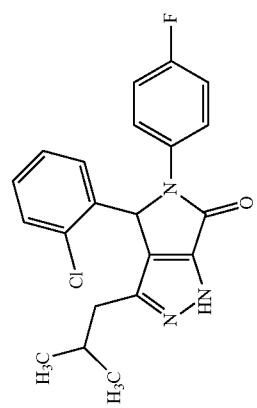 | 4.2 | | | 4.0c | 20.0 | | | 5.0 | | | | |

TABLE 1-continued

Compiled Leishmania Data after Treatment with Antileishmanial Compounds

| Compound | Structure | LogPa | *L. donovani* amast- igotes % GI at 10 µM (THP- 1 cells)b | THP-1 host cell % growth inhib- ition at 10 µMb | *L. donovani* amast- igotes EC50 (µM, THP-1c or B10Rd cells) | THP-1 Host Cell CC50 (µM)c | *L. donovani* amast- igotes EC75 (µM B10R cells)d | B10R Host Cell CC50 (µM)d | SI (Host cell potency/ *L. donovani* potency) | *L. braziliensis* amastigotes EC75 (µM J774 cells)e | *L. major* amastigotes EC75 (µM, THP-1 b or J774 cells) | *L. donovani* promast- igotes EC50 (µM)f | *L. major* promast- igotes EC50 (µM)f |
|---|---|---|---|---|---|---|---|---|---|---|---|---|---|
| CMLD011090 | 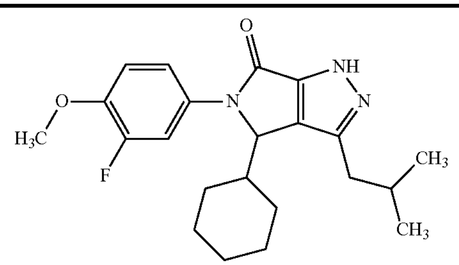 | 4.8 | | | 5.0c | 50.1 | | | 10.0 | | | | |
| CMLD011044 | 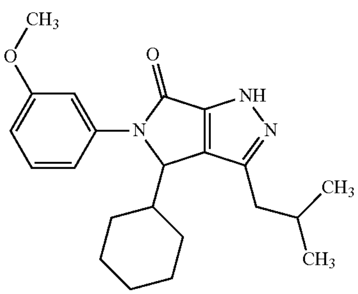 [SMILES: COc1cccc(N2C(=O)c3[nH]nc(CC(C)C)c3C2C2CCCCC2)c1] | 3.2 | | | 6.3c | 50.1 | | | 7.9 | | | | |
| CMLD011087 | 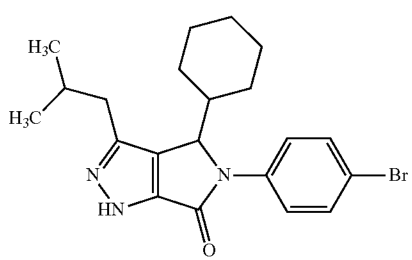 [SMILES: CC(C)Cc1n[nH]c2c1C(C1CCCCC1)N(c1ccc(Br)cc1)C2=O] | 4.9 | | | 6.3c | 7.9 | | | 1.3 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD013629 | 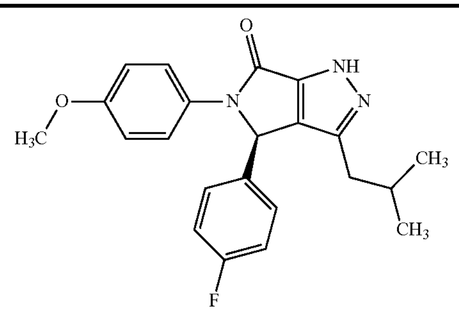 | 4.2 | | | 10.0c | 25.1 | >10 | 4.7 | 2.5 | | | | |
| CMLD010986 | 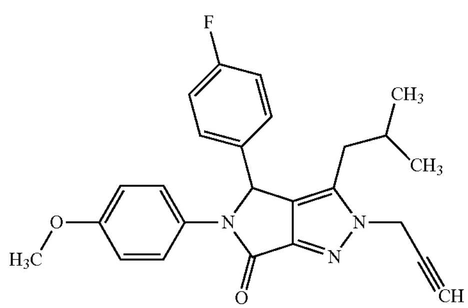 [SMILES: C#CCn1nc2c(c1CC(C)C)C(c1ccc(F)cc1)N(c1ccc(OC)cc1)C2=O] | 4.9 | | | 3.2c | 25.1 | >10 | >5 | 7.9 | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| CMLD011139 | 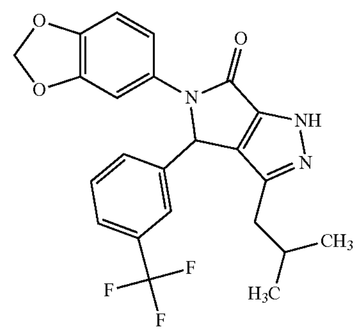 [SMILES: CC(C)Cc1n[nH]c2c1C(c1cccc(C(F)(F)F)c1)N(c1ccc3c(c1)OCO3)C2=O] | 4.8 | | | 3.2c | 20.0 | >10 | 4.9 | 6.3 | | | | |
| BUCMD00647 | 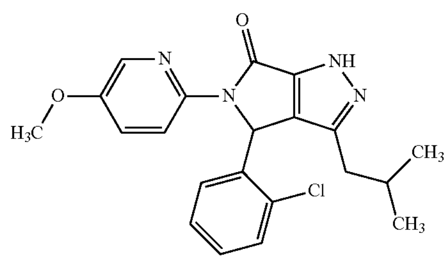 [SMILES: COc1ccc(N2C(=O)c3[nH]nc(CC(C)C)c3C2c2ccccc2Cl)nc1] | 4.1 | | | | | >10 | 5.0 | | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00627 | 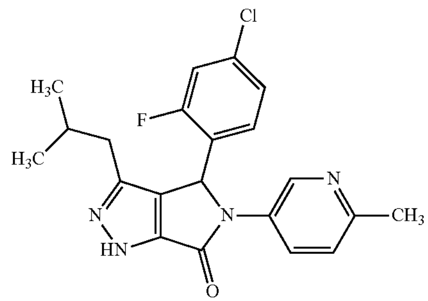 | 3.9 | | | | | >10 | 5.0 | | | | | |
| BUCMD00653 | 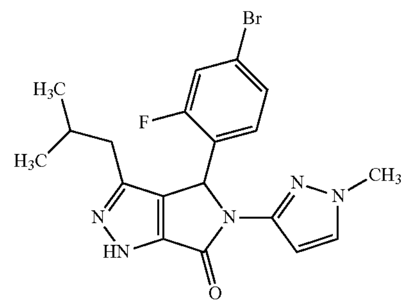 [SMILES: CC(C)Cc1n[nH]c2c1C(c1ccc(Br)cc1F)N(c1ccn(C)n1)C2=O] | 4.2 | | | | | >10 | >5 | | | | | |

TABLE 1-continued

Compiled Leishmania Data after Treatment with Antileishmanial Compounds

| Compound | Structure | LogPa | *L. donovani* amastigotes % GI at 10 μM (THP-1 cells)b | THP-1 host cell % growth inhibition at 10 μMb | *L. donovani* amastigotes EC50 (μM, THP-1c or B10Rd cells) | THP-1 Host Cell CC50 (μM)c | *L. donovani* amastigotes EC75 (μM B10R cells)d | B10R Host Cell CC50 (μM)d | SI (Host cell potency/ *L. donovani* potency) | *L. braziliensis* amastigotes EC75 (μM J774 cells)e | *L. major* amastigotes EC75 (μM, THP-1 b or J774e cells) | *L. donovani* promastigotes EC50 (μM)f | *L. major* promastigotes EC50 (μM)f |
|---|---|---|---|---|---|---|---|---|---|---|---|---|---|
| BUCMD00641 | 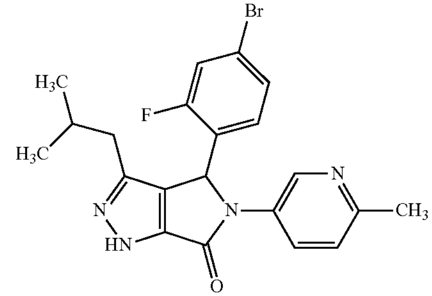 | 4.1 | | | | | >10 | 4.9 | | | | | |
| BUCMD00645 | 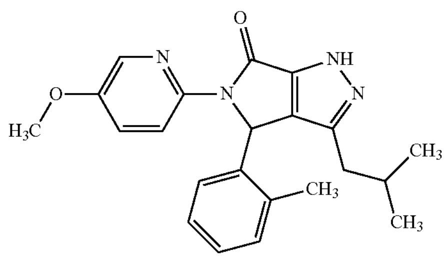 | 4.0 | | | | | >10 | 4.7 | | | | | |
| BUCMD00646 | 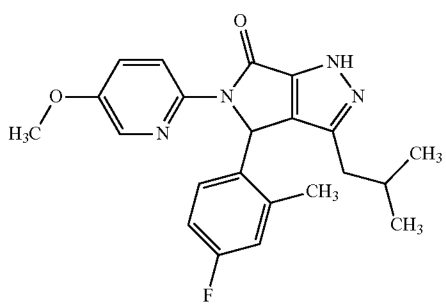 | 4.1 | | | | | >10 | 4.9 | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00648 | 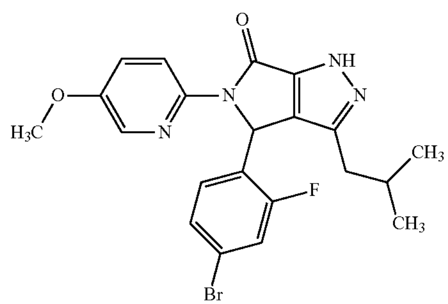 [SMILES: COc1ccc(N2C(=O)c3[nH]nc(CC(C)C)c3C2c2ccc(Br)cc2F)nc1] | 4.4 | | | | | >10 | 5.4 | | | | | |
| BUCMD00652 | 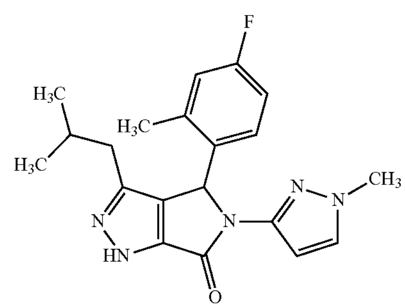 [SMILES: Cc1cc(F)ccc1C1c2c(CC(C)C)n[nH]c2C(=O)N1c1ccn(C)n1] | 3.9 | | | | | >10 | 00 | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00654 | 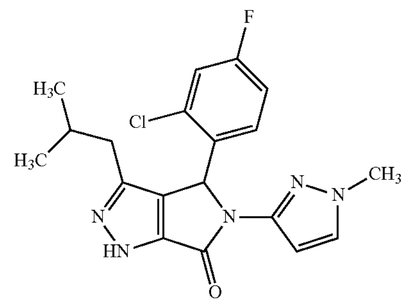 | 4.0 | | | | | >10 | >5 | | | | | |
| BUCMD00655 | 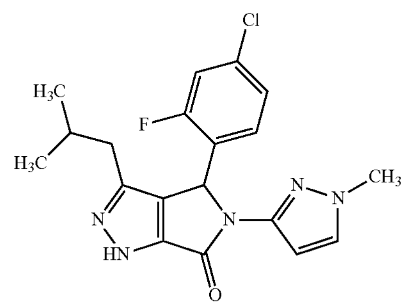 [SMILES: CC(C)Cc1n[nH]c2c1C(c1ccc(Cl)cc1F)N(c1ccn(C)n1)C2=O] | 4.0 | | | | | >10 | >5 | | | | | |
| BUCMD00656 | 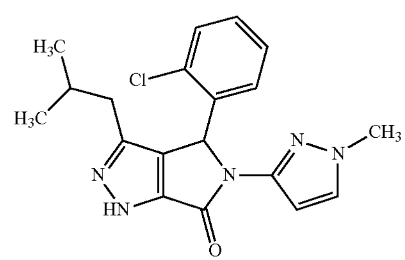 [SMILES: CC(C)Cc1n[nH]c2c1C(c1ccccc1Cl)N(c1ccn(C)n1)C2=O] | 3.9 | | | | | >10 | >5 | | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00657 | 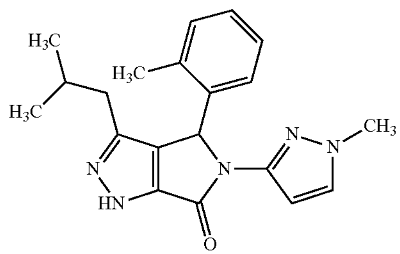 [SMILES: Cc1ccccc1C1c2c(CC(C)C)n[nH]c2C(=O)N1c1ccn(C)n1] | 3.8 | | | | | >10 | >5 | | | | | |
| BUCMD00658 | 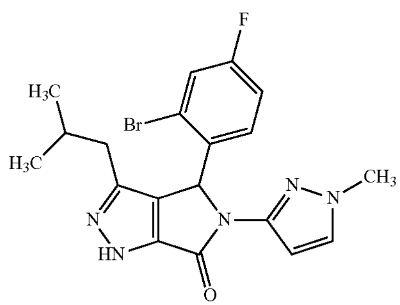 [SMILES: CC(C)Cc1n[nH]c2c1C(c1ccc(F)cc1Br)N(c1ccn(C)n1)C2=O] | 4.2 | | | | | >10 | >5 | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00659 | 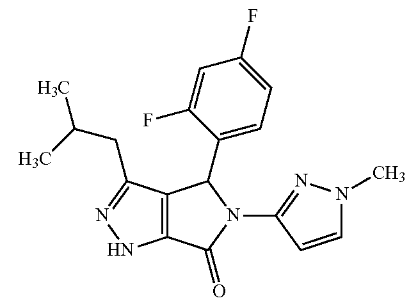 [SMILES: CC(C)Cc1n[nH]c2c1C(c1ccc(F)cc1F)N(c1ccn(C)n1)C2=O] | 3.6 | | | | | >10 | >5 | | | | | |
| BUCMD00660 | 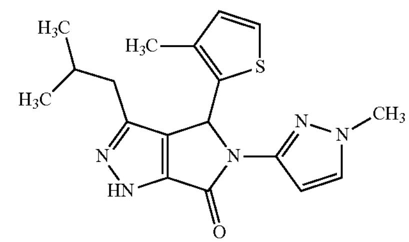 [SMILES: Cc1ccsc1C1c2c(CC(C)C)n[nH]c2C(=O)N1c1ccn(C)n1] | 3.7 | | | | | >10 | >5 | | | | | |
| BUCMD00661 | 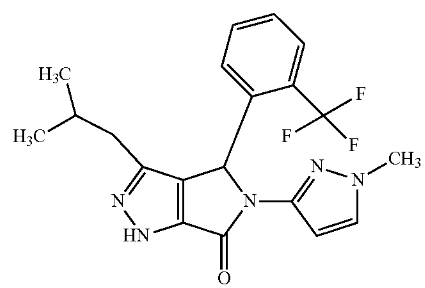 [SMILES: CC(C)Cc1n[nH]c2c1C(c1ccccc1C(F)(F)F)N(c1ccn(C)n1)C2=O] | 4.2 | | | | | >10 | >5 | | | | | |

TABLE 1-continued

Compiled Leishmania Data after Treatment with Antileishmanial Compounds

| Compound | Structure | LogP[a] | L. donovani amastigotes % GI at 10 μM (THP-1 cells)[b] | THP-1 host cell % growth inhibition at 10 μM[b] | L. donovani amastigotes EC50 (μM, THP-1c or B10R[d] cells) | THP-1 Host Cell CC50 (μM)[c] | L. donovani amastigotes EC75 (μM B10R cells)[d] | B10R Host Cell CC50 (μM)[d] | SI (Host cell potency/ L. donovani potency) | L. braziliensis amastigotes EC75 (μM J774 cells)[e] | L. major amastigotes EC75 (μM, THP-1 b or J774 cells)[e] | L. donovani promastigotes EC50 (μM)[f] | L. major promastigotes EC50 (μM)[f] |
|---|---|---|---|---|---|---|---|---|---|---|---|---|---|
| BUCMD00662 | | 4.0 | | | | | >10 | >5 | | | | | |
| BUCMD00664 | | 3.9 | | | | | >10 | >5 | | | | | |
| BUCMD00665 | | 3.8 | | | | | >10 | >5 | | | | | |

TABLE 1-continued

Compiled Leishmania Data after Treatment with Antileishmanial Compounds

| Compound | Structure | LogPa | L. donovani amast- igotes % GI at 10 μM (THP- 1 cells)b | THP-1 host cell % growth inhib- ition at 10 μMb | L. donovani amast- igotes EC50 (μM, THP-1c or B10Rd cells) | THP-1 Host Cell CC50 (μM)c | L. donovani amast- igotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promast- igotes EC50 (μM)f | L. major promast- igotes EC50 (μM)f |
|---|---|---|---|---|---|---|---|---|---|---|---|---|---|
| BUCMD00666 | 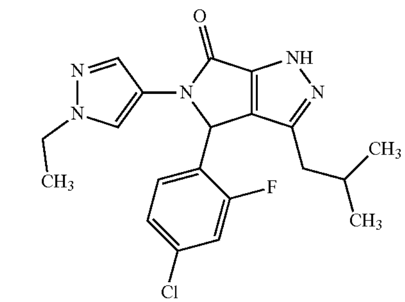 [SMILES: CCn1cc(N2C(=O)c3[nH]nc(CC(C)C)c3C2c2ccc(Cl)cc2F)cn1] | 3.8 | | | | | >10 | >5 | | | | | |
| BUCMD00667 | 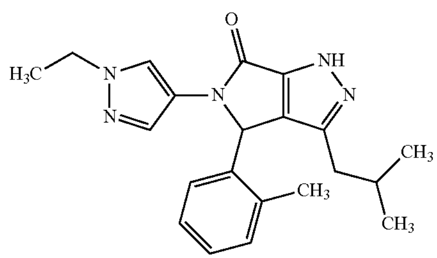 [SMILES: CCn1cc(N2C(=O)c3[nH]nc(CC(C)C)c3C2c2ccccc2C)cn1] | 3.6 | | | | | >10 | >5 | | | | | |
| BUCMD00670 | 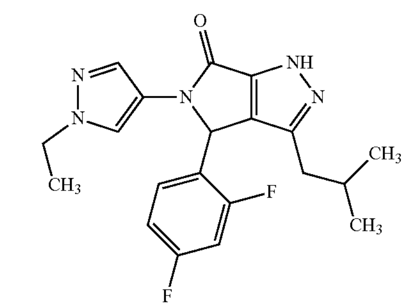 [SMILES: CCn1cc(N2C(=O)c3[nH]nc(CC(C)C)c3C2c2ccc(F)cc2F)cn1] | 3.3 | | | | | >10 | >5 | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00671 | 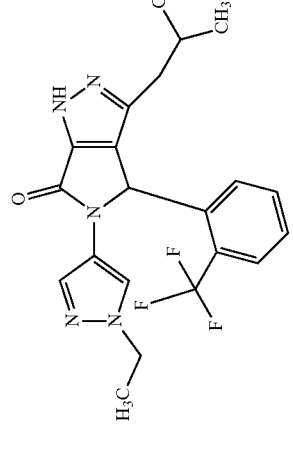 | 3.9 | | | | | >10 | >5 | | | | | |
| BUCMD00675 | 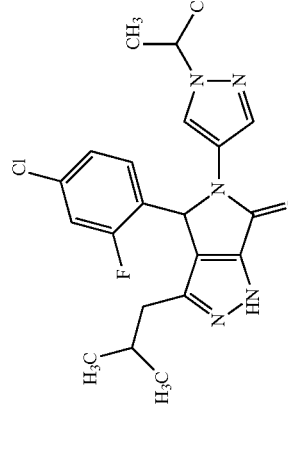 | 4.2 | | | | | >10 | >5 | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| BUCMD00676 | | 4.1 | | | | | >10 | >5 | | | | | |
| BUCMD00677 | | 4.0 | | | | | >10 | >5 | | | | | |
| BUCMD00678 | | 3.7 | | | | | >10 | >5 | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00680 | 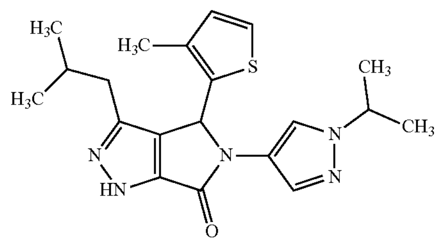 [SMILES: Cc1ccsc1C1c2c(CC(C)C)n[nH]c2C(=O)N1c1cnn(C(C)C)c1] | 3.9 | | | | | >10 | >5 | | | | | |
| BUCMD00693 | 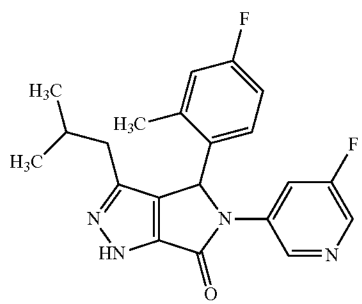 [SMILES: Cc1cc(F)ccc1C1c2c(CC(C)C)n[nH]c2C(=O)N1c1cncc(F)c1] | 3.8 | | | | | >10 | >5 | | | | | |
| BUCMD00696 | 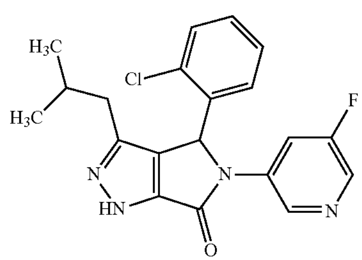 [SMILES: CC(C)Cc1n[nH]c2c1C(c1ccccc1Cl)N(c1cncc(F)c1)C2=O] | 3.8 | | | | | >10 | >5 | | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00701 | 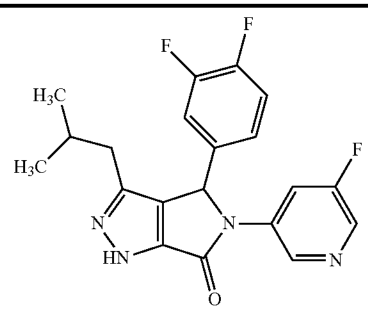 | 3.5 | | | | | >10 | >5 | | | | | |
| BUCMD00711 | 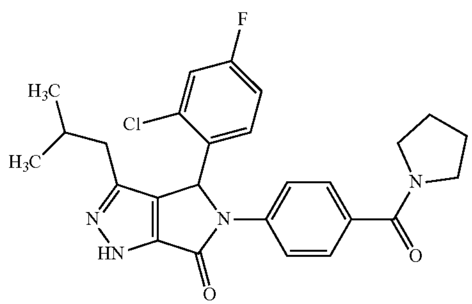 | 4.7 | | | | | >10 | 5.3 | | | | | |

TABLE 1-continued

Compiled Leishmania Data after Treatment with Antileishmanial Compounds

| Compound | Structure | LogPa | *L. donovani* amastigotes % GI at 10 µM (THP-1 cells)b | THP-1 host cell % growth inhibition at 10 µMb | *L. donovani* amastigotes EC50 (µM, THP-1c or B10Rd cells) | THP-1 Host Cell CC50 (µM)c | *L. donovani* amastigotes EC75 (µM B10R cells)d | B10R Host Cell CC50 (µM)d | SI (Host cell potency/ *L. donovani* potency) | *L. braziliensis* amastigotes EC75 (µM J774 cells)e | *L. major* amastigotes EC75 (µM, THP-1 b or J774 cells) | *L. donovani* promastigotes EC50 (µM)f | *L. major* promastigotes EC50 (µM)f |
|---|---|---|---|---|---|---|---|---|---|---|---|---|---|
| BUCMD00712 | 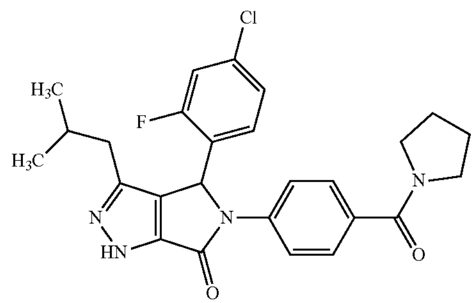 [SMILES: CC(C)Cc1n[nH]c2c1C(c1ccc(Cl)cc1F)N(c1ccc(C(=O)N3CCCC3)cc1)C2=O] | 4.7 | | | | | >10 | 5.8 | | | | | |
| BUCMD00713 | 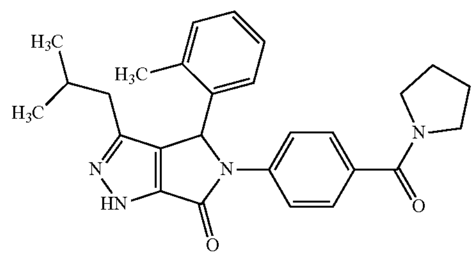 [SMILES: Cc1ccccc1C1c2c(CC(C)C)n[nH]c2C(=O)N1c1ccc(C(=O)N2CCCC2)cc1] | 4.5 | | | | | >10 | 5.0 | | | | | |
| BUCMD00714 | 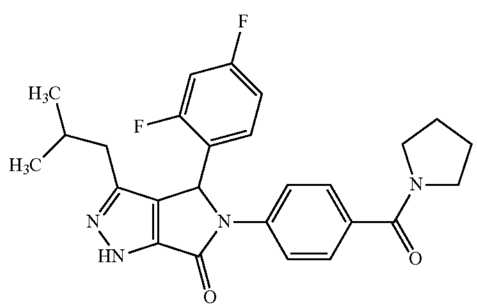 [SMILES: CC(C)Cc1n[nH]c2c1C(c1ccc(F)cc1F)N(c1ccc(C(=O)N3CCCC3)cc1)C2=O] | 4.2 | | | | | >10 | 5.0 | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00715 | 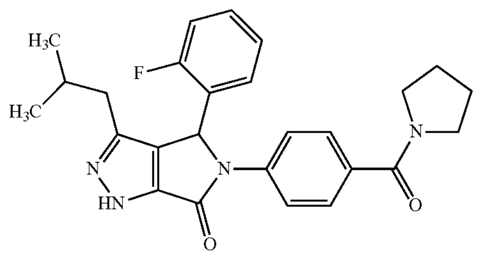 [SMILES: CC(C)Cc1n[nH]c2c1C(c1ccccc1F)N(c1ccc(C(=O)N3CCCC3)cc1)C2=O] | 4.1 | | | | | >10 | >5 | | | | | |
| BUCMD00716 | 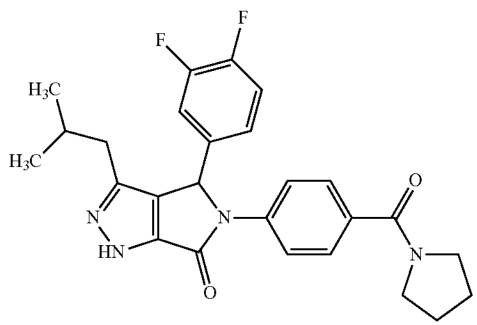 [SMILES: CC(C)Cc1n[nH]c2c1C(c1ccc(F)c(F)c1)N(c1ccc(C(=O)N3CCCC3)cc1)C2=O] | 4.2 | | | | | >10 | >5 | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00719 | 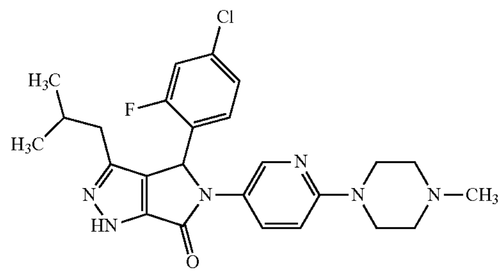 [SMILES: CC(C)Cc1n[nH]c2c1C(c1ccc(Cl)cc1F)N(c1ccc(N3CCN(C)CC3)nc1)C2=O] | 3.9 | | | | | >10 | 5.7 | | | | | |
| BUCMD00722 | 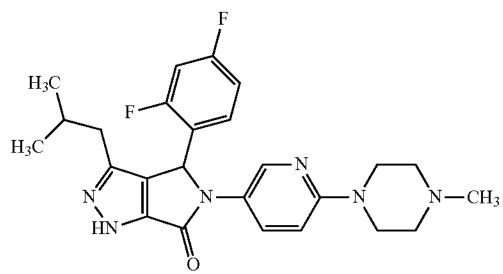 [SMILES: CC(C)Cc1n[nH]c2c1C(c1ccc(F)cc1F)N(c1ccc(N3CCN(C)CC3)nc1)C2=O] | 3.5 | | | | | >10 | 5.1 | | | | | |
| BUCMD00724 | 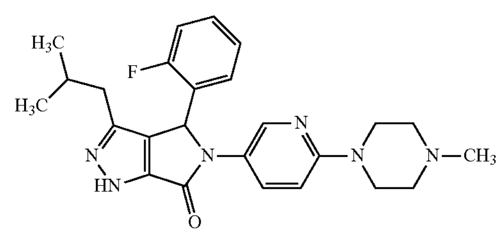 [SMILES: CC(C)Cc1n[nH]c2c1C(c1ccccc1F)N(c1ccc(N3CCN(C)CC3)nc1)C2=O] | 3.3 | | | | | >10 | 5.2 | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| BUCMD00725 | 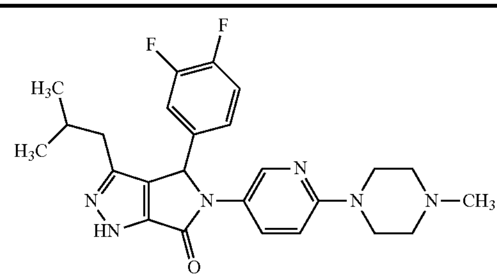 | 3.5 | | | | | >10 | 5.1 | | | | | |
| BUCMD00726 | 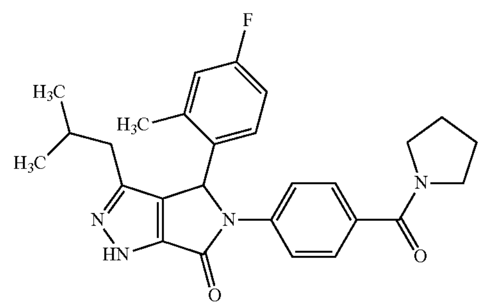 [SMILES: Cc1cc(F)ccc1C1c2c(CC(C)C)n[nH]c2C(=O)N1c1ccc(C(=O)N2CCCC2)cc1] | 4.6 | | | | | >10 | >5 | | | | | |
| BUCMD00727 | 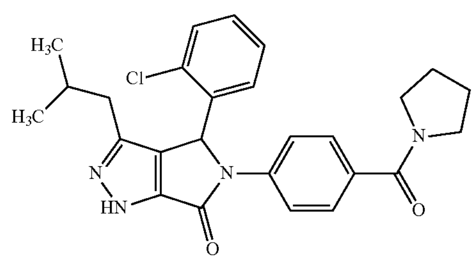 [SMILES: CC(C)Cc1n[nH]c2c1C(c1ccccc1Cl)N(c1ccc(C(=O)N3CCCC3)cc1)C2=O] | 4.6 | | | | | >10 | >5 | | | | | |

TABLE 1-continued

Compiled Leishmania Data after Treatment with Antileishmanial Compounds

| Compound | Structure | LogPa | L. donovani amast-igotes % GI at 10 μM (THP-1 cells)b | THP-1 host cell % growth inhib-ition at 10 μM | L. donovani amast-igotes EC50 (μM, THP-1c or B10Rd cells) | THP-1 Host Cell CC50 (μM)c | L. donovani amast-igotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promast-igotes EC50 (μM)f | L. major promast-igotes EC50 (μM)f |
|---|---|---|---|---|---|---|---|---|---|---|---|---|---|
| BUCMD00731 | 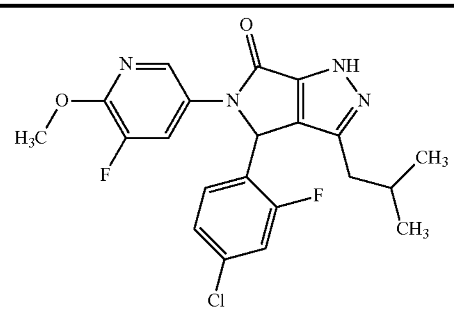 | 4.4 | | | | | >10 | >5 | | | | | |
| BUCMD00739 | 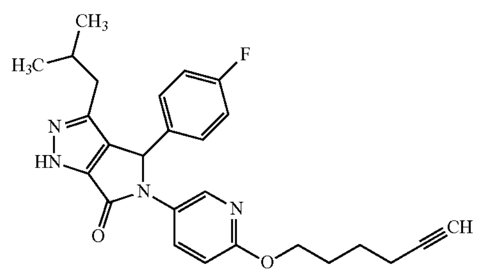 [SMILES: C#CCCCCOc1ccc(N2C(=O)c3[nH]nc(CC(C)C)c3C2c2ccc(F)cc2)cn1] | 5.0 | | | | | >10 | >5 | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00741 | 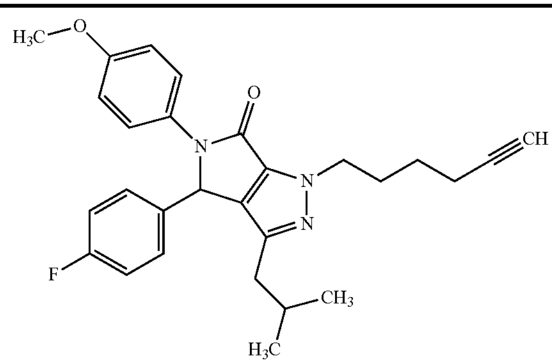 | 5.8 | | | | | >10 | 5.0 | | | | | |
| BUCMD00156 | 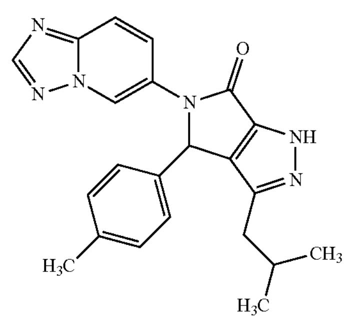 [SMILES: Cc1ccc(C2c3c(CC(C)C)n[nH]c3C(=O)N2c2ccc3ncnn3c2)cc1] | 4.2 | | | | | >10 | | | | | | |

TABLE 1-continued

Compiled Leishmania Data after Treatment with Antileishmanial Compounds

| Compound | Structure | LogPa | L. donovani amast-igotes % GI at 10 µM (THP-1 cells)b | THP-1 host cell % growth inhib-ition at 10 µMb | L. donovani amast-igotes EC50 (µM, THP-1c or B10Rd cells) | THP-1 Host Cell CC50 (µM)c | L. donovani amast-igotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promast-igotes EC50 (µM)f | L. major promast-igotes EC50 (µM)f |
|---|---|---|---|---|---|---|---|---|---|---|---|---|---|
| BUCMD00157 | 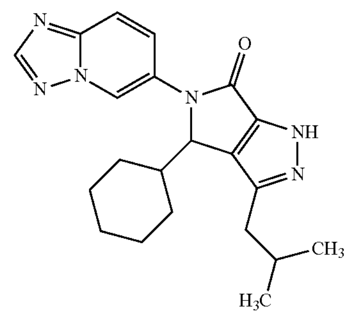 [SMILES: CC(C)Cc1n[nH]c2c1C(C1CCCCC1)N(c1ccc3ncnn3c1)C2=O] | 4.1 | | | | | >10 | | | | | | |
| BUCMD00158 | 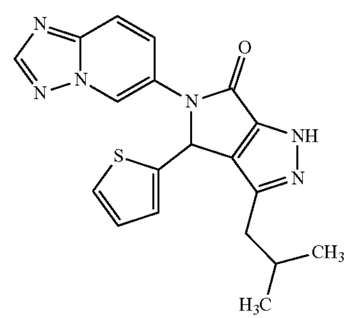 [SMILES: CC(C)Cc1n[nH]c2c1C(c1cccs1)N(c1ccc3ncnn3c1)C2=O] | 4.0 | | | | | >10 | | | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00159 | 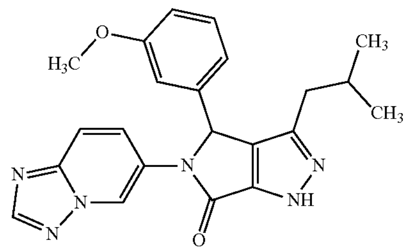 [SMILES: COc1cccc(C2c3c(CC(C)C)n[nH]c3C(=O)N2c2ccc3ncnn3c2)c1] | 4.1 | | | | | >10 | | | | | | |
| BUCMD00160 | 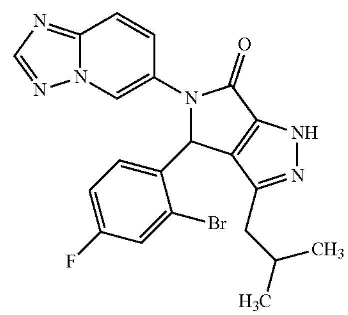 [SMILES: CC(C)Cc1n[nH]c2c1C(c1ccc(F)cc1Br)N(c1ccc3ncnn3c1)C2=O] | 4.4 | | | | | >10 | | | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00161 | 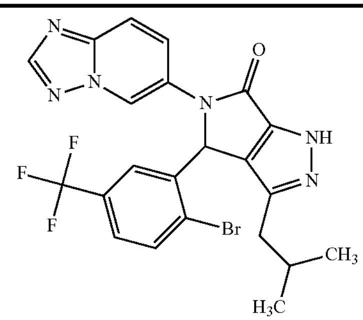 | 4.5 | | | | | >10 | | | | | | |
| BUCMD00162 | 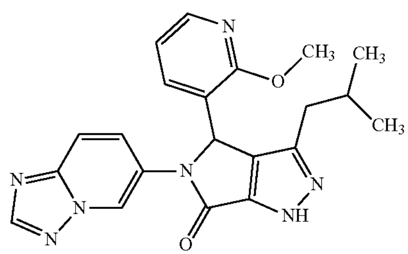 [SMILES: COc1ncccc1C1c2c(CC(C)C)n[nH]c2C(=O)N1c1ccc2ncnn2c1] | 3.9 | | | | | >10 | | | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00163 | 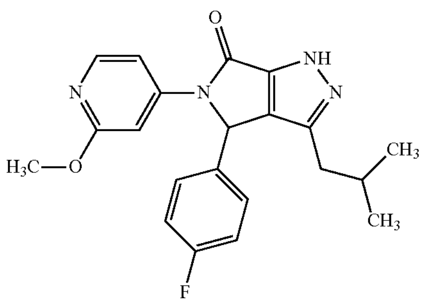 [SMILES: COc1cc(N2C(=O)c3[nH]nc(CC(C)C)c3C2c2ccc(F)cc2)ccn1] | 4.0 | | | | | >10 | | | | | | |
| BUCMD00164 | 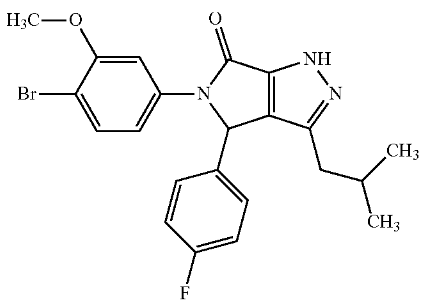 [SMILES: COc1cc(N2C(=O)c3[nH]nc(CC(C)C)c3C2c2ccc(F)cc2)ccc1Br] | 4.0 | | | | | >10 | | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00165 | 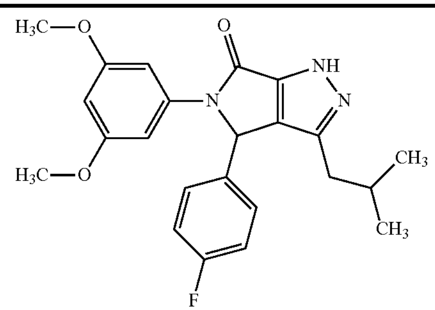 | 3.9 | | | >10 | | | | | | | | |
| BUCMD00166 | 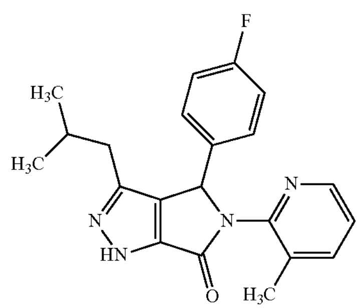 [SMILES: Cc1cccnc1N1C(=O)c2[nH]nc(CC(C)C)c2C1c1ccc(F)cc1] | 3.8 | | | >10 | | | | | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00167 | 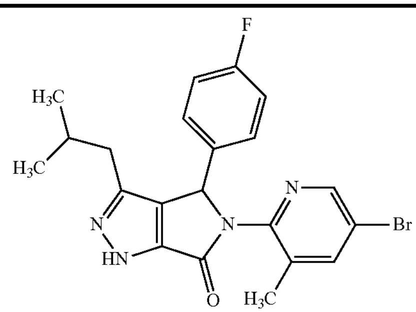 | 4.2 | | | | | >10 | | | | | | |
| BUCMD00168 | 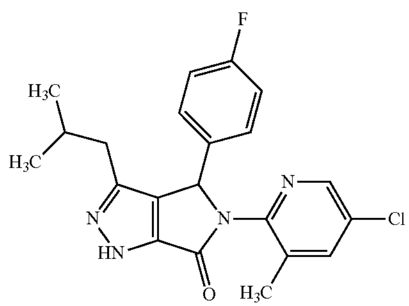 [SMILES: Cc1cc(Cl)cnc1N1C(=O)c2[nH]nc(CC(C)C)c2C1c1ccc(F)cc1] | 3.6 | | | | | >10 | | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00169 | 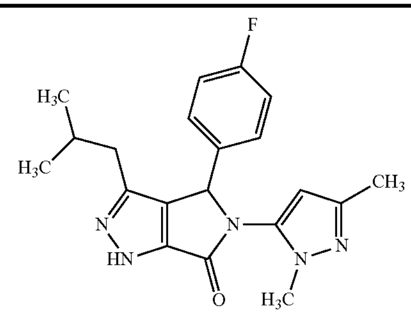 | 3.7 | | | | | >10 | | | | | | |
| BUCMD00170 | 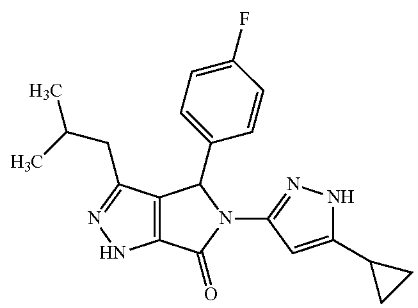 [SMILES: CC(C)Cc1n[nH]c2c1C(c1ccc(F)cc1)N(c1cc(C3CC3)[nH]n1)C2=O] | 4.2 | | | | | >10 | | | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00171 | 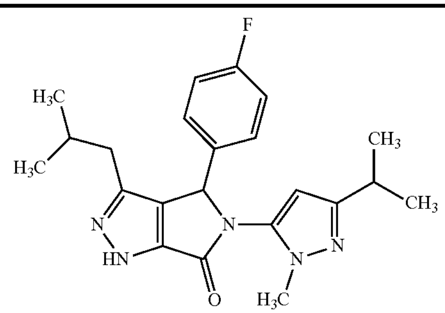 | 4.0 | | | | | >10 | | | | | | |
| BUCMD00172 | 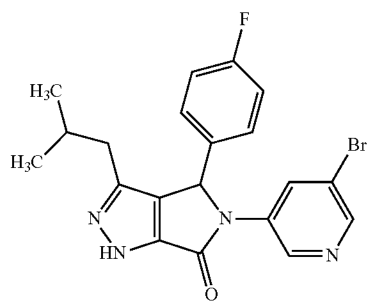 [SMILES: CC(C)Cc1n[nH]c2c1C(c1ccc(F)cc1)N(c1cncc(Br)c1)C2=O] | 3.9 | | | | | >10 | | | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00173 | | 3.8 | | | | | >10 | | | | | | |
| BUCMD00174 | | 3.8 | | | | | >10 | | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00175 | 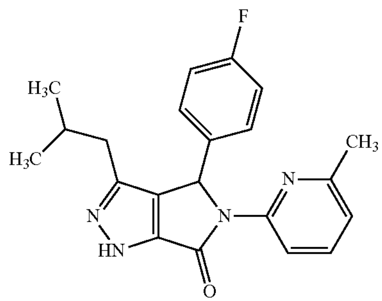 [SMILES: Cc1cccc(N2C(=O)c3[nH]nc(CC(C)C)c3C2c2ccc(F)cc2)n1] | 3.6 | | | | | >10 | | | | | | |
| BUCMD00176 | 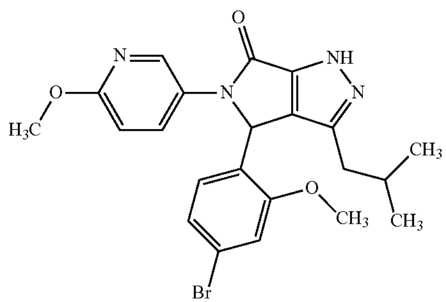 [SMILES: COc1ccc(N2C(=O)c3[nH]nc(CC(C)C)c3C2c2ccc(Br)cc2OC)cn1] | 3.3 | | | | | >10 | | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00177 | 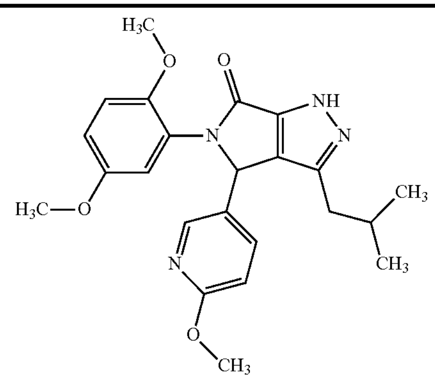 | 3.9 | | | | | >10 | | | | | | |
| BUCMD00178 | 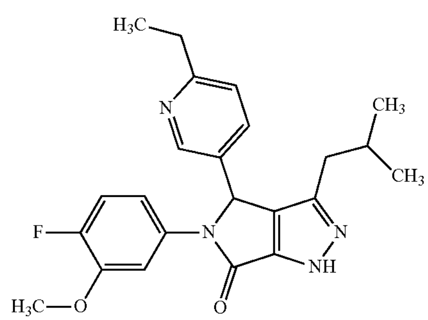 [SMILES: CCc1ccc(C2c3c(CC(C)C)n[nH]c3C(=O)N2c2ccc(F)c(OC)c2)cn1] | 4.1 | | | | | >10 | | | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774 cells) | L. donovani promastigotes EC50 (µM)f | L. major promastigotes EC50 (µM)f |
|---|---|---|---|---|---|---|---|---|---|---|---|---|---|
| BUCMD00179 | 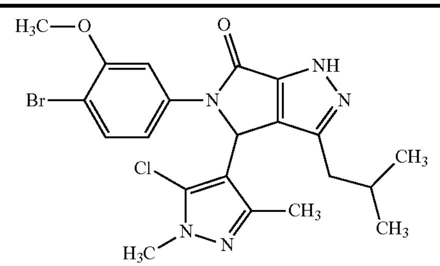 | 4.2 | | | | | >10 | | | | | | |
| BUCMD00180 | 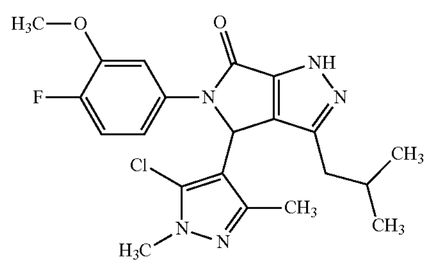 [SMILES: COc1cc(N2C(=O)c3[nH]nc(CC(C)C)c3C2c2c(C)nn(C)c2Cl)ccc1F] | 4.1 | | | | | >10 | | | | | | |
| BUCMD00181 | 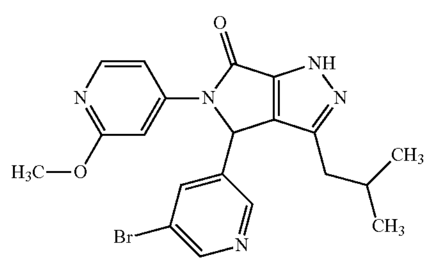 [SMILES: COc1cc(N2C(=O)c3[nH]nc(CC(C)C)c3C2c2cncc(Br)c2)ccn1] | 4.0 | | | | | >10 | | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00182 | 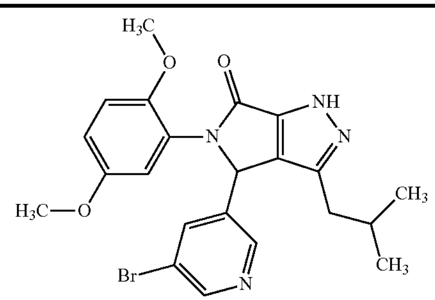 | 3.7 | | | | | >10 | | | | | | |
| BUCMD00183 | 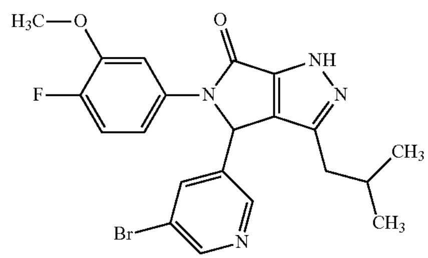 [SMILES: COc1cc(N2C(=O)c3[nH]nc(CC(C)C)c3C2c2cncc(Br)c2)ccc1F] | 3.9 | | | | | >10 | | | | | | |
| BUCMD00184 | 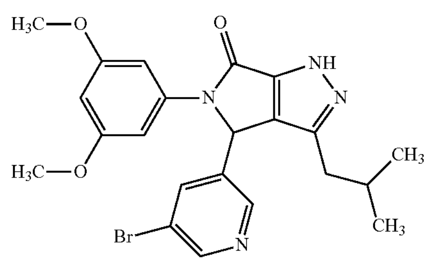 [SMILES: COc1cc(OC)cc(N2C(=O)c3[nH]nc(CC(C)C)c3C2c2cncc(Br)c2)c1] | 4.2 | | | | | >10 | | | | | | |

TABLE 1-continued

Compiled Leishmania Data after Treatment with Antileishmanial Compounds

| Compound | Structure | LogPa | L. donovani amastigotes % GI at 10 µM (THP-1 cells)b | THP-1 host cell % growth inhibition at 10 µMb | L. donovani amastigotes EC50 (µM, THP-1c or B10Rd cells) | THP-1 Host Cell CC50 (µM)c | L. donovani amastigotes EC75 (µM B10R cells)d | B10R Host Cell CC50 (µM)d | SI (Host cell potency/ L. donovani potency) | L. braziliensis amastigotes EC75 (µM J774 cells)e | L. major amastigotes EC75 (µM, THP-1 b or J774e cells) | L. donovani promastigotes EC50 (µM)f | L. major promastigotes EC50 (µM)f |
|---|---|---|---|---|---|---|---|---|---|---|---|---|---|
| BUCMD00185 | | 4.3 | | | | | >10 | | | | | | |
| BUCMD00186 | | 3.8 | | | | | >10 | | | | | | |
| BUCMD00187 | | 3.8 | | | | | >10 | | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00188 | 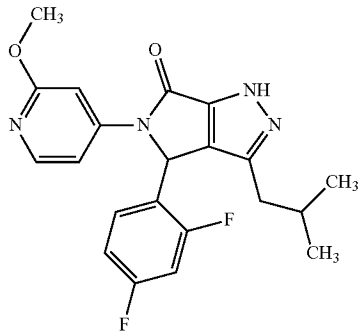 [SMILES: COc1cc(N2C(=O)c3[nH]nc(CC(C)C)c3C2c2ccc(F)cc2F)ccn1] | 3.8 | | | | | >10 | | | | | | |
| BUCMD00189 | 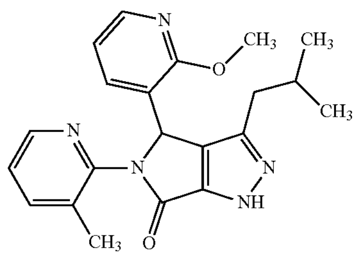 [SMILES: COc1ncccc1C1c2c(CC(C)C)n[nH]c2C(=O)N1c1ncccc1C] | 3.5 | | | | | >10 | | | | | | |

TABLE 1-continued

Compiled Leishmania Data after Treatment with Antileishmanial Compounds

| Compound | Structure | LogPa | *L. donovani* amastigotes % GI at 10 µM (THP-1 cells)b | THP-1 host cell % growth inhibition at 10 µM b | *L. donovani* amastigotes EC50 (µM, THP-1c or B10Rd cells) | THP-1 Host Cell CC50 (µM)c | *L. donovani* amastigotes EC75 (µM B10R cells)d | B10R Host Cell CC50 (µM)d | SI (Host cell potency/ *L. donovani* potency) | *L. braziliensis* amastigotes EC75 (µM J774 cells)e | *L. major* amastigotes EC75 (µM, THP-1 b or J774 cells)e | *L. donovani* promastigotes EC50 (µM)f | *L. major* promastigotes EC50 (µM)f |
|---|---|---|---|---|---|---|---|---|---|---|---|---|---|
| BUCMD00190 | 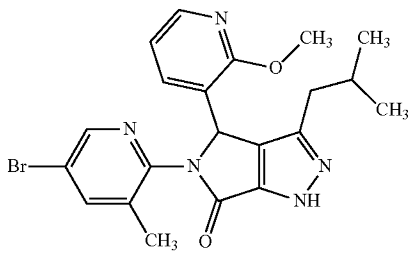 [SMILES: COc1ncccc1C1c2c(CC(C)C)n[nH]c2C(=O)N1c1ncc(Cl)cc1C] | 4.7 | | | | | >10 | | | | | | |
| BUCMD00191 | 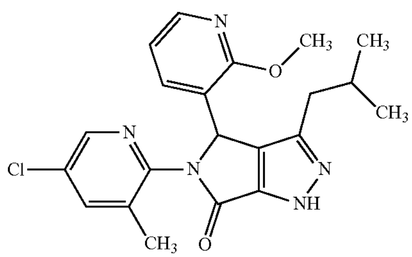 | 4.7 | | | | | >10 | | | | | | |
| BUCMD00192 | 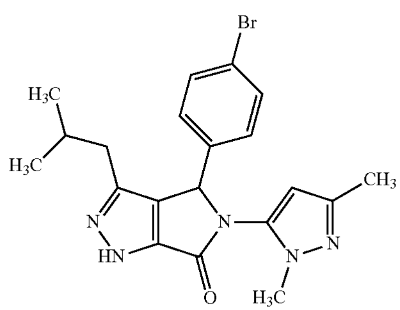 [SMILES: Cc1cc(N2C(=O)c3[nH]nc(CC(C)C)c3C2c2ccc(Cl)cc2)n(C)n1] | 4.5 | | | | | >10 | | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00193 | 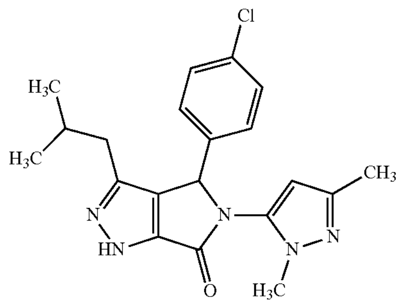 | 4.2 | | | | | >10 | | | | | | |
| BUCMD00194 | 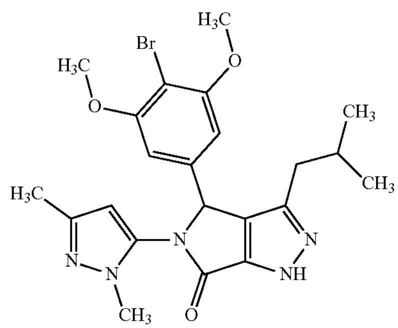 [SMILES: COc1cc(C2c3c(CC(C)C)n[nH]c3C(=O)N2c2cc(C)nn2C)cc(OC)c1Br] | 4.1 | | | | | >10 | | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774e cells) | L. donovani promastigotes EC50 (μM)f | L. major promastigotes EC50 (μM)f |
|---|---|---|---|---|---|---|---|---|---|---|---|---|---|
| BUCMD00195 | 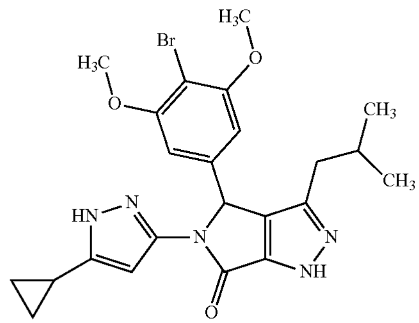 [SMILES: COc1cc(C2c3c(CC(C)C)n[nH]c3C(=O)N2c2cc(C3CC3)[nH]n2)cc(OC)c1Br] | 4.2 | | | | | >10 | | | | | | |
| BUCMD00196 | 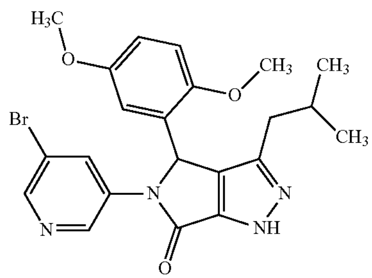 [SMILES: COc1ccc(OC)c(C2c3c(CC(C)C)n[nH]c3C(=O)N2c2cncc(Br)c2)c1] | 3.9 | | | | | >10 | | | | | | |

TABLE 1-continued

Compiled Leishmania Data after Treatment with Antileishmanial Compounds

| Compound | Structure | LogPa | L. donovani amastigotes % GI at 10 μM (THP-1 cells)b | THP-1 host cell % growth inhibition at 10 μMb | L. donovani amastigotes EC50 (μM, THP-1c or B10Rd cells) | THP-1 Host Cell CC50 (μM)c | L. donovani amastigotes EC75 (μM B10R cells)d | B10R Host Cell CC50 (μM)d | SI (Host cell potency/ L. donovani potency) | L. braziliensis amastigotes EC75 (μM J774 cells)e | L. major amastigotes EC75 (μM, THP-1 b or J774 cells) | L. donovani promastigotes EC50 (μM)f | L. major promastigotes EC50 (μM)f |
|---|---|---|---|---|---|---|---|---|---|---|---|---|---|
| BUCMD00197 | 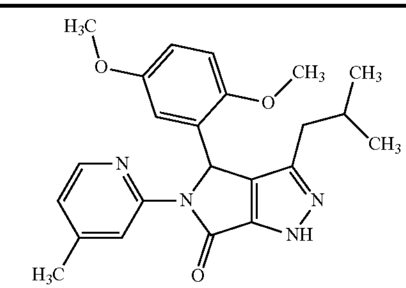 | 3.5 | | | | | >10 | | | | | | |
| BUCMD00198 | 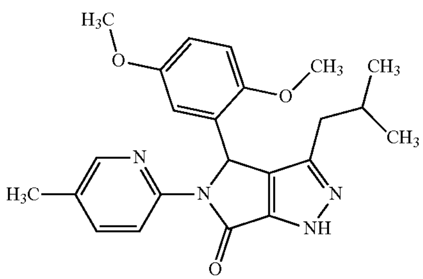 [SMILES: COc1ccc(OC)c(C2c3c(CC(C)C)n[nH]c3C(=O)N2c2ccc(C)cn2)c1] | 3.3 | | | | | >10 | | | | | | |
| BUCMD00199 | 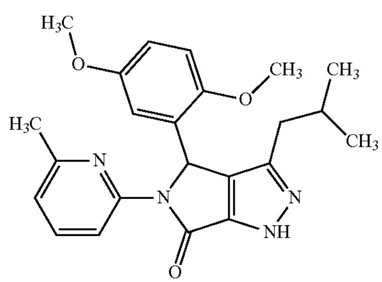 [SMILES: COc1ccc(OC)c(C2c3c(CC(C)C)n[nH]c3C(=O)N2c2cccc(C)n2)c1] | 3.5 | | | | | >10 | | | | | | |

Table 1 Footnotes:
Measured using ChemAxon's JChem calculator.

Assay Conditions B: THP-1 cells (human acute monocytic leukemia cell line—ATCC TIB202) were grown in RPMI supplemented with 10% Fetal Bovine Serum (FBS) and 50 µM 2-mercaptoethanol at 37° C. in 5% $CO_2$. THP-1 were seeded in microwell plates at $5 \times 10^5$ cells/mL density and treated with 0.1 µM phorbol myristate acetate (PMA, Sigma) at 37° C. for 48 h for differentiation into adherent, non-dividing macrophages. After activation by PMA, cells were washed and incubated with complete RPMI medium containing stationary phase Leishmania promastigotes (L. major: strain LV39; L. donovani, strain 1 S/Cl2D) at a 1:15 parasite-cell ratio. Compounds were added and incubated at 37° C. for 72 h. Cells were then washed with phosphate-buffered saline (PBS), fixed for 30 minutes with 4% formaldehyde, rinsed again with PBS, stained for 2 h with 4',6'-diamidino-2-phenylindole (DAPI 300 nM) and finally washed with PBS.

Assay Conditions C: The intramacrophage Leishmania donovani activity assay was performed as described in Antimicrob Agents Chemother (2013) 57(7):2913-22.

Assay Conditions D: B10R cells (CVCL_0155) were seeded at 300 cells/well, and L. donovani WT promastigotes in stationary phase (7th day after passage) were added at 6,000 parasites/well (ratio of 20 parasites/cell). Both cells and parasites were seeded in DMEM High-Glucose medium (Gibco, cat. no. 11995065) containing 5% Fetal Bovine Serum (Sigma-Aldrich, cat. no. F2442) and 1% Penicillin-Streptomycin (Gibco, cat. no. 15140122). Cells and parasites were incubated in the presence of the compounds for 72 h at 37° C. and 5% $CO_2$. Plates were then fixed with 4% formaldehyde solution for at least 1 h, then washed with 1×PBS and stained with 5 µg/mL DAPI. Plates were read using an ImageXpress microscope (Molecular Devices) and analyzed by MetaXpress software (Molecular Devices) using a custom module optimized for this assay. Compounds that showed relevant antiparasitic activity in the primary screening were retested in serial dilution to obtain a dose-response curve (DRC). Compounds were tested in a 10-point 2-fold serial dilution in 3 technical replicates, and 2 biological replicates. After 72 h, plates were fixed and stained with DAPI as described above. Images were acquired on an ImageXpress microscope, and analyzed using the MetaXpress custom module. The DRCs were plotted, effective concentration inducing 75% activity ($EC_{75}$) and half-cytotoxic concentration ($CC_{50}$) were calculated using GraphPad Prism Software, version 6.05 (GraphPad Software, San Diego, CA).

Assay Conditions E: J774 cells (ATCC J774A.1 were grown in DMEM supplemented with 10% Fetal Bovine Serum (FBS) and 1% Penicillin-Streptomycin at 37° C. in 5% $CO_2$. Leishmania parasites expressing luciferase and GFP were grown as described in Front. Cell. Infect. Microbiol (2019) 9:237. J774 cells were seeded in microwell plates at $3 \times 10^5$ cells/mL density. Cells were washed with PBS and incubated with complete DMEM medium containing stationary phase Leishmania promastigotes (L. major: strain Friedlin; L. braziliensis, strain BA788) at a 1:10 parasite-cell ratio for 24 h. Cells were washed with PBS. Cells and compounds were incubated for 48 h at 37° C. and 5% $CO_2$. Compounds were tested in 8-point 2-fold serial dilution in 4 technical replicates, and 2 biological replicates. After 48 h, OneTiterGlo (Promega) (100 µl) was added to each well. Plates were incubated for 15 min and bioluminescence was measured using a plate reader (Molecular Devices). Effective concentration inducing 75% activity ($EC_{75}$) was calculated using GraphPad Prism Software (version 9.0).

Assay Conditions F: Leishmania promastigotes (L. major: strain LV39; L. donovani, strain 1 S/Cl2D) were maintained as previously described in PloS Negl Trop Dis (2015) 9(3):e0003588 and Pathogens (2021) 10(5):593) at 28° C. in M199 media supplemented with glutamine, adenosine, folic acid, hemin, HEPES, 10% Fetal Bovine Serum (Sigma-Aldrich, cat. no. F2442) and 1% Penicillin-Streptomycin (Gibco, cat. no. 15140122). For the promastigote assay, we followed the method previously described in PloS Negl Trop Dis (2011) 5(7):e1253. Briefly, promastigotes were incubated with the compounds for 72 h at 27° C., then lysed by adding 50 µL of CellTiter-Glo (Promega) and placed on an orbital shaker for 5 min at room temperature. After lysis, the resulting ATP-bioluminescence was measured using the Analyst HT plate reader (Molecular Devices).

Example 2

Introduction

Leishmaniases are a group of parasitic diseases caused by a variety of species of parasites of the genus Leishmania, which are exist on all continents. About 350 million people are living in high-risk areas. The form and severity of the disease depend on the Leishmania species and the host's immune status. While Leishmania major causes most CL infections in North Africa, the Middle East, and Central Asia, L. braziliensis is the leading causative agent of CL in South America, responsible for the majority of the 300,000 total cases. In Brazil, 21,000 new cases are registered per year. CL infection by L. braziliensis presents as several clinical forms, which range from a localized ulcerated lesion (localized cutaneous leishmaniasis, or LCL) to disfiguring lesions in mucosal areas. In Brazil, LCL is caused mainly by L. amazonensis and L. braziliensis. LCL also can produce a large number of skin ulcers on exposed parts of the body, such as the face, legs and arms, which later become permanent scars. L. braziliensis can also cause disseminated leishmaniasis, characterized by the appearance of dozens to thousands of skin lesions that spread across non-contiguous body segments, also with frequent involvement of mucosal areas.

Treatment alternatives for leishmaniasis are limited to a small number of drugs that, due to the high cost and significant adverse effects, becomes one of the major barriers to cure the disease. In Brazil, the first drug of choice is pentavalent antimonial (Sb v), with two commercial presentations: antimoniate-N-methyl-glucamine (Glucantime®) and sodium stibogluconate (Pentostam®). Pentavalent antimonials interfere with the oxidative metabolism of the Leishmania amastigote, causing an inhibition in both glycolysis and oxidation of fatty acids, processes primarily located in the glycosomes. The recommended dose of Glucantime® varies between 10 to 20 mg of $Sb^v$/kg/day/20 days and in the absence of complete healing two weeks after the end of treatment, the regimen is repeated. If the failure persists, the diagnosis should be reassessed in a specialized service to verify the possibility of indicating the drugs of second choice, which in these cases are Amphotericin B and Pentamidine.

Pentavalent antimonials have been used worldwide for the treatment leishmaniasis for more than six decades and, lately, acquired resistance has become a clinical threat. Therefore other alternatives to using of $Sb^v$ have emerged such as Miltefosine, which replaced sodium stibogluconate (Pentostan) in the Indian subcontinent. Amphotericin B is also highly effective, but relatively toxic when injected in its deoxycholate free form. Administration in a liposomal formulation improves the risk of toxicity, although the high cost of this formulation has restricted its use. Lastly, Paromomycin has a relatively narrow range of target species of Leishmania which makes the range of treatment difficult. In parallel to the search for new therapeutic alternatives for leishmaniasis, another goal is to develop novel forms of therapy besides the intravenous or intramuscular routes used for pentavalent antimonials. Towards this end, the use of bacterial cellulose or biocellulose (BC) membranes was investigated for the topical treatment of LCL. Several microorganisms have the ability to produce BC, however Gram-negative bacteria of Gluconacetobacter genus are capable of producing cellulose in commercial quantities. Cellulose membrane are synthesized at the air/liquid interface of the static culture medium, they highly porous structures constituted of a random microfibrillar 3D-network of cellulose chains aligned in parallel with high permeability to fluids, this being favorable for cell adhesion and proliferation. BC membranes are thus a promising biomaterial for healing wounds, burns and the treatment of tissue implants due to their unique properties such as high crystallinity, high mechanical strength, ultrafine fiber network structure and high water-uptake capability (water content 90%). BC membranes also provide a humid environment to the affected region, promoting exudate absorption and acceleration of wound healing without any toxicity. Efforts to develop new BC-based materials to add new characteristics and therapeutic possibilities have generated a BC-based hydrogel. BC-based-hydrogel has been shown to accelerate the healing processes, suggesting its demonstrating potential for the treatment of dermal lesions, such as those observed in LCL.

A new class of pyrazolopyrrolidinone antileishmanials has recently been exposed and exemplified by early lead CMLD011128 with potent inhibition of both the VL-causative species L. donovani, and CL-causative species L. major. From this work, two advanced leads CMLD011494 and CMLD010948 showed significant leishmanicidal activity, in micromolar quantities, against the amastigote and promastigote forms, suggesting their therapeutic potential in leishmaniasis.

Given the recent findings describing the use of BC biocuratives formulated with DETC, Diethyldithiocarbamate, a superoxide dismutase 1 inhibitor, herein the leishmanicial potential of CMLD011494 and CMLD010948 was investigated against L. braziliensis. Experiments conducted in vitro and in vivo, using BC-based hydrogel containing CMLD011494 and CMLD010948 showed that both leads display leishmanicidal activity.

Figures 4A, 4B, 4C:
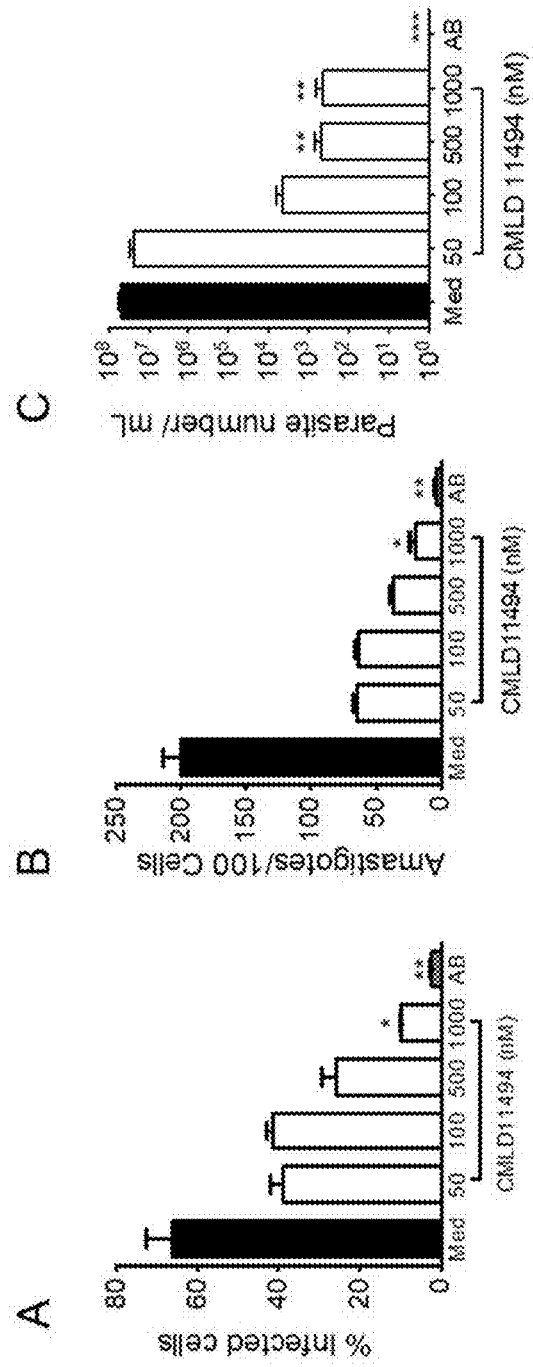
FIG. 4A-4C shows CMLD011494 reduces L. braziliensis infection in vitro. Macrophages were infected with L. braziliensis for 24 h, and exposed to different concentrations of CMLD011494 for 24 h. Cells were stained with H&E and evaluated.

Pyrazolopyrrolidinones Reduce the Parasite Load In Vitro, in a Dose-Dependent Manner Initially, the leishmanicidal effect of (S)-1 was evaluated and a subset of high-potency advanced leads, including CMLD011494, CMLD0010948, and CMLD010947 against marine macrophages infected with L. braziliensis. It was found that CMLD011494 significantly reduced the percentage of infected macrophages (FIG. 4A) and the number of amastigotes (FIG. 4B) in a dose dependent manner. To confirm that CMLD011494 compromised parasite viability, intracellular parasite survival was quantified by transformation of amastigotes into proliferating promastigotes in Schneider's medium, as described. L. braziliensis promastigotes were also significantly reduced following exposure of infected BMDM to CMLD011494 (FIG. 4C).

Figures 5A, 5B:
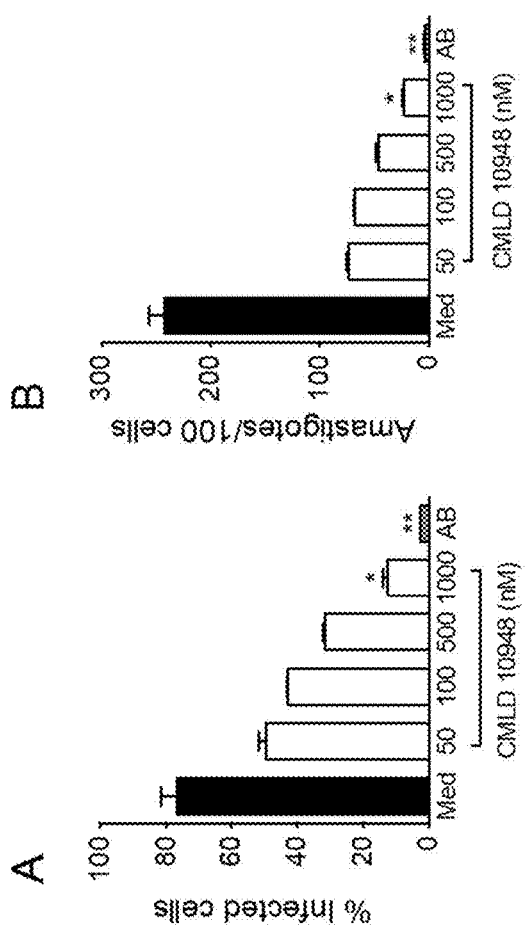
FIG. 5A-5B show CMLD010948 reduces L. braziliensis infection in vitro. Macrophages were infected with L. braziliensis for 24 h, and exposed to different concentrations of CMLD010948 for 24 h. Cells were stained with H&E and evaluated.
Figures 8A, 8B, 8C, 8D:
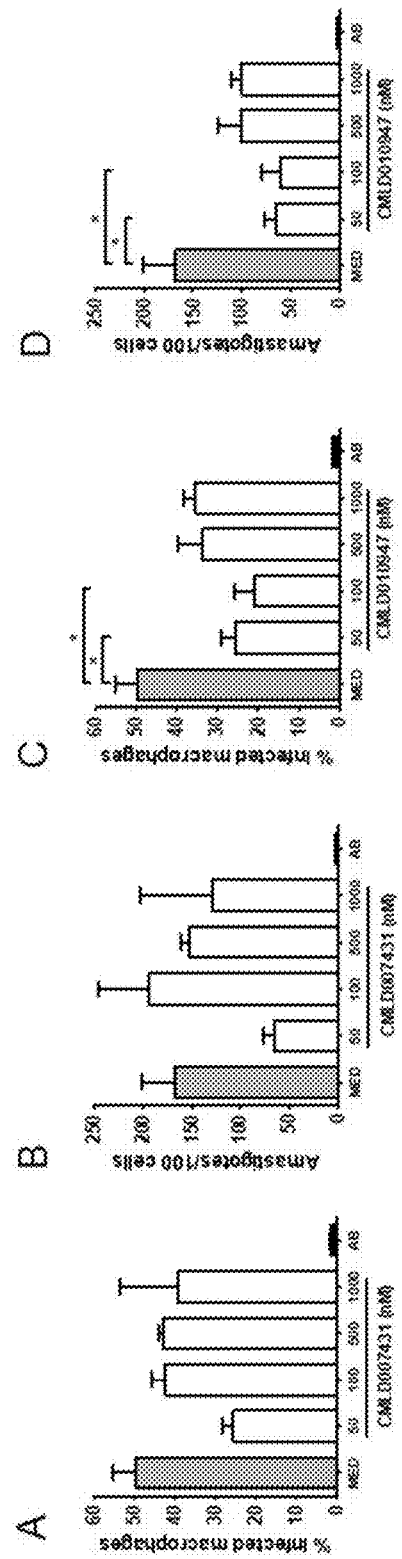
FIG. 8A-8D examine dose-dependent effect of small molecules targeting intracellular L. braziliensis infection in vitro. Macrophages were infected with L. braziliensis for 24 h and exposed to different concentrations of CMLDs 007431 and 10947 for 24 h. Cells were stained with H&E and evaluated.

In similar experiments, compound CMLD010948 also induced a significant decrease in the percentage of infected cells (FIG. 5A) and of intracellular amastigotes (FIG. 5B). These results again confirm that these small molecules are targeting the intracellular amastigote, leading to parasite killing. Of note, however, is that compounds CMLD010947 and CMLD011128, both potent inhibitors of L. donovani, and the latter an inhibitor of L. major, did not show leishmanicidal effects when probed against L. braziliensis infection. The percentage of infected macrophages did not decrease upon treatment with CMLD011128 (FIGS. 8A and 8B). However, killing effect was seen with for CMLD010947, at the two lowest concentrations tested (50 and 100 nM) (FIGS. 8C and 8D) but not at the higher concentration range (500 and 1000 nM).

Figures 6A, 6B, 6C, 6D:
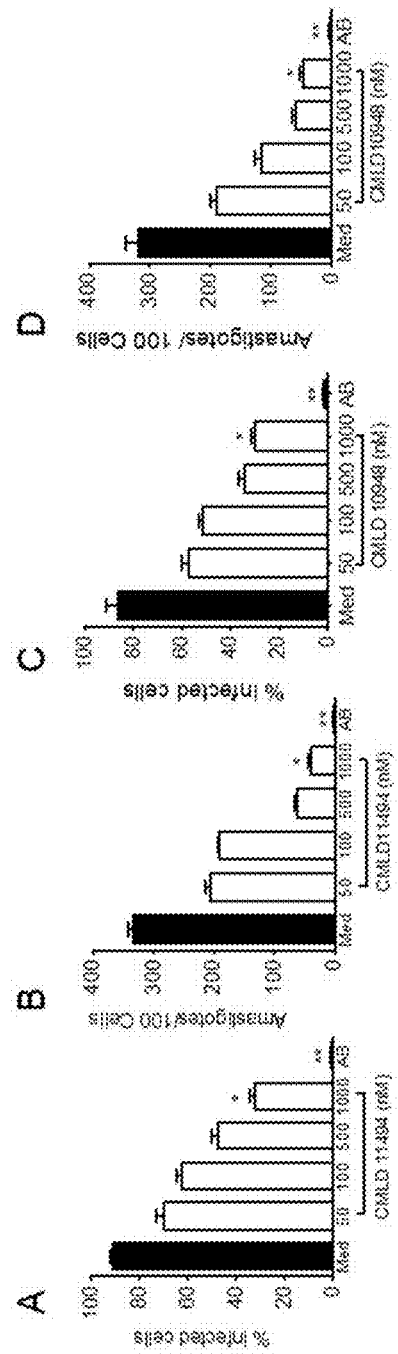
FIG. 6A-6D show CMLD011494 and CMLD010948 reduce L. major infection in vitro. Macrophages were infected with L. major for 24 h, and exposed to different concentrations of CMLD011494 and CMLD010948 for another 24 h. Cells were stained with H&E and evaluated.
Figures 9A, 9B:
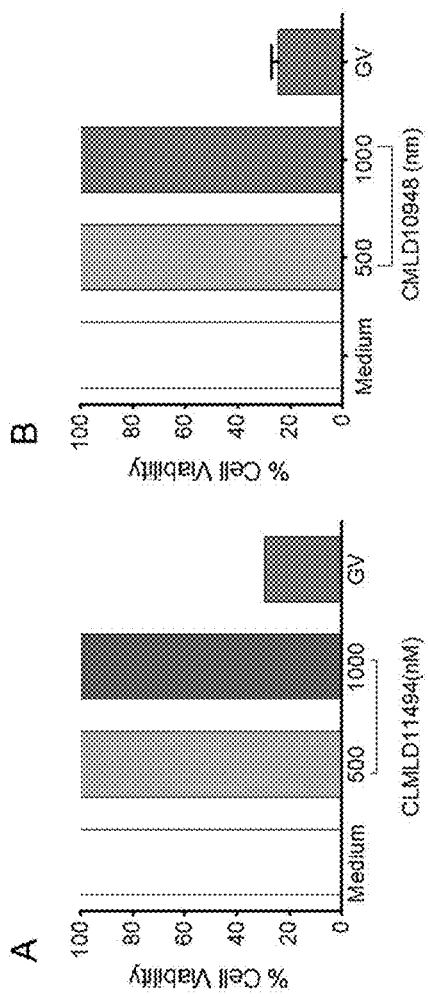
FIGS. 9A and 9B show effect of bacterial CMLDs on cell viability. Macrophages were exposed to empty CMLD011494 (FIG. 9A) or CMLD010948 (FIG. 9B) at different concentrations. Cell viability was evaluated after 24 h. Data are from one representative experiment and are expressed in percent of untreated control (100%).

Given the dose dependent effect of compounds CMLD011494 (FIG. 5A) and CMLD010948 (FIG. 5B), the investigation was extended to L. major since this is the main etiological agent of LCL in the Middle East. Differently from L. braziliensis, L. major does not cause disfigurative disease such as mucosal leishmaniasis. The results show that exposure of L. major-infected murine macrophages to both CMLD011494 and CMLD010948 also leads to a significant decreased percentage of infected cells (FIG. 6A and FIG. 6C, respectively) and number of intracellular amastigotes (FIG. 6B and FIG. 6D, respectively). However, these effects were only observed at the highest dose (1 µM). Exposure of macrophages to CMLD011494 and CMLD010948 at concentrations ranging from 500-1000 nM did not change cell viability (FIGS. 9A and 9B). The $EC_{50}$ of CMLD011494 against L. braziliensis-infected macrophages was 1.64 µM and for CMLD010948 was >5 µM.

The in vitro data collectively show that CMLD011494 and CMLD010948 display a leishmanicidal potential against L. braziliensis and L. major, as seen by the reduction in the percentage of infected cells as well the number of intracellular amastigotes.

Figures 7A, 7B, 7C:
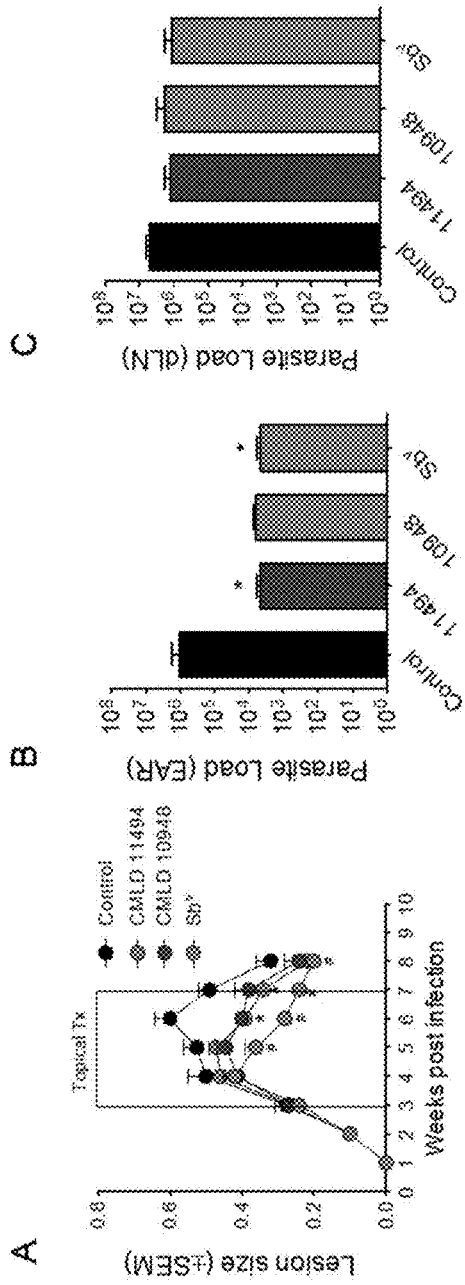
FIG. 7A-7C examine in vivo leishmanicidal effect of small molecules in L. braziliensis-infected mice. BALB/c mice (5 per group) were infected with $10^5$ L. braziliensis promastigotes in the ear dermis. Three weeks post infection, treatment was started on alternate days (boxed area).
Figure 10:
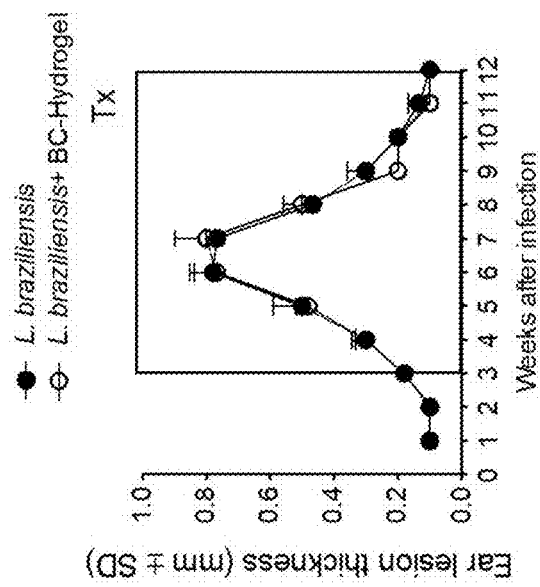
FIG. 10 examines leishmanicidal effect of BC Hydrogel in mice infected with L. braziliensis. BALB/c mice (5 per group) were infected with $10^5$ L. braziliensis promastigotes in the ear dermis. Three weeks post infection, BC-Hydrogel treatment was started on alternate days (boxed area). Lesion development was measured weekly.

Topically-Applied BC-Hydrogel Containing Pyrazolopyrrolidinones Reduces the Lesion Size and Parasite Load In Vivo Next, the effect of the compounds was tested using an in vivo experimental model of CL. Mice were inoculated with L. braziliensis and three weeks later, treated with BC-hydrogel containing CMLD011494 at 10 µg. The hydrogel was applied to cutaneous lesions, with treatment applied three times a week, for eight weeks. BC-hydrogel alone (control) did not interfere with lesion development; however, the BC-hydrogel containing CMLD011494 significantly impaired lesion development (FIG. 7A). Of note, L. braziliensis treatment with BC-Hydrogel alone did not change lesion development in comparison to untreated mice (FIG. 10), indicating that BC-hydrogel containing CMLD011494 or CMLD010948 exert therapeutic effects in vivo. Six weeks after parasite inoculation, parasite load was determined at the infection site and in draining lymph nodes. As shown in FIG. 7, treatment with BC-hydrogel containing CMLD011494 significantly reduced parasite load at the ear (FIG. 7B), in levels compared to pentavalent antimony (the current standard care treatment for LCL caused by L. braziliensis, in Brazil). In comparison, the parasite load was similar amongst the four groups (FIG. 7C) in the draining lymph nodes, indicating that the local topical exposure to CMLD011494 does not impact distal sites.

Experimental Methods

Ethics Statements

Female BALB/c mice, 6-8 weeks of age, were obtained from the IGM-FIOCRUZ animal facility where they were maintained under pathogen-free conditions. All animal experimentation was conducted in accordance with the Guidelines for Animal Experimentation established by the Brazilian Council for Animal Experimentation Control (CONCEA). All procedures involving animals were approved by the local Institutional Review Board for Animal Care and Experimentation (CEUA-IGM-FIOCRUZ-002/2019-2068.

Cells

Leishmania braziliensis (MHOM/BR/00/BA788) and L. major (Friedlin) promastigotes were maintained in Schneider's medium (SIGMA) supplemented with 10% heat-inactivated FCS, 100 U/ml penicillin, 100 µg/ml streptomycin (all from Invitrogen).

Macrophage Infection with L. braziliensis and Exposure to CMLDs.

BMDM were obtained as described above. Cells were resuspended in DMEM medium supplemented with 100 U/mL penicillin, 100 mg/mL streptomycin, and 10% heat-inactivated Fetal Bovine Serum (all from Invitrogen) and seeded at a density of $3 \times 10^5$ cells per well in 24-well culture plates. Monolayers received $3 \times 10^6$ cells L. braziliensis promastigotes and were incubated at 37° C. in supplemented DMEM medium for 24 h. Infected macrophages were then washed to remove non-internalized parasites. Compounds CMLD 011128, CMLD010947, CMLD010498, and CMLD011494 were added at different concentrations. After 24 hours, cells were extensively washed, fixed and stained with hematoxylin and eosin (H&E). The number of infected cells and of intracellular amastigotes were counted by optical microscopy in 200 macrophages. Positive controls consisted of cultures treated with Amphotericin B (0.25 µg/mL, Invitrogen). Cultures were performed in quintuplicate. Alternatively, infected macrophages were treated as described, monolayers were extensively washed and the medium was replaced by 0.5 ml of supplemented Schneider medium. Cells were cultured for seven additional days at 26° C., when number of viable promastigotes was determined using hemocytometer.

To calculate the half-maximal effective concentration ($EC_{50}$), L. braziliensis-infected macrophages were exposed to different concentrations of CMLD011494 (10, 25, 50, 100, 250, 500 and 1000 nM) After 24 hours, the percentage of infected macrophages was determined by optical microscopy. Results were expressed as the mean percentage reduction of infected cells compared with untreated control wells. Half-maximal effective concentrations ($EC_{50}$) were determined by sigmoidal regression curves using Prism 7.0 software (GraphPad Software Inc.)

Cellular Viability

Briefly, macrophages were obtained from bone marrow and seeded at a density of $1 \times 10^6$ cells per well in 24-well culture plates. After 2 hours, cells were treated with compounds at two concentrations (500 and 1000 nm) for 24 hours. Cell viability was determined using Cell Titer Glo (Promega), according to manufacturer's instructions. For positive control, pararosaniline chloride was used.

Superoxide and Cytokine Quantification in Culture Supernatants.

BMDM were seeded at a density of $1 \times 10^6$ cells per well in 24-well culture plates and cells were infected with L. braziliensis as described above. To determine superoxide production, BC-DETC or empty BC were placed within wells containing infected cells for 48 h in presence of 0.5 mM hydroxylamine hydrochloride (Acros Organics). Superoxide was quantified in culture supernatants using Griess reagent.

Cytokine levels were determined in culture supernatants using commercial ELISA kits, following manufacturer's instructions.

L. braziliensis Intradermal Inoculation and Therapeutic Scheme.

BALB/c mice were inoculated intradermally with L. braziliensis promastigotes ($10^5$ parasites in 10 µl of saline) using a 27.5-gauge needle18. Ear thickness (as a surrogate for lesion development) was recorded weekly using a digital caliper (Thomas Scientific). Three weeks after parasite inoculation mice were randomly assigned into three groups: one group was topically treated with BC-11494 or BC-10948. BC-based hydrogel was kindly provided by Seven Industria de Produtos Biotecnologicos Ltda. (Ibipord, PR, Brazil). BC-based hydrogel (Nexfill® Hydrogel) composition was obtained according to the PI 0601330-9 A2 patent. CMLD011494 or CMLD010498 solution (10 mM) were mixed to BC-hydrogel (20 uL) and placed on the lesions of infected mice, three times a week, for three consecutive weeks. Ear thickness continued to be recorded weekly. Controls consisted of mice treated with BC-hydrogel alone or with $Sb^V$ (50 mg/kg), following the same regime described for BC-hydrogel. Six weeks after infection, parasite load was determined using by limiting-dilution analysis, as described previously.

REFERENCES

1. Organization. WECotCotLWH. Control of the Leishmaniases: Report of a WHO Expert Committee. Geneva: World Health Organization, 1990.
2. Cunningham A C. Parasitic Adaptive Mechanisms in Infection by Leishmania. Experimental and Molecular Pathology. 2002; 72(2):132-41. doi: https://doi.org/10.1006/exmp.2002.2418.
3. Burza S, Croft S L, Boelaert M. Leishmaniasis. Lancet (London, England). 2018; 392(10151):951-70. Epub 2018/08/22. doi: 10.1016/s0140-6736(18)31204-2. PubMed PMID: 30126638.
4. Cutaneous Leishmaniasis (LT): what it is, causes, symptoms, treatment, diagnosis and prevention: Brazilian Ministry of Health; 2019 [cited 2019 Jun. 5]. Available from: http://saude.gov.br/saude-de-a-z/leishmaniose-tegumentar.
5. Guimaraes L H, Queiroz A, Silva J A, Silva S C, Magalhaes V, Lago E L, et al. Atypical Manifestations of Cutaneous Leishmaniasis in a Region Endemic for Leishmania braziliensis: Clinical, Immunological and Parasitological Aspects. PLoS neglected tropical diseases. 2016; 10(12):e0005100. doi: 10.1371/journal.pntd.0005100.
6. Carvalho E M, Banal A, Costa J M L, Bittencourt A, Marsden P. Clinical and immunopathological aspects of disseminated cutaneous leishmaniasis. Acta Tropica. 1994; 56(4):315-25. doi: 10.1016/0001706x(94)90103-1.
7. Croft S L, Olliaro P. Leishmaniasis chemotherapy—challenges and opportunities. Clin Microbiol Infect. 2011; 17(10):1478-83. Epub 2011/09/22. doi: 10.1111/j.1469-0691.2011.03630.x. PubMed PMID: 21933306.
8. Ponte-Sucre A, Gamarro F, Dujardin J C, Barrett M P, Lopez-Velez R, Garcia-Hernandez R, et al. Drug resistance and treatment failure in leishmaniasis: A 21st century challenge. PLoS neglected tropical diseases. 2017;

11(12):e0006052. Epub 2017/12/15. doi: 10.1371/journal.pntd.0006052. PubMed PMID: 29240765; PubMed Central PMCID: PMCPMC5730103.
9. Ullah H, Wahid F, Santos H A, Khan T. Advances in biomedical and pharmaceutical applications of functional bacterial cellulose-based nanocomposites. Carbohydr Polym. 2016; 150:330-52. Epub2016/06/18. doi: 10.1016/j.carbpol.2016.05.029. PubMed PMID: 27312644.
10. Picheth G F, Pinch C L, Sierakowski M R, Woehl M A, Sakakibara C N, de Souza C F, et al. Bacterial cellulose in biomedical applications: A review. Int J Biol Macromol. 2017; 104(Pt A):97-106. Epub 2017/06/08. doi: 10.1016/j.ijbiomac.2017.05.171. PubMed PMID: 28587970.
11. Oliveira Barud H G, Barud Hda S, Cavicchioli M, do Amaral T S, de Oliveira Junior O B, Santos D M, et al. Preparation and characterization of a bacterial cellulose/silk fibroin sponge scaffold for tissue regeneration. Carbohydr Polym. 2015; 128:41-51. Epub 2015/05/26. doi: 10.1016/j.carbpol.2015.04.007. PubMed PMID: 26005138.
12. Shao W, Wu J, Liu H, Ye S, Jiang L, Liu X. Novel bioactive surface functionalization of bacterial cellulose membrane. Carbohydr Polym. 2017; 178:270-6. Epub 2017/10/21. doi: 10.1016/j.carbpol.2017.09.045. PubMed PMID: 29050594.
13. Carbinatto F M, Sabio R M, Meneguin A B, Cestari S E, Cruz S A, Barud H D S. Bacterial cellulose-based hydrogel for wound healing: characterization and in vitro evaluation. International Journal of Advances in Medical Biotechnology—IJAMB. 2018; 1(2). doi: 10.25061/25953931/IJAMB/2018.v1i2.21.
14. Celes F S, Trovatti E, Khouri R, Van Weyenbergh J, Ribeiro S J, Borges V M, et al. DETC-based bacterial cellulose bio-curatives for topical treatment of cutaneous leishmaniasis. Sci Rep. 2016; 6:38330. Epub 2016/12/07. doi: 10.1038/srep38330. PubMed PMID: 27922065; PubMed Central PMCID: PMCPMC5138610.
15. de Moura T R, Novais F O, Oliveira F, Clarencio J, Noronha A, Banal A, et al. Toward a Novel Experimental Model of Infection To Study American Cutaneous Leishmaniasis Caused by *Leishmania braziliensis*. Infect Immun. 2005; 73(9):5827-34. doi: 10.1128/iai.73.9.5827-5834.2005.
16. Novais F O, Carvalho L P, Graff J W, Beiting D P, Ruthel G, Roos D S, et al. Cytotoxic T cells mediate pathology and metastasis in cutaneous leishmaniasis. PLoS pathogens. 2013; 9(7):e1003504. Epub 2013/07/23. doi: 10.1371/journal.ppat.1003504. PubMed PM ID: 23874205; PubMed Central PMCID: PMCPMC3715507.

Example 3

Leishmaniasis is a disease caused by the *Leishmania* genus of parasites that affects approximately 2 million people worldwide, with 700,000-1 million new cases and as many as 50 thousand deaths annually. It is the second deadliest parasitic disease after Malaria. Leishmaniasis has different clinical manifestations depending on the leishmanial species and patient immune system. Visceral leishmaniasis (VL) is a febrile condition affecting internal organs that can lead to death if left untreated. Current first line treatment for VL, predominantly caused by the species *L. donovani* and *L. infantum/L. chagasi*, is based on antimonials, a drug formulation using the toxic metal antimony. Second line treatments include IV-administered liposomal amphotericin B (AmBisome), and miltefosine as an orally administered pill. AmBisome is the most effective but prohibitively expensive for the disease population most affected by leishmanial infections. Availability and supply is often a challenge, with the additional requirement that it must be administered in a clinical setting. Miltefosine is teratogenic, toxic to the kidneys and causes gastrointestinal discomfort at the doses necessary to treat the disease, leading to poor compliance in completing a full treatment regimen. Resistance has already become an issue with miltefosine, and there are supply challenges due to the public-private partnership model.

Cutaneous leishmaniasis (CL) is a generally non-fatal skin condition that produces lesions ultimately leading to permanent scarring and disfigurement. *Leishmania major* causes most CL infections in North Africa, the Middle East, and Central Asia, while *L. braziliensis* and *L. amazonensis* are the leading causative agents of CL in South America. In total, CL infects 1.5 million people worldwide, and the current first line treatment is a pentavalent antimony compound that is delivered by painful intralesional needle injection. Additional challenges in supply, administration, toxicity, and resistance also make this treatment less than ideal. Advances have been made using topically-administered miltefosine, however, there have already been documented failures in this approach due to the rate of parasite mutation.

All current approved small-molecule treatments for leishmaniasis are "repurposed" drugs that were developed for other diseases, especially cancer. The current pipeline is underdeveloped. Drugs for Neglected Diseases (DNDi: dndi.org) lists five new compound classes in their clinical antileishmanial portfolio; none have yet progressed beyond Phase I. GlaxoSmithKline's lead CRK12 inhibitor GSK3186899 (VL only) completed a Phase I single ascending dose study in 2019, but further clinical evaluation of this compound has been paused following the emergence of non-clinical data for a non-GSK asset with a similar mode-of-action. Oxaborole DNDI-6148 (CL/VL) and nitroimidazole DNDI-0690 (CL/VL), have both completed Phase I single ascending dose studies with multiple ascending dose trials underway. Oligo-deoxynucleotide CpG-D35 (CL only) and GSK's recently-reported proteasome inhibitor GSK3494245 are also both slated for Phase I study. There remains an unmet clinical need to develop new treatments against leishmaniasis that are ideally inexpensive, readily produced, and orally available as a short course of chemotherapy. Herein, the discovery of a novel antileishmanial compound class is described, with potent activity against the intracellular stage of the parasite (the most relevant for human disease) in multiple *Leishmania* species.

Methods

Chemistry

All pyrazolopyrrolidinones were synthesized via a two-step sequence in which pyrrolidinones 4 were first synthesized via Mannich condensation/cyclization of a/y diketo esters 5 with either pre-isolated or in-situ-generated imines 6, followed by Knorr pyrazole condensation with a requisite hydrazine 3 (Scheme 1) produced the desired pyrazolopyrrolidinones. All compounds tested had a purity of >90% as measured by UPLC-MS-ELSD. Full details for compound synthesis and characterization for select pyrazolopyrrolidinones are provided in the Supplementary Information.

High-Throughput Screen for Antileishmanial Compounds at UCSD

Compounds were obtained as 0.2 µmoles of dried film for primary single point screening. Each compound was diluted in DMSO to 10 µM final testing concentration. These compounds were tested in 2 biological replicates. The compounds were pre-spotted onto 384-well assay plates in single concentration. B10R cells (CVCL_0155) were seeded at 300 cells/well, and *L. donovani* WT promastigotes in stationary phase (7th day after passage) were added at 6,000 parasites/well (ratio of 20 parasites/cell). Both cells and parasites were seeded in DMEM High-Glucose medium (Gibco, cat. no. 11995065) containing 5% Fetal Bovine Serum (Sigma-Aldrich, cat. no. F2442) and 1% Penicillin-Streptomycin (Gibco, cat. no. 15140122). Cells and parasites were incubated in the presence of the compounds for 72 h at 37° C. and 5% $CO_2$. Plates were then fixed with 4% formaldehyde solution for at least 1 h, then washed with 1×PBS and stained with 5 µg/mL DAPI. Plates were read using an ImageXpress microscope (Molecular Devices) and analyzed by MetaXpress software (Molecular Devices) using a custom module optimized for this assay. Compounds that showed relevant antiparasitic activity in the primary screening were retested in serial dilution to obtain a dose-response curve (DRC). Compounds were tested in a 10-point 2-fold serial dilution in 3 technical replicates, and 2 biological replicates. After 72 h, plates were fixed and stained with DAPI as described above. Images were acquired on an ImageXpress microscope, and analyzed using the MetaXpress custom module. The DRCs were plotted, half-effective concentration (EC50) and half-cytotoxic concentration (CC50) were calculated using GraphPad Prism Software, version 6.05 (GraphPad Software, San Diego, CA).

In Vitro *L. donovani* (LD AMMAC) Assay at GlaxoSmithKline

The intramacrophage *Leishmania donovani* activity assay (LD AMMAC) at GlaxoSmithKline was performed as described.

Solubility Assays

Solubility of compounds using ChemiLuminescent Nitrogen Detection (CLND) was measured as described. Solubility of compounds using Charged Aerosol Detection (CAD) was measured as described. Solubility of solid compounds in Fasted Simulated Intestinal Fluid (FaSSIF) was measured as described.

Artificial Membrane Permeability (AMP) Assays

Passive permeability of compounds via rate of permeation through an artificial phospholipid membrane at pH 7.4 was measured in a high-throughput format, in duplicate. A solution of 1.8% phosphatidylcholine in 1% decane was added to a 96-well Millicell filter plate along with 250 µL of 50 mM phosphate buffer, pH 7.4 on the donor side, and 100 µL of the same buffer solution on the receiver side. The assay plate was shaken for 45 minutes before adding test compounds. Test compounds were then added to the filter plate and then incubated at room temperature with shaking for three hours. The donor and receiver solutions were next transferred to a 384-well plate for analysis by LC/MS.

Microsomal Stability Assays

Mouse microsomal stability assays were performed as described. Test compound (0.5 µM) was incubated with female CD 1 mouse (Xenotech) liver microsomes and their action started with addition of excess NADPH (8 mg/mL 50 mM potassium phosphate buffer, pH 7.4). Aliquots (50 µL) of the incubation mixture were removed immediately (at time 0) and at 3, 6, 9, 15, and 30 min and mixed with acetonitrile (100 µL) to stop the reaction. Internal standard was added to all samples, the samples were centrifuged to sediment precipitated protein, and the plates were then sealed prior to UPLC-MS/MS analysis using a Quattro Premier XE (Waters Corporation, USA). XLfit (IDBS, UK) was used to calculate the exponential decay and consequently the rate constant (k) from the ratio of the peak area of test compound to internal standard at each time point. The rate of intrinsic clearance ($Cl_i$) of each test compound was then calculated using the equation $Cl_i$ (mL/min/g liver)=k× V×microsomal protein yield, where V (mL/mg protein) is the incubation volume/mg protein added and microsomal protein yield is taken as 52.5 mg protein/g liver. Verapamil (0.5 µM) was used as a positive control to confirm acceptable assay performance.

Human Serum Albumin (HSA) Assay

The Percentage of Compound Bound to Human Serum Albumin was Measured Using a chromatographic method as described. Briefly, each compound was assayed on an immobilized HSA column and gradient retention times measured, with chromatographic peak detection by UV. Each retention time was then converted to a % HSA bound value using a calibration set of compounds with a known % HSA binding.

Plasma Protein Binding (PPB) Assay

The unbound fraction of compound 1 in plasma was measured using a commercial RED (Rapid Equilibrium Dialysis) plate with inserts (Thermo) with a molecular weight membrane cut off of 8K. The relevant volume of spiked sample matrix was added into the corresponding sample chambers of the RED insert. Three volume equivalents of dialysis buffer were added to the buffer chamber. The dialysis plate was sealed and incubated at 37° C. on a plate shaker for approximately 4 h at 100 rpm. An equivalent volume was removed from each of the three buffer sample chambers and placed into its own well in a clean plate. A specific volume of control matrix was added to each buffer sample for matrix matching. Next, >3× volume of precipitation solvent (acetonitrile+internal standard) was added and the plate was centrifuged. A measured volume of the resulting supernatants was transferred into a clean plate and a specific volume of analytical grade water was added to all samples. Samples were analyzed using a compound-specific LC-MS/MS method to generate analyte peak area ratios which are representative of bound and free drug.

Chiral Chromatographic Resolution of 1

Figure 12B:
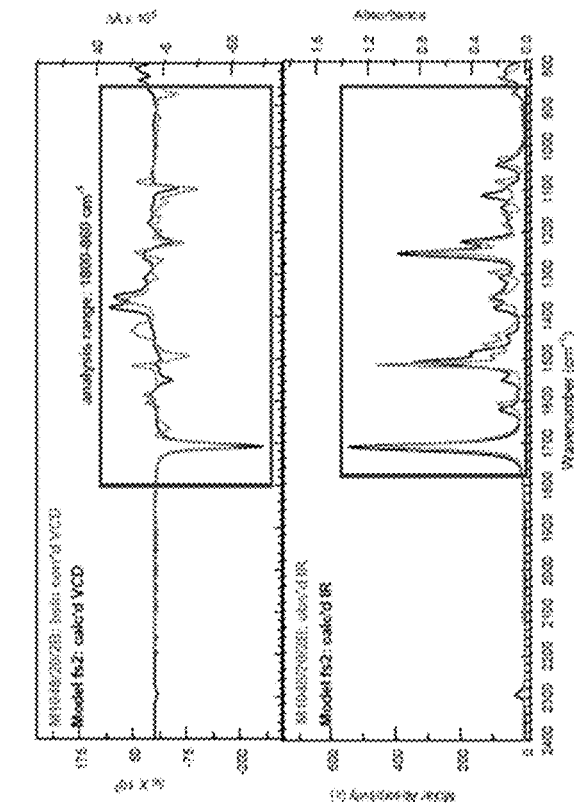
FIGS. 12A-12B shows vibrational circular dichroism to determine absolute configuration of bioactive (S)-enantiomer of compound 1.
Figure 12A:
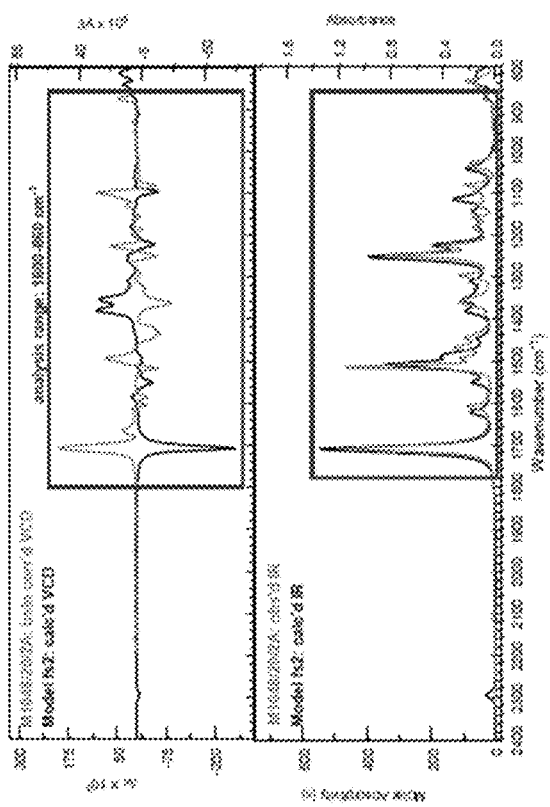

The enantiomers of compound 1 were resolved using semi-preparative chiral HPLC on a Chiralpak IC column (0.46×25 cm) using an isocratic mobile phase of 70:30 heptane:ethanol with a 1 mL/min flowrate for 30 minutes. The first- and second-eluding enantiomers of 1 had retention times of 13.9 minutes, and 22.6 minutes, respectively (FIG. 12A-12B). Independent biological testing of each enantiomer in the LD AMMAC assay indicated that the first-eluting enantiomer (1a, $T_R$=13.9 min) had an $EC_{50}$ of 0.398 µM, and the second-eluting enantiomer (1b, $T_R$=22.6 min) had an $EC_{50}$ of ~10 µM. The separated enantiomers were next subjected to VCD analysis for absolute stereochemistry assignment as described below.

VCD Analysis

A VCD spectrum for each of the separated enantiomers of 1 was obtained in deuterated acetonitrile (~9.8 mg/175 µL concentration) on a BioTools ChirallR-2× FT-VCD spectrometer operated at 4 $cm^{-1}$. VCD frequency range was measured from 2400-800 $cm^1$ with PEM calibrated at 1400 $cm^{-1}$ and PEM retardation applied. The first-eluting enantiomer (1a) was analyzed using a single two-hour block scan (6240 total scans) and the second-eluting enantiomer (1b) was analyzed using the average of six two-hour block scans (37,440 total scans). These experimentally-obtained VCD spectra were utilized in the computational enantiomer assignment as described below.

Computational Methods and Enantiomer Determination

Predicted VCD and IR spectra for the (R) enantiomer of compound 1 were generated according to the following computational workflow: first, a conformational search was performed using MOE LowMode algorithm and Amber12:EHT force field with a generalized Born implicit solvent model (dielectric constant=1). Each unique conformer was then subjected to DFT optimization (B3LYP/DGDZVP2) with VCD vibrational frequency calculation using a polarizable continuum solvent model for acetonitrile. A VCD spectrum was then predicted with fractional populations of each conformer estimated using Boltzmann statistics with a Lorentzian band width of 8 cm$^1$ and a frequency scale factor of 9.9825. This computationally-predicted spectrum was compared to the experimentally obtained spectra using CompareVOA software (BioTools, Inc.) (FIG. 12A-12B). Inspection of the VCD data in the analysis range indicated that the (R) model spectrum was largely coincident with that measured on the second-eluting enantiomer 1b, and was the mirror image of that obtained for the first-eluting enantiomer 1a. Based on these findings, the bioactive enantiomer 1a was assigned with (S) absolute configuration((S)-1), and enantiomer 1b was assigned with (R) absolute configuration ((R)-1). The confidence limit for these assignments was determined from the absolute values of two parameters in the CompareVOA software: total neighborhood similarity (TNS (VCD)) and the enantiomeric similarity index (ESI). The thresholds for "high" reliability (CL of >99%) are TNS (VCD)≥70 and ESI≥60. In this study, the TNS (VCD) and ESI values were 81.0, and 77.5, respectively, providing an estimated confidence limit of >>99% (very high reliability).

Results and Discussion

High-Content Screening in *Leishmania* Intracellular Amastigotes Reveals a New Antileishmanial Pyrazolopyrrolidinone Chemotype In a collaborative effort to identify new antileishmanial chemotypes with minimal host cell cytotoxicity, compounds from the Boston University Center for Molecular Discovery (BUCMD) screening collection were assessed in a phenotypic, high content primary screen at the University of California's Center for Discovery and Innovation in Parasitic Diseases (CDIPD) for the ability to inhibit growth of *L. donovani* intracellular amastigotes infecting THP-1 cells. From this screen, two pyrazolopyrrolidinones were identified (1 and 2, Table 1) which exhibited >99% inhibition of parasite growth with minimal cytotoxicity to the host THP-1 cells (<13% GI). Dose-response testing in *L. donovani* (both intracellular amastigotes and promastigotes) confirmed concentration-dependent growth inhibition of both morphologies of the parasite at low micromolar EC$_{50}$ values for both compounds (Table 1). Similar activity was subsequently confirmed against both morphologies the cutaneous leishmaniasis-causative species *L. major*, suggestive of broad spectrum antileishmanial activity. Notably, these initial hits had potencies comparable to all existing non-antimonial treatments for the disease (Table 1), as well as to GlaxoSmithKline's current Phase I VL candidates GSK3186899 (intramacrophage EC$_{50}$=1.4 μM) and GSK3494245 (intramacrophage EC$_{50}$=1.6 μM), which both were chosen for advancement over more potent analogues due to favorable drug properties (e.g. safety, solubility).

TABLE 1

Structures and antiparasitic activity profiles of antileishmanial pyrazolopyrrolidinones 1 and 2, first identified in a CDIPD high content screen for compounds inhibiting growth of *L. donovani* intracellular amastigotes infecting THP-1 cells.

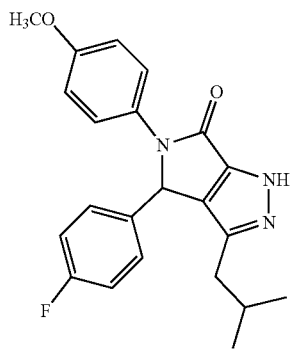

CMLD007431

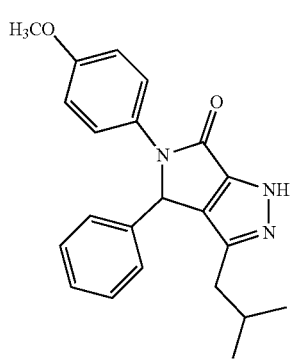

CMLD007427

| Compound | Intracellular Amastigote EC$_{50}$ | Extracellular promastigote EC$_{50}$ |
|---|---|---|
| *Leishmania donovani* | | |
| CMLD007431 (1) | 2.5 μM | 2.0 μM |
| CMLD007427 (2) | 3.7 μM | 2.4 μM |
| *Leishmania major* | | |
| CMLD007431 (1) | 1.3 μM | 4.4 μM |
| CMLD007427 (2) | 1.7 μM | 4.2 μM |
| Host (THP-1) cell CC$_{50}$ | | |
| CMLD007431 (1) | >20 μM | |
| CMLD007427 (2) | >20 μM | |

Compounds 1 and 2 were generated as part of a larger combinatorial library of pyrazolopyrrolidinones (Scheme 1, 3), obtained via Knorr pyrazole condensation of 4-acylated 3-hydroxydihydropyrrol-2-ones 4 with hydrazine hydrate. Precursors 4 are easily produced from a Mannich reaction/intramolecular cyclization between α/γ-diketo esters 5 and pre-formed or in situ-generated imines 6. The lack of activity for several near-neighbor analogues in the primary screen provided some nascent SAR (FIG. 13), hinting at the importance of the para-methoxyphenyl moiety at R$^1$ (vs. phenyl), and the isobutyl group at R$^3$ (vs. methyl, isopropyl and phenyl).

Figure 11:
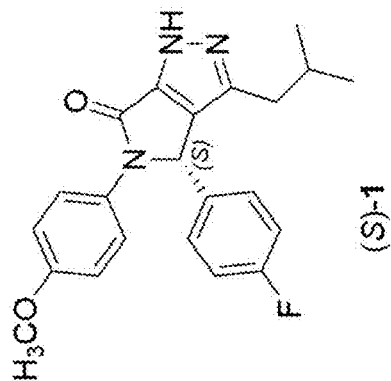
FIG. 11 shows an active enantiomer of (S)-1 as determined by VCD analysis.

At the outset of the project, compound 1 was evaluated against GSK's established criteria for antileishmanial compound advancement (Table 2). Some of these assessments were performed on racemic 1, while chiral separation was also pursued of the 1 racemate to determine the active enantiomer. Preparative chiral-SFC was used to separate enantioenriched 1 on a multigram scale, and vibrational circular dichroism (VCD) analysis confirmed the absolute (S)-stereochemistry of the active enantiomer (FIG. 11, FIGS. 12A-12B), which had an improved $EC_{50}$ of 0.8 μM. As shown in

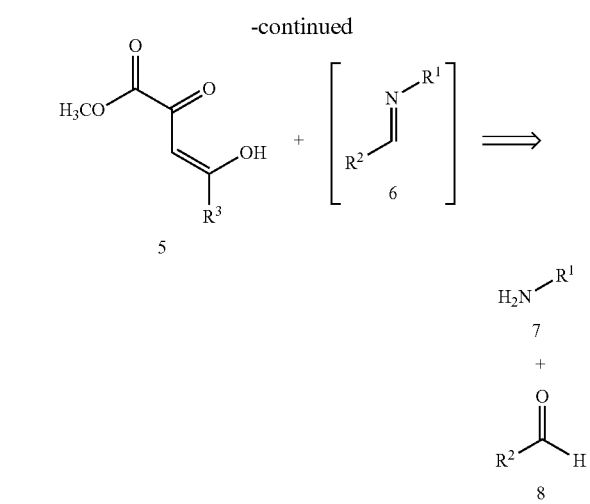

Table 2, compound 1 performed well against most of GSK's lead selection criteria, and met minimum standards toward advancement as a lead compound, human serum albumin binding and property forecast index (PFI), a hydrophobicity metric developed at GSK which considers lipophilicity and aromatic ring count and is predictive of downstream developability. Based on this promising profile, it progressed into medicinal chemistry optimization to better understand structure-activity relationships (SAR) toward improved potency, as well as structure-property relationships (SPR) with an eye toward reducing PFI and plasma protein binding.

TABLE 2

| GlaxoSmithKline lead selection criteria for leishmaniasis | | | |
|---|---|---|---|
| | Lead selection criteria | Compound 1 | Criteria |
| IN VITRO EFFICACY | | | |
| Antiparasitic activity | $EC_{50} < 1$ μM for *L. donovani* amastigotes | $EC_{50} = 0.8$ μM$^a$; 2.5 μM$^b$ | Ideal |
| SI (HepG2, THP-1)$^c$ | >50 | HepG2 $CC_{50} = 63.1$ μM$^a$, SI(HepG2) = 79$^a$; THP-1 $CC_{50} = 31.6$ μM$^{a,d}$; SI(THP-1) = 40$^a$ | Accepted |
| DEVELOPABILITY | | | |
| MW | <500 (<420 ideally) | 379 | Ideal |
| PFI | ≤7 | 8.4 | Accepted |
| Aromatic rings | ≤4 (ideally ≤3) | 3 | Ideal |
| Chemical Tractability | The chemical series is amenable to rapid analogues synthesis. Scale-up of potential lead (>1 g with >95% purity) + consideration of cost of goods. | Pass | Ideal |
| IN VITRO ADME$^b$ | | | |
| Solubility: | | | |
| CLND (μM) | >30 | 107 | Ideal |
| FaSSIF solubility (μg/mL) | >5 | 130 | |
| Microsomal stability (mouse) | $Cl_{int} < 5$ mL/min/g $t_{1/2} > 13.5$ min | $Cl_{int} < 3.4$ mL/min/g $t_{1/2} > 20$ min | Ideal |
| Whole blood stability | No % reduction over 120 min; No reactive functionalities | Pass | Ideal |
| Plasma protein binding | <95% | 97.5% | Accepted |

$^a$Measured on the single enantiomer (S)-1.
$^b$Measured on the racemate (rac)-1.
$^c$SI = selectivity index compared to mammalian cells, calculated as SI = [mammalian cell $CC_{50}$]/[antiparasitic $EC_{50}$].
$^d$THP-1 cytotoxicity as measured in the GlaxoSmithKline LD AMMAC assay.

Medicinal Chemistry of Pyrazolopyrrolidinones Establishing Preliminary Structure-Activity and Structure Property Relationships Toward Improved Leads The pyrazolopyrrolidinone chemotype is well-described in the research and patent literature, with a rich array of reported biological activities, the most prominent of which are p53/MDM2 interaction inhibition, phosphodiesterase inhibition, and GPR55 modulation. In addition, there are examples of pyrazolopyrrolidinones exhibiting P2X3 antagonism, GPR68 agonism, 5-HT1A receptor binding, BET inhibition, 14-3-3-PMA2 interaction stabilization, P-glycoprotein inhibition, antitumor activity, and antimicrobial activity against various parasitic, viral and bacterial species including *T cruzi*, HIV, flaviviruses, *M. tuberculosis*, *P. falciparum*, and *V. cholerae*. Interestingly, most of the aforementioned activities are relegated to pyrazolopyrrolidinones wherein $R^3$ is an aryl substituent. This phenomenon may, however, be attributable to the ease of synthesis of such compounds and their precursors. An important exception to the $R^3$ arylation trend is observed among select inhibitors of the p53/MDM2 interaction. In all of these inhibitors, the $R^1/R^2$ diarylated motif has been shown crystallographically to be a critical binding element at the Leu26 and Trp23 subpockets of MDM2, a similar pharmacophore and binding mode to that exhibited by other diarylated p53/MDM2 inhibitors such as nutlin. Among these inhibitors, non-aryl $R^3$ substitutions such as methyl, isopropyl, and tert-butyl have all been shown to confer some degree of inhibition. Other scattered exceptions include a class of purinoreceptor antagonists with similarly broad tolerance for $R^3$ substitution, and two examples of $R^3$-methyl substituted inhibitor chemotypes: EPX-107979, annotated as a folding corrector of F508del-CFTR and 11β-hydroxysteroid dehydrogenase inhibitors ZINC01292412 and ZINC01260941. Importantly, however, there are no reported examples to-date of pyrazolopyrrolidinones bearing the $R^3={}^iBu$ substitution, which from the primary screen SAR (FIG. 13) appeared to be critical for antileishmanial activity in the absence of host toxicity. While the target of antileishmanial pyrazolopyrrolidinones has yet to be defined, and it cannot conclusively rule out any of the aforementioned targets as being implicated in this activity, the consistent lack of antileishmanial activity among the many $R^3$ phenyl-, isopropyl- and methyl-substituted pyrazolopyrrolidiones tested in the primary screen is suggestive of a target for the $R^3$ isobutylated compounds which is orthogonal to those already appearing in the vast pyrazolopyrrolidinone literature.

Concurrent with the evaluation of screening hit 1 against GSK TCOLF's lead advancement criteria (Table 2), a preliminary medicinal chemistry campaign was executed to improve the understanding of structure-activity relationships (SAR) for this series, in order to target compounds with improved potencies and physicochemical properties to potentially supersede compound 1 as an advanced lead.

Given the literature precedents described above and the apparent narrow tolerance for $R^3$ substitutions observed in the primary screen compounds, a thorough and methodical assessment was undertaken of tolerated groups at the three points of diversity ($R^1/R^2/R^3$) for the core. At this stage of the project, all analogues were assessed using a battery of assays performed in-house at GlaxoSmithKline. For antileishmanial activity, GSK's inMac assay was utilized. This assay provides two readouts of compound potency: average number of intracellular amastigotes per infected cell (AM-MAC) $EC_{50}$, percentage of infected cells per well (INF-CELL) $EC_{50}$, as well as a toxicity output derived from the number of host cells (MAC $EC_{50}$). In addition, compounds were assessed for toxicity against HepG2 cells (HEPG2 $EC_{50}$). Here, AMMAC EC50 values were focused on for relative potency assessments. Using this data, a selectivity index (SI) was calculated for each compound, described here as a macrophage SI (MAC SI), using the equation MAC SI=(MAC $EC_{50}$)/(AMMAC $EC_{50}$). It should be noted that for all compounds assessed in this project, the measured toxicity against THP-1 macrophages either equaled or exceeded that of HepG2 hepatocytes, therefore the MAC SI is used here as the more conservative estimate of therapeutic index.

Revisiting the initial profile of compound 1 against GSK's lead selection criteria, a number of properties were identified requiring improvement, including PFI, plasma protein binding, and a larger SI relative to THP-1 and HepG2 cells. While the CLND solubility fell below the ideal range, good FaSSIF solubility suggested viability as an orally available drug. The potency and physiochemical data was used for 1 as a benchmark for guidance as investigation began into the SAR to identify an improved lead compound for series progression and advancement to animal studies. In these studies, human serum albumin (HSA) binding was employed as a surrogate for plasma protein binding.

Starting first at $R^3$, a variety of aliphatic substitutions were explored, determining that some branched aliphatics of similar size to the parent isobutyl (e.g. isopentyl/neopentyl, Table 3, compounds 9-10) exhibited comparable potencies and low host cell toxicities, whereas the linear n-butyl (compound 11) showed a significant increase in potency (~300 nM) that was accompanied by a toxicity increase to the low micromolar range (2.5 μM). Similar effects were observed with n-but-1-ene and 2-methyl-n-but-1-ene substitutions (compounds 12-13). Finally, surveys of additional branched aliphatic (13) and aromatic (compounds 14-17) substituents at $R^3$ failed to produce more potent compounds than 1, and often showed significant decreases in selectivity index. While the isopentyl/neopentyl analogues 9 and 10 showed marginal improvements over 1 with respect to their macrophage toxicity, these improvements were offset by equivalently small increases in HepG2 toxicity and significant reductions in solubility/permeability; as such it was opted to retain the $R^3$ isobutyl substituent in all future analogues.

TABLE 3
Surveying the effects of variations at $R^3$. Values bolded and underlined are considered improved in comparison to initial lead compound rac-1.
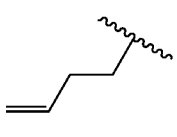
| Cpd | $R^3$ | LD AMMAC $EC_{50}$ (μM)[a] | LD MAC $EC_{50}$ (μM)[b] | SI $MAC^c$ | HEPG2 $EC_{50}$ (μM) | Solubility[d] (μM) | $AMP^e$ (nm/sec) | $HSA^f$ Binding (%) | $PFI^g$ |
|---|---|---|---|---|---|---|---|---|---|
| rac-1 | isobutyl | 2.5 | 15.8 | 6.3 | 63.1 | 107 | 345 | 96.4 | 8.4 |
| 9 | isopentyl | 2.5 | 31.6 | 12.6 | 79.4 | 15 | 100 | 98.0 | 9.1 |
| 10 | neopentyl | 2.5 | 25.1 | 10.0 | 39.8 | 36 | 170 | 97.4 | 9.0 |
| 11 | n-butyl | 0.1 | 2.5 | 25.0 | 50.1 | 49 | 370 | 96.7 | 8.4 |
| 12 | 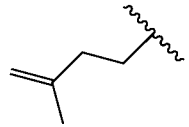 [SMILES: *CCC(=C)C] | 1.6 | 3.2 | 2.0 | 50.1 | 135 | 410 | 97.5 | 8.1 |
| 13 | 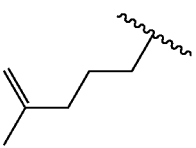 [SMILES: *CCCC(=C)C] | 0.5 | 1.6 | 3.2 | 50.1 | 52 | 370 | 96.8 | 8.5 |
| 14 | 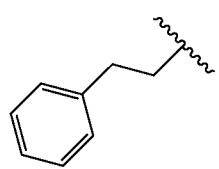 [SMILES: *CCc1ccccc1] | 6.3 | 20.0 | 3.2 | 50.1 | 17 | 270 | 97.9 | 8.9 |
| 15 |  | 6.3 | 25.1 | 4.0 | 50.1 | 6 | 360 | 98.0 | 9.7 |

TABLE 3-continued

Surveying the effects of variations at $R^3$. Values bolded and underlined are considered improved in comparison to initial lead compound rac-1.

| Cpd | $R^3$ | LD AMMAC $EC_{50}$ (µM)$^a$ | LD MAC $EC_{50}$ (µM)$^b$ | SI MAC$^c$ | HEPG2 $EC_{50}$ (µM) | Solubility$^d$ (µM) | AMP$^e$ (nm/sec) | HSA$^f$ Binding (%) | PFI$^g$ |
|---|---|---|---|---|---|---|---|---|---|
| 16 | (indanyl) | 5.0 | 7.9 | 1.6 | 25.1 | 17 | 130 | 97.8 | 10.6 |
| 17 | (4-isobutylphenyl) | 4.0 | 7.9 | 2.0 | 15.8 | <1 | 340 | 98.0 | 11.4 |

$^a$$EC_{50}$ for growth inhibition of *L. donovani* intracellular amastigotes infecting THP-1 macrophages;
$^b$$EC_{50}$ for cytotoxicity against host THP-1 macrophages;
$^c$SI MAC = selectivity index in macrophages, calculated as SI MAC = (LD MAC $EC_{50}$)/(LD AMMAC $EC_{50}$);
$^d$kinetic aqueous solubility as determined by high-throughput CLND (chemoluminescent nitrogen detection);
$^e$artificial membrane permeability;
$^f$human serum albumin binding;
$^g$PFI = ChromLogD$_{7.4}$ + Aromatic rings The effects of modifying the $R^1$ para-methoxyphenyl substituent were examined (Table 4). Direct conversion of the methyl ether to phenol (compound 18) suppressed both antileishmanial activity and toxicity. The ethyl ether analogue 19 exhibited modest improvements in both activity and toxicity as compared to the parent methyl, while the trifluoromethoxy ether (20) ablated antileishmanial activity to levels below that of the inherent THP1-cell toxicity. The dimethylamino analogue 21 showed significantly improved potency and selectivity index, while the ethyl-, fluoro-, bromo-, tert-butyl- and methyl ester-substituted analogues (compounds 22-25) had comparable activities and therapeutic indices to 1. In contrast to methyl ester 25, hydrolyzed carboxylic acid 26 was inactive. Lastly, replacement of the para-methoxy with an N-linked imidazole (compound 27) afforded an equipotent compound with reduced cytotoxicity, leading to an improved SI. However, all improvements in potency (24, 26) or host cell toxicity (26, 28) leading to improved selectivity index were accompanied by significant reductions CLND solubility.

TABLE 4

Surveying effects of various p-substituted aromatics at $R^1$.
Values in bold and underlined are considered improved in comparison to initial lead compound 1.

| Compound | X | LD AMMAC $EC_{50}$ (μM)[a] | LD MAC $EC_{50}$ (μM)[b] | SI MAC[c] | HEPG2 $EC_{50}$ (μM) | Solubility[d] (μM) | AMP[e] (nm/sec) | HSA[f] Binding (%) | PFI[g] |
|---|---|---|---|---|---|---|---|---|---|
| 1 | —OCH$_3$ | 2.5 | 15.8 | 6.3 | 63.1 | 107 | 345 | 96.4 | 8.4 |
| 18 | —OH | 5.0 | 39.8 | 8.0 | >100 | ≥430 | 285 | 95.6 | 7.1 |
| 19 | —OEt | 1.6 | 20.0 | 12.5 | 50.1 | 38 | 250 | 97.5 | 8.9 |
| 20 | —OCF$_3$ | 3.2 | 7.9 | 2.5 | 25.1 | 5 | 290 | 98.1 | 9.8 |
| 21 | —N(CH$_3$)$_2$ | 1.0 | 39.8 | 39.8 | 50.1 | 33 | 160 | 96.1 | 9.0 |
| 22 | —Et | 4.0 | 20.0 | 5.0 | 50.1 | 9 | <10 | 97.4 | 9.7 |
| 23 | —F | 6.3 | 25.1 | 4.0 | 50.1 | 61 | 120 | 97.7 | 8.8 |
| 24 | —Br | 1.3 | 15.8 | 12.2 | 39.8 | 9 | 320 | 97.9 | 9.7 |
| 25 | —t-Bu | 10.0 | >50 | >5.0 | 50.1 | <1 | 130 | 97.9 | 10.5 |
| 26 | —CO$_2$CH$_3$ | 1.6 | 31.6 | 20.0 | 39.8 | 26 | 410 | 97.5 | 8.5 |
| 27 | —CO$_2$H | >50 | >50 | n/a | >100 | ≥389 | <3 | 95.2 | 4.9 |
| 28 | imidazolyl | 2.5 | >50 | >20.0 | >100 | 7 | <3 | 96.3 | 8.1 |

[a]$EC_{50}$ for growth inhibition of *L. donovani* intracellular amastigotes infecting THP-1 macrophages;
[b]$EC_{50}$ for cytotoxicity against host THP-1 macrophages;
[c]SI MAC = selectivity index in macrophages, calculated as SI MAC = (LD MAC $EC_{50}$)/(LD AMMAC $EC_{50}$);
[d]kinetic aqueous solubility as determined by high-throughput CLND (chemoluminescent nitrogen detection);
[e]artificial membrane permeability;
[f]human serum albumin binding;
[g]PFI = ChromLogD$_{7.4}$ + Aromatic rings Next, alternate substitution patterns were examined on the $R^1$ aryl ring (Table 5). Movement of the methoxy group from para- to the ortho- (29) or meta-positions (30) ablated activity, as did nitrogenation of the ring in the presence (31) or absence (32-33) of the para-methoxy group. Additional unsuccessful modifications explored included homologation of the para-methoxyphenyl moiety to a para-methoxybenzyl (34), and additional furyl (35) and non-aromatic substituents (36-41); although several of these modifications led to significant improvements in key properties such as reduced host cell toxicity, and improved solubility, permeability, HSA binding, and PFI, none were able to achieve inhibition of parasite replication below 10 μM $EC_{50}$ values.

TABLE 5
Probing expanded diversity at R[1]. Values in bold and underlined are considered improved in comparison to initial lead compound 1.
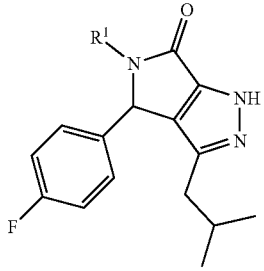
| Cpd | R[1] | LD AMMAC EC$_{50}$ (μM)[a] | LD MAC EC$_{50}$ (μM)[b] | SI MAC[c] | HEPG2 EC$_{50}$ (μM) | Solubility[d] (μM) | AMP[e] (nm/sec) | HSA[f] Binding (%) | PFI[g] |
|---|---|---|---|---|---|---|---|---|---|
| 1 | 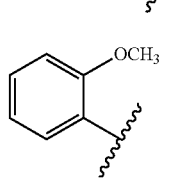 | 2.5 | 15.8 | 6.3 | 63.1 | 107 | 345 | 96.4 | 8.4 |
| 29 | 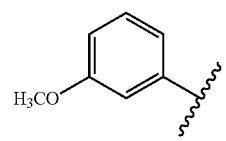 [SMILES: *c1cccc(OC)c1] | 20.0 | >50 | >2.5 | 79.4 | 240 | 590 | 97.5 | 8.5 |
| 30 | 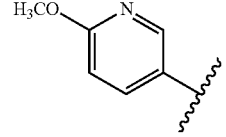 [SMILES: *c1ccc(OC)nc1] | 12.6 | 31.6 | 2.5 | 63.1 | 64 | 370 | 97.3 | 8.4 |
| 31 | 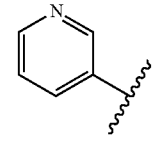 [SMILES: *c1cccnc1] | 10.0 | >50 | >5.0 | >100 | 194 | 260 | 95.5 | 8.0 |
| 32 | 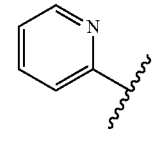 [SMILES: *c1ccccn1] | 25.1 | >50 | >2.0 | >100 | 182 | 470 | 93.4 | 7.2 |
| 33 | 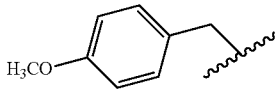 [SMILES: *Cc1ccc(OC)cc1] | 20.0 | >50 | >2.5 | >100 | 219 | 200 | 96.6 | 8.5 |
| 34 | 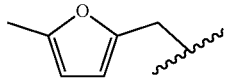 [SMILES: *Cc1ccc(C)o1] | 12.6 | 31.6 | >2.5 | 50.1 | 45 | 550 | 98.2 | 9.0 |
| 35 |  | 15.8 | 39.8 | >2.5 | 50.1 | 19 | 370 | 97.2 | 8.9 |

TABLE 5-continued

Probing expanded diversity at $R^1$. Values in bold and underlined are considered improved in comparison to initial lead compound 1.

| Cpd | $R^1$ | LD AMMAC $EC_{50}$ (µM)[a] | LD MAC $EC_{50}$ (µM)[b] | SI MAC[c] | HEPG2 $EC_{50}$ (µM) | Solubility[d] (µM) | AMP[e] (nm/sec) | HSA[f] Binding (%) | PFI[g] |
|---|---|---|---|---|---|---|---|---|---|
| 36 | H₃CO-cyclohexyl | 25.1 | >50 | >2.0 | >100 | ≥450 | 570 | 92.1 | 7.3 |
| 37 | (CH₃)₂N-cyclohexyl | 25.1 | >50 | >2.0 | >100 | ≥446 | 130 | 81.1 | 4.6 |
| 38 | tetrahydropyran-4-yl | 31.6 | >50 | >1.6 | >100 | ≥381 | 490 | 90.2 | 6.5 |
| 39 | pyrrolidin-1-yl-propyl | 15.8 | >50 | >3.2 | >100 | ≥433 | 230 | 76.7 | 5.3 |
| 40 | 1-methylpyrrolidin-3-yl-methyl | >50 | >50 | >1.0 | >100 | ≥351 | <10 | 77.5 | 4.8 |
| 41 | H₃CO-propyl | >50 | >50 | >1.0 | >100 | ≥421 | 520 | 90.2 | 6.7 |

[a] $EC_{50}$ for growth inhibition of *L. donovani* intracellular amastigotes infecting THP-1 macrophages;
[b] $EC_{50}$ for cytotoxicity against host THP-1 macrophages;
[c] SI MAC = selectivity index in macrophages, calculated as SI MAC = (LD MAC $EC_{50}$)/(LD AMMAC $EC_{50}$);
[d] kinetic aqueous solubility as determined by high-throughput CLND (chemoluminescent nitrogen detection);
[e] artificial membrane permeability;
[f] human serum albumin binding;
[g] PFI = ChromLogD$_{7.4}$ + Aromatic rings.

There was more success in replacing the para-methoxyphenyl group with disubstituted benzene and bicyclic heteroaromatic substituents (Table 6). For example, meta-fluorination of 1 (42) led to modest increases in both potency and selectivity, albeit with the reduction in solubility as would be expected due to the increased lipophilicity. In contrast, addition of an ortho-methoxy substituent to 1 (43) improved solubility, again at the expense of activity. The replacement of the methoxy moiety with various 3,4-fused heterocycles (methylenedioxy 44, ethylenedioxy 45, and triazolopyridine 46) all led to modest improvements in selectivity via reduced host cell toxicity. However, none of these analogues showed improved solubility relative to 1 despite the presence of additional heteroatoms, which was apparently offset by the increased planarity imparted by the bicyclic systems.

TABLE 6

Surveying effects of di- and tri- substitutions at $R^1$. Values in bold and underlined are considered improved in comparison to initial lead compound 1.

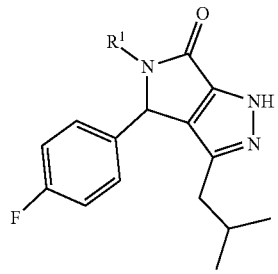

| Cpd | $R^1$ | LD AMMAC $EC_{50}$ (μM)$^a$ | LD MAC $EC_{50}$ (μM)$^b$ | SI MAC$^c$ | HEPG2 $EC_{50}$ (μM) | Solubility$^d$ (μM) | AMP$^e$ (nm/sec) | HSA$^f$ Binding (%) | PFI$^g$ |
|---|---|---|---|---|---|---|---|---|---|
| 1 | H₃CO-phenyl | 2.5 | 15.8 | 6.3 | 63.1 | 107 | 345 | 96.4 | 8.4 |
| 42 | H₃CO, F-phenyl | 1.3 | 25.1 | 19.3 | 50.1 | 39 | 290 | 96.9 | 8.6 |
| 43 | H₃CO, H₃CO-phenyl | 20.0 | 31.6 | 1.6 | 63.1 | 138 | 170 | 96.2 | 8.5 |
| 44 | methylenedioxyphenyl | 0.6 | 25.1 | 41.8 | 63.1 | 63 | 390 | 96.2 | 8.4 |

TABLE 6-continued

Surveying effects of di- and tri- substitutions at $R^1$. Values in bold and underlined are considered improved in comparison to initial lead compound 1.

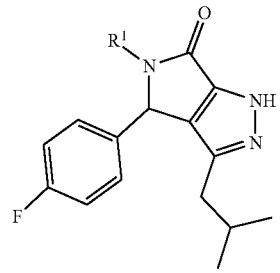

| Cpd | $R^1$ | LD AMMAC $EC_{50}$ (μM)[a] | LD MAC $EC_{50}$ (μM)[b] | SI MAC[c] | HEPG2 $EC_{50}$ (μM) | Solubility[d] (μM) | AMP[e] (nm/sec) | HSA[f] Binding (%) | PFI[g] |
|---|---|---|---|---|---|---|---|---|---|
| 45 | benzodioxane | 3.2 | 25.1 | 7.9 | >50 | 50 | 510 | 96.2 | 8.4 |
| 46 | triazolopyridine | 5.0 | >50 | >10 | >50 | 49 | 920 | 91.8 | 7.8 |

Figure 13:
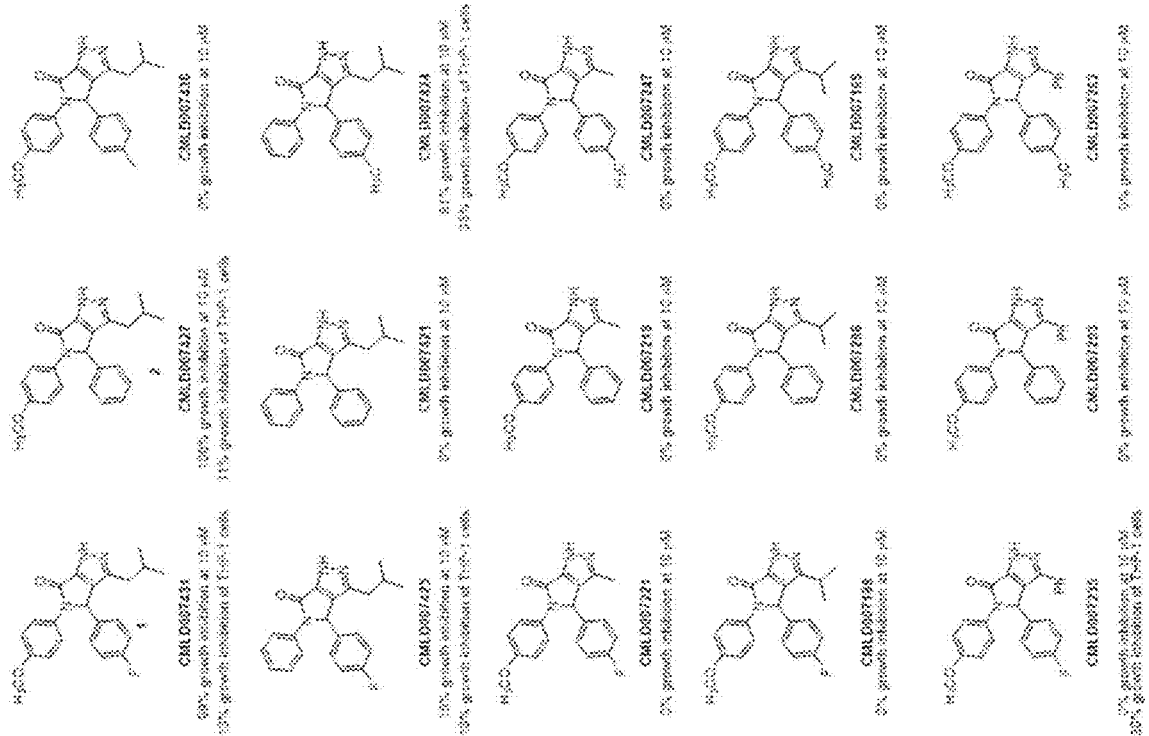
FIG. 13 shows nascent structure-activity relationships from near-neighbor analogues to compounds 1 and 2 from the primary L. donovani intracellular amastigote screen (UCSF).
Figure 15A:
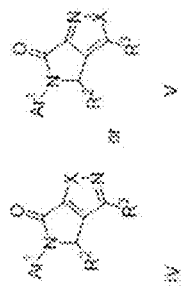
FIGS. 15A and 15B depict some exemplary compounds.
Figure 15A:
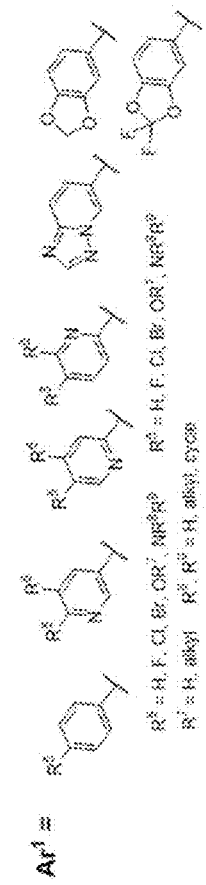
Figure 15A:
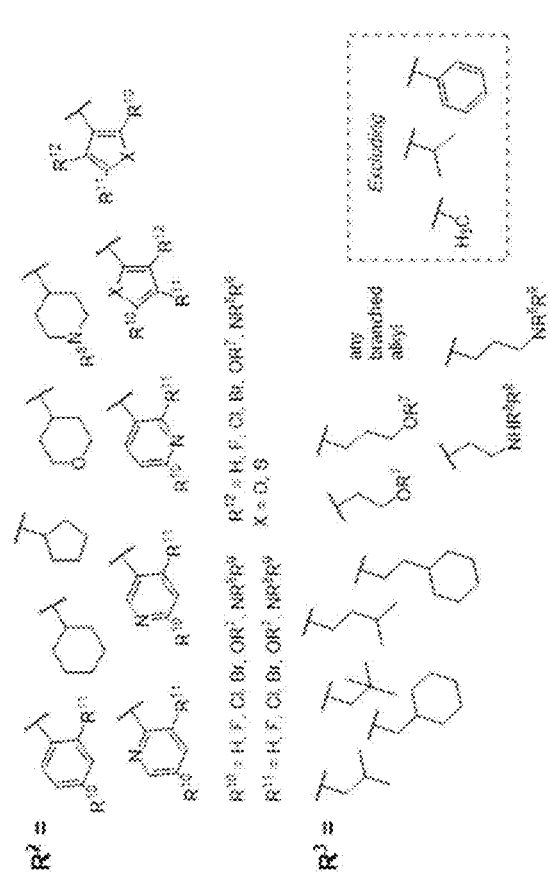
Figure 15B:
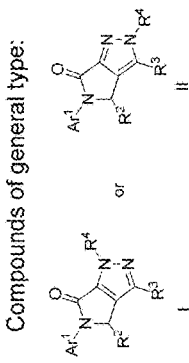
Figure 15B:
Figure 15B:
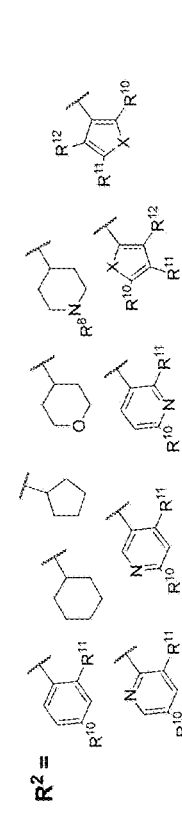
Figure 15B:
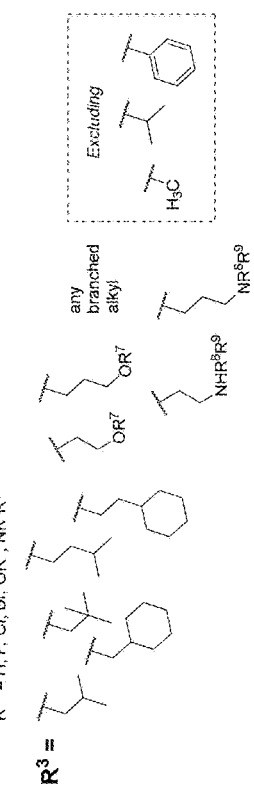
Figure 16:
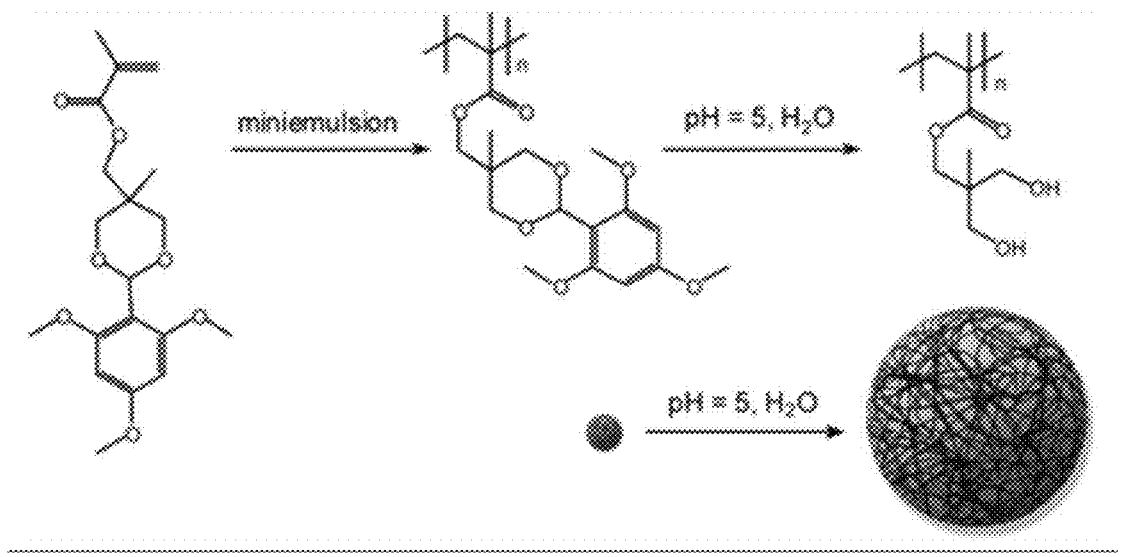
FIG. 16 is a schematic representation showing expansile particles are stable at neutral pH but hydrolyze in the mildly acidic pH (~5) of the cellular endosome.
Figure 17:
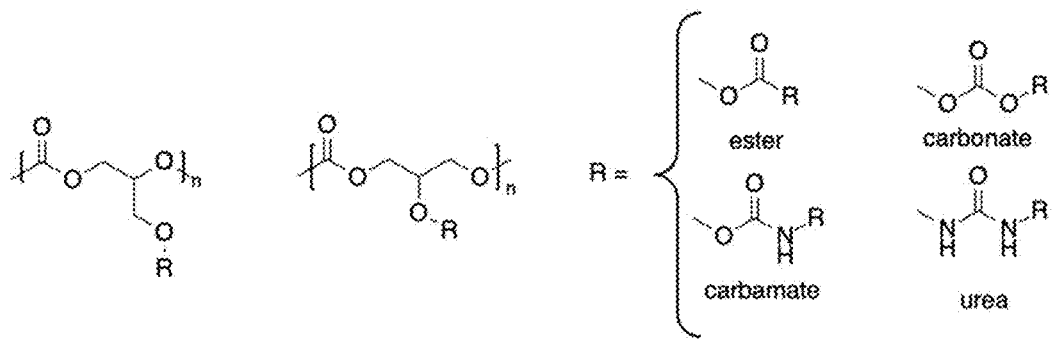
FIG. 17 depicts exemplary 1,2 and 1,3 polyglycerol carbonates monomer.
Figure 18:
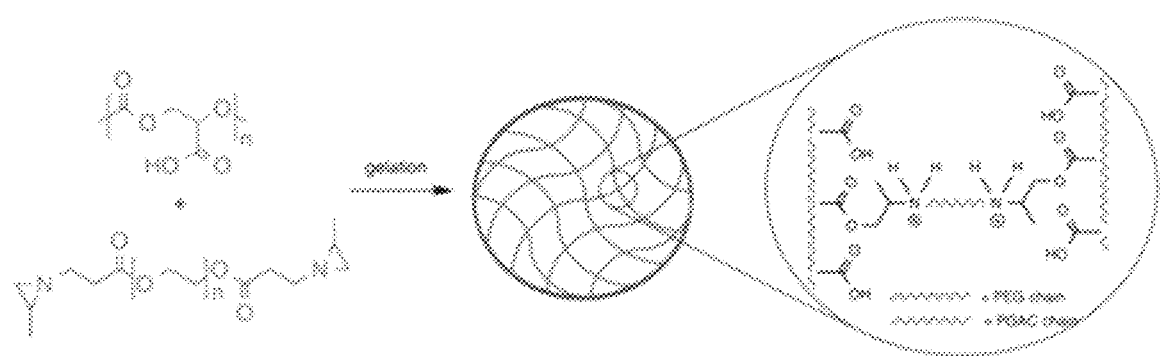
FIG. 18 is a schematic representation of a PEG-diaziridine cross-linked carbonate polymer hydrogel.
Figure 19:
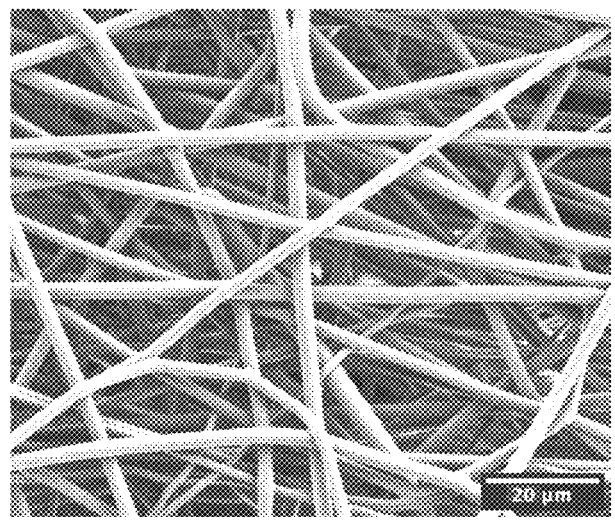
FIG. 19 is a photograph of an electrospun, porous polymer mesh used as durable and moisture permeable backing to the adhesive patch.

[a]$EC_{50}$ for growth inhibition of *L. donovani* intracellular amastigotes infecting THP-1 macrophages;
[b]$EC_{50}$ for cytotoxicity against host THP-1 macrophages;
[c]SI MAC = selectivity index in macrophages, calculated as SI MAC = (LD MAC $EC_{50}$)/(LD AMMAC $EC_{50}$);
[d]kinetic aqueous solubility as determined by high-throughput CLND (chemoluminescent nitrogen detection);
[e]artificial membrane permeability;
[f]human serum albumin binding;
[g]PFI = ChromLogD$_{7.4}$ + Aromatic rings With an improved understanding of $R^1$ and $R^3$ SAR, next was advancing to modifications of $R^2$ (Table 7), where the initial screening SAR indicated that deletion of the para-fluoro substituent (compound 2) afforded a similarly potent compound to 1, whereas replacement of the fluorine with a methyl group resulted in 0% inhibition at 10 μM (CMLD007430, FIG. 13). Consistent with this, the efforts to replace the fluorine with other halogens (47-48), trifluoromethyl (49), carboxylate (50) and methyl carboxylate (51) substituents all reduced potency, as did replacement of the phenyl ring with cyclohexyl and cyclopentyl moieties (compounds 52-53). Interestingly, improved potencies and selectivity indexes were achieved with several types of ortho-substituents, including halogens (53-56) and a methyl ether (57), whereas none such improvements were observed with the equivalent meta-substituents (59-63). Consistent with this trend, addition of ortho-substituents to the para-fluorinated 1 (64-65) led to improved potency, whereas addition of a meta-fluoro to the same scaffold did not (66). Lastly, 2,6-dichloro substitution of the $R^2$ phenyl ring (compound 67) led to improved potency but with a considerable increase in host cell toxicity.

TABLE 7

Surveying effects of simple aliphatic and aromatic R². Values in bold and underlined are considered improved in comparison to initial lead compound 1.

[Structure: core scaffold with H₃CO-phenyl group attached to N, pyrrolopyrazolone with NH, R² substituent, and isobutyl group]

| Cpd | R² | LD AMMAC EC₅₀ (μM)[a] | LD MAC EC₅₀ (μM)[b] | SI MAC[c] | HEPG2 EC₅₀ (μM) | Solubility[d] (μM) | AMP[e] (nm/sec) | HSA[f] Binding (%) | PFI[g] |
|---|---|---|---|---|---|---|---|---|---|
| 1 | 4-F-phenyl | 2.5 | 15.8 | 6.3 | 63.1 | 107 | 345 | 96.4 | 8.4 |
| 2 | Ph— | 3.2 | 31.6 | 9.9 | 79.4 | 90 | 370 | 95.8 | 8.4 |
| 47 | 4-Cl-phenyl | 4.0 | 15.8 | 4.0 | 50.1 | 22 | 330 | 96.9 | 9.2 |
| 48 | 4-Br-phenyl | 6.3 | 15.8 | 2.5 | 50.1 | 9 | 420 | 97.2 | 9.3 |
| 49 | 4-F₃C-phenyl | 8.0 | 15.8 | 2.0 | 50.1 | 12 | 210 | 96.9 | 9.3 |
| 50 | 4-HO₂C-phenyl | >50 | ≥50 | 1.0 | >100 | ≥470 | <3 | 90.7 | 4.5 |
| 51 | 4-MeO₂C-phenyl | 25.1 | 39.8 | 1.6 | 63.1 | 44 | 380 | 95 | 8.2 |
| 52 | cyclohexyl | 7.9 | 25.1 | 3.2 | 50.1 | 29 | 330 | 97.6 | 8.5 |

TABLE 7-continued

Surveying effects of simple aliphatic and aromatic R².
Values in bold and underlined are considered improved in
comparison to initial lead compound 1.

| Cpd | R² | LD AMMAC EC$_{50}$ (μM)$^a$ | LD MAC EC$_{50}$ (μM)$^b$ | SI MAC$^c$ | HEPG2 EC$_{50}$ (μM) | Solubility$^d$ (μM) | AMP$^e$ (nm/sec) | HSA$^f$ Binding (%) | PFI$^g$ |
|---|---|---|---|---|---|---|---|---|---|
| 53 | cyclopentyl | 12.6 | 20.0 | 1.6 | >100 | 119 | 590 | 96.3 | 8.1 |
| 54 | 2-F-phenyl | 3.2 | 31.6 | 9.9 | 31.6 | 75 | 230 | 97.3 | 8.6 |
| 55 | 2-Cl-phenyl | 1.3 | 20.0 | 15.3 | 31.6 | 30 | 330 | 97.8 | 8.8 |
| 56 | 2-Br-phenyl | 0.5 | 25.1 | 50.2 | 39.8 | 12 | 300 | 97.1 | 9.2 |
| 57 | 2-OCH₃-phenyl | 0.5 | 25.1 | 50.2 | 6.3 | 57 | 350 | 95.7 | 8.6 |
| 58 | 3-F-phenyl | 5.0 | 12.6 | 2.5 | 50.1 | 91 | 370 | 96.9 | 8.3 |
| 59 | 3-Cl-phenyl | 7.9 | 39.8 | 5.0 | 39.8 | 19 | 280 | 96.8 | 9.0 |

TABLE 7-continued

Surveying effects of simple aliphatic and aromatic R².
Values in bold and underlined are considered improved in
comparison to initial lead compound 1.

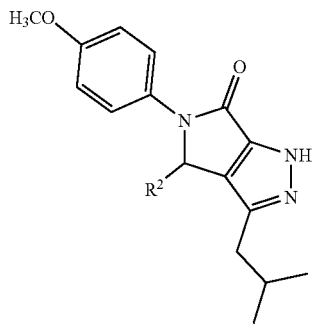

| Cpd | R² | LD AMMAC EC$_{50}$ (μM)$^a$ | LD MAC EC$_{50}$ (μM)$^b$ | SI MAC$^c$ | HEPG2 EC$_{50}$ (μM) | Solubility$^d$ (μM) | AMP$^e$ (nm/sec) | HSA$^f$ Binding (%) | PFI$^g$ |
|---|---|---|---|---|---|---|---|---|---|
| 60 | 3-Br-phenyl | 7.9 | <u>25.1</u> | 3.2 | 39.8 | 10 | <u>370</u> | 97 | 9.1 |
| 61 | 3-MeO-phenyl | 4.0 | <u>20.0</u> | 5.0 | 63.1 | 63 | 290 | <u>95</u> | 8.4 |
| 62 | 3-CF₃-phenyl | 6.3 | 15.8 | 2.5 | 50.1 | 20 | 220 | 97.8 | 8.9 |
| 63 | 2,4-diF-phenyl | 2.0 | <u>25.1</u> | <u>12.6</u> | 63.1 | 52 | 140 | <u>96.1</u> | 8.8 |
| 64 | 4-F-2-Me-phenyl | 0.5 | <u>25.1</u> | <u>50.2</u> | <u>50.1</u> | 43 | 110 | 97.2 | 8.8 |
| 65 | 3,4-diF-phenyl | 5.0 | <u>25.1</u> | 5.0 | 50.1 | 44 | 140 | <u>96.2</u> | 8.7 |

TABLE 7-continued

Surveying effects of simple aliphatic and aromatic $R^2$.
Values in bold and underlined are considered improved in
comparison to initial lead compound 1.

[Structure: pyrrolo-pyrazolone core with 4-methoxyphenyl N-substituent, $R^2$ group, isobutyl group, and NH]

| Cpd | $R^2$ | LD AMMAC $EC_{50}$ (µM)[a] | LD MAC $EC_{50}$ (µM)[b] | SI MAC[c] | HEPG2 $EC_{50}$ (µM) | Solubility[d] (µM) | AMP[e] (nm/sec) | HSA[f] Binding (%) | PFI[g] |
|---|---|---|---|---|---|---|---|---|---|
| 66 | 2,6-dichlorophenyl | 1.0 | 2.5 | 2.5 | 6.3 | 6 | 330 | 97.1 | 9.1 |

[a]$EC_{50}$ for growth inhibition of *L. donovani* intracellular amastigotes infecting THP-1 macrophages;
[b]$EC_{50}$ for cytotoxicity against host THP-1 macrophages;
[c]SI MAC = selectivity index in macrophages, calculated as SI MAC = (LD MAC $EC_{50}$)/(LD AMMAC $EC_{50}$);
[d]kinetic aqueous solubility as determined by high-throughput CLND (chemoluminescent nitrogen detection);
[e]artificial membrane permeability;
[f]human serum albumin binding;
[g]PFI = ChromLogD$_{7.4}$ + Aromatic rings In an effort to improve solubility via $R^2$ modifications, a diverse array of substituted and unsubstituted heteroaromatic groups were also surveyed at this position (Table 9). While several of these compounds exhibited the expected improvements in CLND solubility and reduction in HSA binding, potency was also significantly compromised for this set.

Figure 14:
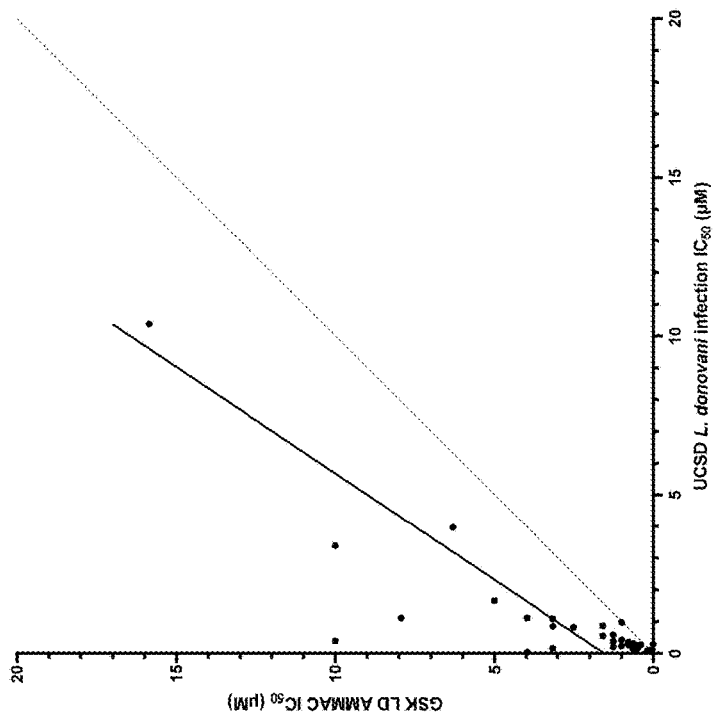
FIG. 14 depicts a plot of comparative potencies of select compounds in the GSK and UCSD L. donovani infection assays show higher comparative potency in the UCSD assay, with good overall correlation. Solid line: simple linear regression ($r^2$=0.5529); dashed line: x=y.

With the scope and limitations of $R^1/R^2$ substitutions mapped with respect to potency and property improvements, it was next attempted to pair promising groups at each site to arrive at optimized new inhibitors. Based on the trends observed in the initial series, it was clear that improvements in solubility and reduced human serum albumin binding would require reduced lipophilicity (C Log P), a modification which generally also correlated with reduced potency in the initial analogues. To offset this, global Log P were reduced via modifications to $R^1$ (where increased polarity appeared to be more tolerable), in combination with the apparent potency-enhancing ortho-substituents at $R^2$. Table 8 depicts the most successful of these pairings with respect to potency, selectivity, HSA binding, and solubility. Of note, at this later stage in the project solubility was measured using charged aerosol detection (CAD), due to a change in standard in vitro ADME methods employed at GSK. In addition, infection $EC_{50}$ and host cell $CC_{50}$ measurements were obtained in a comparable *L. donovani* infection model performed at the University of California, San Diego (see Methods). In order to benchmark compound performance across the two assays, a random sampling of compounds was selected for re-assessment in the UCSD infection assay (Table 10). Most compounds showed slightly improved potency in the UCSD assay than was observed in the LD AMMAC assay run at GSK; as a representative example, the UCSD potency for racemic 1 was found to be 0.82 µM (Table 8, entry 1), compared to 2.5 µM in the GSK LD AMMAC assay. Despite the change in absolute potency values, the two assays were well-correlated with respect to relative potencies, with a Pearson's correlation coefficient of 0.74. (Table 10 and FIG. 14).

From this compound series, the ortho-substituted $R^2$ groups (B1-B4) significantly improved potency and selectivity, even when paired with groups at $R^1$ which had conferred reduced potency when paired with the $R^2$ para-fluorophenyl moiety (e.g. A4/A5, Compounds 78-87). Several inhibitors in this series, 69, 86 and 87, exhibited the desired improvements across all key physicochemical properties, in addition to improved potency and selectivity. However, for a large proportion of these compounds the most significant gains in potency were offset by an increase in toxicity, PFI and HSA binding, and a reduction in solubility owing to increased lipophilicity. Efforts to optimize from 69, 86 and 87 toward further improved analogues are ongoing in the laboratory.

TABLE 8
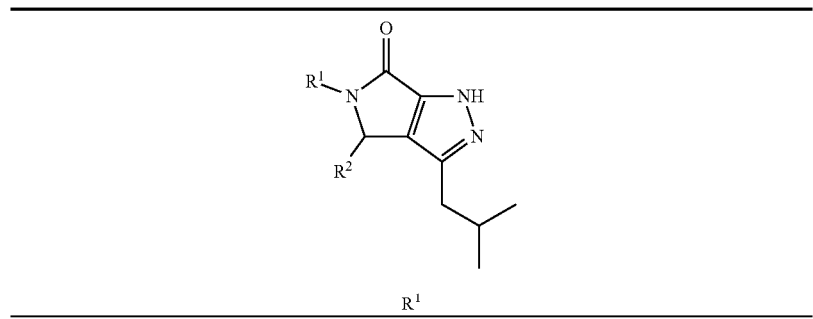
| R¹ | |
|---|---|
| 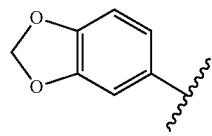 | A1 |
| 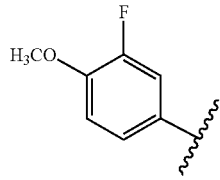 [SMILES: *c1ccc(OC)c(F)c1] | A2 |
| 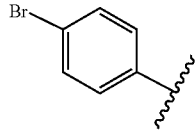 | A3 |
| 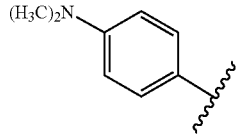 | A4 |
| 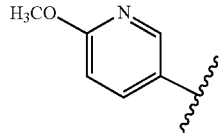 [SMILES: *c1ccc(OC)nc1] | A5 |
| 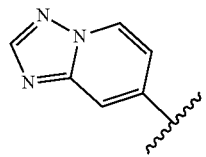 [SMILES: *c1ccn2ncnc2c1] | A6 |
| R² | |
|---|---|
| 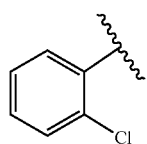 | B1 |
| 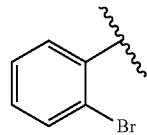 [SMILES: *c1ccccc1Br] | B2 |

TABLE 8-continued

B3

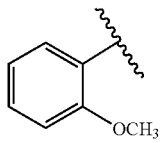

B4

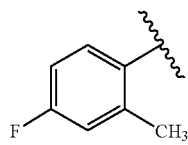

B5

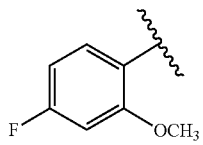 [SMILES: *c1ccc(F)cc1OC]

Pairing of promising $R^1/R^2$ moieties toward improved inhibitors. Values in bold and underlined are considered improved in comparison to initial lead compound 1.

| Cpd | $R^1$ | $R^2$ | *L. donovani* $EC_{50}$ (μM)[a] | $CC_{50}$ (μM)[b] | $SI^c$ | Solubility[d] (μM) | $HSA^e$ binding (%) | $PFI^g$ |
|---|---|---|---|---|---|---|---|---|
| (rac)-1 | — | — | 0.82 | >20.00 | >24.4 | 89[f] | 96.4 | 8.4 |
| 67 | A1 | B1 | 0.16 | 12.22 | 76.4 | 35 | 98.0 | 8.7 |
| 68 | A1 | B2 | 0.29 | >20.00 | >69.0 | 27 | 97.0 | 8.8 |
| 69 | A1 | B3 | 0.27 | >20.00 | >74.1 | 66 | 95.3 | 8.2 |
| 70 | A1 | B4 | 0.10 | 12.08 | 120.8 | 46 | 97.6 | 8.6 |
| 71 | A2 | B2 | 0.42 | 3.04 | 7.2 | 20 | 96.9 | 9.2 |
| 72 | A2 | B3 | 0.38 | 0.26 | 0.7 | 43 | 95.9 | 8.5 |
| 73 | A2 | B4 | 0.16 | 10.89 | 68.1 | 35 | 96.3 | 8.8 |
| 74 | A3 | B2 | 0.39 | 4.98 | 12.8 | <1 | 98.0 | 10.4 |
| 75 | A3 | B3 | 0.24 | 1.14 | 4.8 | <1 | 97.5 | 9.6 |
| 76 | A3 | B4 | 0.12 | 3.04 | 25.3 | <1 | 97.7 | 9.8 |
| 77 | A3 | B5 | 0.12 | 4.04 | 33.7 | <1 | 98.5 | 9.7 |
| 78 | A4 | B1 | 0.26 | 7.32 | 28.2 | 21 | 96.7 | 9.4 |
| 79 | A4 | B2 | 0.08 | 5.72 | 71.5 | <1 | 96.9 | 9.4 |
| 80 | A4 | B3 | 0.07 | 3.45 | 49.3 | 66 | 95.7 | 8.6 |
| 81 | A4 | B4 | 0.11 | 7.51 | 68.3 | 27 | 96.5 | 9.1 |
| 82 | A4 | B5 | 0.04 | 8.50 | 212.5 | 45 | 97.1 | 8.8 |
| 83 | A5 | B1 | 1.11 | 9.93 | 8.9 | 77 | 97.0 | 8.7 |
| 84 | A5 | B2 | 0.98 | >20.00 | >54.1 | 63 | 96.6 | 8.8 |
| 85 | A5 | B3 | 1.11 | >20.00 | >76.9 | 176 | 93.9 | 8.0 |
| 86 | A5 | B4 | 0.37 | >20.00 | >36.4 | 119 | 94.7 | 8.3 |
| 87 | A5 | B5 | 0.26 | >20.00 | >23.0 | 145 | 94.1 | 8.1 |
| 88 | A6 | B1 | 0.55 | >20.00 | >55.6 | <1 | 94.1 | 8.0 |
| 89 | A6 | B4 | 0.87 | >20.00 | >24.4 | <1 | 93.2 | 8.1 |

[a]$EC_{50}$ for growth inhibition of *L. donovani* intracellular amastigotes infecting THP-1 macrophages (UCSD assay), average of two biological replicates;
[b]$EC_{50}$ for cytotoxicity against host THP-1 macrophages (UCSD assay);
[c]SI = selectivity index, calculated as SI = (*L. donovani* infection $EC_{50}$)/($CC_{50}$);
[d]kinetic aqueous solubility as determined by high-throughput CAD (charged aerosol detection);
[e]human serum albumin binding.
[f]Obtained on the single enantiomer (S)-1;
[g]PFI = ChromLogD$_{7.4}$ + Aromatic rings

CONCLUSION

In this study, it was discovered a novel antileishmanial pyrazolopyrrolidinone chemotype that is effective against the intracellular amastigote parasite morphology in multiple *Leishmania* species with minimal host cytotoxicity. Compared to all of the advanced leads in the current antileishmanial pipeline, pyrazolopyrrolidinones are extremely facile to produce, without the need for sophisticated reaction apparatus in two synthetic steps from low-cost commodity starting materials—an ideal attribute for a therapeutic targeting a neglected tropical disease. Subsequent medicinal chemistry optimization has produced multiple advanced leads with significantly improved potency and ADME parameters relative to the initial hit, and support further preclinical optimization of the series. Work to advance these and similar candidates into in vivo pharmacokinetic and efficacy assessments is ongoing.

TABLE 9

Surveying effects of heterocycles at R². Values underlined and bolded are considered improved in comparison to initial lead compound 1.
"nd" = not determined.

| Cpd | R² | LD AMMAC EC$_{50}$ (µM)[a] | LD MAC EC$_{50}$ (µM)[b] | SI MAC[c] | HEPG2 EC$_{50}$ (µM) | Solubility[d] (µM) | Permeability[e] (nm/sec) | HSA[f] Binding (%) | PFI[g] |
|---|---|---|---|---|---|---|---|---|---|
| rac-1 | 4-fluorophenyl | 2.5 | 15.9 | 6.3 | 63.1 | 107 | 345 | 96.4 | 8.4 |
| S1 | N-Bn-piperidin-4-yl | 15.8 | 20.0 | 1.3 | 63.1 | 188 | 290 | 94.8 | 9.0 |
| S2 | thiophen-2-yl | 7.9 | >50 | >6.3 | >100 | 8 | 300 | 95.9 | 8.2 |
| S3 | thiophen-3-yl | 6.3 | >50 | >7.9 | >100 | 149 | 470 | 95.4 | 8.3 |
| S4 | thiazol-5-yl | 15.8 | >50 | >3.1 | >100 | ≥534 | 320 | 89.3 | 6.5 |
| S5 | thiazol-2-yl | 20.0 | >50 | >2.5 | >100 | 143 | 420 | 89.5 | 7.2 |
| S6 | pyridin-4-yl | >50 | >50 | 1.0 | >100 | ≥432 | 230 | 87.9 | 6.3 |

TABLE 9-continued
Surveying effects of heterocycles at R². Values underlined and bolded are considered improved in comparison to initial lead compound 1.
"nd" = not determined.
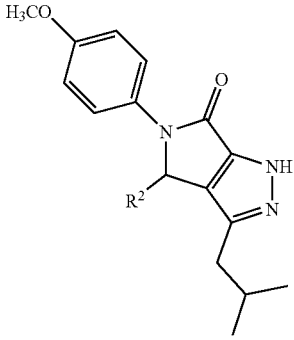
| Cpd | R² | LD AMMAC EC$_{50}$ ($\mu$M)$^a$ | LD MAC EC$_{50}$ ($\mu$M)$^b$ | SI MAC$^c$ | HEPG2 EC$_{50}$ ($\mu$M) | Solubility$^d$ ($\mu$M) | Permeability$^e$ (nm/sec) | HSA$^f$ Binding (%) | PFI$^g$ |
|---|---|---|---|---|---|---|---|---|---|
| S7 | 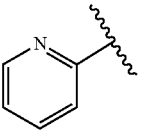 [SMILES: *c1ccccn1] | 31.6 | >50 | >1.6 | >100 | ≥450 | 420 | 86.8 | 7.1 |
| S8 | 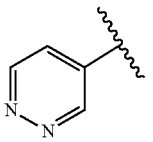 | >50 | >50 | 1.0 | >100 | 273 | 340 | 76.8 | 6.3 |
| S9 | 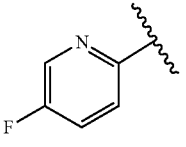 | >50 | >50 | 1.0 | >100 | ≥340 | 50 | 70.5 | 5.5 |
| S10 | 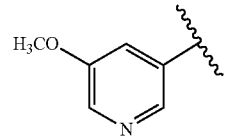 | 10.0 | >50 | >5.0 | >100 | ≥343 | 490 | 90.2 | 7.7 |
| S11 | 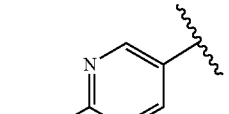 | 10.0 | 20.0 | 2.0 | >100 | 386 | 470 | 91.2 | 6.6 |
| S12 | 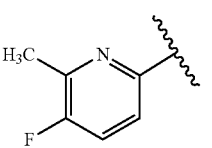 [SMILES: *c1ccc(F)c(C)n1] | >50 | >50 | 1.0 | >100 | 272 | 440 | 92.6 | 7.5 |
| S13 |  | 12.6 | >50 | >4.0 | >100 | 305 | 380 | 94.4 | 8.3 |

TABLE 9-continued

Surveying effects of heterocycles at $R^2$. Values underlined and bolded are considered improved in comparison to initial lead compound 1. "nd" = not determined.

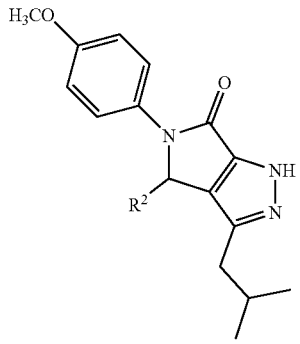

| Cpd | $R^2$ | LD AMMAC $EC_{50}$ (µM)[a] | LD MAC $EC_{50}$ (µM)[b] | SI MAC[c] | HEPG2 $EC_{50}$ (µM) | Solubility[d] (µM) | Permeability[e] (nm/sec) | HSA[f] Binding (%) | PFI[g] |
|---|---|---|---|---|---|---|---|---|---|
| S14 | 2,6-difluoropyridin-4-yl | >50 | >50 | 1.0 | >100 | 367 | 540 | 93 | 7.4 |

[a]$EC_{50}$ for growth inhibition of *L. donovani* intracellular amastigotes infecting THP-1 macrophages;
[b]$EC_{50}$ for cytotoxicity against host THP-1 macrophages;
[c]SI MAC = selectivity index in macrophages, calculated as SI MAC = (LD MAC $EC_{50}$)/(LD AMMAC $EC_{50}$);
[d]kinetic aqueous solubility as determined by high-throughput CLND (chemoluminescent nitrogen detection);
[e]artificial membrane permeability;
[f]human serum albumin binding;
[g]PFI = ChromLogD$_{7.4}$ + Aromatic rings

TABLE 10

Comparative antileishmanial potencies for select compounds in the UCSD vs. GSK infection assays. Pearson correlation r = .7429, n = 34, p < 0.10. A single outlier compound (70) did not demonstrate a measurable $IC_{50}$ value in the GSK LD AMMAC assay and was omitted from this analysis.

| Compound | UCSD *L. donovani* infection $IC_{50}$ (µM) | GSK LD AMMAC $IC_{50}$ (µM) |
|---|---|---|
| (S)-1 | 0.4 | 0.79 |
| rac-1 | 0.8 | 2.5 |
| 2 | 1.1 | 3.2 |
| 21 | 0.2 | 1.0 |
| 39 | 10.4 | 15.9 |
| 42 | 0.6 | 1.3 |
| 44 | 0.3 | 0.6 |
| 45 | 0.9 | 3.2 |
| 46 | 1.7 | 5.0 |
| 55 | 0.2 | 1.3 |
| 67 | 0.2 | 0.5 |
| 68 | 0.3 | 0.0 |
| 69 | 0.3 | 0.4 |
| 70 | 0.1 | >100 |
| 71 | 0.4 | 1.0 |
| 72 | 0.4 | 1.3 |
| 73 | 0.2 | 3.2 |
| 74 | 0.4 | 10.0 |
| 75 | 0.2 | 0.5 |
| 76 | 0.1 | 0.6 |
| 77 | 0.1 | 0.1 |
| 78 | 0.3 | 0.8 |
| 79 | 0.1 | 0.0 |
| 80 | 0.1 | 0.2 |
| 81 | 0.1 | 0.1 |
| 82 | 0.0 | 4.0 |
| 83 | 1.1 | 4.0 |
| 84 | 1.0 | 1.0 |
| 85 | 1.1 | 7.9 |
| 86 | 0.4 | 10.0 |
| 87 | 0.3 | 0.8 |
| 88 | 0.6 | 1.6 |
| 89 | 0.9 | 1.6 |
| S3 | 4.0 | 6.3 |
| S10 | 3.4 | 10.0 |

Supplementary Methods: Chemical Synthesis
General Methods.

All $^1$H NMR spectra were obtained at 400 or 500 MHz and referenced to the CHCl$_3$ singlet at 7.26 ppm, or the center peak of the quintet from the residual $^1$H resonance of DMSO-d$_6$ at 2.50 ppm. $^{13}$C NMR spectra were obtained at 125 or 100 MHz, and referenced to the center peak of the CDCl$_3$ triplet at 77.16 ppm, or the center peak of the DMSO-d$_6$ heptet at 39.52 ppm. Chemical shifts are reported in parts per million as follows: chemical shift, multiplicity (s=singlet, d=doublet, t=triplet, q=quartet, h=heptet m=multiplet, br=broad), coupling constant, and integration. Optical rotations were recorded on a Rudolph AUTOPOL II digital polarimeter at 589 nm, and were reported as $[\alpha]_D$ (concentration in grams/100 mL solvent). Analytical thin layer chromatography was performed using EMD 0.25 mm silica gel 60-F plates. Flash column chromatography was performed on Sorbent Technologies 60 Å silica gel. Chiral HPLC analysis was performed using an Agilent 1100 series HPLC with a multiple wavelength detector. Chiral columns include Chiralcel®OD (Chiral Technologies Inc., 25 cm×4.6 mm I.D.), Chiralpak®IA (Chiral Technologies Inc., 25 cm×4.6 mm I.D.). High resolution mass spectrometry data was obtained on a Waters Qtof (hybrid quadrupolar/time-of-flight) API US system by electrospray (ESI) in the positive mode. Mass correction was done by an external reference using a Waters Lockspray accessory. Mobile phases were water and acetonitrile with 0.1% formic acid. The MS settings were: capillary voltage=3 kV, cone voltage=35, source temperature=120° C. and desolvation temperature=350° C. UPLC-MS analysis was performed on a XBridge C18 column (1.7 mm, 2.1×50 mm) with $CH_3CN$:$H_2O$ gradient as eluent with UV, ELSD and electrospray ionization (ESI) positive ion detection. Purity analysis was performed by HPLC and quantified by UV peak area at the indicated wavelength.

Detailed Synthetic Methods.

Methyl keto-enol esters (5) were prepared analogously to literature precedents (1) via the following representative procedure: An oven dried 250 mL round-bottom flask equipped with a stir bar was charged with methanol (75 mL) and cooled to 0° C. in an ice-water bath. Sodium metal (5.75 g, 250 mmol, 1.00 equiv.) was added portion-wise, and the flask was stirred and allowed to warm to room temperature. A separate flame-dried 100 mL flask was charged with dimethyl oxalate (29.5 g, 250 mmol, 1.00 equiv.) and 4-methylpentan-2-one (31.3 mL, 250 mmol, 1.00 equiv) and methanol (75 mL). After the sodium metal had completely dissolved, the contents of the 100 mL flask were transferred by cannula to the freshly prepared sodium methoxide solution. The 250 mL flask was fitted with an Ar balloon, and the reaction was stirred at 22° C. for 16 h, at which time the reaction was cooled to 0° C. in an ice-water bath, and quenched by the addition of 80 mL 4 M aq. sulfuric acid. The solution was poured into a 1 L separatory funnel, diluted with 250 mL water, and extracted 3×250 mL dichloromethane. The combined organics were dried over anhydrous $Na_2SO_4$, and concentrated by rotary evaporation. The crude oil was distilled under reduced pressure (8 mbar, 105° C.) to yield methyl (Z)-2-hydroxy-6-methyl-4-oxohept-2-enoate as a light yellow oil. Yield: 27.2 g, 59.5%. $^1$H NMR: (400 MHz, $CDCl_3$) δ 6.34 (s, 1H), 3.89 (s, 3H), 2.34 (d, J=7.1 Hz, 2H), 2.14 (dh, J=7.1, 6.6 Hz, 1H), 0.96 (d, J=6.6 Hz, 7H).

Pyrrolidinones of general structure 4 (FIG. 1) were prepared based on a modified literature precedent (2) at ~0.5 mmol scales according to the following representative procedure: A 2 dram vial equipped with a stir bar was charged with 4-fluorobenzaldehyde (57.6 μL, 536 μmol, 1.00 equiv.), N1,N1-dimethylbenzene-1,4-diamine (73.1 mg, 536 μmol, 1.00 equiv.), and (Z)-2-hydroxy-6-methyl-4-oxohept-2-enoate (300 mg, 1.61 mmol, 3.00 equiv.). The reactants were suspended in dichloromethane (5.00 mL), the vial was capped and stirred at 22° C. for 3 days, at which point the vial was concentrated under reduced pressure (typically Genevac evaporator with multiple reactions in parallel). The crude residue was dissolved in a minimal amount of chloroform, and solid 1-[4-(dimethylamino)phenyl]-2-(4-fluorophenyl)-4-hydroxy-3-(3-methylbutanoyl)-2H-pyrrol-5-one (S21) was precipitated as an off-white solid by the addition of excess hexanes. The solid was collected by vacuum filtration, and carried forward to the next step without further purification. Yield: 154 mg, 72.6%. Purity: >95% @ 254 nm by HPLC. $^1$H NMR: (400 MHz, $CDCl_3$) δ 7.14 (d, J=9.1 Hz, 2H), 6.9 (dd, J=8.7 Hz, 2H), 6.59 (d, J=9.1 Hz, 2H), 5.67 (s, 1H), 2.90 (s, 6H) 2.44 (dd, J=15.3, 6.4 Hz, 1H), 2.15 (m, 1H), 2.05 (m, 1H), 0.88 (d, J=6.6 Hz, 3H), 0.74 (d, J=6.6 Hz, 3H). LCMS: (ESI+) m/z calc' for $(C_{23}H_{25}FN_2O_3+H)^+$ 397.48; found 397.10.

Pyrazolopyrrolidinones (1, 9-89) were synthesized on a ~60 mg scale, as a modification of a literature precedent, according to the following representative procedure:

5-(4-(dimethylamino)phenyl)-4-(4-fluorophenyl)-3-isobutyl-4,5-dihydropyrrolo[3,4-c]pyrazol-6(1H)-one (21). A 1 dram vial equipped with a stir bar was charged with 1-[4-(dimethylamino)phenyl]-2-(4-fluorophenyl)-4-hydroxy-3-(3-methylbutanoyl)-2H-pyrrol-5-one S21 (60.0 mg, 151 μmol, 1.00 equiv.) and acetic acid (1.5 mL). Hydrazine monohydrate (23 μL, 454 μmol, 3.00 equiv) was added to the vial by microsyringe. The vial was capped with a Teflon-backed screw cap, and heated in a 120° C. metal heating block for 1 h, at which point the mixture was concentrated under reduced pressure (typically Genevac evaporator with multiple reactions in parallel). The residue was dissolved in 1.0 mL DMSO, and purified by reverse-phase preparative HPLC (XBridge C18 column, basic conditions, 40-100% $CH_3CN$ gradient in water). Fractions containing the desired product were concentrated under reduced pressure (Genevac evaporator or lyophilizer) to yield 2.22 as an off-white solid. Yield: 26.9 mg, 41.1% yield. Purity: >95% @ 254 nm by HPLC. $^1$H NMR: (400 MHz, $CDCl_3$) δ 10.65 (br. s., 1H), 7.14-7.11 (overlap, 4H), 6.95 (m, 2H), 6.62 (d, J=9.1 Hz, 2H), 5.77 (s, 1H), 2.90 (s, 6H), 2.40 (m, 1H), 2.28 (m, 1H), 1.65 (m, 2H), 0.81 (d, J=6.5 Hz, 3H), 0.78 (d, J=6.8 Hz, 3H). LCMS: (ESI+) m/z=393 $[M+H]^+$.

Full characterization of select pyrazolopyrrolidinones 1, 24, 42, 44, 46, 55, 57, 64, 65, 67, 70, 72-78, 80-82, 85, 86 and 89, and corresponding pyrrolidinone precursors S1, S24, S42, S44, S46, S55, S57, S64, S65, S67, S70, S72-S78, S80-S82, S85, S86 and S89.

5-(4-fluorophenyl)-3-hydroxy-1-(4-methoxyphenyl)-4-(3-methylbutanoyl)-1,5-dihydro-2H-pyrrol-2-one (S1). Yield: 13.3 g, 89.3%. $^1$H NMR: (400 MHz, $CDCl_3$) δ 7.24 (d, J=9.0 Hz, 2H), 7.17 (m, 2H), 6.97 (dd, J=8.6, 8.6 Hz, 2H), 6.82 (d, J=9.0 Hz, 2H), 5.71 (s, 1H), 3.75 (s, 3H), 2.42 (dd, J=15.4, 6.6 Hz, 1H), 2.22 (dd, J=15.4, 6.7 Hz), 2.06 (m, 1H), 0.88 (d, J=6.6 Hz, 3H), 0.74 (d, J=6.6 Hz, 3H). LCMS: (ESI+) m/z=384.20 $[M+H]^+$.

4-(4-fluorophenyl)-3-isobutyl-5-(4-methoxyphenyl)-4,5-dihydropyrrolo[3,4-c]pyrazol-6(1H)-one (1). Yield: 313 mg, 77.9% yield from S1. $^1$H NMR: (400 MHz, $CDCl_3$) δ 11.36 (br s, 1H), 7.23 (d, J=9.1 Hz, 2H), 7.13 (m, 2H), 6.96 (dd, J=8.6, 8.6 Hz, 2H), 6.82 (d, J=9.1 Hz, 2H), 5.83 (s, 1H), 3.76 (s, 3H), 2.50 (dd, J=14.5, 6.8 Hz, 1H), 2.33 (dd, J=14.5, 7.2 Hz, 1H), 1.67 (m, 1H), 0.81 (d, J=6.6 Hz, 3H), 0.78 (d, J=6.6 Hz, 3H). LCMS: (ESI+) m/z=380 $[M+H]^+$.

1-(4-bromophenyl)-5-(4-fluorophenyl)-3-hydroxy-4-(3-methylbutanoyl)-1,5-dihydro-2H-pyrrol-2-one (S24). Yield: 162 mg, 37.5%. $^1$H NMR: (500 MHz, $CDCl_3$) δ 7.41 (d, J=8.9 Hz, 2H), 7.33 (d, J=8.9 Hz, 2H), 7.21 (dd, J=8.6, 5.1 Hz, 2H), 6.96 (dd, J=8.6, 8.5 Hz, 2H), 5.79 (s, 1H), 2.52 (dd, J=15.5, 6.4 Hz, 1H), 2.33 (dd, J=15.5, 7.5 Hz, 1H), 2.05 (ddqq, J=7.5, 6.7, 6.7, 6.4 Hz, 1H), 0.86 (d, J=6.7 Hz, 3H), 0.73 (d, J=6.7 Hz, 3H). $^{13}$C NMR: (126 MHz, $CDCl_3$) δ 197.1, 164.4, 163.8, 161.8, 154.3, 134.9, 132.3, 130.8, 130.7, 129.5, 129.4, 124.1, 120.5, 119.9, 116.3, 116.1, 61.7, 50.3, 24.9, 22.7, 22.3. $^{19}$F NMR: (470 MHz, CDCl$_3$) δ −112.07 (tt, 8.5, 5.1 Hz). HRMS: (ESI+) m/z calc'd for (C$_{21}$H$_{19}$BrFNO$_3$+H)$^+$432.0611; found: 432.0611.

5-(4-bromophenyl)-4-(4-fluorophenyl)-3-isobutyl-4,5-dihydropyrrolo[3,4-c]pyrazol-6(1H)-one (24). Yield: 99.0 mg, 99.9% yield from S24. $^1$H NMR: (500 MHz, CDCl$_3$) δ 7.39 (d, J=8.9 Hz, 2H), 7.34 (d, J=8.9 Hz, 2H), 7.15 (dd, J=8.5, 5.2 Hz, 2H), 6.96 (t, J=8.5, 8.5 Hz, 2H), 5.96 (s, 1H), 2.71 (dd, J=14.5, 7.1 Hz, 1H), 2.46 (dd, J=14.5, 7.1 Hz, 1H), 1.66 (m, 1H), 0.80 (d, J=6.6 Hz, 3H), 0.76 (d, J=6.6 Hz, 3H). $^{13}$C NMR: (126 MHz, CDCl$_3$) δ 163.7, 161.8, 161.7, 148.0, 139.9, 136.8, 132.54, 132.51, 132.1, 128.9, 128.8, 127.2, 124.8, 118.8, 116.3, 116.2, 60.7, 33.7, 28.9, 22.21, 22.19. $^{19}$F NMR: (470 MHz, CDCl$_3$) δ −112.56 (tt, J=8.5, 5.5 Hz). HRMS: (ESI+) m/z calc'd for (C$_{21}$H$_{19}$BrFN$_3$O+H)$^+$ 428.0774; found: 428.0763.

1-(3-fluoro-4-methoxy-phenyl)-2-(4-fluorophenyl)-4-hydroxy-3-(3-methylbutanoyl)-2H-pyrrol-5-one (S42). Yield: 60.2 mg, 23.3%; Purity: 94.7% @ 210 nm by HPLC. $^1$H NMR: (400 MHz, CDCl$_3$) δ 7.24 (d, J=2.53 Hz, 1H), 7.17-7.23 (overlap, 3H), 7.03-7.09 (m, 1H), 6.99 (t, J=8.6 Hz, 2H), 6.86 (t, J=9.0 Hz, 1H), 5.69 (s, 1H), 3.84 (s, 4H), 2.42 (dd, J=16.0, 8.0 Hz, 1H), 2.22 (dd, J=16.0, 8.0 Hz, 1H), 2.05 (m, 1H), 0.88 (d, J=6.6 Hz, 3H), 0.73 (d, J=6.6 Hz, 3H). LCMS: (ESI+) m/z=401.0 [M+H]$^+$.

5-(3-fluoro-4-methoxyphenyl)-4-(4-fluorophenyl)-3-isobutyl-4,5-dihydropyrrolo[3,4-c]pyrazol-6(2H)-one (42). Yield: 29.4 mg, 59.4% from S42; Purity: >95% @ 240 nm by HPLC. $^1$H NMR: (400 MHz, CDCl$_3$) δ 10.70 (br. s., 1H), 7.21 (dd, J=12.63, 2.53 Hz, 1H), 7.14 (dd, J=8.72, 5.18 Hz, 2H), 7.07 (m, 1H), 6.98 (m, 2H), 6.87 (m, 1H), 5.84 (s, 1H), 3.84 (s, 3H), 2.44 (dd, J=10.0, 6.0, 1H), 2.30 (dd, J=10.0, 6.0 Hz, 1H), 1.66 (m, 1H), 0.82 (d, J=6.6 Hz, 3H), 0.77 (d, J=6.8 Hz, 3H). LCMS: (ESI+) m/z=398 [M+H]$^+$.

1-(benzo[d][1,3]dioxol-5-yl)-5-(4-fluorophenyl)-3-hydroxy-4-(3-methylbutanoyl)-1,5-dihydro-2H-pyrrol-2-one (S44). Yield: 310 mg, 78.1%. $^1$H NMR: (500 MHz, CD$_3$OD) δ 7.15 (dd, J=8.5, 5.3 Hz, 2H), 6.89 (d, J=8.6 Hz, 2H), 6.87 (m, 1H), 6.71 (dd, J=8.4, 1.9 Hz, 1H), 6.65 (d, J=8.4 Hz, 1H), 5.87 (d, J=6.7 Hz, 2H), 5.66 (s, 1H), 2.72 (dd, J=14.8, 6.2 Hz, 1H), 2.48 (dd, J=14.8, 7.8 Hz, 1H), 2.04 (m, 1H), 0.83 (d, J=6.7 Hz, 3H), 0.72 (d, J=6.7 Hz, 3H). $^{13}$C NMR: (126 MHz, CDC$_3$OD) δ 196.7, 164.7, 163.2, 161.2, 152.9, 147.7, 145.8, 131.5, 131.4, 129.4, 129.1, 129.0, 120.3, 116.8, 115.1, 115.0, 107.7, 104.9, 101.3, 61.9, 50.7, 24.8, 22.1, 21.6. $^{19}$F NMR: (470 MHz, CDCl$_3$) δ −110.23 (m). HRMS: (ESI+) m/z calc'd for (C$_{22}$H$_{20}$FNO$_5$+H)$^+$398.1402; found: 398.1411.

5-(benzo[d][1,3]dioxol-5-yl)-4-(4-fluorophenyl)-3-isobutyl-4,5-dihydropyrrolo[3,4-c]pyrazol-6(1H)-one (44). Yield: 104 mg, quant. yield from S44. $^1$H NMR: (500 MHz, CDCl$_3$) δ 7.02 (m, 2H), 6.86 (dd, J=8.5, 8.5 Hz, 2H), 6.73 (d, J=7.9 Hz, 1H), 6.59 (d, J=9.2 Hz, 2H), 5.81 (m, 2H), 5.71 (s, 1H), 5.22 (s, 1H), 2.31 (dd, J=14.5, 7.2 Hz, 1H), 2.16 (dd, J=14.5, 7.2 Hz, 1H), 1.53 (dt, J=13.4, 6.7, 6.7 Hz, 1H), 0.68 (d, J=6.6 Hz, 3H), 0.64 (d, J=6.6 Hz, 3H). $^{13}$C NMR: (126 MHz, CDCl$_3$) δ 163.6, 162.1, 161.6, 147.8, 145.9, 139.1, 132.31, 132.29, 130.9, 129.1, 129.0, 127.0, 118.4, 115.9, 115.7, 108.0, 106.6, 101.4, 61.7, 53.4, 34.0, 28.4, 21.97, 21.96. $^{19}$F NMR: (470 MHz, CDCl$_3$) δ −109.12 (tt, J=8.4, 5.0 Hz). HRMS: (ESI+) m/z calc'd for (C$_{22}$H$_{20}$FN$_3$O$_3$)$^+$ 396.1479; found: 396.1481.

1-([1,2,4]triazolo[1,5-a]pyridin-6-yl)-5-(4-fluorophenyl)-3-hydroxy-4-(3-methylbutanoyl)-1,5-dihydro-2H-pyrrol-2-one (S46). Yield: 394 mg, 62.5%. $^1$H NMR: (500 MHz, DMSO) δ 9.29 (dd, J=2.0, 0.6 Hz, 1H), 8.48 (s, 1H), 7.89 (dd, J=9.6, 2.0 Hz, 1H), 7.81 (dd, J=9.6, 0.6 Hz, 1H), 7.39 (dd, J=8.8, 5.4 Hz, 2H), 7.02 (dd, J=8.8, 8.8 Hz, 2H), 6.20 (s, 1H), 2.72 (dd, J=15.0, 6.2 Hz, 1H), 2.51 (m, 1H), 1.98 (m, 1H), 0.78 (d, J=6.7 Hz, 3H), 0.70 (d, J=6.6 Hz, 3H). $^{13}$C NMR: (126 MHz, DMSO) δ 165.0, 162.5, 160.6, 154.5, 147.9, 132.4, 129.92, 129.85, 127.2, 125.2, 123.8, 115.7, 115.2, 115.0, 60.3, 50.6, 24.5, 22.5, 22.0. $^{19}$F NMR: (470 MHz, DMSO) δ −114.06 (tt, J=8.8, 5.5 Hz). HRMS: (ESI+) m/z calc'd for (C$_{21}$H$_{19}$FN$_4$O$_3$)$^+$395.1519; found: 395.1515.

(5-([1,2,4]triazolo[1,5-a]pyridin-6-yl)-4-(4-fluorophenyl)-3-isobutyl-4,5-dihydropyrrolo[3,4-c]pyrazol-6(1H)-one) (46). Yield: 95.6 mg, 88.0% yield from S46. $^1$H NMR: (500 MHz, CDCl$_3$) δ 8.80 (d, J=1.9 Hz, 1H), 8.17 (s, 1H), 7.60 (dd, J=9.6, 1.9 Hz, 1H), 7.54 (d, J=9.6 Hz, 1H), 7.09 (dd, J=8.6, 5.1 Hz, 2H), 6.86 (t, J=8.5, 8.5 Hz, 2H), 5.92 (s, 1H), 2.29 (dd, J=14.6, 7.2 Hz, 1H), 2.14 (dd, J=14.6, 7.2 Hz, 1H), 1.50 (m, 1H), 0.65 (d, J=6.6 Hz, 3H), 0.60 (d, J=6.6 Hz, 3H). $^{13}$C NMR: (126 MHz, CDCl$_3$) δ 163.7, 161.8, 153.6, 131.6, 128.9, 128.8, 127.7, 127.1, 123.8, 116.4, 116.2, 115.7, 60.9, 33.7, 28.4, 21.9, 21.8. $^{19}$F NMR: (470 MHz, CDCl$_3$) δ −108.16 (tt, J=8.5, 5.2 Hz). HRMS: (ESI+) m/z calc'd for (C$_{21}$H$_{19}$FN$_6$O+H)$^+$391.1683; found: 391.1675.

5-(2-chlorophenyl)-3-hydroxy-1-(4-methoxyphenyl)-4-(3-methylbutanoyl)-1,5-dihydro-2H-pyrrol-2-one (S55). Yield: 170 mg, 42.4%. $^1$H NMR: (500 MHz, CDCl$_3$) δ 7.34 (d, J=9.0 Hz, 2H), 7.31 (d, J=2.3 Hz, 1H), 7.16-7.14 (overlap, 2H), 6.98 (dd, J=6.0, 3.4 Hz, 1H), 6.79 (d, J=9.0 Hz, 2H), 6.43 (s, 1H), 3.72 (s, 3H), 2.45 (dd, J=15.4, 6.8 Hz, 1H), 2.21 (dd, J=15.4, 7.1 Hz, 1H), 2.02 (m, 1H), 0.88 (d, J=6.6 Hz, 3H), 0.71 (d, J=6.6 Hz, 3H). $^{13}$C NMR: (126 MHz, CDCl$_3$) δ 197.5, 163.5, 159.4, 158.1, 134.9, 133.2, 130.1, 128.6, 127.8, 127.5, 124.9, 124.6, 119.7, 114.4, 57.6, 55.4, 48.9, 25.0, 22.6, 22.4. HRMS: (ESI+) m/z calc'd for (C$_{22}$H$_{22}$ClNO$_4$+H)$^+$400.1316; found: 400.1308.

4-(2-chlorophenyl)-3-isobutyl-5-(4-methoxyphenyl)-4,5-dihydropyrrolo[3,4-c]pyrazol-6(1H)-one (55). Yield: 106 mg, 86.3% yield from S55. $^1$H NMR: (500 MHz, CDCl$_3$) δ 7.40 (d, J=8.9 Hz, 2H), 7.35 (br d, J=7.9 Hz, 1H), 7.14 (ddd, J=7.9, 7.4, 1.0 Hz, 1H), 7.09 (br dd, J=7.4, 7.4 Hz, 1H), 6.99 (br d, J=7.6 Hz, 1H), 6.81 (br d, J=9.0 Hz, 2H), 6.62 (s, 1H), 3.72 (s, 3H), 2.73 (dd, J=14.3, 7.3 Hz, 1H), 2.58 (dd, J=14.3, 7.2 Hz, 1H), 1.64 (m, 1H), 0.78 (d, J=6.6 Hz, 3H), 0.72 (d, J=6.6 Hz, 3H). $^{13}$C NMR: (126 MHz, CDCl$_3$) δ 162.1, 157.1, 148.4, 139.8, 134.8, 133.3, 130.9, 129.7, 129.5, 127.9, 127.8, 127.0, 124.3, 114.3, 57.1, 55.4, 33.9, 29.1, 22.2, 22.0. HRMS: (ESI+) m/z calc'd for (C$_{22}$H$_{22}$ClN$_2$O$_2$+H)$^+$394.1567; found: 394.1568.

3-hydroxy-5-(2-methoxyphenyl)-1-(4-methoxyphenyl)-4-(3-methylbutanoyl)-1,5-dihydro-2H-pyrrol-2-one (S57). Yield: 124 mg, 58.5%. $^1$H NMR: (400 MHz, CDCl$_3$) δ 7.40 (d, J=9.1 Hz), 7.22 (ddd, J=7.8, 7.8, 1.8 Hz, 1H), 6.96 (d, J=8.1 Hz, 1H), 6.83-6.90 (overlap, 2H), 6.78 (d, J=9.1 Hz, 2H), 6.34 (br s, 1H), 3.90 (br s, 3H), 3.74 (s, 3H), 2.31 (dd, J=14.0, 6.0 Hz, 1H), 2.02 (dd, J=14.0, 6.0 Hz, 1H), 0.88 (d, J=6.6 Hz, 3H), 0.67 (d, J=6.3 Hz, 3H). LCMS: (ESI+) m/z=396.10 [M+H]$^+$.

3-isobutyl-4-(2-methoxyphenyl)-5-(4-methoxyphenyl)-4,5-dihydropyrrolo[3,4-c]pyrazol-6(1H)-one (57). Yield: 48.4 mg, 81.5% yield from S57. Purity: >95% @ 272 nm by HPLC. $^1$H NMR: (400 MHz, CDCl$_3$) δ 7.41 (d, J=9.1 Hz, 2H), 7.19 (ddd, J=8.3, 7.1, 1.7 Hz, 1H), 6.95 (m, 1H), 6.88 (dd, J=8.3, 1.7 Hz, 1H), 6.81 (d, J=9.1 Hz, 3H), 6.50 (br. s., 1H), 3.88 (br. s., 3H), 3.75 (s, 3H), 2.40 (m, 1H), 2.30 (m, 1H), 1.68 (m, 1H), 0.80 (d, J=6.8 Hz, 3H), 0.73 (d, J=6.6 Hz, 3H). LCMS: (ESI+) m/z=392 [M+H]$^+$.

5-(4-fluoro-2-methylphenyl)-3-hydroxy-1-(4-methoxyphenyl)-4-(3-methylbutanoyl)-1,5-dihydro-2H-pyrrol-2-one (S64). Yield: 114 mg, 53.2%. ¹H NMR: (400 MHz, CDCl₃) δ 7.09 (d, J=8.8 Hz, 2H), 6.90 (m, 1H), 6.75-6.85 (overlap, 4H), 5.93 (s, 1H), 3.76 (s, 3H), 2.41-2.51 (overlap, 4H), 2.27 (dd, J=8.0, 4.0 Hz, 1H), 2.06 (m, 1H), 0.88 (d, J 6.6 Hz, 3H), 0.75 (d, J=6.6 Hz, 3H). LCMS: (ESI+) m/z=398.2 [M+H]⁺.

4-(4-fluoro-2-methylphenyl)-3-isobutyl-5-(4-methoxyphenyl)-4,5-dihydropyrrolo[3,4-c]pyrazol-6(1H)-one (64). Yield: 61.0 mg, 93.4% yield from S64; Purity: >95% @ 254 nm by HPLC. ¹H NMR: (400 MHz, CDCl₃) δ 8.39 (d, J=4.0 Hz, 1H), 7.45 (d, J=9.1 Hz, 2H), 7.28-7.24 (overlap, 2H), 7.05 (dd, J=8.8, 4.0 Hz, 1H), 6.84 (d, J=9.1 Hz, 2H), 6.17 (s, 1H), 3.76 (s, 3H), 2.48 (m, 1H), 2.39 (m, 1H), 1.72 (m, 1H), 1.44 (s, 3H), 0.83 (d, J=6.6 Hz, 3H), 0.77 (d, J=6.6 Hz, 3H). LCMS: (ESI+) m/z=394 [M+H]⁺.

5-(3,4-difluorophenyl)-3-hydroxy-1-(4-methoxyphenyl)-4-(3-methylbutanoyl)-1,5-dihydro-2H-pyrrol-2-one (S65). Yield: 404 mg, 71.4%. ¹H NMR: (500 MHz, CDCl₃) δ 7.26 (m, 2H), 7.06-6.98 (overlap, 3H), 6.83 (m, 2H), 5.71 (s, 1H), 3.75 (s, 3H), 2.59 (dd, J=15.5, 6.4 Hz, 1H), 2.44 (dd, J=15.5, 7.5 Hz, 1H), 2.09 (m, 1H), 0.88 (d, J=6.7 Hz, 3H), 0.78 (d, J=6.7 Hz, 3H). ¹³C NMR: (126 MHz, CDCl₃) δ 196.4, 164.5, 158.3, 153.9, 151.6, 151.5, 151.4, 151.3, 149.6, 149.5, 149.4, 149.3, 132.74, 132.70, 132.67, 128.3, 124.7, 124.23, 124.20, 124.18, 124.15, 120.2, 117.8, 117.7, 116.7, 116.5, 114.6, 62.1, 55.5, 50.5, 24.9, 22.8, 22.4. ¹⁹F NMR: (470 MHz, CDCl₃) δ −136.14 (m), −136.91 (m). HRMS: (ESI+) m/z calc'd for (C₂₂H₂₁F₂NO₄+H)⁺402.1517; found: 402.1516.

4-(3,4-difluorophenyl)-3-isobutyl-5-(4-methoxyphenyl)-4,5-dihydropyrrolo[3,4-c]pyrazol-6(1H)-one (65). Yield: 99.0 mg, quant. yield from S65. ¹H NMR: (500 MHz, CDCl₃) δ 7.24 (d, J=9.0 Hz, 2H), 7.05 (ddd, J=8.2, 8.2, 8.1 Hz, 1H), 6.95-6.92 (overlap, 2H), 6.82 (d, J=9.0 Hz, 2H), 5.84 (s, 1H), 3.74 (s, 3H), 2.72 (dd, J=14.5, 7.1 Hz, 1H), 2.46 (dd, J=14.5, 7.1 Hz, 1H), 1.68 (dt, J=13.4, 6.7, 6.7 Hz, 1H), 0.81 (d, J=6.6 Hz, 3H), 0.78 (d, J=6.6 Hz, 3H). ¹³C NMR: (126 MHz, CDCl₃) δ 161.9, 157.8, 151.7, 151.6, 151.3, 151.2, 149.7, 149.6, 149.4, 149.3, 139.8, 134.3, 130.2, 126.6, 126.0, 123.7, 117.9, 117.8, 116.4, 116.2, 114.4, 61.2, 55.5, 33.8, 28.9, 22.24, 22.21. ¹⁹F NMR: (470 MHz, CDCl₃) δ −136.08 (m), −137.16 (dddd, J=17.9, 13.4, 8.9, 4.4 Hz). HRMS: (ESI+) m/z calc'd for (C₂₂H₂₁F₂N₃O₂+H)⁺ 398.1680; found: 398.1679.

1-(benzo[d][1,3]dioxol-5-yl)-5-(2-chlorophenyl)-3-hydroxy-4-(3-methylbutanoyl)-1,5-dihydro-2H-pyrrol-2-one (S67). Yield: 259 mg, 62.7%. ¹H NMR: (500 MHz, CDCl₃) δ 7.34 (m, 1H), 7.17 (m, 2H), 6.99-6.96 (overlap, 2H), 6.82 (d, J=7.2 Hz, 1H), 6.68 (d, J=8.4 Hz, 1H), 6.38 (s, 1H), 5.90 (d, J=7.6 Hz, 2H), 2.43 (dd, J=15.5, 6.8 Hz, 1H), 2.19 (dd, J=15.5, 7.0 Hz, 1H), 2.00 (m, 1H), 0.88 (d, J=6.5 Hz, 3H), 0.71 (d, J=6.6 Hz, 3H). ¹³C NMR: (126 MHz, CDCl₃) δ 197.6, 163.6, 159.2, 148.0, 146.3, 134.9, 133.0, 130.2, 130.1, 129.7, 127.9, 127.4, 119.6, 116.8, 108.3, 105.2, 101.7, 57.9, 48.9, 24.9, 22.6, 22.4. HRMS: (ESI+) m/z calc'd for (C₂₂H₂₀ClNO₅+H)⁺414.1108; found: 414.1108.

5-(benzo[d][1,3]dioxol-5-yl)-4-(2-chlorophenyl)-3-isobutyl-4,5-dihydropyrrolo[3,4-c]pyrazol-6(1H)-one (67). Yield: 118 mg, quant. yield from S67. ¹H NMR: (500 MHz, CDCl₃) (mixture of rotamers—major rotamer) δ 7.36 (d, J=7.9 Hz, 1H), 7.16 (ddd, J=9.1, 7.8, 1.4 Hz, 1H), 7.12-7.09 (overlap, 2H), 6.97 (dd, J=7.7, 1.5 Hz, 1H), 6.82 (dd, J=8.4, 2.0 Hz, 1H), 6.69 (d, J=8.4 Hz, 1H), 6.58 (s, 1H), 5.90 (dd, J=5.6, 1.4 Hz, 2H), 2.69 (dd, J=14.4, 7.3 Hz, 1H), 2.54 (dd, J=14.4, 7.2 Hz, 1H), 1.63 (m, 1H), 0.78 (d, J=6.6 Hz, 3H), 0.72 (d, J=6.6 Hz, 3H). ¹³C NMR: (126 MHz, CDCl₃) (mixture of rotamers) δ 161.9, 148.0, 145.3, 140.0, 134.6, 133.4, 131.9, 129.8, 129.6, 127.9, 127.1, 116.4, 108.2, 105.3, 101.5, 57.3, 34.8, 34.7, 34.0, 31.7, 29.2, 29.1, 27.0, 25.4, 22.8, 22.2, 22.0, 20.8, 14.2, 11.6. HRMS: (ESI+) m/z calc'd for (C₂₂H₂₀ClN₃O₃+H)⁺410.1271; found: 410.1263.

1-(benzo[d][1,3]dioxol-5-yl)-5-(4-fluoro-2-methylphenyl)-3-hydroxy-4-(3-methylbutanoyl)-1,5-dihydro-2H-pyrrol-2-one (S70). Yield: 442 mg, 29.9%. ¹H NMR: (500 MHz, CDCl₃) (mixture of rotamers—major rotamer) δ6.86 (dd, J=8.5, 5.8 Hz, 1H), 6.82-6.76 (overlap, 2H), 6.74 (d, J=2.0 Hz, 1H), 6.69 (d, J=8.3 Hz, 1H), 6.60 (dd, J=8.3, 2.1 Hz, 1H), 5.92 (m, 3H), 2.54 (dd, J=15.4, 6.4 Hz, 1H), 2.50 (s, 3H), 2.34 (dd, J=15.4, 7.5 Hz, 1H), 2.05 (m, 1H), 0.86 (d, J=6.7 Hz, 3H), 0.74 (d, J=6.6 Hz, 3H). ¹³C NMR: (126 MHz, CDCl₃) (mixture of rotamers) δ 196.8, 164.9, 163.2, 161.3, 148.2, 146.8, 139.9, 139.8, 129.7, 129.14, 129.12, 127.2, 127.1, 121.2, 117.8, 117.7, 117.5, 116.8, 114.0, 113.9, 108.4, 106.0, 105.0, 101.8, 64.5, 58.5, 50.3, 49.4, 25.0, 24.9, 22.8, 22.5, 22.4, 22.2, 19.7, 18.8. ¹⁹F NMR: (470 MHz, CDCl₃) δ −113.63 (m). HRMS: (ESI+) m/z calc'd for (C₂₃H₂₂FNO₅+H)⁺412.1560; found 412.1570.

5-(benzo[d][1,3]dioxol-5_yl)-4-(4-fluoro-2-methylphenyl)-3-iSObutyl-4,5-dihydropyrrolo[3,4-c]pyrazol-6(1H)-one (70). Yield: 99.0 mg, quant. yield from S70. ¹H NMR: (500 MHz, CDCl₃) (Mixture of rotamers—major rotamer) 6.88-6.81 (overlap, 3H), 6.76 (m, 1H), 6.68 (d, J=8.3 Hz, 1H), 6.63 (d, J=8.0 Hz, 1H), 6.11 (s, 1H), 5.90 (d, J=3.5 Hz, 2H), 2.62 (dd, J=14.5, 7.1 Hz, 1H), 2.48 (dd, J=14.4, 7.1 Hz, 1H), 2.42 (s, 2H), 1.57 (m, 1H), 0.75 (d, J=6.6 Hz, 3H), 0.72 (d, J=6.6 Hz, 3H). ¹³C NMR: (126 MHz, CDCl₃) (mixture of rotamers) δ 163.1, 162.3, 161.1, 148.0, 146.1, 139.5, 137.9, 131.7, 130.7, 128.5, 127.6, 118.3, 117.2, 117.0, 114.3, 114.2, 108.2, 106.8, 105.7, 101.5, 63.3, 57.5, 34.8, 34.6, 34.1, 31.7, 29.2, 28.9, 25.4, 22.8, 22.20, 22.18, 20.8, 19.5, 14.2. ¹⁹F NMR: (470 MHz, CDCl₃) (minor rotamer) δ 113.83 (m); (major rotamer) δ −113.97 (m). HRMS: (ESI+) m/z calc'd for (C₂₃H₂₂FN₃O₃+H)⁺408.1723; found 408.1719.

1-(3-fluoro-4-methoxyphenyl)-3-hydroxy-5-(2-methoxyphenyl)-4-(3-methylbutanoyl)-1,5-dihydro-2H-pyrrol-2-one (S72). Yield: 413 mg, 80.3%. ¹H NMR: (500 MHz, CDCl₃) δ 7.35 (dd, J=12.9, 2.0 Hz, 1H), 7.29 (d, J=6.4 Hz, 1H), 7.21 (ddd, J=8.5, 8.4, 1.7 Hz, 1H), 6.88 (d, J=8.2 Hz, 1H), 6.85 (d, J=7.4 Hz, 1H), 6.81 (dd, J=9.1, 9.1 Hz, 1H), 3.94 (s, 2H), 3.78 (s, 3H), 2.33 (dd, J=15.2, 6.8 Hz, 1H), 2.07 (dd, J=15.2, 7.2 Hz, 1H), 1.98 (m, 1H), 0.86 (d, J=6.6 Hz, 3H), 0.66 (d, J=6.6 Hz, 3H). ¹³C NMR: (126 MHz, CDCl₃) δ 163.2, 157.4, 152.8, 150.9, 145.6, 145.5, 130.3, 129.7, 129.6, 122.9, 121.6, 117.9, 113.3, 111.5, 110.5, 56.4, 55.8, 48.1, 24.9, 22.6, 22.3. ¹⁹F NMR: (470 MHz, CDCl₃) δ −133.14 (m). HRMS:

(ESI+) m/z calc'd for (C₂₃H₂₄FNO₅+H)⁺414.1717 Found 414.1722.

5-(3-fluoro-4-methoxyphenyl)-3-isobutyl-4-(2-methoxyphenyl)-4,5-dihydropyrrolo[3,4-c]pyrazol-6(1H)-one (72). Yield: 99.9 mg, quant. yield from S72. ¹H NMR: (500 MHz, CDCl₃) δ 7.42 (dd, J=13.4, 2.1 Hz, 1H), 7.24 (d, J=8.8 Hz, 1H), 7.19 (m, 1H), 6.89 (d, J=8.0 Hz, 2H), 6.83 (dd, J=9.1, 9.1 Hz, 1H), 6.78 (dd, J=7.5, 7.5 Hz, 1H), 6.50 (s, 1H), 3.92 (s, 3H), 3.81 (s, 3H), 2.64 (dd, J=14.4, 7.4 Hz, 1H), 2.47 (dd, J=14.4, 7.2 Hz, 1H), 1.69 (m, 1H), 0.80 (d, J=6.6 Hz, 3H), 0.74 (d, J=6.6 Hz, 3H). ¹³C NMR: (126 MHz, CDCl₃) δ 162.1, 157.0, 153.0, 151.0, 144.8, 144.7, 139.6, 131.9, 131.8, 129.5, 124.7, 121.4, 118.0, 113.42, 110.8, 56.5, 55.6, 33.9, 28.8, 22.3, 22.2, 22.1. ¹⁹F NMR: (470 MHz, CDCl₃) δ −133.59 (m). HRMS: (ESI+) m/z calc'd for (C₂₃H₂₄FN₃O₃+H)⁺410.1880; found 410.1873.

5-(4-fluoro-2-methylphenyl)-1-(3-fluoro-4-methoxyphenyl)-3-hydroxy-4-(3-methylbutanoyl)-1,5-dihydro-2H-pyrrol-2-one (S73). Yield: 415 mg, 26.8%. $^1$H NMR: (500 MHz, CDCl$_3$) δ 7.12 (dd, J=12.2, 2.4 Hz, 1H), 6.92 (m, 1H), 6.85 (d, J=8.8 Hz, 2H), 6.85-6.80 (overlap, 3H), 6.76 (ddd, J=8.5, 8.3, 2.5 Hz, 1H), 5.93 (s, 1H), 3.82 (s, 4H), 2.60 (dd, J=15.4, 6.3 Hz, 2H), 2.56 (s, 3H), 2.40 (dd, J=15.4, 7.6 Hz, 1H), 2.06 (m, 1H), 0.86 (d, J=6.7 Hz, 4H), 0.74 (d, J=6.6 Hz, 3H). $^{13}$C NMR: (126 MHz, CDCl$_3$) δ 196.7, 165.2, 163.2, 161.2, 153.4, 153.0, 151.0, 146.7, 146.6, 139.9, 139.8, 129.01, 128.98, 128.84, 128.77, 127.0, 126.9, 121.7, 119.5, 119.4, 117.7, 117.6, 114.0, 113.9, 113.48, 113.46, 112.4, 112.3, 64.2, 58.2, 56.4, 50.5, 49.7, 25.0, 24.9, 22.8, 22.4, 22.2, 19.7, 18.7. $^{19}$F NMR: (470 MHz, CDCl$_3$) δ −113.56 (m), 132.18 (m). HRMS: (ESI+) m/z calc'd for (C$_{23}$H$_{23}$F$_2$NO$_4$+H)$^+$416.1673; found 416.1666.

4-(4-fluoro-2-methylphenyl)-5-(3-fluoro-4-methoxyphenyl)-3-isobutyl-4,5-dihydropyrrolo[3,4-c]pyrazol-6(1H)-one (73). Yield: 103 mg, quant. yield from S73. $^1$H NMR: (500 MHz, CDCl$_3$) (mixture of rotamers—major rotamer) δ7.17 (d, J=12.1 Hz, 1H), 6.96 (d, J=7.5 Hz, 1H), 6.85-6.82 (overlap, 3H), 6.75 (s, 1H), 6.14 (s, 1H), 3.81 (s, 3H), 2.62 (dd, J=14.5, 7.1 Hz, 1H), 2.54-2.48 (overlap, 3H), 1.56 (m, 1H), 0.75 (d, J=6.4 Hz, 3H), 0.72 (d, J=6.6 Hz, 3H). $^{13}$C NMR: (126 MHz, CDCl$_3$) (mixture of rotamers)$^{13}$C NMR (126 MHz, cdcl$_3$) δ 163.2, 162.1, 161.2, 153.0, 151.0, 137.8, 130.9, 130.6, 128.3, 119.8, 117.3, 117.2, 114.5, 114.3, 113.5, 112.8, 112.6, 57.1, 56.4, 34.1, 29.0, 22.3, 22.17, 22.16, 19.5. $^{19}$F NMR: (470 MHz, CDCl$_3$) (major rotamer) δ −113.79 (m), −132.93 (m); (minor rotamer) δ −113.60 (m), −133.07 (m). HRMS: (ESI+) m/z calc'd for (C$_{23}$H$_{23}$F$_2$N$_3$O$_2$+H)$^+$ 412.1837; found 412.1827.

5-(2-bromophenyl)-1-(4-bromophenyl)-3-hydroxy-4-(3-methylbutanoyl)-1,5-dihydro-2H-pyrrol-2-one (S74). Yield: 406 mg, 82.3%. $^1$H NMR: (500 MHz, CDCl$_3$)$^1$H NMR (500 MHz, cdcl$_3$) δ 7.53 (br d, J=7.8 Hz, 1H), 7.43-7.36 (overlap, 4H), 7.20 (br dd, J=7.4, 7.4 Hz, 1H), 7.11 (br dd, J=7.6, 7.6 Hz, 111), 6.95 (br d, J=7.8 Hz, 1H), 6.42 (s, 1H), 2.49 (dd, J=15.6, 6.9 Hz, 1H), 2.20 (dd, J=15.6, 7.0 Hz, 1H), 2.00 (m, 1H), 0.89 (d, J=6.6 Hz, 3H), 0.71 (d, J=6.7 Hz, 3H). $^{13}$C NMR: (126 MHz, CDCl$_3$) $^{13}$C NMR (126 MHz, cdcl$_3$) δ 198.0, 163.6, 158.7, 134.9, 134.3, 133.6, 132.25, 132.16, 130.6, 128.7, 127.6, 125.5, 124.3, 120.0, 119.9, 60.0, 49.1, 24.9, 22.6, 22.4. HRMS: (ESI+) m/z calc'd for (C$_{21}$H$_{19}$Br$_2$NO$_3$+H)$^+$491.9810; found 491.9993.

4-(2-bromophenyl)-5-(4-bromophenyl)-3-isobutyl-4,5-dihydropyrrolo[3,4-c]pyrazol-6(1H)-one (74). Yield: 112 mg, quant. yield from S74. $^1$H NMR: (500 MHz, CDCl$_3$) $^1$H NMR (500 MHz, cdcl$_3$) δ 7.57 (dd, J=7.8, 1.4 Hz, 1H), 7.47 (d, J=9.0 Hz, 2H), 7.40 (d, J 9.0 Hz, 2H), 7.13 (ddd, J=7.6, 7.6, 1.4 Hz, 1H), 7.09 (ddd, J=7.6, 7.4, 1.9 Hz, 1H), 6.92 (dd, J=7.6, 1.9 Hz, 1H), 6.62 (s, 1H), 2.73 (dd, J=14.4, 7.4 Hz, 1H), 2.60 (dd, J=14.4, 7.3 Hz, 1H), 1.61 (m, 1H), 0.78 (d, J=6.6 Hz, 3H), 0.70 (d, J=6.6 Hz, 3H). $^{13}$C NMR: (126 MHz, CDCl$_3$) $^{13}$C NMR (126 MHz, cdcl$_3$) δ 161.8, 137.1, 136.0, 133.2, 132.1, 130.2, 128.7, 127.8, 123.4, 118.2, 59.4, 34.8, 34.1, 31.7, 29.2, 25.4, 22.8, 22.2, 22.0, 20.8, 14.3. HRMS: (ESI+) m/z calc'd for (C$_{21}$H$_{19}$Br$_2$N$_3$O+H)$^+$ 489.9973; found 489.9964.

1-(4-bromophenyl)-3-hydroxy-5-(2-methoxyphenyl)-4-(3-methylbutanoyl)-1,5-dihydro-2H-pyrrol-2-one (S75). Yield: 365 mg, 82.3%. $^1$H NMR: (500 MHz, CDCl$_3$) δ 7.47 (d, J=8.9 Hz, 2H), 7.36 (d, J=8.9 Hz, 2H), 7.22 (m, 1H), 6.88 (br d, J=8.3 Hz, 1H), 6.84 (br dd, J=7.4, 7.4 Hz, 1H), 6.38 (s, 1H), 3.94 (s, 3H), 2.34 (dd, J=15.2, 6.8 Hz, 1H), 2.07 (dd, J=15.2, 7.1 Hz, 1H), 1.98 (m, 1H), 0.87 (d, J=6.6 Hz, 3H), 0.66 (d, J=6.6 Hz, 3H). $^{13}$C NMR: (126 MHz, CDCl$_3$) δ 163.3, 157.3, 135.6, 132.0, 130.4, 123.3, 122.7, 121.7, 119.0, 111.5, 77.4, 77.2, 76.9, 55.9, 48.2, 24.9, 22.7, 22.3. HRMS: (ESI+) m/z calc'd for (C$_{22}$H$_{22}$BrNO$_4$+H)$^+$ 444.0810; found 444.0820.

5-(4-bromophenyl)-3-isobutyl-4-(2-methoxyphenyl)-4,5-dihydropyrrolo[3,4-c]pyrazol-6(1H)-one (75). Yield: 111 mg, quant. yield from S75. $^1$H NMR: (500 MHz, CDCl$_3$) (mixture of rotamers—major rotamer) δ 7.50 (d, J=8.8 Hz, 2H), 7.36 (d, J=8.9 Hz, 2H), 7.18 (m, 1H), 6.89 (d, J=8.2 Hz, 2H), 6.76 (dd, J=7.5, 7.5 Hz, 1H), 6.57 (s, 1H), 3.93 (s, 3H), 2.72 (dd, J=14.3, 7.3 Hz, 1H), 2.53 (dd, J=14.3, 7.2 Hz, 1H), 1.69 (m, 1H), 0.81 (d, J=6.6 Hz, 3H), 0.74 (d, J=6.6 Hz, 3H). $^{13}$C NMR: (126 MHz, CDCl$_3$) (mixture of rotamers) δ 162.2, 156.9, 148.3, 139.6, 137.6, 131.8, 129.5, 127.6, 127.0, 124.6, 123.3, 121.5, 117.6, 110.8, 55.6, 34.8, 33.7, 29.2, 28.9, 27.0, 25.4, 22.8, 22.2, 22.1, 20.8, 14.2. HRMS: (ESI+) m/z calc'd for (C$_{22}$H$_{22}$BrN$_3$O$_2$+H)$^+$440.0974; found 440.0961.

1-(4-bromophenyl)-5-(4-fluoro-2-methylphenyl)-3-hydroxy-4-(3-methylbutanoyl)-1,5-dihydro-2H-pyrrol-2-one (S76). Yield: 211 mg, 47.3%. $^1$H NMR: (500 MHz, CDCl$_3$) (mixture of rotamers—major rotamer) δ 7.41 (d, J=8.9 Hz, 2H), 7.19 (d, J=8.9 Hz, 2H), 6.84-6.81 (overlap, 2H), 6.76 (m, 1H), 5.99 (s, 1H), 2.63-2.59 (overlap, 4H), 2.41 (dd, J=15.4, 7.6 Hz, 1H), 2.07 (m, 1H), 0.86 (d, J=6.7 Hz, 3H), 0.75 (d, J=6.6 Hz, 3H). $^{13}$C NMR: (126 MHz, CDCl$_3$) (mixture of rotamers) δ 196.7, 165.2, 163.2, 161.3, 139.8, 139.8, 135.0, 132.4, 132.3, 128.84, 128.81, 126.9, 126.8, 124.7, 123.9, 121.8, 120.4, 117.8, 117.7, 114.1, 113.9, 63.8, 57.8, 50.6, 49.8, 25.0, 24.9, 22.8, 22.4, 22.2, 19.7, 18.7. $^{19}$F NMR: (470 MHz, CDCl$_3$) (major rotamer) δ −113.40 (m); (minor rotamer) δ −112.87 (m). HRMS: (ESI+) m/z calc'd for (C$_{22}$H$_{21}$BrFNO$_3$+H)$^+$446.0767; found 446.0762.

5-(4-bromophenyl)-4-(4-fluoro-2-methylphenyl)-3-isobutyl-4,5-dihydropyrrolo[3,4-c]pyrazol-6(1H)-one (76). Yield: 108 mg, quant. yield from S76. $^1$H NMR: (500 MHz, CDCl$_3$) (mixture of rotamers—major rotamer) δ 7.40-7.38 (overlap, 3H), 7.26 (m, 1H), 6.86 (m, 1H), 6.74 (m, 1H), 6.21 (br s, 1H), 2.58 (dd, J=14.5, 7.2 Hz, 1H), 2.55-2.50 (overlap, 2H), 1.56 (d, J=5.6 Hz, 1H), 0.76 (d, J=6.4 Hz, 3H), 0.72 (d, J=6.6 Hz, 3H). $^{19}$F NMR: (470 MHz, CDCl$_3$) (major rotamer) δ −113.59 (m); (minor rotamer) δ −113.32 (m). HRMS: (ESI+) m/z calc'd for (C$_{22}$H$_{21}$BrFN$_3$O+H)$^+$ 442.0930; found 442.0924.

1-(4-bromophenyl)-5-(4-fluoro-2-methoxyphenyl)-3-hydroxy-4-(3-methylbutanoyl)-1,5-dihydro-2H-pyrrol-2-one (S77). Yield: 194 mg, 39.1%. $^1$H NMR: (500 MHz, CDCl$_3$) δ 7.42 (d, J=9.0 Hz, 2H), 7.37 (d, J=9.0 Hz, 2H), 6.90 (br s, 1H), 6.60 (br d, J 10.5 Hz, 1H), 6.56 (ddd, J=8.3, 8.3, 2.4 Hz, 1H), 6.29 (br s, 1H), 3.92 (s, 3H), 2.38 (dd, J=15.3, 6.7 Hz, 1H), 2.13 (dd, J=15.2, 7.2 Hz, 1H), 2.02 (m, 1H), 0.88 (d, J=6.6 Hz, 3H), 0.71 (d, J=6.6 Hz, 3H). $^{13}$C NMR: (126 MHz, CDCl$_3$) δ 164.8, 163.5, 162.8, 158.9, 158.6, 135.3, 132.1, 123.4, 119.3, 118.6, 108.5, 100.0, 99.8, 56.2, 48.7, 24.9, 22.7, 22.4. $^{19}$F NMR: (470 MHz, CDCl$_3$) δ −108.71 (br s). HRMS: (ESI+) m/z calc'd for (C$_{22}$H$_{21}$BrFNO$_4$+H)$^+$ 462.0716; found 462.0711.

5-(4-bromophenyl)-4-(4-fluoro-2-methoxyphenyl)-3-isobutyl-4,5-dihydropyrrolo[3,4-c]pyrazol-6(1H)-one (77). Yield: 71.0 mg, 71.6% yield from S77. $^1$H NMR: (500 MHz, CDCl$_3$) (mixture of rotamers—major rotamer) δ 7.45 (d, J=8.9 Hz, 2H), 7.37 (d, J=8.9 Hz, 2H), 6.84 (br s, 1H), 6.62 (br d, J=9.8 Hz, 1H), 6.50-6.47 (overlap, 2H), 3.91 (s, 3H), 2.72 (dd, J=14.3, 7.2 Hz, 1H), 2.52 (dd, J=14.3, 7.2 Hz, 1H), 1.70 (m, 1H), 0.81 (d, J 6.6 Hz, 3H), 0.76 (d, J=6.6 Hz, 3H). $^{13}$C NMR: (126 MHz, CDCl$_3$) (mixture of rotamers) δ 164.4, 162.4, 162.2, 158.1, 139.5, 137.3, 131.9, 123.6, 121.5, 120.5, 117.9, 108.2, 108.1, 99.5, 99.2, 56.0, 36.2, 34.8, 34.6, 33.8, 31.7, 29.2, 28.9, 27.0, 25.4, 22.8, 22.20, 22.15, 20.8, 18.9, 14.2, 11.5. $^{19}$F NMR: (470 MHz, CDCl$_3$) δ −110.19 (m). HRMS: (ESI+) m/z calc'd for (C$_{22}$H$_{21}$BrFN$_3$O$_2$+H)$^+$458.0879; found 458.0874.

5-(2-chlorophenyl)-1-(4-(dimethylamino)phenyl)-3-hydroxy-4-(3-methylbutanoyl)-1,5-dihydro-2H-pyrrol-2-one (S78). Yield: 246 mg, quant. yield. $^1$H NMR: (400 MHz, CDCl$_3$) δ 7.33 (dd, J=6.1, 3.3 Hz, 1H), 7.26 (m, 2H), 7.19-7.16 (overlap, 2H), 7.03 (m, 1H), 6.60 (d, J=9.1 Hz, 2H), 6.41 (s, 1H), 2.90 (s, 6H), 2.40 (dd, J=15.3, 7.0 Hz, 1H), 2.15 (dd, J=15.3, 6.7 Hz, 1H), 2.00 (m, 1H), 0.90 (d, J=6.8 Hz, 3H), 0.71 (d, J=6.8 Hz, 3H). LCMS: (ESI+) m/z calc'd for (C$_{23}$H$_{25}$ClN$_2$O$_3$+H)$^+$413.16; found 413.10.

4-(2-chlorophenyl)-5-(4-(dimethylamino)phenyl)-3-isobutyl-4,5-dihydropyrrolo[3,4-c]pyrazol-6(1H)-one (78). Yield: 25.0 mg, 43.6% yield from S78. $^1$H NMR: (400 MHz, CDCl$_3$) δ 10.36 (br s, 1H), 7.29-7.38 (overlap, 3H), 7.17-7.09 (overlap, 2H), 7.03 (dd, J=7.6, 2.3 Hz, 1H), 6.64 (d, J=9.4 Hz, 2H), 6.57 (s, 1H), 2.89 (s, 6H), 2.45 (m, 1H), 2.38 (m, 1H), 1.59 (m, 1H), 0.78 (d, J=6.6 Hz, 3H), 0.71 (d, J=6.8 Hz, 3H). LCMS: (ESI+) m/z calc'd for (C$_{23}$H$_{25}$ClN$_4$O+H)$^+$ 409.18; found 409.10.

1-(4-(dimethylamino)phenyl)-3-hydroxy-5-(2-methoxyphenyl)-4-(3-methylbutanoyl)-1,5-dihydro-2H-pyrrol-2-one (S80). Yield: 292 mg, 71.5%. $^1$H NMR: (500 MHz, CDCl$_3$) δ 7.32 (d, J=8.7 Hz, 2H), 7.18 (m, 1H), 6.95 (s, 1H), 6.83 (dd, J=7.5, 7.5 Hz, 2H), 6.58 (d, J=8.7 Hz, 2H), 6.32 (s, 1H), 3.88 (s, 3H), 2.86 (s, 6H), 2.33 (dd, J=15.1, 6.8 Hz, 1H), 2.09 (dd, J=15.1, 7.2 Hz, 1H), 1.98 (m, 1H), 0.87 (d, J=6.6 Hz, 3H), 0.66 (d, J=6.6 Hz, 3H). $^{13}$C NMR: (126 MHz, CDCl$_3$) δ 163.0, 157.6, 148.7, 129.9, 125.9, 123.7, 121.4, 112.5, 111.4, 55.8, 47.9, 40.6, 25.0, 22.7, 22.3. HRMS: (ESI+) m/z calc'd for (C$_{24}$H$_{28}$N$_2$O$_4$+H)$^+$409.2127; found 409.2125.

5-(4-(dimethylamino)phenyl)-3-isobutyl-4-(2-methoxyphenyl)-4,5-dihydropyrrolo[3,4-c]pyrazol-6(1H)-one (80). Yield: 98.1 mg, 99.1% yield from S80. $^1$H NMR: (500 MHz, DMSO) (mixture of rotamers—major rotamer) δ 7.29 (d, J=9.0 Hz, 2H), 7.17 (m, 1H), 7.00 (s, 1H), 6.77 (dd, J=7.4, 7.4 Hz, 1H), 6.64 (d, J=9.0 Hz, 2H), 6.46 (d, J=8.6 Hz, 1H), 3.84 (s, 3H), 2.82 (s, 6H), 2.33 (dd, J=13.9, 7.4 Hz, 1H), 2.23 (dd, J=13.9, 7.1 Hz, 1H), 1.57 (m, 1H), 0.70 (d, J=6.5 Hz, 3H), 0.58 (d, J=6.6 Hz, 3H). $^{13}$C NMR: (126 MHz, DMSO) (mixture of rotamers) δ 161.9, 156.8, 149.3, 147.7, 136.1, 128.9, 127.5, 125.4, 124.7, 124.2, 120.7, 112.3, 111.3, 55.6, 53.0, 40.2, 33.1, 29.9, 28.0, 22.0, 21.7. HRMS: (ESI+) m/z calc'd for (C$_{24}$H$_{28}$N$_4$O$_2$+H)$^+$405.2291; found 405.2301.

1-(4-(dimethylamino)phenyl)-5-(4-fluoro-2-methylphenyl)-3-hydroxy-4-(3-methylbutanoyl)-1,5-dihydro-2H-pyrrol-2-one (S81). Yield: 208 mg, 50.6%. $^1$H NMR: (500 MHz, CDCl$_3$) δ 7.05 (d, J=9.0 Hz, 2H), 6.89 (dd, J=8.4, 5.8 Hz, 1H), 6.76 (m, 2H), 6.59 (d, J=9.0 Hz, 2H), 5.92 (s, 1H), 2.89 (s, 7H), 2.62 (dd, J=15.4, 6.3 Hz, 1H), 2.49 (s, 3H), 2.43 (dd, J=15.4, 7.6 Hz, 1H), 2.08 (m, 1H), 0.86 (d, J=6.7 Hz, 3H), 0.76 (d, J=6.6 Hz, 3H). $^{13}$C NMR: (126 MHz, CDCl$_3$) δ 196.5, 165.2, 163.0, 161.1, 154.1, 149.4, 139.94, 139.89, 129.7, 127.1, 127.0, 125.2, 124.7, 124.1, 121.4, 117.4, 117.3, 113.7, 113.5, 112.5, 58.4, 50.5, 40.5, 25.0, 24.9, 22.8, 22.4, 19.7. $^{19}$F NMR: (470 MHz, CDCl$_3$) δ −114.32 (m). HRMS: (ESI+) m/z calc'd for (C$_{24}$H$_{27}$FN$_2$O$_3$+H)$^+$411.2084; found 411.2083.

5-(4-(dimethylamino)phenyl)-4-(4-fluoro-2-methylphenyl)-3-isobutyl-4,5-dihydropyrrolo[3,4-c]pyrazol-6(1H)-one (81). Yield: 105 mg, quant. yield from S81. $^1$H NMR: (500 MHz, CDCl$_3$) (mixture of rotamers—major rotamer) δ 7.06 (d, J=8.2 Hz, 2H), 6.90 (m, 1H), 6.79-6.75 (overlap, 2H), 6.59 (d, J=8.5 Hz, 2H), 6.44 (m, 1H), 6.08 (s, 1H), 2.88 (s, 6H), 2.59 (dd, J=14.4, 7.0 Hz, 1H), 2.45 (m, 1H), 2.37 (s, 3H), 1.57 (m, 1H), 0.75 (d, J=6.6 Hz, 3H), 0.72 (d, J=6.6 Hz, 3H). $^{13}$C NMR: (126 MHz, CDCl$_3$) (mixture of rotamers) δ 163.0, 162.2, 161.0, 149.1, 138.1, 131.1, 128.7, 126.9, 126.2, 124.9, 117.0, 116.8, 114.1, 113.9, 112.7, 57.4, 40.6, 34.8, 34.6, 34.3, 31.7, 29.2, 28.8, 28.5, 27.0, 25.4, 22.8, 22.3, 22.23, 22.20, 20.8, 19.5, 18.9, 14.2, 11.5. $^{19}$F NMR: (470 MHz, CDCl$_3$) (major rotamer) δ −114.48 (m). HRMS: (ESI+) m/z calc'd for (C$_{24}$H$_{27}$FN$_4$O+H)$^+$407.2247; found 407.2249.

1-(4-(dimethylamino)phenyl)-5-(4-fluoro-2-methoxyphenyl)-3-hydroxy-4-(3-methylbutanoyl)-1,5-dihydro-2H-pyrrol-2-one (S82). Yield: 269 mg, 63.1%. $^1$H NMR: (500 MHz, CDCl$_3$) δ 7.27 (d, J=8.6 Hz, 2H), 6.93 (br s, 1H), 6.59 (d, J=8.6 Hz, 2H), 6.55-6.52 (overlap, 2H), 6.23 (br s, 1H), 3.86 (s, 3H), 2.88 (s, 6H), 2.38 (dd, J=15.1, 6.7 Hz, 1H), 2.15 (dd, J=15.1, 7.3 Hz, 1H), 2.02 (m, 1H), 0.88 (d, J=6.6 Hz, 3H), 0.71 (d, J=6.6 Hz, 3H). $^{13}$C NMR: (126 MHz, CDCl$_3$) δ 164.5, 163.2, 162.6, 158.8, 148.8, 123.9, 119.6, 112.5, 99.9, 99.7, 56.2, 48.4, 40.6, 25.0, 22.7, 22.4. $^{19}$F NMR: (470 MHz, CDCl$_3$) δ−109.79 (br s). HRMS: (ESI+) m/z calc'd for (C$_{24}$H$_{27}$FN$_2$O$_4$+H)$^+$427.2033; found 427.2025.

5-(4-(dimethylamino)phenyl)-4-(4-fluoro-2-methoxyphenyl)-3-isobutyl-4,5-dihydropyrrolo[3,4-c]pyrazol-6(1H)-one (82). Yield: 100 mg, quant. yield from S82. $^1$H NMR: (500 MHz, CDCl$_3$) δ 7.29 (d, J=9.0 Hz, 2H), 6.91 (m, 1H), 6.63 (d, J=9.0 Hz, 2H), 6.56 (dd, J=10.7, 2.2 Hz, 1H), 6.48 (ddd, J=8.4, 8.3, 2.3 Hz, 1H), 6.40 (s, 1H), 3.82 (s, 3H), 2.88 (s, 6H), 2.63 (dd, J=14.3, 7.3 Hz, 1H), 2.46 (dd, J=14.3, 7.2 Hz, 1H), 1.68 (m, 1H), 0.79 (d, J=6.6 Hz, 3H), 0.74 (d, J=6.6 Hz, 3H). $^{13}$C NMR: (126 MHz, CDCl$_3$) δ 164.2, 162.2, 162.1, 158.3, 148.4, 139.6, 128.6, 127.7, 127.4, 124.6, 121.1, 112.8, 107.9, 107.7, 99.3, 99.1, 55.9, 40.8, 34.1, 28.8, 22.24, 22.19. $^{19}$F NMR: (470 MHz, CDCl$_3$) δ −111.17 (br s). HRMS: (ESI+) m/z calc'd for (C$_{24}$H$_{27}$FN$_4$O$_2$+H)$^+$423.2196; found 423.2191.

3-hydroxy-5-(2-methoxyphenyl)-1-(6-methoxypyridin-3-yl)-4-(3-methylbutanoyl)-1,5-dihydro-2H-pyrrol-2-one (S85). Yield: 280 mg, 70.6%. $^1$H NMR: (500 MHz, CDCl$_3$) δ 8.18 (d, J=2.4 Hz, 1H), 7.76 (br d, J=7.8 Hz, 1H), 7.22 (ddd, J=8.4, 8.4, 1.7 Hz, 1H), 6.94 (br s, 1H), 6.85 (dd, J=7.2, 7.2 Hz, 2H), 6.63 (d, J=9.0 Hz, 1H), 6.38 (br s, 1H), 3.88 (s, 3H), 3.84 (s, 3H), 2.33 (dd, J=15.2, 6.8 Hz, 1H), 2.07 (dd, J=15.2, 7.2 Hz, 1H), 1.98 (m, 1H), 0.86 (d, J=6.6 Hz, 3H), 0.66 (d, J=6.6 Hz, 3H). $^{13}$C NMR: (126 MHz, CDCl$_3$) δ 163.5, 161.9, 157.5, 141.0, 133.8, 130.5, 127.2, 122.6, 121.6, 111.5, 110.8, 55.9, 53.7, 48.2, 24.9, 22.7, 22.3. HRMS: (ESI+) m/z calc'd for (C$_{22}$H$_{24}$N$_2$O$_5$+H)$^+$397.1763; found 397.1761.

3-isobutyl-4-(2-methoxyphenyl)-5-(6-methoxypyridin-3-yl)-4,5-dihydropyrrolo[3,4-c]pyrazol-6(1H)-one (85). Yield: 111 mg, quant. yield from S85. $^1$H NMR: (500 MHz, CDCl$_3$) (mixture of rotamers—major rotamer) δ 8.17 (d, J=2.6 Hz, 1H), 7.91 (d, J 7.8 Hz, 1H), 7.19 (ddd, J=8.8, 7.7, 1.7 Hz, 1H), 6.91 (br s, 1H), 6.86 (d, J=8.3 Hz, 1H), 6.79 (dd, J=7.5, 7.5 Hz, 1H), 6.67 (d, J=8.9 Hz, 1H), 6.51 (br s, 1H), 3.86 (s, 6H), 2.66 (dd, J=14.3, 7.3 Hz, 1H), 2.48 (dd, J=14.4, 7.1 Hz, 1H), 1.69 (m, 1H), 0.79 (d, J=6.6 Hz, 3H), 0.74 (d, J=6.6 Hz, 3H). $^{13}$C NMR: (126 MHz, CDCl$_3$) (mixture of rotamers) δ 162.3, 161.3, 157.1, 140.9, 134.2, 129.6, 129.2, 124.3, 121.4, 110.9, 110.7, 55.6, 53.7, 34.8, 33.9, 31.7, 29.2, 28.8, 25.4, 22.8, 22.2, 22.1, 20.8, 14.2, 11.6. HRMS: (ESI+) m/z calc'd for (C$_{22}$H$_{24}$N$_4$O$_3$+H)$^+$393.1927; found 292.1920.

5-(4-fluoro-2-methylphenyl)-3-hydroxy-1-(6-methoxypyridin-3-yl)-4-(3-methylbutanoyl)-1,5-dihydro-2H-pyrrol-2-one (S86). Yield: 119 mg, 29.9%. $^1$H NMR: (500 MHz, CDCl$_3$) (mixture of rotamers—major rotamer) δ 7.98 (d, J=2.5 Hz, 1H), 7.45 (dd, J=8.9, 2.6 Hz, 1H), 6.88 (dd, J=8.5, 5.8 Hz, 1H), 6.82-6.77 (overlap, 2H), 6.66 (d, J=8.9 Hz, 1H), 5.94 (s, 1H), 3.87 (s, 3H), 2.57 (dd, J=15.5, 6.3 Hz, 1H), 2.50 (s, 3H), 2.38 (dd, J=15.5, 7.6 Hz, 1H), 2.07 (dd, J=14.5, 7.7 Hz, 2H), 0.86 (d, J=6.7 Hz, 3H), 0.75 (d, J=6.6 Hz, 3H). $^{13}$C NMR: (126 MHz, CDCl$_3$) (mixture of rotamers) δ 196.8, 165.3, 163.3, 162.8, 161.3, 142.5, 141.4, 140.6, 139.93, 139.87, 135.0, 133.8, 128.81, 128.79, 127.1, 127.0, 126.5, 121.7, 117.8, 117.7, 114.2, 114.0, 111.4, 111.3, 111.0, 100.5, 64.3, 58.2, 53.9, 53.0, 52.3, 50.4, 50.1, 26.2, 25.0, 24.9, 22.81, 22.79, 22.6, 22.4, 22.2, 19.7, 18.7. $^{19}$F NMR: (470 MHz, CDCl$_3$) (major rotamer) δ −113.29 (m); (minor rotamer) δ −112.82 (br s). HRMS: (ESI+) m/z calc'd for (C$_{22}$H$_{23}$FN$_2$O$_4$+H)$^+$ 399.1720; found 399.1729.

4-(4-fluoro-2-methylphenyl)-3-isobutyl-5-(6-methoxypyridin-3-yl)-4,5-dihydropyrrolo[3,4-c]pyrazol-6(1H)-one (86). Yield: 112 mg, quant. yield from S86. $^1$H NMR: (500 MHz, CDCl$_3$) (mixture of rotamers—major rotamer) δ 7.88 (s, 1H), 7.54 (d, J=8.4 Hz, 1H), 6.83-6.77 (overlap, 2H), 6.72 (dd, J=7.9, 7.9 Hz, 1H), 6.63 (d, J=8.9 Hz, 1H), 6.08 (s, 1H), 3.80 (s, 3H), 2.36-2.32 (overlap, 4H), 2.24 (dd, J=14.4, 7.3 Hz, 1H), 1.50 (m, 1H), 0.69 (d, J=6.6 Hz, 3H), 0.65 (d, J=6.6 Hz, 3H). $^{13}$C NMR: (126 MHz, CDCl$_3$) (mixture of rotamers) δ 163.1, 162.2, 161.2, 142.6, 141.6, 137.9, 136.0, 134.8, 132.9, 130.1, 128.5, 128.4, 128.2, 117.3, 117.1, 114.4, 114.2, 111.0, 63.0, 57.2, 53.7, 34.3, 31.6, 28.6, 22.6, 22.04, 22.03, 19.3, 14.0. $^{19}$F NMR: (470 MHz, CDCl$_3$) (major rotamer) δ-113.62 (m); (minor rotamer) δ-113.45 (br s). HRMS: (ESI+) m/z calc'd for (C$_{22}$H$_{23}$FN$_4$O$_2$+H)$^+$ 395.1883; found 395.1893.

1-([1,2,4]triazolo[1,5-a]pyridin-6-yl)-5-(4-fluoro-2-methylphenyl)-3-hydroxy-4-(3-methylbutanoyl)-1,5-dihydro-2H-pyrrol-2-one (S89). Yield: 284 mg, 64.7%. $^1$H NMR: (500 MHz, CD$_3$OD) (mixture of rotamers—major rotamer) δ8.95 (m, 1H), 8.29 (s, 1H), 7.65 (d, J=9.5 Hz, 1H), 7.53 (dd, J=9.6, 2.0 Hz, 1H), 6.85 (dd, J=8.7, 5.7 Hz, 1H), 6.80 (dd, J=9.6, 2.4 Hz, 1H), 6.73 (ddd, J=8.4, 8.4, 2.5 Hz, 1H), 6.05 (s, 1H), 2.79 (dd, J=14.8, 6.2 Hz, 1H), 2.64 (s, 2H), 2.54 (dd, J=14.8, 7.9 Hz, 1H), 2.05 (m, 1H), 0.84 (d, J=6.7 Hz, 3H), 0.73 (d, J=6.7 Hz, 3H). $^{13}$C NMR: (126 MHz, CD$_3$OD) (mixture of rotamers) δ197.4, 166.5, 163.6, 161.6, 154.3, 150.3, 148.6, 140.7, 140.6, 129.7, 127.1, 127.03, 126.96, 126.7, 124.0, 122.9, 118.0, 117.9, 116.4, 115.0, 114.2, 114.1, 112.2, 58.0, 51.7, 25.6, 22.9, 22.4, 19.7. $^{19}$F NMR: (470 MHz, CD$_3$OD) (major rotamer) (δ-114.42 (ddd, J=10.0, 8.6, 5.7 Hz); (minor rotamer) −δ 114.25 (m). HRMS: (ESI+) m/z calc'd for (C$_{22}$H$_{21}$FN$_4$O$_3$+H)$^+$ 409.1676; found 409.1678.

5-([1,2,4]triazolo[1,5-a]pyridin-6-yl)-4-(4-fluoro-2-methylphenyl)-3-isobutyl-4,5-dihydropyrrolo[3,4-c]pyrazol-6(1H)-one (89). Yield: 99.9 mg, quant. yield from S89. $^1$H NMR: (500 MHz, DMSO) (mixture of rotamers) δ 13.49 (s, 1H), 9.24 (s, 1H), 8.48 (s, 1H), 7.87-7.84 (overlap, 2H), 7.07-6.99 (overlap, 2H), 6.84 (m, 1H), 6.69 (s, 1H), 2.56 (s, 3H), 2.37 (m, 2H), 2.27 (dd, J=14.1, 7.2 Hz, 1H), 1.49 (m, 1H), 0.68 (d, J=6.6 Hz, 3H), 0.59 (d, J=6.0 Hz, 3H). $^{13}$C NMR: (126 MHz, DMSO) (mixture of rotamers) δ 162.2, 160.2, 154.5, 147.9, 138.5, 131.0, 128.4, 127.5, 126.7, 124.7, 123.3, 116.9, 116.7, 115.6, 113.9, 113.7, 60.6, 56.2, 33.3, 28.2, 28.0, 21.9, 21.7, 18.8, 17.6. $^{19}$F NMR: (470 MHz, DMSO) (major rotamer) δ −114.51 (br s); (minor rotamer) δ −113.89 (br s). HRMS: (ESI+) m/z calc'd for (C$_{22}$H$_{21}$FN$_6$O+H)$^+$ 405.1839; found 405.1834.

REFERENCES

1. Control of the leishmaniases: report of a meeting of the WHO Expert Committee on the Control of Leishmaniases, Geneva, 22-26 Mar. 2010. Geneva: World Health Organization, 2010.
2. Vos T, Allen C, Arora M, Barber R M, Bhutta Z A, Brown A, et al. Global, regional, and national incidence, prevalence, and years lived with disability for 310 diseases and injuries, 1990-2015: a systematic analysis for the Global Burden of Disease Study 2015. The Lancet. 2016; 388 (10053):1545-602. doi: 10.1016/s0140-6736(16)31678-6.
3. Vakil N H, Fujinami N, Shah R I. Pharmacotherapy for leishmaniasis in the United States: focus on miltefosine. Pharmacotherapy. 2015; 35(5):536-45. Epub 2015/05/06. doi: 10.1002/phar.1585. PubMed PMID: 25940658.
4. Srivastava S, Mishra J, Gupta A K, Singh A, Shankar P, Singh S. Laboratory confirmed miltefosine resistant cases of visceral leishmaniasis from India. Parasites & vectors. 2017; 10(1):49. Epub2017/02/01. doi: 10.1186/513071-017-1969-z. PubMed PMID: 28137296; PubMed Central PMCID: PMCPMC5282768.
5. Bhattacharya A, Ouellette M. New insights with miltefosine unresponsiveness in Brazilian Leishmania infantum isolates. EBioMedicine. 2018; 37:13-4. Epub 2018/10/14. doi:10.1016/j.ebiom.2018.10.016. PubMed PMID: 30314891; PubMed Central PMCID: PMCPMC6286654.
6. Sunyoto T, Potet J, Boelaert M. Why miltefosine—a life-saving drug for leishmaniasis—is unavailable to people who need it the most. BMJ global health. 2018; 3(3):e000709. Epub 2018/05/08.doi: 10.1136/bmjgh-2018-000709. PubMed PMID: 29736277; PubMed Central PMCID: PMCPMC5935166.
7. Frezard F, Demicheli C, Ribeiro R R. Pentavalent antimonials: new perspectives for old drugs. Molecules (Basel, Switzerland). 2009; 14(7):2317-36. Epub 2009/07/28. doi:10.3390/molecules14072317. PubMed PM ID: 19633606.
8. Sundar S, Sinha P R, Agrawal N K, Srivastava R, Rainey P M, Berman J D, et al. A cluster of cases of severe cardiotoxicity among kala-azar patients treated with a high-osmolarity lot of sodium antimony gluconate. Am J Trop Med Hyg. 1998; 59(1):139-43. Epub 1998 Jul. 31. doi: 10.4269/ajtmh.1998.59.139. PubMed PMID: 9684642.
9. Sundar S, Chakravarty J. Antimony toxicity. Int J Environ Res Public Health. 2010; 7(12):4267-77. Epub 2011/02/15. doi: 10.3390/ijerph7124267. PubMed PMID: 21318007; PubMed Central PMCID: PMCPMC3037053.
10. Ait-Oudhia K, Gazanion E, Vergnes B, Oury B, Sereno D. Leishmania antimony resistance: what we know what we can learn from the field. Parasitology research. 2011; 109(5):1225-32. Epub2011/07/30. doi: 10.1007/s00436-011-2555-5. PubMed PMID: 21800124.
11. Jha R K, Sah A K, Shah D K, Sah P. The treatment of visceral leishmaniasis: safety and efficacy. JNMA; journal of the Nepal Medical Association. 2013; 52(192):645-51. Epub 2014/10/21. PubMed PMID: 25327244.
12. Vieira-Goncalves R, Fagundes-Silva G A, Heringer J F, Fantinatti M, Da-Cruz A M, Oliveira-Neto M P, et al. First report of treatment failure in a patient with cutaneous leishmaniasis infected by Leishmania (Viannia) naiffi carrying Leishmania RNA virus: a fortuitous combination? Revista da Sociedade Brasileira de Medicina Tropical. 2019; 52:e20180323. Epub 2019/04/18. doi: 10.1590/0037-8682-0323-2018. PubMed PMID: 30994803.

13. Tahir M, Bashir U, Hafeez J, Ghafoor R. Safety and efficacy of miltefosine in cutaneous leishmaniasis: An open label, non-comparative study from Balochistan. Pakistan journal of medical sciences. 2019; 35(2):495-9. Epub 2019/05/16. doi: 10.12669/pjms.35.2.54. PubMed PMID: 31086539; PubMed Central PMCID: PMCPMC6500830.
14. Van Bocxlaer K, Caridha D, Black C, Vesely B, Leed S, Sciotti R J, et al. Novel benzoxaborole, nitroimidazole and aminopyrazoles with activity against experimental cutaneous leishmaniasis. Int J Parasitol Drugs Drug Resist. 2019. Epub 2019/03/30. doi: 10.1016/j.ijpddr.2019.02.002. PubMed PMID: 30922847.
15. Van den Kerkhof M, Mabille D, Chatelain E, Mowbray C E, Braillard S, Hendrickx S, et al. In vitro and in vivo pharmacodynamics of three novel antileishmanial lead series. Int J Parasitol Drugs Drug Resist. 2018; 8(1):81-6. Epub 2018/02/10. doi: 10.1016/j.ijpddr.2018.01.006. PubMed PMID: 29425734; PubMed Central PMCID: PMCPMC6114106.
16. Singh N, Kumar M, Singh R K. Leishmaniasis: current status of available drugs and new potential drug targets. Asian Pacific journal of tropical medicine. 2012; 5(6): 485-97. Epub 2012/05/12. doi: 10.1016/s1995-7645(12) 60084-4. PubMed PMID: 22575984.
17. Sundar S, Singh A. Chemotherapeutics of visceral leishmaniasis: present and future developments. Parasitology. 2018; 145(4):481-9. Epub 2017/12/08. doi: 10.1017/s0031182017002116. PubMed PMID: 29215329; PubMed Central PMCID: PMCPMC5984184.
18. Health products in the pipeline for infectious diseases: World Health Organization; 2018 [cited 2019 Jun. 5]. Available from: who.int/research-observatory/en/.
19. Portfolio—DNDi: Drugs for Neglected Diseases Initiative; 2019 [cited 2019 Jun. 5]. Available from: dndi.org/diseases-projects/leishmaniasis/leish-portfolio/.
20. Thomas M G, De Rycker M, Ajakane M, Albrecht S, Alvarez-Pedraglio A I, Boesche M, et at. Identification of GSK3186899/DDD853651 as a Preclinical Development Candidate for the Treatment of Visceral Leishmaniasis. J Med Chem. 2019; 62(3):1180-202. Epub 2018/12/21. doi: 10.1021/acs.jmedchem.8b01218. PubMed PMID: 30570265; PubMed Central PMCID: PMCPMC6407917.
21. Wyllie S, Thomas M, Patterson S, Crouch S, De Rycker M, Lowe R, et al. Cyclin-dependent kinase 12 is a drug target for visceral leishmaniasis. Nature. 2018; 560 (7717):192-7. Epub 2018/07/27. doi:10.1038/541586-018-0356-z. PubMed PMID: 30046105; PubMed Central PMCID: PMCPMC6402543.
22. Jacobs R T, Plattner J J, Keenan M. Boron-based drugs as antiprotozoals. Curr Opin Infect Dis. 2011; 24(6):586-92. Epub 2011/10/18. doi: 10.1097/QCO.0b013e32834c630e. PubMed PMID: 22001943.
23. Thompson A M, O'Connor P D, Blaser A, Yardley V, Maes L, Gupta S, et al. Repositioning Antitubercular 6-Nitro-2,3-dihydroimidazo[2,1-b][1,3]oxazoles for Neglected Tropical Diseases: Structure-Activity Studies on a Preclinical Candidate for Visceral Leishmaniasis. J Med Chem. 2016; 59(6):2530-50. Epub 2016/02/24. doi: 10.1021/acs.jmedchem.5b01699. PubMed PMID: 26901446.
24. Thompson A M, O'Connor P D, Marshall A J, Blaser A, Yardley V, Maes L, et al. Development of (6R)-2-Nitro-6-[4-(trifluoromethoxy)phenoxy]-6,7-dihydro-5H-imidazo[2,1-b][1,3]oxazine (DNDI-8219): A New Lead for Visceral Leishmaniasis. J Med Chem. 2018; 61(6):2329-52. Epub 2018/02/21. doi:10.1021/acs.jmedchem.7b01581. PubMed PMID: 29461823; PubMed Central PMCID: PMCPMC5867678.
25. Thompson A M, O'Connor P D, Marshall A J, Yardley V, Maes L, Gupta S, et al. 7-Substituted 2-Nitro-5,6-dihydroimidazo[2,1-b][1,3]oxazines: Novel Antitubercular Agents Lead to a New Preclinical Candidate for Visceral Leishmaniasis. J Med Chem. 2017; 60(10):4212-33. Epub 2017/05/02. doi:10.1021/acs.jmedchem.7b00034. PubMed PMID: 28459575.
26. Flynn B, Wang V, Sacks D L, Seder R A, Verthelyi D. Prevention and treatment of cutaneous leishmaniasis in primates by using synthetic type D/A oligodeoxynucleotides expressing CpG motifs. Infect Immun. 2005; 73(8): 4948-54. Epub 2005/07/26. doi: 10.1128/IAI.73.8.4948-4954.2005. PubMed PMID: 16041009; PubMed Central PMCID: PMCPMC1201230.
27. Verthelyi D, Gursel M, Kenney R T, Lifson J D, Liu S, Mican J, et al. CpG oligodeoxynucleotides protect normal and SIV-infected macaques from *Leishmania* infection. Journal of immunology (Baltimore, Md: 1950). 2003; 170(9):4717-23. Epub 2003/04/23. doi: 10.4049/jimmunol.170.9.4717. PubMed PMID: 12707351.
28. Walker P S, Scharton-Kersten T, Krieg A M, Love-Homan L, Rowton E D, Udey M C, et al. Immunostimulatory oligodeoxynucleotides promote protective immunity and provide systemic therapy for leishmaniasis via IL-12- and IFN-gamma-dependent mechanisms. Proceedings of the National Academy of Sciences of the United States of America. 1999; 96(12):6970-5. Epub 1999/06/09. doi:10.1073/pnas.96.12.6970. PubMed PMID: 10359823; PubMed Central PMCID: PMCPMC22026.
29. Zimmermann S, Egeter O, Hausmann S, Lipford G B, Rocken M, Wagner H, et al. Cutting edge: CpG oligodeoxynucleotides trigger protective and curative Th1 responses in lethal murine leishmaniasis. Journal of immunology (Baltimore, Md: 1950). 1998; 160(8):3627-30. PubMed PMID: WOS:000072970400001.
30. Wyllie S, Brand S, Thomas M, De Rycker M, Chung C W, Pena I, et al. Preclinical candidate for the treatment of visceral leishmaniasis that acts through proteasome inhibition. Proc Natl Acad Sci USA. 2019; 116(19):9318-23. Epub 2019/04/10. doi: 10.1073/pnas.1820175116. PubMed PMID: 30962368.
31. De Rycker M, Hallyburton I, Thomas J, Campbell L, Wyllie S, Joshi D, et al. Comparison of a high-throughput high-content intracellular *Leishmania donovani* assay with an axenic amastigote assay. Antimicrobial agents and chemotherapy. 2013; 57(7):2913-22. Epub 2013 Apr. 11. doi:10.1128/AAC.02398-12. PubMed PMID: 23571538; PubMed Central PMCID: PMCPMC3697379.
32. Valko K, Nunhuck S, Bevan C, Abraham M H, Reynolds D P. Fast gradient HPLC method to determine compounds binding to human serum albumin. Relationships with octanol/water and immobilized artificial membrane lipophilicity. J Pharm Sci. 2003; 92(11):2236-48. Epub 2003 Nov. 7. doi:10.1002/jps.10494. PubMed PMID: 14603509.
33. Bunally S, Young R J. The role and impact of high throughput biomimetic measurements in drug discovery. ADMET and DMPK. 2018; 6(2):74-84. doi: 10.5599/admet.530.
34. Debie E, Bultinck P, Nafie L, Dukor R. CompareVOA. Jupiter, FL: BioTools, Inc.; 2010.

35. Debie E, De Gussem E, Dukor R K, Herrebout W, Nafie L A, Bultinck P. A confidence level algorithm for the determination of absolute configuration using vibrational circular dichroism or Raman optical activity. Chemphyschem. 2011; 12(8):1542-9. Epub 2011/05/05. doi: 10.1002/cphc.201100050. PubMed PMID: 21542094.
36. De Muylder G, Ang K K H, Chen S, Arkin M R, Engel J C, McKerrow J H. A Screen against *Leishmania* Intracellular Amastigotes: Comparison to a Promastigote Screen and Identification of a Host Cell-Specific Hit. PLoS neglected tropical diseases. 2011; 5(7):e1253. doi: 10.1371/journal.pntd.0001253. PubMed Central PMCID: PMCPMC3139667.
37. Leeson P D, Young U. Molecular Property Design: Does Everyone Get It? ACS Med Chem Lett. 2015; 6(7):722-5. doi: 10.1021/acsmedchemlett. 5b00157. PubMed Central PMCID: PMCPMC4499821.
38. Young R J, Green D V, Luscombe C N, Hill A P. Getting physical in drug discovery II: the impact of chromatographic hydrophobicity measurements and aromaticity. Drug discovery today. 2011; 16(17-18):822-30. Epub 2011/06/28. doi: 10.1016/j.drudis.2011.06.001. PubMed PMID: 21704184.
39. Furet P, Guagnano V, Holzer P, Kallen J, Mah R, Masuya K, et al., inventors; Novartis Pharma AG, Switz.; Novartis AG. assignee. Pyrazolo[3,4-d]pyrimidinone compounds as inhibitors of the p53/mdm2 interaction patent US20150353563A1. 2015.
40. Furet P, Guagnano V, Holzer P, Kallen J, Mah R, Masuya K, et al., inventors; Novartis AG, Switz. assignee. Preparation of pyrazolo[3,4-d]pyrimidinone compounds as inhibitors of the p53/MDM2 interaction patent WO2014115080A1. 2014.
41. Furet P, Guagnano V, Holzer P, Mah R, Masuya K, Schlapbach A, et al., inventors; Novartis AG, Switz. assignee. Preparation of pyrazolopyrrolidine compounds as modulators of MDM2 and MDM4 for therapy patent WO2013080141 A1. 2013.
42. Furet P, Masuya K, Kallen J, Stachyra-Valat T, Ruetz S, Guagnano V, et al. Discovery of a novel class of highly potent inhibitors of the p53-MDM2 interaction by structure-based design starting from a conformational argument. Bioorg Med Chem Lett. 2016; 26(19):4837 41. doi:10.1016/j.bmcl.2016.08.010.
43. Zhou W—H, Xu X-G, Li J, Min X, Yao J-Z, Dong G-Q, et al. Design, synthesis and structure-activity relationship of 4,5-dihydropyrrolo[3,4-c]pyrazol-6(1H)-ones as potent p53-MDM2 inhibitors. Chin Chem Lett. 2017; 28(2):422-5. doi: 10.1016/j.cclet.2016.09.001.
44. Zhuang C, Miao Z, Wu Y, Guo Z, Li J, Yao J, et al. Double-Edged Swords as Cancer Therapeutics: Novel, Orally Active, Small Molecules Simultaneously Inhibit p53-MDM2 Interaction and the NF-KB Pathway. J Med Chem. 2014; 57(3):567-77. doi: 10.1021/jm401800k.
45. Devegowda V N, Kim J H, Han K—C, Yang E G, Choo H, Pae A N, et al. Novel 6-N-Arylcarboxamidopyrazolo [4,3-D]Pyrimidin-7-One Derivatives as Potential Anti-Cancer Agents. *Bioorg Med Chem Lett* (2010) 20(5): 1630-3. doi: https://doi.org/1 0.1016/j.bmcl.2010.01.029.
46. Gein V L, Kasimova N N, Aliev Z G, Vakhrin M I. Three-Component Reaction of Methyl 2,4-Dioxo-4-Phenylbutanoate and Methyl 2,4-Dioxopentanoate with Aromatic Aldehydes and Propane-1,2-Diamine and Chemical Properties of the Products. *Russ J Org Chem* (2010) 46(6):875-83. doi: 10.1134/S1070428010060163

Example 4

Formulations of Pyrazolopyrrolidinones or Other Anti-Leishmanial Compounds Loaded into Biocompatible Expansile Particles (eNPs) for Systemic Delivery Expansile particles (eNPs) that possess either a 2,4,6-trimethoxyaldene actetal or a benzaldehyde acetal protecting group (control). The specific monomer unit is (5-methyl-2-(2,4,6-trimethoxyphenyl)-1,3-dioxan-5-yl)methyl methacrylate, prepared from the 1,1,1-tris (hydroxymethyl)ethane acetal of the aldehyde reacted with methacryloyl chloride.

Particle size and monodispersity controlled by varying the crosslinker, surfactant, and sonication parameters during preparation. For example, 1,4-O-methacryloylhydroquinone and 1,4-phenylene bis(2-methylacrylate) can be used as crosslinkers.

Expansile particles are stable at neutral pH, but hydrolyze in the mildly acidic pH (~5) of the cellular endosome where *Leishmania* parasites are intracellularly compartmentalized. See FIG. 16.

Expansile particles have been demonstrated to show significant uptake in the liver (~40%) and spleen (~2%) following IV injection; *Leishmania* parasites predominantly infect monocytes in the reticulo-endothelial system.

Example 5

Formulations of Pyrazolopyrrolidinones or Other Anti-Leishmanial Compounds Loaded into Biocompatible, Biodegradable Glycerol Carbonate Polymer and Polycaprolactone Particles for Systemic Delivery Poly(glycerol carbonate) is prepared from the tin-catalyzed ring opening polymerization of various trimethylene carbonates substituted at the 5-position with hydroxyl, benzyl, ester, or other similar functionality. Poly(glycerol carbonate is additionally prepared through the copolymerization of $CO_2$ with various oxiranyl monomers. Additional copolymers are prepared with poly(glycerol carbonate) and polycaprolactone through a similarly catalyzed ring opening polymerization reaction.

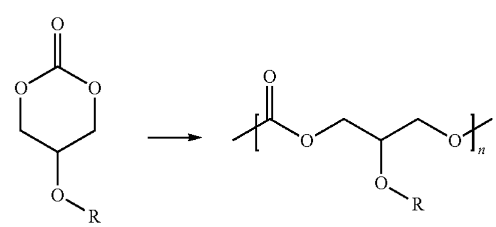

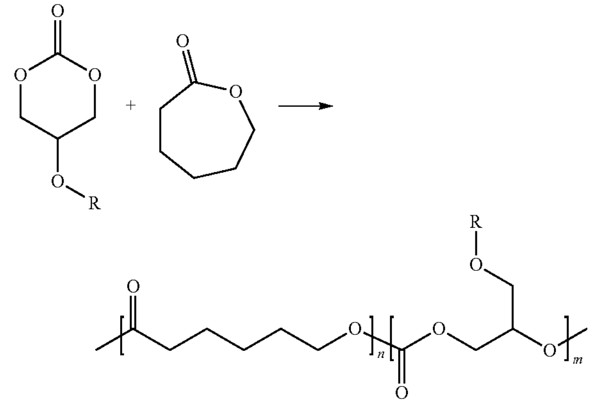

-continued

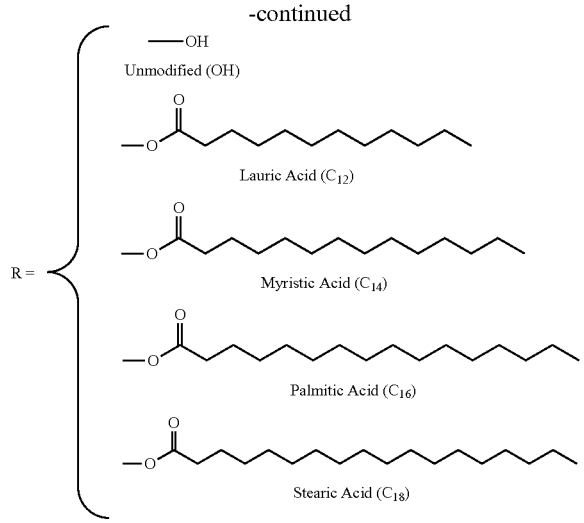

Unmodified (OH)

Lauric Acid ($C_{12}$)

Myristic Acid ($C_{14}$)

Palmitic Acid ($C_{16}$)

Stearic Acid ($C_{18}$)

Particles are formulated through water-in-oil ultrasonication methods and purified via dialysis. Particle size and monodispersity is controlled through sonication time, sonication pulse parameters, and polymer-to-surfactant ratio.

Polymer nanoparticles of similar size and composition to the aforementioned systems have been shown to demonstrate significant uptake in the liver following IV injection; *Leishmania* parasites predominantly infect monocytes in the reticulo-endothelial system.

Example 6

Formulations of Pyrazolopyrrolidinones or Other Anti-Leishmanial Compounds Loaded into Biocompatible, Biodegradable Glycidyl Carbonate Polymeric Adhesive for Topical Delivery Poly(Alkyl Glycidate Carbonate)s are prepared from copolymerization of $CO_2$ and the various oxiranyl glycidyl monomers as well as those polymerized from a carbonate monomer. Monomer units include 1,2 and 1,3 polyglycerol carbonates. See FIG. 17.

Another variation of this carbonate polymer hydrogel can be cross-linked hydrogels using PEG-diaziridine. See FIG. 18.

Pyrazolopyrrolidinones or other antileishmanial compounds can be loaded into these hydrogels through solvent evaporation or similar methods and applied to cutaneous leishmaniasis skin lesions with a brush or as a patch. Additives, tackifiers, or plasticizers may be included to improve adhesive performance.

Electrospun, porous polymer meshes are generated as a durable and moisture permeable backing to the adhesive patch. These meshes are flexible and conformable to the site of intended application. Polymer or hydrogel adhesives are coated onto the backing through dip coating, extrusion, gravure, or other similar methods. See FIG. 19.

Liners are included to protect the adhesive's integrity until the time of application. Liner composition may include silicone coated paper, polymer, or similar material.

In order to improve topical administration to CL lesions, development begun of an adhesive that can be formulated into a transdermal patch. The structure of the polymer, 1,3-poly(glycerol carbonate) (1,3-PGC), is promising as an adhesive in that it is biodegradable into natural metabolites, tunable in adhesive strength via pendant chain modifications, and structurally similar to poly(acrylate) adhesives. Proof-of-concept was demonstrated in drug-loading the adhesive through a solvent evaporation method in ethyl acetate with 5% glycerol. Including the glycerol as an additive slowed down the rate of solvent evaporation, ultimately yielding a more uniform adhesive disk.

New poly(glycerol carbonate) co-polymer nanoparticles were developed and used for the delivery of active agent to the liver in systemic VL infections. This polymer, 1,3-poly(glycerol carbonate)-C18-co-poly(ε-caprolactone) is formulated into nanoparticles via a oil-in-water nanoemulsion sonication method. This method was optimized to achieve particle sizes of 100-130 nm, which is ideal for cellular uptake and in vivo delivery to the liver. Drug release in physiologically relevant buffer demonstrates sustained release over three weeks.

For CL, the pendant chain character of the polymer was modified to achieve optimal adhesion to human skin. The adhesive layer was developed into an easy-to-apply patch using an electrospun poly(lactic acid) backing. Drug release from the adhesive will be optimized once fully formulated.

For VL a more comprehensive drug release study will be performed with more replicates over a longer duration of time to obtain a formulation with optimal release profile.

What is claimed is:

1. A composition comprising:

a. a polymer selected from the group consisting of polycarbonates, polyesters, polyacrylates, polyamides, and copolymers and mixtures thereof; and b. a compound of Formula (I) or (II):

(Formula I)

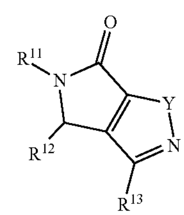

or (Formula II)

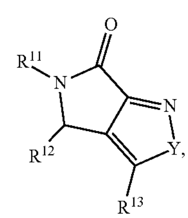

wherein:

Y is $NR^{14}$, $CH_2$, O or S;

$R^{11}$ is aryl, or heteroaryl, each optionally substituted with 1, 2 or 3 substituents selected independently from the group consisting of halogen, hydroxyl, alkoxy, alkyl, cycloalkyl, carboxyl, oxo, nitro, amino, alkylamino dialkylamino, carboxy, sulfonyl, sulfonamide, thiol, and cyano, or $R^{11}$ is alkyl, or alkenyl, each optionally substituted with 1 or 2 substituents selected independently from the group consisting of halogen, hydroxyl, alkoxy, cycloalkyl, aryl, heteroaryl, carboxyl, oxo, nitro, amino, alkylamino dialkylamino, carboxy, sulfonyl, sulfonamide, and cyano;

R$^{12}$ is cycloalkyl, aryl or heteroaryl, optionally the aryl and heteroaryl is substituted with 1, 2 or 3 substituents selected independently from the group consisting of halogen, hydroxyl, alkoxy, alkyl, cycloalkyl, carboxyl, oxo, nitro, amino, alkylamino dialkylamino, carboxy, sulfonyl, sulfonamide, and cyano;

R$^{13}$ is —CH$_2$—R$^{15}$;

R$^{14}$ is H, alkyl, alkenyl, alkynyl, or aryl, optionally the alkyl, alkenyl, alkynyl, and aryl is substituted with 1 or 2 substituents selected independently from the group consisting of halogen, hydroxyl, alkoxy, carboxyl, oxo, nitro, amino, alkylamino dialkylamino, carboxy, sulfonyl, sulfonamide, thiol, and cyan; and R$^{15}$ is alkyl, alkenyl, alkynyl, aryl, a nucleophile, optionally the alkyl, alkenyl, alkynyl and aryl is substituted with 1 or 2 substituents selected independently from the group consisting of halogen, hydroxyl, alkoxy, carboxyl, oxo, nitro, haloalkyl, aryl, heteroaryl, cycloalkyl, amino, alkylamino dialkylamino, carboxy, sulfonyl, sulfonamide, and cyano; and a pharmaceutically acceptable salt thereof.

2. The composition of claim 1, wherein Y is N—R$_4$, e.g., the compound is of Formula (I-A) or (II-A):

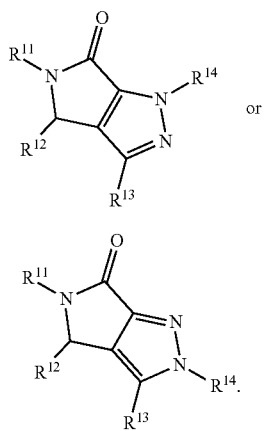

(Formula I-A)

or (Formula II-A)

3. The composition of claim 2, wherein R$^{15}$ is alkyl, or alkenyl, wherein the alkyl and alkenyl is optionally substituted with one substituent selected from the group consisting of halogen, hydroxy, carboxyl, oxo, nitro, aryl, heteroaryl, amino, alkylamino dialkylamino, thiol, sulfinyl, sulfonyl, sulfonamide, sulfate, phosphate, haloalkyl, thioalkyl, cyanomethylene, alkylaminyl, cyano and ureido.

4. The composition of claim 3, wherein R$^{15}$ is isopropyl, isobutyl, t-butyl, propyl, propen-3-yl, 2-methylpropen-3-yl, 2-methylbutene-4-yl, cyclohexylmethyl, 2-cyclohexylethyl, benzyl, —CH$_2$—OR$^{17}$, —CH$_2$CH$_2$—OR$^{17}$, —CH$_2$—NR$^{18}$N$^{19}$ or —CH$_2$CH$_2$—NR$^{18}$N$^{19}$, wherein R$^{17}$ is H or alkyl; and wherein R$^{18}$ and R$^{19}$ are independently H, alkyl or cycloalkyl.

5. The composition of claim 1, wherein R$^{14}$ is H, C$_1$-C$_6$alkyl, C$_2$-C$_6$alkenyl, C$_2$-C$_6$alkynyl, or 5-12 membered aryl, wherein the C$_1$-C$_6$alkyl, C$_2$-C$_6$alkenyl, C$_2$-C$_6$alkynyl, and 5-12 membered aryl is optionally substituted with one substituent selected from the group consisting of halogen, hydroxyl, alkoxy, haloalkyl, and cyano.

6. The composition of claim 5, wherein R$^{14}$ is H, methyl, ethyl, propyl, isopropyl, butyl, isobutyl, but-2-yl, t-butyl, pentyl, 5-hexyn-1-yl, 2-propyn-1-yl, propargyl, methoxymethyl, phenyl, or 4-trifluoromethylphenyl or —(CH$_2$)$_a$—R$^{16}$, where a is 0, 1, 2, 3, 4, 5, 6, 7, 8, 9 or 10, optionally, a is 0, 1, 2, 3 or 4 (e.g., a is 1 or 2); and R$^{16}$ is cycloalkyl, —OR$^{17}$, —NR$^{18}$R$^{19}$, where R$^7$ is H or alkyl, and R$^8$ and R$^9$ are independently H, alkyl, or cycloalkyl.

7. The composition of claim 1, wherein R$^{12}$ is 5-12 membered cycloalkyl, 5-12 membered aryl or 5-12 membered heteroaryl, wherein the 5-12 membered cycloalkyl, 5-12 membered aryl and 5-12 membered heteroaryl is optionally substituted with 1, 2 or 3 substituents selected independently from the group consisting of halogen, hydroxyl, alkoxy, carboxyl, amino, alkylamino dialkylamino, cyano and ureido.

8. The composition of claim 7, wherein R$^{12}$ is 4-fluorophenyl, 4-chlorophenyl, 4-bromophenyl, 4-trifluoromethylphenyl, 4-methoxyphenyl, 4-carboxylphenyl, 4-methoxycarbonylphenyl, 4-methylphenyl, 3-fluorophenyl, 3-chloropehnyl, 3-bromophenyl, 3-trifluoromethylphenyl, 3-methoxyphenyl, 2-fluorophenyl, 2-chloropehnyl, 2-bromophenyl, 2-trifluoromethylphenyl, 2-methoxyphenyl, 2-methylphenyl, 3,4-difluorophenyl, 2,4-difluorophenyl, 4-fluoro-2-methylphenyl, 2-chloro-4-fluorophenyl, 2-bromo-4-fluorophenyl, 2-fluoro-4-chlorophenyl, 2-fluoro-4-bromophenyl, 1,6-dichlorophenyl, phenyl, cyclohexyl, cyclopentyl, 3-methoxypyridin-2-yl, 2-methoxypyridin-3-yl, 2-methoxypyridin-5-yl, thiophen-3-yl, thiopen-2-yl, 3-methylthiophen-2-yl, 2-methylthiophen-5-yl, pyridine-4-yl, 4-fluoro-2-methoxyphenyl, 3-methoxypyridin-5-yl, 3-fluoropyridin-6-yl, 4-carboxylphenyl, 2-bromo-5-trifluoromethylphenyl, 1,3-thiazol-5-yl, 3-trifluoromethyl-4-fluorophenyl, pyrimidin-4-yl, 4-cholor-pyridin-3-yl, 2,6-difluoropyridin-4-yl, 4-trifloromethoxyphenyl, pyridazine-4-yl, 2,5-ditrifluromethylphenyl, thiaz-5-yl, 3-triflluromethyl-4-fluorophenyl, 3-trifluoromethylphenyl, 4-fluoro-2-methylphenyl, 3-fluropyridin-6-yl, and 3-bromothiophen-2-yl.

9. The composition of claim 1, wherein R$^{11}$ is 5-12 membered aryl, or 5-12 membered heteroaryl, wherein the 5-12 membered aryl, and 5-12 membered heteroaryl, is optionally substituted with 1, 2 or 3 substituents selected independently from the group consisting of halogen, hydroxyl, alkoxy, carboxyl, amino, alkylamino dialkylamino, thiol, and cyano; or R$^{11}$ is C$_1$-C$_{10}$alkyl, optionally substituted with 1 or 2 substituents selected independently from the group consisting of halogen, hydroxyl, alkoxy, amino, alkylamino dialkylamino, aryl or heteroaryl.

10. The composition of claim 9, wherein R$^{11}$ is 4-methoxyphenyl, 2-methoxyphenyl, 2-methoxypyridin-5-yl, 3-fluoropyridin-5-yl, 1,3-benzodioxolyl, 4-(methoxycarbonyl)phenyl, 4-carboxyphenyl, 4-dimethylaminoaphenyl, benzimidazole-5-yl, 4-sulfamoylphenyl, 4-trifluromethoxyphenyl, 3-methoxyphenyl, 3-fluoro-4-methoxyphenyl, 4-bromophenyl, 4-fluorophenyl, 4-chlorophenyl, 2-pyridinylethyl, N-methylpiperazinyl, N-isopropylpyrazol-4-yl, 4-pyrrolidonylphenyl, 2,3-dihydro-1,4-benzodioxinyl, 1,3, 3a-triazaindenyl, 1-acetyl-3-hydroxypropyl, 4-imidazolylphenyl, 3-fluoropyridin-5-yl, 4-dimethylaminophenyl, N-methylpyrrolidin-3-yl, 2-hydroxymethyl-2-methyl-3-hydroxypropyl, 2-methoxyethyl, 5-hexyn-1-yl, 4-hydroxyphenyl, 2-(3-butyn-1-yl)pyridin-4-yl, N-ethylpyrrolidin-3-yl, hydrogen, phenyl, 2-methoxypyridin-5-yl, 3-fluoro-2-methoxypyridin-5-yl, 4-methoxyphenylmethyl, 4-(1-Pyrrolidinylsulfonyl)phenyl, 4-imidazole-1-ylphenyl, 2-hydroxybenzimidazoly-5-yl, 3,4,5-trimethoxyphenyl, 4-ethoxyphenyl, 2,4-dimethoxyphenyl, 4-t-butylphenyl, 4-ethylphenyl, 3-methoxypyridin-6-yl-methyl, 4-cyanophenyl, 3-trifluoromethylpyridin-6-yl, 2-pyrrolidinylethyl, tetrahydropyran-4-yl, 3-caynophenyl, 4-trifluoromethoxyphenyl, 1,3-dihydroxypropy-2-yl, 2-methylpyridin-4-yl, N-ethylpyrrolidin-4-yl, 3-oxo-3,4-dihydro-2H-1,4-benzoxazine-7-yl, 4-(2-oxo-1-pyrrolidinyl)phenyl, 2-methylpyridin-5-yl, 2-(N-methylpiperazinyl)pirpdin-5-yl, 3-fluoropyridin-5-yl, 2-methoxy-3-methylpyridin-5-yl, 4-(1-ethyl-1H-pyrazol-4-yl)phenyl, 4-(1-ethyl-1H-pyrazol-3-yl)phenyl, 2-fluoropyridin-5-yl, 4-(1-isopropyl-1H-pyrazol-4-yl)phenyl, 4-(1-isopropyl-1H-pyrazol-3-yl)phenyl, 4-(1-ethyl-1H-pyrazol-3-yl)phenyl, 4-(1-methyl-1H-pyrazol-4-yl)phenyl, 3-methoxypyridin-6-yl, 4-(1-methyl-1H-pyrazol-3-yl)phenyl, 4-(1-pyrrolidinylcarbonyl)-phenyl, 2-(1-methylpiperzin-4-yl)pyridine-5-yl, 4-(5-hexyn-1-oxy)phenyl, 4-triflouromethoxyphenyl, 4-methylphenyl, 4-ethylphenyl, pyridine-3-yl, pyridine-2-yl, 2-methylfuran-5-yl, 4-methoxycyclohexyl, 4-dimethylaminohexyl, and 1-methylpyrrolidin-3-yl methyl.

11. The composition of claim 1, wherein the composition is formulated for topical, intravenous (iv) or oral administration.

12. The composition of claim 1, wherein the polymer and the compound are comprised in a particle comprising the polymer and the compound.

13. The composition of claim 12, wherein the particle is an expansile particle.

14. The composition of claim 12, wherein the particle comprises a first volume at a neutral pH and a second volume at an acidic pH, wherein the second volume is at least 1× greater than the first volume.

15. The composition of claim 12, wherein the particle accumulates in the liver of a subject after administering to said subject and releases the compound in the liver.

16. The composition of claim 12, wherein the particle is from about 10 nm to about 1000 nm in size.

17. The composition of claim 1, wherein the composition is in the form of an adhesive.

18. The composition of claim 1, wherein the composition is in the form of a film, a sheet, a dressing, a cream, a spray, a liquid, a gel, a hydrogel, an emulsion, or a suspension.

19. The composition of claim 1, wherein the polymer comprises one or more monomers of Formula (A), Formula (B), and/or Formula (C):

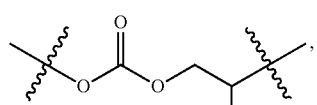
(Formula A)

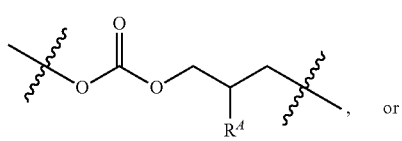
(Formula B), or

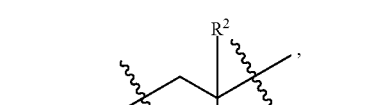
(Formula C)

wherein:

each $R^A$ is independently —OC(O)—$R^{A1}$, —OC(O)O—$R^{A1}$, —OC(O)NH—$R^{A1}$, —NHC(O)O—$R^{A1}$, —NHC(O)NH—$R^{A1}$, —OR$^{A1}$, —C(O)—$R^{A1}$, —C(O)O—$R^{A1}$, or —C(O)NH—$R^{A1}$; and each $R^{A1}$ is independently hydrogen, alkyl, alkenyl, cycloalkyl, aryl, heteroaryl, silyl, alkylsilyl, arylsilyl, alkylaryl, arylalkyl, poly(ethylene glycol), poly(ethylene oxide), poly(hydroxyacid)), a carbohydrate, a protein, a polypeptide, an amino acid, a nucleic acid, a nucleotide, a lipid, an oligosaccharide, a polysaccharide, an antibody, a pharmaceutical agent, an imaging agent, an epitope for a biological receptor, a photocrosslinkable group, or an ionically crosslinkable group, wherein alkyl, alkenyl, cycloalkyl, aryl, heteroaryl, silyl, alkylsilyl, arylsilyl, alkylaryl, and arylalkyl is optionally substituted by one or more substituents selected independently from the group consisting of hydroxyl, hydroxyether, carboxyl, carboxyester, carboxyamide, amino, mono- or di-substituted amino, thiol, thioester, sulfate, phosphate, phosphonate, and halogen;

each $R^C$ is independently:

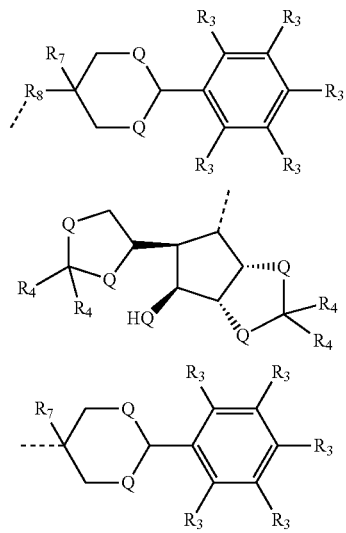

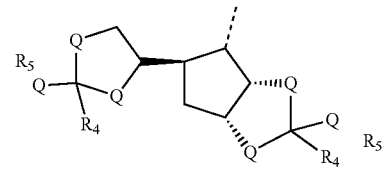

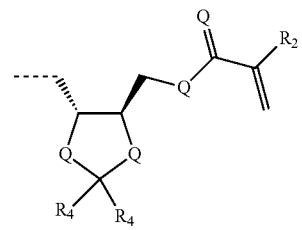

433
-continued

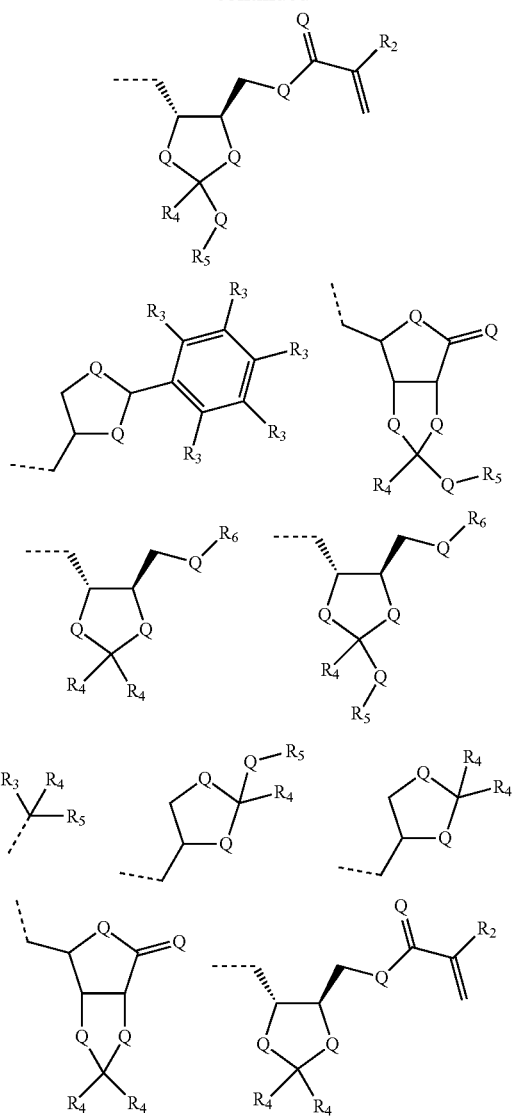

434
-continued

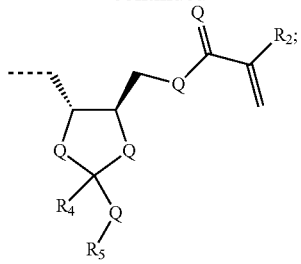

where each Q is O;

each $R^2$ is independently selected from the group consisting of hydrogen, a straight or branched alkyl, cycloalkyl, aryl, olefin, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

one $R_3$ is selected from the group consisting of methoxy, ethoxy, amino, nitro, cycloalkyl, aryl, and olefin;

and the remaining $R_3$ are each independently selected from the group consisting of hydrogen, methoxy, ethoxy, amino, a straight and branched alkyl, cycloalkyl, aryl, and olefin;

$R_4$, $R_5$, and $R_6$ are each independently selected from the group consisting of a straight or branched alkyl, cycloalkyl, aryl, and olefin; and $R_7$ and $R_8$ are each independently selected from the group consisting of hydrogen, a straight or branched alkyl, cycloalkyl, aryl, olefin, alkylaryl, and arylalkyl.

20. The composition of claim 1, wherein the polymer is a poly(glycerol carbonate) or a copolymer thereof.

21. The composition of claim 19, polymer is poly(1,3-glycerol carbonate)-$C_{18}$-co-poly(ε-caprolactone) copolymer.

22. The composition of claim 1, wherein the composition further comprises a pharmaceutically acceptable carrier or excipient.

23. The composition of claim 1, wherein the composition further comprises an active agent.

* * * * *